US011649444B1

(12) United States Patent
Zhang et al.

(10) Patent No.: US 11,649,444 B1
(45) Date of Patent: May 16, 2023

(54) CRISPR-CAS12I SYSTEMS

(71) Applicant: HuidaGene Therapeutics Co., Ltd., Shanghai (CN)

(72) Inventors: Hainan Zhang, Shanghai (CN); Xiangfeng Kong, Shanghai (CN); Qijia Chen, Shanghai (CN)

(73) Assignee: HuidaGene Therapeutics Co., Ltd., Shanghai (CN)

( * ) Notice: Subject to any disclaimer, the term of this patent is extended or adjusted under 35 U.S.C. 154(b) by 0 days.

(21) Appl. No.: 17/819,795

(22) Filed: Aug. 15, 2022

(51) Int. Cl.
*C12N 9/22* (2006.01)
*C12N 15/10* (2006.01)

(52) U.S. Cl.
CPC ............. *C12N 9/22* (2013.01); *C12N 15/102* (2013.01); *C12N 2310/20* (2017.05)

(58) Field of Classification Search
CPC .................................................. C12N 2310/20
See application file for complete search history.

(56) References Cited

U.S. PATENT DOCUMENTS

| | | | |
|---|---|---|---|
| 4,186,183 | A | 1/1980 | Alving et al. |
| 4,217,344 | A | 8/1980 | Handjani et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,774,085 | A | 9/1988 | Fidler |
| 4,797,368 | A | 1/1989 | Carter |
| 4,837,028 | A | 6/1989 | Allen |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,173,414 | A | 12/1992 | Lebkowski et al. |
| 5,580,859 | A | 12/1996 | Felgner |
| 5,589,466 | A | 12/1996 | Felgner |
| 5,593,972 | A | 1/1997 | Weiner et al. |
| 6,410,319 | B1 | 6/2002 | Raubitschek |
| 7,446,191 | B2 | 11/2008 | Jensen |
| 7,514,537 | B2 | 4/2009 | Jensen |
| 9,765,342 | B2 | 9/2017 | Kochenderfer |
| 10,619,154 | B2 | 4/2020 | Reik et al. |
| 10,808,245 | B2 | 10/2020 | Chong et al. |
| 11,021,696 | B2 | 6/2021 | Orkin et al. |
| 11,168,324 | B2 | 11/2021 | Chong et al. |
| 11,447,771 | B1 | 9/2022 | Cheng et al. |
| 2003/0087817 | A1 | 5/2003 | Cox et al. |
| 2007/0059298 | A1 | 3/2007 | Volkmann |
| 2010/0025177 | A1 | 2/2010 | Fukushima |
| 2010/0065818 | A1 | 3/2010 | Kim |
| 2012/0164118 | A1 | 6/2012 | Trobridge et al. |
| 2020/0063126 | A1* | 2/2020 | Cheng .................... C12N 15/90 |
| 2020/0407716 | A1 | 12/2020 | Chong et al. |
| 2021/0395784 | A1 | 12/2021 | Lai et al. |

FOREIGN PATENT DOCUMENTS

| | | | |
|---|---|---|---|
| CN | 111767889 | A | 10/2020 |
| CN | 112041444 | A | 12/2020 |
| CN | 113106081 | A | 7/2021 |
| CN | 113151215 | A | 7/2021 |
| CN | 113308451 | A | 8/2021 |
| CN | 114015674 | A | 2/2022 |
| WO | 199116024 | A1 | 10/1991 |
| WO | 199117424 | A1 | 11/1991 |
| WO | 199324641 | A2 | 12/1993 |
| WO | 199324641 | A3 | 5/1994 |
| WO | 199426877 | A1 | 11/1994 |
| WO | 2002077029 | A2 | 10/2002 |
| WO | 2002077029 | A3 | 5/2003 |
| WO | 2014093622 | A2 | 6/2014 |
| WO | 2014093622 | A3 | 8/2014 |
| WO | 2015142675 | A3 | 9/2015 |
| WO | 2015142675 | A3 | 11/2015 |

(Continued)

OTHER PUBLICATIONS

Ahmad, I. et al. (Sep. 1, 1992). "Antibody-Mediated Specific Binding nd Cytotoxicity of Liposome-Entrapped Doxorubicin to Lung Cancer Cells In Vitro," Cancer Res. 54(17):4817-4820.

Anderson, W.F. (May 8, 1992). "Human Gene Therapy," Science 256:808-813.

Anzalone, A.V. et al. (2020). "Genome Editing With CRISPR-Cas Nucleases, Base Editors, Transposases and Prime Editors," Nature Biotechnology 38:824-844.

Bae, S. et al. (2014, e-pub. Jan. 24, 2014). "Cas-OFFinder: A Fast and Versatile Algorithm That Searches for Potential Off-Target Sites of Cas9 RNA-Guided Endonucleases," Bioinformatics 30:1473-1475.

(Continued)

*Primary Examiner* — Neil P Hammell
(74) *Attorney, Agent, or Firm* — Morrison & Foerster LLP

(57) ABSTRACT

The present disclosure provides a Cas12i protein (e.g., non-naturally occurring, engineered) comprising an amino acid sequence having at least about 80% (e.g., at least about any of 81%, 82%, 83%, 84%, 85%, 86%, 87%, 88%, 89%, 90%, 91%, 92%, 93%, 94%, 95%, 96%, 97%, 98%, 99%, 99.5%, or 100%) identity to the amino acid sequence as set forth in any one of SEQ ID NOs: 1-10 (preferably, SEQ ID NOs: 1-3 and 6, and more preferably, SEQ ID NO: 1). The present disclosure further provides an engineered, non-naturally occurring CRISPR-Cas12i system comprising: (1) any of the Cas12i proteins described herein or a polynucleotide encoding any of the Cas12i proteins described herein; and (2) a CRISPR RNA (crRNA) or a polynucleotide encoding the crRNA, wherein the crRNA comprises: (i) a spacer capable of hybridizing to a target sequence of a target DNA, and (ii) a Direct Repeat (DR) linked to the spacer and capable of guiding the binding of the Cas12i protein to the crRNA to form a CRISPR-Cas12i complex targeting the target sequence.

27 Claims, 6 Drawing Sheets

Specification includes a Sequence Listing.

(56) References Cited

FOREIGN PATENT DOCUMENTS

| | | | |
|---|---|---|---|
| WO | 2017025038 | A1 | 2/2017 |
| WO | 2021257730 | A2 | 12/2021 |
| WO | 2022120520 | A1 | 6/2022 |
| WO | 2022256619 | A2 | 12/2022 |

OTHER PUBLICATIONS

Bauer, D.E. et al. (Oct. 11, 2013). "An Erythroid Enhance of BCL11A Subject To Genetic Variation Determines Fetal Hemoglobin Level," Science 342:253-257.
Behr, J-P. (Sep. 1, 1994). "Gene Transfer Wth Synthetic Cationic Amphiphiles: Prospects for Gene Therapy," Bioconjugate Chem. 5:382-389.
Bennetzen, J.L. et al. (Mar. 25, 1982). "Codon Selection in Yeast," J. Biol. Chem. 257(6):3026-2031.
Berger, C. et al. (Jan. 2008). "Adoptive Transfer Of Effector CD8+ T Cells Derived From Central Memory Cells Establishes Persistent T Cell Memory In Primates," The Journal Of Clinical Investigation 118(1):294-305.
Bravo, J. P. K. et al. (2022, e-pub. Mar. 2, 2022). "Structural Basis for Mismatch Surveillance by CRISPR-Cas," Nature 603:343-347.
Buchscher, G.L. et al. (May 1992). "Human Immunodeficieny Virus Vectors for Inducible Expression of Foreign Genes," J. Virol. 66(3):2731-2739.
Campbell, W.H. (1990). Codon Usage in Higher Plants, Green Algae and Cyanobacteria, Plant Physiol. 92(1):1-11.
Canver, M.C. et al. (2015). "BCL11A Enhancer Dissection By Cas9-Mediated In Situ Saturating Mutagenesis," Nature 527:192-197.
Chen, Y. et al. (Jul. 12, 2022). "Synergistic Engineering of CRISPR-Cas Nucleases Enables Robust Mammalian Genome Editing," Innovation 3(4):100264:1-8.
Cho, S. et al. (2010), "Lipid-Like Nanoparticles for Small Interfering RNA Delivery to Endothelial Cells," Advanced Functional Materials 19:3112-3118.
Cong, L. et al. (Feb. 15, 2013). "Multiplex Genome Engineering Using CRISPR/Cas Systems," Science 339 (6121):819-823, 9 pages.
Cox, D. B. T. et al. (Nov. 24, 2017). "RNA Editing With CRISPR-Cas13," Science 358:1019-1027.
Crystal, R.D. (Oct. 20, 1995). "Transfer Of Genes To Humans: Early Lessons and Obstacles to Success," Science 270:404-410.
Dillon, N. (May 1993). "Regulating Gene Expression in Gene Therapy," Trends Biotechnol. 11(5):167-173.
Doudna, J. A. (Feb. 13, 2020). "The Promise and Challenge of Therapeutic Genome Editing," Nature 578:229-236.
El-Andaloussi, S. et al. (2012, e-pub. Nov. 15, 2012). "Exosome-Mediated Delivery of siRNA in Vitro and in Vivo," Nat. Protoc. 7(12):2112-2126.
Fellmann, C, et al. (2016). "Cornerstones of CRISPR-Cas in Drug Discovery and Therapy," Nature Review Drug Discovery 16:89-100, 27 pages.
Fukui, K. (2010). "Dna Mismatch Repair in Eukaryotesand Bacteria," J. Nucleic Acids 260512, 16 pages.
Gao, X. (Dec. 1, 1995), "Cationic Liposome-Mediated Gene Transfer," Gene Therapy 2:710-722.
Gaudelli, N. M. et al. (Nov. 23, 2017). "Programmable Base Editing Of A*T To G*C In Genomic DNA Without DNA Cleavage," Nature 551:464-471.
Genbank Accession No. NC_000001.11. (Apr. 6, 2022). "*Homo sapients* Chromosome 1, GRCh38.p14 Primary Assembly," 3 pages.
Genbank Accession No. NC_000009.12. (Apr. 6, 2022). "*Homo sapiens* Chromosome 9, GRCh38.p14 Primary Assembly," 3 pages.
Genbank Accession No. NC_000012.12. (Apr. 6, 2022). "*Homo sapiens* Chromosome 12, GRCh38.p14 Primary Assembly," 3 pages.
Genbank Accession No. NC_000012.12. (Aug. 31, 2020). "*Homo sapiens* Programmed Cell Death 1 (PDCD1), RefSeqGene on Chromosome 2," 7 pages.
Genbank Accession No. NC_000017.11. (Apr. 6, 2022). "*Homo sapiens* Chromosome 17, GRCh38.p14 Primary Assembly," 3 pages.
Genbank Accession No. NC_00003.12. (Apr. 6, 2022). "*Homo sapiens* Chromosome 3. GRCh38.p14 Primary Assembly," 402 pages.
Genbank Accession No. NC_00019.10. (Apr. 6, 2022). "Homo Sapiens Chromosome 19, GRCh38.p14 Primary Assembly," 3 pages.
Genbank Accession No. NG_001332.3. (Jul. 2, 2020). "*Homo sapiens* T Cell Receptor Alpha Delta L0cus (TCRA/TCRD) on Chromosome 14," 47 pages.
Genbank Accession No. NG_001333.2. (Sep. 3, 2019). "*Homo sapiens* T Cell Receptor Beta Locus (TRB) on Chromosome 7," 48 pages.
Genbank Accession No. NG_007073.2. (Oct. 14, 2020). "*Homo sapiens* Glyceraldehyde-3-Phosphate Dehydrogenase (GAPDH), RefSeqGene on Chromosome 12," 10 pages.
Genbank Accession No. NG_007383.1. (Feb. 25. 2022). "*Homo sapiens* CD3 Epsilon Subunit of T-Cell Receptor Complex (CD3E), ReFSeqGene (LRG_38) on Chromosome 11," 7 pages.
Genbank Accession No. NG_007490.1. (Aug. 21, 2022), "*Homo sapiens* Transforming Growth Factor Beta Receptor 2 (TGFGR2), Ref SeqGene (LRG_779) on Chromsome 3," 25 pages.
Genbank Accession No. NG_007566.1. (Feb. 25. 2022). "*Homo sapiens* CD3 Gamma Subunit of T-Cell Receptor Complex (CD3G), RefSeqGene (LRG39) on Chromosome 11," 8 pages.
Genbank Accession No. NG_009066.1. (Jun. 14, 2022). "*Homo sapiens* Fc Gamma Receptor IIIa(FCGR3A). RefSeqGene (LRG_60) on Chromosome 1" 6 pages.
Genbank Accession No. NG_009088.1. (Aug. 21, 2022). "*Homo sapien* Interleukin 2 Receptor Subunit Gamma (IL2RG), RefSEqGene (LRG150) on Chromosome X," 7 pages.
Genbank Accession No. NG_009628.1. (Jun. 21, 2020). "*Homo sapiens* Class II Major Histocompatibility Complex Transactivator (CIITA), RefSeqGene (LRG_49) on Chromosome 16," 16 pages.
Genbank Accession No. Ng 009770.2. (Aug. 22, 2022). "*Homo sapiens* Hexosaminidase Sunbunit Beta (HEXB), RefSeqGene on Chromosome 5; Nuclear Gene for Mitochondrial Product," 29 pages.
Genbank Accession No. NG_009891.1, (Feb. 25, 2022). "*Homo sapiens* CD3 Delta Subunit of T-Cell Receptor Complex (CD3D), RefSeqGene (LRG_37) on Chromosome 11," 6 pages.
Genbank Accession No. NG_011502.1. (Oct. 5, 2020). "*Homo sapiens* Cytotoxic T-Lymphocyte Associated Protein 4 (CTLA4), RefSeqGene (LRG_1220) on Chromosome 2," 6 pages.
Genbank Accession No. NG_011587.1. (Jul. 9, 2021). "*Homo sapiens* C-X-C Motif Chemokine Receptor 4 (CXCR4), RefSeqGene (LRG51) on Chromosome 2," 8 pages.
Genbank Accession No. NG_011968.1. (Aug. 21, 2022). "*Homo sapiens* BAF Chromatin Remodeling Complex Subunit BCL11A (BCL11A), RefSeqGene on Chromosome 2," 28 pages.
Genbank Accession No. NG_012110.1. (Aug. 31, 2020). "*Homo sapiens* Programmed Cell Death 1 (PDCD1), RefSeqGene on Chromosome 2," 7 pages.
Genbank Accession No. NG_012637.1 . (May 31, 2021). "*Homo sapiens* C-C Motif Chemokine Receptors (CCR5), RefSeqGene on Chromosome 3," 7 pages.
Genbank Accession No. NG_012920.2. (Oct. 14. 2020). "*Homo sapiens* Beta-2-Microglobulin (B2M), RefSeqGene (LRG_1215) on Chromosome 15," 6 pages.
Genbank Accession No. NG_023194.1. (Aug. 31, 2020). "*Homo sapiens* Cytokine Inducible SH2 Containing Protein (CISH), RefSeqGene on Chromosome 3," 5 pages.
Genbank Accession No. NG_027762.1. (Jul. 25. 2022). "*Homo sapiens* Killer Cell Lectin Like Receptor K1 (KLRK1), RefSeqGene on Chromosome 12," 9 pages.
Genbank Accession No. NG_030444.1 . (Oct. 5, 2020). "*Homo sapiens* Hepatitis A. Virus Cellular Receptor 2 (HAVCR2), RefSeqGene on Chromosome 5," 10 pages.
Genbank Accession No. NG_052804.1. (Nov. 23, 2020). "*Homo sapiens* Adenosine A2a Receptor (ADORA2A), RefSeqGene on Chromosome 22," 9 pages.

(56) References Cited

OTHER PUBLICATIONS

Genbank Accession No. NG_059281.1. (Jun. 20, 2022). "*Homo sapiens* Hemoglobin Subunit Beta (HBB), RefSeqGene (LRG_1232) on Chromosome 11," 7 pages.
Gillmore, J.D. et al. (Aug. 5, 2021, e-pub. Jun. 26, 2021). "CRISPR-Cas9 In Vivo Gene Editing for Transthyretin Amyloidosis," New England Journal Medicine 385:493-502.
Gootenberg, J.S. (2017). "Nucleic Acid detection With CRISP-Cas13/a/C2c2," Science 356:438-442.
Grunebaum, E. et al. (Dec. 2013). "Recent Advances in Understanding and Managing Adenosine Deaminase and Purine Nucleoside Phosphorylase Deficiencies," Curr. Opin. Allergy Clin. Cimmunol. 13(6):630-638.
Hermonat, P.L. et al. (Oct. 1984). "Use of Adeno-Associated Virus as a Mammalian DNA Cloning Vector: Transduction of Neomycin Resistance Into Mammalian Tissue Culture Cells," PNAS 81:6466-6470.
Huang, X. et al. (2020). "Structural Basis for Two Metal-Ion Catalysis of DNA Cleavage by Cas12i2,". Nat Communication 11(5241):1-14.
Johann, S.V..et al. (Mar. 1992). "GLVR1, A Receptor for Gibbon Ape Leukemia Virus, Is Homologous to a Phosphate Permease of Neuropora Crassa and Is Expressed at High Levels in the Brain and Thymus," J. Virol. 66(3):1635-1640.
Kim, D.Y. et al. (Jan. 2022). "Efficient CRISPR Editing With a Hypercompact Cas12f1 and Engineered Guide RNAs Delivered by Adeno-Associated Virus," Nat Biotechnol. 40:94-102.
Kim, J. et al. (2006, e-pub. Apr. 29, 2006). "Structural and Kinetic Characterization of *Escherichia coli* TadA, the Wobble-Specific tRNA Deaminase," Biochemistry 45:6407-6416.
Kim, Y.B. (Apr. 2017), "Increasing the Genome-Targeting Scope and Precision of Base Editing With Engineered Cas9-Cytidine Deaminase Fusions," Nature Biotechnology 35(4):371-377, 15 pages.
Kleinstiver, B. P. et al. (2016). "High-fidelity CRISPR-Cas9 Nucleases With no Detectable Genome-Wide Off-Target Effects," Nature 529:490-495.
Kleinstiver, B. P. et al. (Aug. 2016). "Genome-Wide Specificities of CRiSPR-Cas Cpf1 Nucleases in Human Cells," Nature Biotechnology 34:869-874, 14 pages.
Kleinstiver, B. P. et al. (Mar. 2019). "Engineered CRISPR-Cas12a Variants With Increased Activities and Improved Targeting Ranges for Gene, Epigenetic and Base Editing," Nat, Biotechnol. 37(3):276-282, 22 pages.
Komore, A.C. (2016). "Programmable Editing of a Target Base in Genomic DNA Without Double-Stranded DNA Cleavage," Nature 533(7603):420-424, 25 pages.
Konermann, S. et al. (Jan. 29, 2015). "Genome-Scale Transcriptional Activation by an Engineered CRISPR-Cas9 Complex," Nature 517:583-588.
Kotin, R. (Jul. 1994). "Prospects for the Use of Adeno-Associated Virus as a Vector for Human Gene Therapy," Hum. Gene Ther. 5(7):793-801.
Kotin, R.M. et al. (1992). "Characterization of a Preferred Site on Human Chromosome 19q for Integration of Adeno-Associated Virus DNA by Non-Homoiogous Recombination," Embo J. 11(13):5071-5078.
Kremer, E.J. et al. (1995), "Adenovirus and Adeno-Associated Virus Mediated Gene Transfer," British Medical Bulletin 51(1):31-44.
Lewis, D.L. et al. (Sep. 2002, e-pub. Jul. 29, 2002). "Efficient Delivery of siRNA for Inhibition of Gene Expression in Postnatal Mice," Nat. Gen. 32:107-108.
Li, X. et al. (Apr. 2018). "Base Editing With a Cpf1-Cytidine Deaminase Fusion," Nat Biotechnol 36(4):324-327.
Makarova, K. S. et al. (Feb. 2020). "Evolutionary Classification of CRISPR-Cas Systems: A Burst of Class 2 and Derived Variants," Nat. Rev. Microbiol. 18(2):67-83, 36 pages.
Mcgaw, C. et al. (2022). "Engineered Cas12i2 is a Versatile High-Efficiency Platform for Therapeutic Genome Editing," Nat. Commun. 13:2833, 1-11 pages.
Miller, A.D. (Jun. 11, 1992). "Human Gene Therapy Comes of Age" Nature 357(6378):455-460.
Miller, A.D. et al. (May 1991). "Construction and Properties of Retrovirus Packaging Cells Based on Gibbon Ape Leukemia Virus," J. Virol. 65(5):2220-2224.
Mitani, M. et al., (May 1993). "Delivering Therapeutic Genes—Matching Approach and Application," Trends Biotechnol. 11(5):162-166.
Morton, B.R. (Apr. 1998). "Selection on the Codon Bias of Chloroplast and Cyanelle Genes in Different Plant and Algal Lineages," J. Mol. Evol. 46(4):449-459.
Murray, E.E. et al. (1989). "Codon Usage in Plant Genes," Nucleic Acids Res. 17(2):477-498.
Musunuru, K. et al. (May 20, 2021, e-pub. May 19, 2021). "In Vivo CRISPR Base Editing of PCSK9 Durably Lowers Cholesterol in Primates," Nature 593:429-434.
Muzyczka, N. (Oct. 1994). "Adeno-Associated Virus (AAV) Vectors: Will They Work?," J. Clin. Invest. 94:1351.
Myers, E.W. et al. (Mar. 1988), Optimal Alignments in Liner Space, CABIOS 4(1):11-17.
Nabel, G.J. et al. (May 1993). "Direct Gene Transfer for Immunotherapy and Immunization," Trends Biotechnol 11(5):211-215.
Nakamura, M. et al. (Jan. 2021). "CRISPR Technologies for Precise Epigenome Editing," Nature Cell Biology 23:11-22.
Nakamura, Y., et al. (Jan. 1, 2000). "Codon Usage Tabulated From The International DNA Sequence Databases: Status For The Year 2000," Nucl. Acids Res. 28:292.
NCBI Gene ID 567, B2M Beta-2-Microglobulin [*Homo sapiens* (human)], Ensembl: ENSG00000166710 MIM: 109700; AllianceGenome: HGNC: 914, upated on Sep. 11, 2022, 13 pages.
NCBI Gene ID 10219, KLRG1 Killer Cell Lectin Like Receptor G1 [*Homo sapiens* (human)], EnsembL: ENSG00000139187 MIM: 604874; AllianceGenome: HGNC: 6380, updated Aug. 5, 2022, 10 pages.
NCBI Gene ID 1043, CD52 CD42 Molecule [*Homo sapiens* (human)], Ensembl: ENSG00000169442 MIM: 114280; AllianceGenome: HGNC: 1804, updated Aug. 5, 2022, 7 pages.
NCBI Gene ID 1154, CISH Cytokine Inducible SH2 Containing Protein [*Homo sapiens* (human)], ENSG0000114737 MIM: 602441; AllianceGenome: HGNC: 1984, updated Aug. 5, 2022, 11 pages.
NCBI Gene ID 1234, CCR5 C-C Motif Chemokine Receptor 5 [*Homo sapiens* (human)], Ensembl: ENSG00000160791 MIM: 601373; AllianceGenome: HGNC: 1606, updated Sep. 4, 2022, 13 pages.
NCBI Gene ID 135, ADORA2A Adenosine A2a Receptor [*Homo sapiens* (human)], Ensembl:; ENSG00000128271 MIM: 102776; AllianceGenome: HGNC: 263, updated Aug. 5, 2022, 13 pages.
NCBI Gene ID 1493, CTLA4 Cytotoxic T-Lymphocyte Associated Protein 4 [*Hono sapiens* (human)], Ensembl: ENSG00000163599 MIM: 123890; AllianceGenome: HGNC: 2505, updated Sep. 4, 2022, 13 pages.
NCBI Gene ID 201633, TIGIT T Cell Immunoreceptor With Ig and ITIM Domains [*Homo sapiens* (human)], Ensembl: ENSG00000181847 MIM:612859; AllianceGenome: HGNC: 26838, updated Sep. 4, 2022, 9 pages.
NCBI Gene ID 2214, FCGR3A Fc Gamma Receptor IIIa [*Homo sapiens* (human)], Ensembl: ENSG00000203747 MIM:146740; AllianceGenome: HGNC: 3619, updated Sep. 4, 2022, 14 pages.
NCBI Gene ID 22914, KLRK1 Killer Cell Lectin Like Receptor K1 [*Homo sapiens* (human)], Ensembl: ENSG00000213809 MIM: 611817; AllianceGenome: HGNC: 18788, updated Sep. 4, 2022, 10 pages.
NCBI Gene ID 2597, GAPDH Glyceraldehyde-3-Phosphate Dehydrogenase [*Homo sapiens* (human)], Ensembl: ENSG0000011640 MIM: 1384000; AllianceGenome: HGNC: 4141, updated Sep. 6, 2022, 14 pages.
NCBI Gene ID 28638, TRBC2 T Cell Receptor Beta Constant 2 [*Homo sapiens* (human)], Ensembl: ENSG0000011772 IMGT/GENE-DB: TRBC2; MIM: 615445; AllianceGenome: HGNC: 12157, updated May 13, 2022, 6 pages.

(56) References Cited

OTHER PUBLICATIONS

NCBI Gene ID 28639, TRBC1 T Cell Receptor Beta Constant 1 [*Homo sapiens* (human)], Ensembl: ENSG00000211751 IMGT/GENE-DB:TRBC1; MIM: 186930; AllianceGenome: HGNC: 12156, updated May 13, 2022, 6 pages.
NCBI Gene ID 28755, Trac T Cell Receptor Alpha Constant [*Homo sapiens* (human)], Ensembl: ENSG00000277734 IMGT/GENE-DB: Trac: MIM: 186880: AllianceGenome: HGNC: 12029, updated on May 13, 2022, 6 pages.
NCBI Gene ID 29126, CD274 CD274 Molecule {*Homo sapien* (human)], Ensembl: ENSG00000120217 MIM: 605042; AllianceGenome: HGNC: 17635, updated Sep. 11, 2022, 11 pages.
NCBI Gene ID 3074, HEXB Hexosaminidase Subunit beta [*Homo sapiens* (human)], Ensembl: ENSG00000049860 MIM: 606873; AllianceGenome: HGNC: 4879, updated Sep. 6, 2022, 13 pages.
NCBI Gene ID 3561, IL2RG Interleukin 2 Receptor Subunit Gamma [*Homo sapiens* (human)], Ensembl: ENSG00000147168 MIM: 308380; AllianceGenome: HGNC:6010, updated Aug. 5, 2022, 12 pages.
NCBI Gene ID 3821, KLRC1 Killer Cell Lectin Like Receptor C1 [*Homo sapiens* (human)}, Ensembl: ENSG00000134545 MIM: 161555; AllianceGenome: HGNC: 6374, updated on Sep. 4, 2022, 10 pages.
NCBI Gene ID 3902, LAG3 Lymphocyte Activating 3 [*Homo sapiens* (human)], Ensembl: ENSG00000089692 MIM: 153337; AllianceGenome: HGNC: 6476, updated Sep. 11, 2022, 8 pages.
NCBI Gene ID 4261, CIITA Class II Major Histocompatibility Complex Transactivator [*Homo sapiens* (human)], Ensembl: ENSG00000179583 MIM: 600005; AllianceGenome: HGNC: 7067, updated Aug. 12, 2022, 18 pages.
NCBI Gene ID 5133, PDCD1 Programmed Cell Death 1 [*Homo sapiens* (human)], Ensembl: ENSG00000188389 MIM: 600244; AllianceGenome: HGNC: 8760, updated Sep. 11, 2022, 11 pages.
NCBI Gene ID 53335, BCL11A BAF Chromatin Remodeling Complex Subunit BCLA11A [*Homo sapiens* (human)}, Ensembl: ENSG000001 19866 MIM: 606557; AllianceGenome: HGNC: 13221, updated Sep. 6, 2022, 19 pages.
NCBI Gene ID 54776, PPP1R12C Protein Phosphatase 1 Regulatory Sunbunit 120 [*Homo sapiens* (human)], Ensembl: ENSG000001 25503 MIM: 61324; AllianceGenome: HGNC: 14947, updated Aug. 5, 2022, 11 pages.
NCBI Gene ID 6964, TRD T Cell Receptor Delta Locus [*Homo sapiens* (human)], AllianceGenome: HGNC: 12252, updated May 13, 2022, 6 pages.
NCBI Gene ID 6965, TRG T Cell Receptor Gamma Locus {*Homo sapiens* (human)], AllianceGenome: HGNC: 12271, updated May 13, 2022, 6 pages.
NCBI Gene ID 7048, TGFBR2 Transforming Growth Factor Beta Receptor 2 {*Homo sapiens* (human)], Ensembl: ENSG00000163513 MIM: 190182; Alliance Genome: HGNC: 11773, updated Aug. 28, 2022, 16 pages.
NCBI Gene ID 7852, CXCR4 C-X-C motif Chemokine Receptor 4 [*Homo sapiens* (human)], Ensembl: ENSG00000121966 MIM: 162643; AllianceGenome: HGNC: 2561, updated Sep. 4, 2022, 16 pages.
NCBI Gene ID 84868, HAVCR2 Hepatitis A Virus Cellular Receptor 2 [*Homo sapiens* (human)], Ensembl: ENSG00000315077 MIM: 606652: AllianceGenome: HGNC: 18437, updated Aug. 28, 2022, 11 pages.
NCBI Gene ID 915, CD3D CD3 Delta Subunit of T-Cell Receptor Complex [*Homo sapiens* (human)], Ensembl: ENSG000001 67286 MIM: 186790; AllianceGenome: HGNC:1673, updated on Aug. 5, 2022, 13 pages.
NCBI Gene ID 916, CD3E CDE Epsilon Subunit of T-Cell Receptor Complex [*Homo sapiens* (human)], Ensembl: ENSG00000198851 MIM: 186830; AllianceGenome: HGNC: 1674, updated Aug. 5, 2022, 13 pages.
NCBI Gene ID 917, GD3G CD3 Gamma Subunit of T-Cell Receptor Complex [*Homo sapiens* (human)], Ensembl: ENSG00000160654 MIM: 186740; AllianceGenome: HGNC: 1675, updated Aug. 5, 2022, 13 pages.
NCBI Gene ID 924, CD7 Molecule [*Homo sapiens* (human)], Ensembl: ENSG00000173762 MIM: 186820; AllianceGenome: HGNC: 1695, updated May 13, 2022, 8 pages.
Needleman, S. B. et al. (1970). "A General Method Applicable to the Search for Similarities in the Amino Acid sequence of Two Proteins," J. Mol. Biol. 48:443-453.
Reich, S.J. et al. (May 30, 2003). "Small Interfering RNA (siRNA) Targeting VEGH Effectively inhibits Ocular Neovascularization in a Mouse Model," Mol. Vision. 9:210-216.
Remy, J-S. et al. (1994). "Gene Transfer With a Series of Lipophilic DNA-Binding Molecules," Bioconjugate Chem. 5:647-654.
Richter, M. F. et al. (Jul. 2020). "Phage-Assisted Evolution of an Adenine Base Editor With Improved Cas Domain Compatibility and Activity," Nat. Biotechnol. 38(7):883-891, 31 pages.
Samulski, R. J. et al. (Jun. 1989). "Helper-Free Stocks Of Recombinant Adeno-Associated Viruses: Normal Integration Does Not Require Viral Gene Expression," Journal Of Virology 63(9):3822-3828.
Schroeder, A. et al. (Jan. 2010). "Lipid-Based Nanotherapeutics for siRNA Delivery," Journal of Internal Medicine 267:9-21,21 pages.
Shen, C. et al. (Mar. 5, 2003). "Gene Silencing by Adenovirus-Delivered siRNA," FEBS Let. 539:111-114.
Simeoni, F et al. (Jun. 1, 2003). "Insight into the Mechanism of the Peptide-Based Gene Delivery System MPG: Implications for Delivery of siRNA into Mammalian Cells," Nucleic Acids Research 31(11):2717-2724.
Sommnerfelt, M.A. et al. (May 1990). "Receptor Interference Groups of 20 Retroviruses Plating on Human Cells," Virol. 176:58-59.
Sorensen, D.R. et al. (2003). "Gene Silencing by Systemic Delivery of Synthetic siRNAs in Adult Mice," J. Mol. Biol. 327-761-766.
Strecker, J. et al. (2019). "Engineering of CRISPR-Cas12b for Human Genome Editing," Nat Communications 10(212):1-8.
Tolentino, M. et al. (Feb. 2004). "Intravitreal Injection of Vascular Endothelial Growth Factor Small Interfering RNA inhibits Growth And Leakage In A Nonhuman Primate, Laser-Induced Model of Choroidal Neovascularization," Retina 24(1):132-138.
Tolentino, M. et al. (Jul. 12, 2004). "Dear Editor: Erratum," Retina 24(4):660.
Tratschin, J-D. et al. (Nov. 1985). "Adeno-Associated Virus Vector For High-Frequency Integration, Expression, And Rescue Of Genes In Mammalian Cells," Mol. Cell Biol. 5(11):3251-3260.
Tratschin, J-D. et al. (Oct. 1984). "A Human Parvovirus, Adeno-Associated Virus, as a Eucaryotic Vector Transient Expression and Encapsidatlon of the Procaryotic Gene for Chloramphenicol Acetyltransferase," Mol. Cell. Biol. 4(10):2072-2081.
Travassos Da Rosa, A.P.A. et al. (1984). "Carajas And Maraba Viruses, Two New Vesiculoviruses Isolated From Phlebotomine Sand Files in Brazil," Am. J. Tropical Med. & Hygiene 33(5):999-1006.
Uno, Y. et al. (Jun. 2011). "High-Density Lipoprotein Facilitates in Vivo Delivery of α-Tocopherol-Conjugated Short-Interfering RNA to the Brain," Human Gene Therapy 22:711-719.
Van Brut, J. (Oct. 1988), Molecular Farming: Transgenic Animals as Bioreactors, Biotechnology 6(10):1149-1154.
Vigne, E. et al., (1995). "Third-Generation Adenovectors for Gene Therapy," Restor. Neurol. Neurosci. 8(1):35-36.
Wang, D. et al. (Apr. 2, 2020). "CRISPR-Based Therapeutic Genome Editing: Strategies and In Vivo Delivery by AAV Vectors," Cell 181:136-150.
Wang, H. et al. (Nov. 15, 2018). "CRISPR-Mediated Programmable 3D Genome Positioning and Nuclear Organization," Cell 175:1405-1417.
Wang, X. et al. (Jun. 2, 2020). "Cas12a Base Editors Induce Efficient and Specific Editing with Low DNA Damage Response," Cell Reports 31:107723, 1-21 pages.
Ward, P. et al, (2012, e-pub, Sep. 13, 2012). "Targeted Integration of a rAAV Vector into the AAVS1 Region," Virology 433(2):356-366.

(56) References Cited

OTHER PUBLICATIONS

West, M.H-P. et al. (Sep. 1987). "Gene Expression in Adeno-Associated Virus Vectors: The Effects of Chimeric mRNA Structure, Helper Virus, and Adenovirus VA, RNA," Virology 160(1):38-47.
Wilson, C. et al. (May 1989). "Formation of Infectious Hybrid Virions With Gibbon Ape Leukemia Virus and Human T-Cell Leukemia Virus Retroviral Envelope Glycoproteins and the Gag and Pol Proteins of Moloney Murine Leukemia Virus," J. Virol. 63(5):2374-2378.
Wolf, J. et al. (2002). tadA, An Essential tRNA-Specific Adenosine Deaminase From *Escherichia coli*, EMBO J. 21(14):3841-3851.
Xia, H. et al. (Oct. 2002, e-pub. Sep. 16, 2002). "siRNA-Mediated Gene Silencing in Vitro and in Vivo," Nat. Biotech. 20:1006-1010.
Xu, X. et al. (Oct. 21, 2021). "Engineered Miniature CRISPR-Cas System for Mammalian Genome Regulation and Editing," Mol. Cell 81:4333-4345.
Yan, W. X. et al. (Jan. 4, 2019). "Functionally Diverse Type V CRISPR-Cas Systems," Science 363:88-91.
Yang, Y. et al. (2016). "Highly Efficient and Rapid Detection of the Cleavage Activity of Cas9/gRNA via a Fluorescent Reporter," Appl. Biochem. Biotechnol. 180:655-667.
Yu, M. et al. (1994). "Progress Towards Gene Therapy for HIV Infection," Gene Ther. 1(1):13-26.
Yuen, C.T. L. et al. (2022, e-pub. Jan. 21, 2022). "High-Fidelity KKH Variant of *Staphylococcus aureus* Cas9 Nucleases with Improved Base Mismatch Discrimination," Nucleic Acids Res 50(3):1650-1660.
Zetsche, B. et al. (Jan. 2017). "Multiplex Gene Editing by CRISPR-Cpf1 Through Autonomous Processing of a Single crRNA Array," Nature Biotechnology 35(1):31-34, 8 pages.
Zetsche. B. et al. (Oct. 22, 2015). "Cpf1 Is A Single RNA-Guided Endonuclease Of A Class 2 CRISPR-Cas System," Cell 163:759-771.
Zhang, B. et al. (2021). "Mechanistic insights Into the R-Loop Formation and Cleavage in CRISPR-Cas12i1," Nat. Commun. 12(3476):1-13.
Zhang, H. et al. (Jun. 17, 2022). "An Engineered xCasl 2i With High, Activity, High Specificity and Broad PAM Range," Cold Spring Harbor, 29 pages.
Zhang, H. et al., (Nov. 2020). "Mechanisms for Target Recognition and Cleavage by the Cas12i RNA-Guided Endonuclease," Nat. Struct. Mol. Biol. 27:1069-1076, 28 pages.
Zhang, L. et al. (2021). "AsCas12a Ultra Nuclease Facilitates the Rapid Generation of Therapeutic Cell Medicines," Nat. Commun. 12(3908):1-15.
Zheng, Y. et al. (2017, e-pub. Jan. 28, 2017). "DNA Editing in DNA/RNA Hybrids By Adenosine Deaminases That Act On RNA," Nucleic Acids Res 45(6):3369-3377.
Zou, W. et al. (Apr. 2011, e-pub. Nov. 19, 2010). "Intrathecal Lentiviral-Mediated RNA Interference Targeting PKCγ Attenuates Chronic Constriction Injury-Induced Neuropathic Pain In Rats," Human Gene Therapy 22(4):465-475.
Finn, J.D. et al. (Feb. 27, 2018). A Single Administration of CRISPR/Cas9 Lipid Nanoparticles Achieves Robust and Persistent In Vivo Genome Editing. Cell Rep 22:2227-2235.
Yin, J. (2019). "Optimizing Genome Editing Strategy by Primer-Extension-Mediated Sequencing," Cell Discov. 5:18, 1-11.

* cited by examiner (SEQ ID NO: 101)

DR-P 5'- AGAAAT GTGTC CCCAGTT GACAC -3' (SEQ ID NO: 113)
DR-A 5'- AGAAAT CCGTC CTTAGTT GACGG -3' (SEQ ID NO: 108)
DR-B 5'- AGACAT GTGTC CCCAGT GACAC -3' (SEQ ID NO: 109)
DR-C 5'- AGAAAT GTTTC CCCAGTT GAAAC -3' (SEQ ID NO: 110)
DR-D 5'- AGAAAT GTGTT CCCAGTT AACAC -3' (SEQ ID NO: 111)
DR-E 5'- AGAAAT TTGTC CCCAGTT GACAA -3' (SEQ ID NO: 112)

CRISPR-CAS12I SYSTEMS

CROSS REFERENCE TO RELATED APPLICATIONS

This application claims the priority benefit of Chinese Patent Application No. 202111290670.8 filed on Nov. 2, 2021, the content of which is incorporated herein by reference in its entirety.

REFERENCE TO AN ELECTRONIC SEQUENCE LISTING

The contents of the electronic sequence listing (233462000100SUBSEQLIST.xml; Size: 282,490 bytes; and Date of Creation: Sep. 2, 2022) is herein incorporated by reference in its entirety.

FIELD OF THE INVENTION

The invention relates to novel CRISPR-Cas12i systems and uses thereof.

BACKGROUND OF THE INVENTION

Clustered regularly interspaced short palindromic repeat (CRISPR) and CRISPR-associated (Cas) genes, collectively referred to as CRISPR-Cas or CRISPR/Cas system, are now understood to provide immunity to bacteria and archaea against phage infection. CRISPR-Cas systems of adaptive immunity in prokaryotes consist of extremely diverse effectors, non-coding elements, and locus structures that can be engineered and used for applications such as gene editing, target detection, and disease treatment. Zhang Feng et al. found that Cas12a proteins (formerly known as Cpf1 proteins) can be used for gene editing and gene diagnosis. Later, more Cas12 proteins were discovered, including Cas12b (C2c1), Cas12c (C2c3), Cas12d (CasY), Cas12e (CasX), Cas12f (C2c10/Cas14) and Cas12k (C2c5). However, each of them has its own advantages and disadvantages.

SUMMARY OF THE INVENTION

The present application provides Cas12i proteins and CRISPR-Cas systems thereof with diverse applications. The present application also provides uses based on the CRISPR-Cas12i system, such as target DNA editing (e.g., DNA insertion, excision, transfer, modification (such as single base modification)), regulation or detection, or disease therapy (e.g., transthyretin-related amyloidosis (ATTR)).

In one aspect, there is provided a Cas12i protein (e.g., isolated, engineered, non-naturally occurring Cas12i protein) comprising an amino acid sequence having at least about any of 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identity to the amino acid sequence as set forth in any one of SEQ ID NOs: 1-10 (preferably, SEQ ID NOs: 1-3 and 6, more preferably, SEQ ID NO: 1).

In some embodiments according to any one of the Cas12i proteins described above, the Cas12i protein comprises (or consists essentially of, or consists of) the sequence of any of SEQ ID NOs: 1-10, such as any of SEQ ID NOs: 1-3 and 6, or SEQ ID NO: 1. In some embodiments, the Cas12i protein is a variant of the Cas12i protein as set forth in any of SEQ ID NOs: 1-10, such as a native variant. In some embodiments, the Cas12i protein is non-naturally occurring, such as a Cas12i protein mutant, or an engineered Cas12i protein. In some embodiments, the Cas12i protein is an SiCas12i protein. In some embodiments, the SiCas12i variant comprises one or more mutations, such as single amino acid substitution(s), relative to parental SiCas12i (SEQ ID NO: 1). The present invention also provides polynucleotides or vectors encoding any of the Cas12i proteins described herein, host cells comprising such Cas12i proteins, polynucleotides or vectors, and hosts (e.g., mammal) comprising such host cells.

In some embodiments according to any one of the Cas12i proteins described above, the Cas12i protein substantially lacks (e.g., retains less than about any of 50%, 40%, 35%, 30%, 27.5%, 25%, 22.5%, 20%, 17.5%, 15%, 12.5%, 10%, 7.5%, 5%, 4%, 3%, 2.5%, 2%, 1% or less) spacer-specific endonuclease cleavage activity of the corresponding parental or reference Cas12i protein (e.g., Cas12i protein comprising any of SEQ ID NOs: 1-10) for a target sequence of a target DNA complementary to a guide sequence. In some embodiments, the Cas12i protein is a dead Cas12i (dCas12i). In some embodiments, the Cas12i protein is linked to one or more functional domains (e.g., deaminase such as TadA).

In one aspect, the invention provides a polynucleotide encoding any of the Cas12i proteins described herein (e.g., SiCas12i protein or variant thereof, or TadA8e-dSiCas12i). In another aspect, the invention provides a vector comprising such polynucleotide. In another aspect, the invention provides a delivery system comprising (1) a delivery medium (e.g., liposome or lipid nanoparticle); and (2) any of the Cas12i protein described herein, polynucleotide or vector.

In one aspect, there is provided an engineered, non-naturally occurring CRISPR-Cas system comprising:

(1) any one of the Cas12i proteins described herein (e.g., SiCas12i protein or variant thereof, or TadA8e-dSiCas12i) or a polynucleotide encoding the Cas12i protein; and (2) a CRISPR RNA (crRNA) or a polynucleotide encoding the crRNA, the crRNA comprising:

(i) a spacer capable of hybridizing to a target sequence of a target DNA, and (ii) a Direct Repeat (DR) linked to the spacer and capable of guiding the Cas12i protein to bind to the crRNA to form a CRISPR-Cas complex targeting the target sequence. In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

In another aspect, there is provided a CRISPR-Cas system (e.g., engineered, non-naturally occurring) comprising one or more vectors comprising:

(1) a first regulatory element operably linked to a first polynucleotide sequence encoding any one of the Cas12i proteins described herein (e.g., SiCas12i protein or variant thereof, or TadA8e-dSiCas12i); and (2) a second regulatory element operably linked to a second polynucleotide encoding a crRNA, the crRNA comprising:

(i) a spacer capable of hybridizing to a target sequence of a target DNA, and (ii) a DR linked to the spacer and capable of guiding the Cas12i protein to bind to the crRNA to form a CRISPR-Cas complex targeting the target sequence;

wherein the first regulatory element and the second regulatory element are located on the same or different vectors of the CRISPR-Cas system. In some embodiments, the first regulatory element and the second regulatory element are the same. In some embodiments, the first regulatory element and the second regulatory element are different. In some embodiments, the first regulatory element operably linked to the first polynucleotide, and the second regulatory element operably linked to the second polynucleotide are located on different vectors of the CRISPR-Cas system. In some embodiments, the first regulatory element operably linked to the first polynucleotide, and the second regulatory element operably linked to the second polynucleotide are located on the same vector of the CRISPR-Cas system. In some embodiments, the first regulatory element operably linked to the first polynucleotide are located upstream of the second regulatory element operably linked to the second polynucleotide. In some embodiments, the first regulatory element operably linked to the first polynucleotide are located downstream of the second regulatory element operably linked to the second polynucleotide. In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

In another aspect, there is provided an engineered, non-naturally occurring CRISPR-Cas complex comprising:

(1) any one of the Cas12i proteins described herein (e.g., SiCas12i protein or variant thereof, or TadA8e-dSiCas12i); and (2) a crRNA, the crRNA comprising:

(i) a spacer capable of hybridizing to a target sequence of a target DNA, and (ii) a DR linked to the spacer; wherein the DR guides the Cas12i protein to bind to the crRNA. In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

In another aspect, there is provided a CRISPR-Cas system (e.g., engineered, non-naturally occurring) comprising a vector comprising:

(1) a first polynucleotide encoding any of the Cas12i proteins described herein (e.g., SiCas12i protein or variant thereof, or TadA8e-dSiCas12i);

(2) a second polynucleotide encoding a crRNA, wherein the crRNA comprises:

(i) a spacer capable of hybridizing to a target sequence of a target DNA, and (ii) a DR linked to the spacer and capable of guiding the Cas12i protein to bind to the crRNA to form a CRISPR-Cas complex targeting the target sequence; and (3) a regulatory element operably linked to the first polynucleotide and the second polynucleotide. In some embodiments, the vector comprises, from 5' to 3', the regulatory element, the first polynucleotide, and the second polynucleotide. In some embodiments, the vector comprises, from 5' to 3', the regulatory element, the second polynucleotide, and the first polynucleotide. In some embodiments, the first polynucleotide and the second polynucleotide are connected by a linker sequence, e.g., a nucleic acid encoding any of P2A, T2A, E2A, F2A, BmCPV 2A, BmIFV 2A, $(GS)_n$ (SEQ ID NO: 190), $(GGGS)_n$ (SEQ ID NO: 191), $(GGGGS)_n$ (SEQ ID NO: 192) (wherein n is an integer of at least 1), or a nucleic acid of any one of IRES, SV40, CMV, UBC, EF1α, PGK, and CAGG, or any combination thereof. In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

In one aspect, there is provided a method of modifying (e.g., cleaving or single base editing) a target DNA, comprising contacting the target DNA with any of the CRISPR-Cas systems or complexes described herein (e.g., CRISPR-SiCas12i, or TadA8e-dSiCas12i), the contacting resulting in modification of the target DNA by the Cas12i protein. In some embodiments, the method further comprises providing a repair/donor template (e.g., a wild-type TTR nucleic acid), which is introduced into the modified target DNA (e.g., inserted between cleavage sites, or replacing the target sequence by homologous recombination). In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

Hence in some embodiments, there is provided a method of modifying (e.g., cleaving or single base editing) a target DNA (e.g., a TTR sequence), comprising contacting (e.g., in vitro, ex vivo, or in vivo) the target DNA with a CRISPR-Cas system (e.g., engineered, non-naturally occurring), wherein the CRISPR-Cas system comprises:

(1) any one of the Cas12i proteins described herein (e.g., SiCas12i protein or variant thereof, or TadA8e-dSiCas12i) or a polynucleotide encoding the Cas12i protein; and (2) a crRNA or a polynucleotide encoding the crRNA, the crRNA comprising:

(i) a spacer capable of hybridizing to a target sequence of the target DNA, and (ii) a DR linked to the spacer and capable of guiding the Cas12i protein to bind to the crRNA to form a CRISPR-Cas complex targeting the target sequence;

wherein the hybridization of the spacer sequence and the target sequence of the target DNA mediates the contact of the Cas12i protein with the target sequence of the target DNA, resulting in the modification of the target DNA by the Cas12i protein. In some embodiments, the method further comprises providing a repair/donor template comprising a repair/donor nucleic acid, wherein the repair/donor nucleic acid is capable of being incorporated into the modified target DNA at the target sequence. In some embodiments, the modification of the target DNA repairs a mutation (e.g., loss of function mutation) in the target DNA to a wild-type (or non-deleterious version) sequence. In some embodiments, the modification of the target DNA introduces an exogenous sequence. In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

In some embodiments, there is provided a cell or descendant thereof modified using any of the target DNA modification methods described herein. In some embodiments, the modified cell or descendant thereof has a change (quantity and/or quality) of a product compared to a cell or descendant thereof without such modification. In another aspect, the invention provides a cell product from the cell or descendant thereof, wherein the cell product is modified qualitatively or quantitatively compared to that from a cell not subjected to the modification method. For example, in some embodiments, the modified cell or descendant thereof has higher amount, activity, and/or stability of a wild-type protein (or protein existing in heathy individuals), lower amount, activity, and/or stability of a mutant protein (e.g., disease-related protein), compared to a cell or descendant thereof without such modification. For example, in some embodiments, the modified cell or descendant thereof with modification to the target DNA (e.g., TTR sequence) has lower (e.g., at least about any of 10%, 20%, 30%, 40%, 50%, 60%, 70%, 80%, 90%, or 100% lower) expression of the target DNA encoded product (e.g., protein) compared to that from a cell or descendant thereof without such modification. In some embodiments, the modified cell or descendant thereof with modification to the target DNA (e.g., TTR sequence) has higher (e.g., at least about any of 1.2, 1.5, 2, 3, 5, 10, 20, 50, 100 fold, or higher) stability of the target DNA encoded product (e.g., protein) compared to that from a cell or descendant thereof without such modification.

In one aspect, the invention provides a cell or descendant thereof comprising any of the Cas12i proteins described herein, polynucleotide encoding any of the Cas12i proteins described herein, vector encoding any of the Cas12i proteins described herein, delivery system encoding or comprising any of the Cas12i proteins described herein, CRISPR-Cas system or complex comprising any of the Cas12i proteins described herein. In some embodiments, the cell is selected from the group consisting of prokaryotic cells, eukaryotic cells, animal cells, plant cells, fungal cells, vertebrate cells, invertebrate cells, rodent cells, mammalian cells, primate cells, non-human primate cells, and human cells.

In another aspect, the invention provides a non-human multicellular organism comprising any of the modified cells or descendants thereof described herein, such as a cell or descendant thereof modified by any of the CRISPR-Cas12i system or complex described herein. In some embodiments, the non-human multicellular organism is an animal (e.g., rodent or non-human primate) model for human gene related diseases.

In one aspect, the invention provides a method of non-specifically cleaving a non-target DNA, comprising contacting a target DNA with any of the CRISPR-Cas12i systems or complexes described herein, whereby hybridization of the spacer to a target sequence of the target DNA mediates the contact of the Cas12i protein with the target sequence of the target DNA and cleavage of the target sequence by the Cas12i protein, leading to the Cas12i protein's cleavage of the non-target DNA by spacer non-specific endonuclease collateral activity. In some embodiments, the non-target DNA is close to the target DNA (e.g., in cis), such as within at most about 500 bp (e.g., at most about any of 400, 300, 200, 100, 50, 20, or 10 bp) from the target DNA. In some embodiments, the Cas12i protein comprises the sequence of any of SEQ ID NOs: 1-10 (e.g., any of SEQ ID NOs: 1-3 and 6).

In another aspect, the invention provides a method of detecting a target DNA in a sample, the method comprising: (1) contacting the sample with any of the CRISPR-Cas12i (e.g., CRISPR-SiCas12i) systems or complexes described herein and a reporter nucleic acid capable of releasing a detectable signal after being cleaved, whereby hybridization of the spacer to a target sequence of the target DNA and cleavage of the target sequence by the Cas12i protein make the Cas12i protein cleave the reporter nucleic acid by spacer non-specific endonuclease collateral activity; and (2) measuring the detectable signal generated by cleavage of the reporter nucleic acid, thereby detecting the presence of the target DNA in the sample. In some embodiments, the Cas12i protein comprises the sequence of any of SEQ ID NOs: 1-10 (e.g., any of SEQ ID NOs: 1-3 and 6).

In some embodiments, there is provided a method of treating a disease or condition (e.g., ATTR) in an individual (e.g., human), comprising administering (e.g., intravenous injection or infusion) to the individual an effective amount of any of the CRISPR-Cas12i (e.g., CRISPR-SiCas12i, or TadA8e-dSiCas12i) systems or complexes described herein. In some embodiments, the disease or condition is associated with an abnormality (e.g., pathogenic point mutation) in a target DNA of the individual. In some embodiments, the disease or condition is treated due to modification (e.g., cleavage, base editing, or repair) of the target DNA (e.g., fix the abnormality) by the CRISPR-Cas12i system or complex. In some embodiments, the disease is caused by over-expression or mis-expression (e.g., missense mutation, frameshift mutation, nonsense mutation) of one or more target gene, wherein the CRISPR-Cas12i systems or complexes can target the one or more target genes for targeted modification, such as cleavage, based editing, or sequence repair (e.g., by further introducing a repair/donor template for repairing the cleaved target gene by the CRISPR-Cas12i systems or complexes by homologous recombination). In some embodiments, the disease or condition is selected from the group consisting of ATTR, cystic fibrosis, hereditary angioedema (HAE), diabetes, progressive pseudohypertrophic muscular dystrophy, Becker muscular dystrophy (BMD), alpha-1 antitrypsin deficiency (AAT deficiency), Pompe disease, myotonic dystrophy, Huntington's disease, Fragile X syndrome (FXS), Friedreich ataxia (FRDA), amyotrophic lateral sclerosis (ALS), frontotemporal dementia (FTD), hereditary chronic kidney disease, hyperlipidemia, hypercholesterolemia, Leber congenital amaurosis (LCA), sickle cell disease (SCD), and β-thalassemia. In some embodiments, the disease or condition is ATTR, such as transthyretin-related wild-type amyloidosis (ATTRwt), transthyretin-related hereditary amyloidosis (ATTRm), familial amyloid polyneuropathy (FAP, ATTR-PN), or familial amyloid cardiomyopathy (FAC, ATTR-CM). In some embodiments, the disease or condition is transthyretin instability caused by abnormal expression (e.g., high expression) of the TTR gene. In some embodiments, the disease or condition is other disease or condition or derived disease or condition caused by abnormal expression (e.g., high expression) of the TTR gene. In some embodiments, the CRISPR-Cas12i system or complex is packaged and delivered via a lipid nanoparticle. In some embodiments, the lipid nanoparticle is administered via intravenous injection or infusion to the individual.

Hence in some embodiments, there is provided a method of treating an ATTR in an individual (e.g., human), comprising administering (e.g., intravenous infusion or injection) to the individual an effective amount of a CRISPR-Cas12i (e.g., CRISPR-SiCas12i, such as engineered or non-naturally existing) system or complex, wherein the CRISPR-Cas12i system or complex comprises:

(1) any one of the Cas12i proteins described herein (e.g., SiCas12i protein or variant thereof, or TadA8e-dSiCas12i) or a polynucleotide encoding the Cas12i protein; and (2) a crRNA or a polynucleotide encoding the crRNA, the crRNA comprising:

(i) a spacer capable of hybridizing to a target sequence of the TTR gene, and (ii) a DR linked to the spacer and capable of guiding the Cas12i protein, wherein the hybridization of the spacer sequence and the target sequence of the TTR gene mediates the contact of the Cas12i protein with the target sequence of the TTR gene, resulting in the modification (e.g., cleavage, base editing) of the TTR gene by the Cas12i protein. In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

In some embodiments, there is provided a method of treating an ATTR in an individual (e.g., human), comprising administering (e.g., intravenous infusion or injection) to the individual an effective amount of a CRISPR-Cas12i (e.g., CRISPR-SiCas12i, such as engineered or non-naturally existing) system comprising one or more vectors (e.g., viral vectors), wherein the one or more vectors comprise:

(1) a first regulatory element operably linked to a first polynucleotide encoding any one of the Cas12i proteins described herein (e.g., SiCas12i protein or variant thereof, or TadA8e-dSiCas12i); and (2) a second regulatory element operably linked to a second polynucleotide encoding a crRNA, the crRNA comprising:

(i) a spacer capable of hybridizing to a target sequence of the TTR gene, and (ii) a DR linked to the spacer and capable of guiding the Cas12i protein to bind to the crRNA to form a CRISPR-Cas complex targeting the target sequence;

wherein the first regulatory element and the second regulatory element are located on the same or different vectors of the CRISPR-Cas system; wherein the Cas12i protein is expressed in vivo, and the crRNA is transcribed in vivo; wherein the hybridization of the spacer sequence and the target sequence of the TTR gene mediates the contact of the Cas12i protein with the target sequence of the TTR gene, resulting in the modification (e.g., cleavage, base editing) of the TTR gene by the Cas12i protein. In some embodiments, the first regulatory element and the second regulatory element are the same. In some embodiments, the first regulatory element and the second regulatory element are different. In some embodiments, the first regulatory element operably linked to the first polynucleotide, and the second regulatory element operably linked to the second polynucleotide are located on different vectors of the CRISPR-Cas system. In some embodiments, the first regulatory element operably linked to the first polynucleotide, and the second regulatory element operably linked to the second polynucleotide are located on the same vector of the CRISPR-Cas system. In some embodiments, the first regulatory element operably linked to the first polynucleotide are located upstream of the second regulatory element operably linked to the second polynucleotide. In some embodiments, the first regulatory element operably linked to the first polynucleotide are located downstream of the second regulatory element operably linked to the second polynucleotide. In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

In some embodiments, there is provided a method of treating an ATTR in an individual (e.g., human), comprising administering (e.g., intravenous infusion or injection) to the individual an effective amount of a CRISPR-Cas12i (e.g., CRISPR-SiCas12i, such as engineered or non-naturally existing) system comprising a vector (e.g., viral vector), wherein the vector comprises:

(1) a first polynucleotide encoding any one of the Cas12i proteins described herein (e.g., SiCas12i protein or variant thereof, or TadA8e-dSiCas12i);

(2) a second polynucleotide encoding a crRNA, the crRNA comprising:

(i) a spacer capable of hybridizing to a target sequence of the TTR gene, and (ii) a DR linked to the spacer and capable of guiding the Cas12i protein to bind to the crRNA to form a CRISPR-Cas complex targeting the target sequence; and (3) a regulatory element operably linked to the first polynucleotide and the second polynucleotide;

wherein the regulatory element regulates the expression of the Cas12i protein and the transcription of the crRNA in vivo; wherein the hybridization of the spacer and the target sequence of the TTR gene mediates the contact of the Cas12i protein with the target sequence of the TTR gene, resulting in the modification (e.g., cleavage, base editing) of the TTR gene by the Cas12i protein. In some embodiments, the first polynucleotide is upstream of the second polynucleotide. In some embodiments, the first polynucleotide is downstream of the second polynucleotide. In some embodiments, the first polynucleotide and the second polynucleotide are connected by a linker sequence, e.g., a nucleic acid encoding any of P2A, T2A, E2A, F2A, BmCPV 2A, BmIFV 2A, (GS)n, (GGGS)n, (GGGGS)n (wherein n is an integer of at least 1), or a nucleic acid of any one of IRES, SV40, CMV, UBC, EF1α, PGK, and CAGG, or any combination thereof. In some embodiments, the Cas12i protein comprises the sequence of any of SEQ ID NOs: 1-10 (e.g., any of SEQ ID NOs: 1-3 and 6). In some embodiments, the Cas12i protein is a fusion protein comprising a dCas12i (e.g., any of dCas12i described herein) fused to TadA8e or a functional fragment thereof. In some embodiments, the fusion protein comprises the amino acid sequence of SEQ ID NO: 85 or 184.

In one aspect, the invention provides a kit comprising any of the CRISPR-Cas12i systems described herein. In some embodiments, the components of the CRISPR-Cas12i system are in the same container. In some embodiments, the components of the CRISPR-Cas12i system are in separate containers. In another aspect, the invention provides a sterile container comprising any of the CRISPR-Cas12i system described herein; preferably, wherein the sterile container is a syringe. In another aspect, the invention provides an implantable device comprising any of the CRISPR-Cas12i system described herein; preferably, wherein the CRISPR-Cas12i system is stored in a reservoir.

DETAILED DESCRIPTION OF THE INVENTION

Figure 1:
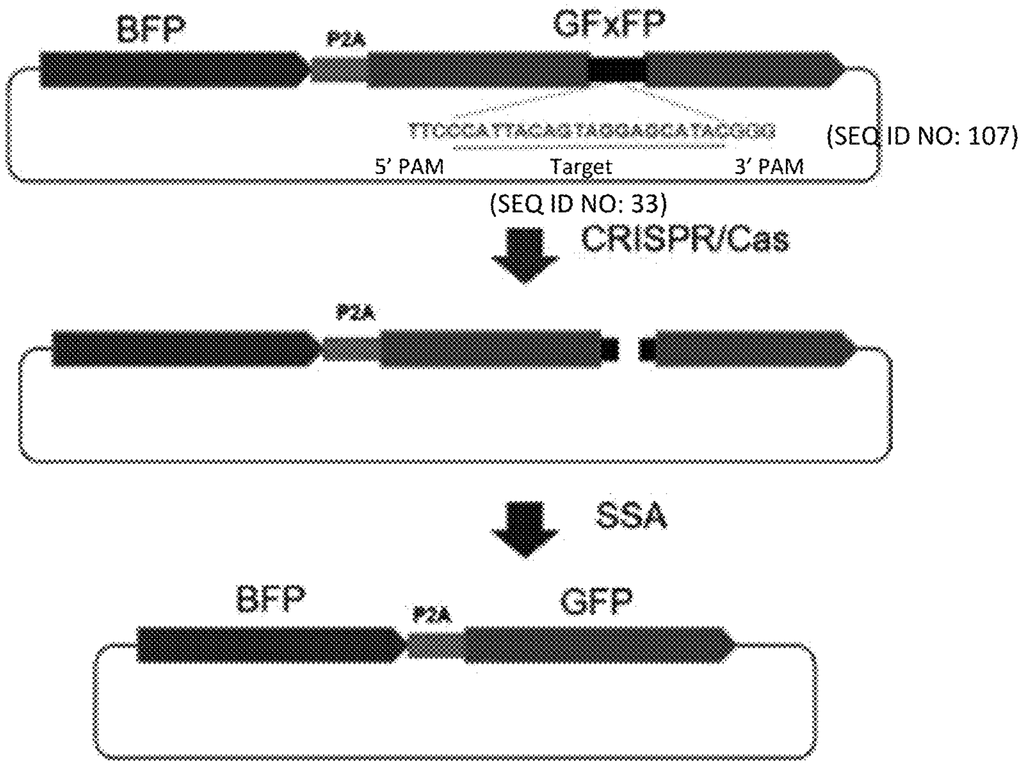
FIG. 1 shows schematic diagram of the BFP-P2A-GFxFP fluorescence reporting system.

The present application provides Cas12i proteins, and CRISPR-Cas12i systems and complexes based on said Cas12i proteins. In addition, there is provided Cas12i mutants or engineered Cas12i proteins (such as dCas12i) that lack (such as almost lost or completely lost) cleavage activity on double-stranded DNA (dsDNA), and CRISPR- Cas12i gene editing systems based on said Cas12i protein mutants. For example, transfer RNA adenosine deaminase (TadA) or other DNA editing proteins are fused with dCas12i described herein to form fusion proteins, which are used to perform base editing, such as A-to-I (or A-to-G), on target DNA. The present invention also provides the application of the CRISPR-Cas12i systems or complexes based on the Cas12i proteins described herein, mutants or engineered proteins thereof, and fusion proteins thereof, such as for gene editing, cutting, repairing, DNA identification or detection, and treatment and/or prevention of diseases (such as transthyretin amyloidosis, ATTR).

The Cas12i proteins (and mutants thereof) and CRISPR-Cas12i systems thereof have at least below advantages.

First, compared to widely used SpCas9 and Cas12a, the Cas12i proteins described herein are smaller (about 1,050 amino acids (aa) on average, nearly about 300 aa smaller than SpCas9, and nearly about 150 aa smaller than Cas12a), with simpler components of crRNA (unlike Cas9 which further requires tracrRNA), and with simpler PAM sequences. The smaller Cas12i protein size also allows for greater versatility in protein delivery or expression, such as easier packaging using a single AAV vector. The Cas12i proteins described herein recognize the PAM sequences of 5' TTN in mammalian cells, while Cas12a generally recognizes 5'-TTTV PAM sequences in mammalian cells, hence the Cas12i proteins described herein have broader targeting range. Compared with SpCas9, the Cas12i proteins described herein have crRNA processing function and do not require tracrRNA, so easier to target multiple sites in vivo.

Second, some Cas12i proteins described herein have significant cleavage activity on target DNA (such as SiCas12i, Si2Cas12i, WiCas12i, and SaCas12i), even higher than the conventionally used Cas9 and Cas12a, and other types of Cas12i (such as Cas12i.3). Further, a great variety of PAM sequences suitable for the efficient recognition and editing by Cas12i proteins of the present invention, as well as a great range of spacer length, are identified through a large number of screenings on the PAM sequences and various lengths of the spacer, therefore providing more and better choices for the design of target gene editing and/or regulation. Since PAM sequences limit the targeting ability of different Cas to target DNA, the present invention can not only cleave/edit certain target sites more efficiently, but also expand the scope of applicable gene editing sites of the entire CRISPR-Cas system (for example, some target genes do not have a PAM that can be recognized by Cas9 or Cas12a and could not be edited previously, but they may have a PAM that can be recognized by the Cas12i proteins of the present invention and can now be edited), thereby expanding the scope of disease prevention and treatment by the CRISPR-Cas system.

Third, through screening of direct repeat (DR) variants, the inventors discovered that when the secondary structure of DR is maintained (i.e., the secondary structure of the DR variant is substantially the same as that of parental DR), the CRISPR-Cas12i systems of the present invention can tolerate mismatches or deletions in DR without affecting cleavage activity, demonstrating the broad adaptability of the present invention to DR changes. Moreover, as described above, the CRISPR-Cas12i systems of the present invention also have extensive adaptability to spacer length variations.

Fourth, the Cas12i proteins described herein and CRISPR-Cas12i systems thereof can not only achieve excellent gene editing efficiency (such as about 92% to about 100% cleavage or gene inactivation efficiency for mouse and human TTR genes) in vitro (such as in mammalian cells, such as human cells), but also achieve excellent gene editing or regulation efficiency in vivo (for example, about 86% cleavage or gene inactivation efficiency for the TTR gene in mouse liver), demonstrating promising application of the present invention in clinical treatment. Moreover, the gene editing efficiency of the present invention can be even higher than the conventionally used Cas9, Cas12a, and other Cas12i proteins (e.g., Cas12i3) (see Examples 5 and 6). For some target sites that cannot be cleaved by Cas12i.3, the Cas12i proteins of the present invention (such as SiCas12i) can still have great cleavage efficiency. These further demonstrate the contribution of the present invention in the expansion of the editing scope of the CRISPR-Cas system.

Fifth, the subject application also provides engineered Cas12i proteins with reduced or no DNA cleavage activity, such as dCas12i. These Cas12i mutant proteins have broad applications in gene editing and regulation, including in disease treatment. For example, by fusing a protein of interest (e.g., TadA) with dCas12i of the present application, the protein of interest can be targeted to a gene of interest for gene editing and/or regulation, or for interaction with biomolecules (such as proteins) near the gene locus. For example, as demonstrated in Example 7, by fusing a gene editing protein (e.g., a single base editing protein, such as a deaminase like TadA, APOBEC, etc.) with dCas12i of the present invention, gene editing (e.g., single base editing, such as A-to-G, C-to-T) of the target DNA can be mediated by crRNA.

These advantages make the present invention have broad application prospects in in vitro and in vivo gene editing (such as DNA insertion, excision, transfer, modification), gene regulation, and disease prevention and/or treatment, and adaptable to gene perturbation such as genetic variation.

Transthyretin (TTR or TBPA) is a transport protein in serum and cerebrospinal fluid that transports the thyroid hormone thyroxine (T4) and retinol to the liver. The liver secretes TTR into the blood, and the choroid plexus secretes TTR into the cerebrospinal fluid. Mis-folding and aggregation of TTR is associated with amyloid diseases, including transthyretin-related wild-type amyloidosis (ATTRwt), transthyretin-related hereditary amyloidosis (ATTRm), familial amyloid polyneuropathy (FAP, ATTR-PN), and familial amyloid cardiomyopathy (FAC, ATTR-CM). Among them, ATTRm is caused by mutations in the TTR gene, which makes the TTR protein more unstable and more prone to the formation of amyloid fibrils, which may endanger the cardiovascular, peripheral, and autonomic nervous systems. Gene editing of TTR to reduce TTR protein production (especially diseased, unstable TTR proteins) may have therapeutic effects in TTR-associated amyloid diseases. Examples provided herein demonstrate that the CRISPR-Cas12i systems (such as CRISPR-SiCas12i) described herein can effectively cleave TTR target site in vivo (e.g., delivered by LNP to target liver TTR gene), with an cleavage efficiency of about 86%, demonstrating that the present invention has very promising prospects for the treatment of TTR-related amyloid diseases, such as ATTR (e.g., ATTRwt or ATTRm).

General Definitions

Unless otherwise specifically indicated, the invention will be practiced using conventional methods of chemistry, biochemistry, organic chemistry, molecular biology, microbiology, recombinant DNA technology, genetics, immunology, cell biology, stem cell protocols, cell culture, and transgenic biology in the art, many of which are described below for illustrative purposes. Such technologies are well described in the literature.

All publications, patents and patent applications cited herein are incorporated herein by reference in their entirety.

Unless otherwise specified, all technical and scientific terms used herein have the meaning commonly understood by one of ordinary skill in the art to which this invention belongs. For the purposes of the invention, the following terms are defined to conform to the meanings commonly understood in the art.

The articles "a/an" and "the" are used herein to refer to one or more than one (i.e., at least one) grammatical object of the article. For example, "element" means one element or more than one element.

The use of alternatives (e.g. "or") is to be understood to mean either, both, or any combination thereof.

The term "and/or" should be understood to mean either or both of the alternatives.

As used herein, the term "about" or "approximately" refers to an amount, level, value, quantity, frequency, percentage, dimension, size, mass, weight, or length that is changed by up to 15%, 10%, 9%, 8%, 7%, 6%, 5%, 4%, 3%, 2%, or 1% as compared to the reference amount, level, value, quantity, frequency, percentage, dimension, size, mass, weight, or length. In one embodiment, the term "about" or "approximately" refers to a range of amount, level, value, quantity, frequency, percentage, dimension, size, mass, weight, or length that is ±15%, ±10%, ±9%, ±8%, ±7%, ±6%, ±5%, ±4%, ±3%, ±2%, or ±1% around the reference amount, level, value, frequency, frequency, percentage, scale, size, weight, quantity, weight, or length.

As used herein, the term "substantially/essentially" refers to a degree, amount, level, value, quantity, frequency, percentage, dimension, size, mass, weight, or length that is about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or more of the reference degree, amount, level, value, quantity, frequency, percentage, dimension, size, mass, weight, or length.

A numerical range includes the end values of the range, and each specific value within the range, for example, "16 to 100 nucleotides" includes 16 and 100, and each specific value between 16 and 100.

Throughout this specification, the terms "comprise", "include", "contain", and "have" are to be understood as implying that a stated step or element or a group of steps or elements is included, but not excluding any other step or element or group of steps or elements, unless the context requires otherwise. In certain embodiments, the terms "comprise", "include", "contain", and "have" are used synonymously.

"Consist of" means including but limited to any element after the phrase "consist of". Thus, the phrase "consist of" indicates that the listed elements are required or mandatory, and that no other elements can be present.

"Consist essentially of" is intended to include any element listed after the phrase "consist essentially of" and is limited to other elements that do not interfere with or contribute to the activities or actions specified in the disclosure of the listed elements. Thus, the phrase "consist essentially of" is intended to indicate that the listed elements are required or mandatory, but no other elements are optional, and may or may not be present depending on whether they affect the activities or actions of the listed elements.

Throughout the specification, reference to "one embodiment", "embodiment", "a specific embodiment", "a related embodiment", "an embodiment", "another embodiment" or "a further embodiment" or a combination thereof means that specific features, structures, or characteristics described in connection with the embodiment are included in at least one embodiment of the invention. Accordingly, the appearances of the foregoing phrases in various places throughout the specification are not necessarily all referring to the same embodiments. Furthermore, specific features, structures, or characteristics may be combined in any suitable manner in one or more embodiments.

"Sequence identity" between two polypeptides or nucleic acid sequences refers to the percentage of the number of identical residues between the sequences relative to the total number of the residues, and the calculation of the total number of residues is determined based on types of mutations. Types of mutations include insertion (extension) at either end or both ends of a sequence, deletions (truncations) at either end or both ends of a sequence, substitutions/replacements of one or more amino acids/nucleotides, insertions within a sequence, deletions within a sequence. Taking polypeptide as an example (the same for nucleotide), if the mutation type is one or more of the following: replacement/substitution of one or more amino acids/nucleotides, insertion within a sequence, and deletion within a sequence, then the number of residues of the larger molecule in the compared molecules is taken as the total number of residues. If the mutation type also includes an insertion (extension) at either end or both ends of the sequence or a deletion (truncation) at either end or both ends of the sequence, the number of amino acids inserted or deleted at either end or both ends (e.g., less than 20 inserted or deleted at both ends) is not counted in the total number of residues. In calculating the percentage of identity, the sequences being compared are aligned in a manner that produces the largest match between the sequences, and the gaps (if present) in the alignment are resolved by a particular algorithm.

Conservative substitutions of non-critical amino acids may be made without affecting the normal functions of the protein. Conservative substitutions refer to the substitution of amino acids with chemically or functionally similar amino acids. Conservative substitution tables that provide similar amino acids are well known in the art. For example, in some embodiments, the amino acid groups provided below are considered to be mutual conservative substitutions.

In certain embodiments, selected groups of amino acids considered as mutual conservative substitutions are as follows:

| | |
|---|---|
| Acidic residues | D and E |
| Basic residues | K, R and H |
| Hydrophilic uncharged residues | S, T, N, and Q |
| Aliphatic uncharged residues | G, A, V, L and I |
| Nonpolar uncharged residues | C, M and P |
| Aromatic residues | F, Y and W |

In certain embodiments, other selected groups of amino acids considered as mutual conservative substitutions are as follows:

| | |
|---|---|
| Group 1 | A, S and T |
| Group 2 | D and E |
| Group 3 | N and Q |
| Group 4 | R and K |
| Group 5 | I, L and M |
| Group 6 | F, Y and W |

-continued

In certain embodiments, other selected groups of amino acids considered as mutual conservative substitutions are as follows:

| | |
|---|---|
| Group A | A and G |
| Group B | D and E |
| Group C | N and Q |
| Group D | R, K and H |
| Group E | I, L, M, V |
| Group F | F, Y and W |
| Group G | S and T |
| Group H | C and M |

The term "amino acid" means twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y) and valine (Val; V).

As used herein, the term "Cas12i protein" is used in its broadest sense and includes parental or reference Cas12i proteins (e.g., Cas12i protein comprising any of SEQ ID NOs: 1-10), derivatives or variants thereof, and functional fragments such as oligonucleotide-binding fragments thereof.

As used herein, the term "crRNA" is used interchangeably with guide molecule, gRNA, and guide RNA, and refers to nucleic acid-based molecules, which include but are not limited to RNA-based molecules capable of forming complexes with CRISPR-Cas proteins (e.g., any of Cas12i proteins described herein) (e.g., via direct repeat, DR), and comprises sequences (e.g., spacers) that are sufficiently complementary to a target nucleic acid sequence to hybridize to the target nucleic acid sequence and guide sequence-specific binding of the complex to the target nucleic acid sequence.

As used herein, the term "CRISPR array" refers to a nucleic acid (e.g., DNA) fragment comprising CRISPR repeats and spacers, which begins from the first nucleotide of the first CRISPR repeat and ends at the last nucleotide of the last (terminal) CRISPR repeat. Typically, each spacer in the CRISPR array is located between two repeats. As used herein, the term "CRISPR repeat" or "CRISPR direct repeat" or "direct repeat" refers to a plurality of short direct repeat sequences that exhibit very little or no sequence variation in a CRISPR array. Appropriately, V-I direct repeats may form a stem-loop structure.

"Stem-loop structure" refers to a nucleic acid having a secondary structure including a nucleotide region known or predicted to form a double strand (stem) connected on one side by a region (loop) which is mainly a single-stranded nucleotide. The terms "hairpin" and "fold-back" structures are also used herein to refer to stem-loop structures. Such structures are well known in the art and these terms are used in accordance with their well-known meanings in the art. As known in the art, the stem-loop structure does not require accurate base pairing. Thus, the stem may include one or more base mismatches. Alternatively, the base pairing may be accurate, i.e., no mismatch is included.

As use herein, target nucleic acid is used interchangeably with target sequence or target nucleic acid sequence to refer to a specific nucleic acid comprising a nucleic acid sequence complementary to all or part of a spacer in a crRNA. In some examples, the target nucleic acid comprises a gene or a sequence within the gene. In some examples, the target nucleic acid comprises a non-coding region (e.g., a promoter). In some examples, the target nucleic acid is single-stranded. In some examples, the target nucleic acid is double-stranded.

As used herein, "donor template nucleic acid" or "donor template" is used interchangeably to refer to a nucleic acid molecule that can be used by one or more cell proteins to alter the structure of a target nucleic acid after the CRISPR enzyme described herein alters the target nucleic acid. In some examples, the donor template nucleic acid is a double-stranded nucleic acid. In some examples, the donor template nucleic acid is a single-stranded nucleic acid. In some examples, the donor template nucleic acid is linear. In some examples, the donor template nucleic acid is circular (e.g., plasmid). In some examples, the donor template nucleic acid is an exogenous nucleic acid molecule. In some examples, the donor template nucleic acid is an endogenous nucleic acid molecule (e.g., chromosome).

The target nucleic acid should be associated with PAM (protospacer adjacent motif), that is, short sequences recognized by the CRISPR complex. Depending on the nature of the CRISPR-Cas protein, the target sequence should be selected such that its complementary sequence (the complementary sequence of the target sequence) in the DNA duplex is upstream or downstream of PAM. In an embodiment of the invention, the complementary sequence of the target sequence is downstream or 3' of PAM. The requirements for exact sequence and length of PAM vary depending on the Cas12i protein used.

It will be understood by one of ordinary skill in the art that uracil and thymine can both be represented by 't', instead of 'u' for uracil and 't' for thymine; in the context of a ribonucleic acid, it will be understood that 't' is used to represent uracil unless otherwise indicated.

As use herein, the term "cleavage" refers to DNA breakage in a target nucleic acid produced by a nuclease of the CRISPR system described herein. In some examples, the cleavage is double-stranded DNA breakage. In some examples, the cleavage is single-stranded DNA breakage.

As used herein, the meanings of "cleaving target nucleic acid" or "modifying target nucleic acid" may overlap. Modifying a target nucleic acid includes not only modification of a mononucleotide but also insertion or deletion of a nucleic acid fragment.

Cas12i Proteins

The present application provides Cas12i proteins, such as SiCas12i (SEQ ID NO: 1), Si2Cas12i (SEQ ID NO: 2), WiCas12i (SEQ ID NO: 3), Wi2Cas12i (SEQ ID NO: 4), Wi3Cas12i (SEQ ID NO: 5), SaCas12i (SEQ ID NO: 6), Sa2Cas12i (SEQ ID NO: 7), Sa3Cas12i (SEQ ID NO: 8), WaCas12i (SEQ ID NO: 9), and Wa2Cas12i (SEQ ID NO: 10), which have single-stranded or double-stranded DNA cleavage activity. The Cas12i proteins described herein have less than about 50% sequence identity to other known Cas12i, are smaller and have better delivery efficiency than other Cas such as Cas9 or Cas12. In some embodiments, the Cas12i protein comprises a sequence of any of SEQ ID NOs: 1-10, such as any of SEQ ID NOs: 1-3 and 6, or SEQ ID NO: 1. In some embodiments, the Cas12i protein is isolated. In some embodiments, the Cas12i protein is engineered. In some embodiments, the Cas12i protein is man-made.

Cas12i proteins described herein, such as SiCas12i, Si2Cas12i, WiCas12i, and SaCas12i, have excellent cleavage activity for exogenous or endogenous genes in vitro or at the cellular level, comparable to or even better than the cleavage activity of SpCas9, LbCas12a, and Cas12i.3. The cleavage activity of Cas12i proteins described herein, such as SiCas12i, Si2Cas12i, WiCas12i, and SaCas12i, for specific target sequences of exogenous or endogenous genes can be greater than about any of 15%, 20%, 30%, 40%, 50%, 60%, 70%, 80%, 90%, 95% or even greater than 99% at the cellular level. Generally speaking, the cleavage activity of Cas12i proteins described herein for specific target sequences of exogenous or endogenous genes at the cellular level is superior to that of Cas12i.3.

The cleavage activity of SiCas12i for exogenous or endogenous genes in vitro or at the cellular level is comparable to, or even better than that of SpCas9 or LbCas12a, and significantly better than that of Cas12i.3. Its cleavage activity for specific target sequences of exogenous or endogenous genes at the cellular level may be greater than about any of 15%, 20%, 30%, 40%, 50%, 60%, 70%, 80%, 90%, 95% or even greater than 99%. In general, the cleavage activity of SiCas12i for specific target sequences of exogenous or endogenous genes at the cellular level is significantly superior to that of Cas12i.3.

The above Cas12i proteins may also comprise amino acid mutations that do not substantially affect (e.g., affect no more than about any of 5%, 4%, 3%, 2%, 1%, or smaller) the catalytic activity (endonuclease cleavage activity) or nucleic acid binding function of the Cas12i.

In some embodiments, the Cas12i proteins of the present invention (including variants, dCas, nickases, etc.), such as SiCas12i, comprise one or more nuclear localization sequences (NLSs) at its N-terminus and/or C-terminus, preferably one NLS at its N-terminus and one NLS at C-terminus. In some embodiments, the NLS is an SV40 NLS (e.g., as set forth in SEQ ID NO: 179), preferably when the Cas12i protein is used for cleavage. In some embodiments, the NLS is a BP NLS, such as shown in SEQ ID NO: 180 or 181, preferably when the Cas12i protein is used for base editing, more preferably the Cas12i protein is fused at its N-terminus a BP NLS of SEQ ID NO: 180, and fused at its C-terminus a BP NLS of SEQ ID NO: 181.

Cas12i Protein Variants

The present invention also provides variants of any of the Cas12i proteins described herein, such as Cas12i variants with at least about 80% (e.g., at least about any of 81%, 82%, 83%, 84%, 85%, 86%, 87%, 88%, 89%, 90%, 91%, 92%, 93%, 94%, 95%, 96%, 97%, 98%, 99%, 99.5% or higher) but less than 100% identical sequence to any of SEQ ID NOs: 1-10 (preferably, SEQ ID NOs: 1-3 and 6, more preferably, SEQ ID NO: 1). In some embodiments, the Cas12i variant comprises one or more substitutions, insertions, deletions, or truncations relative to the amino acid sequence of a reference Cas12i protein (e.g., a Cas12i protein comprising the amino acid sequence of any one of SEQ ID NOs: 1-10).

As used herein, "variant" refers to a polynucleotide or a polypeptide that differs from a reference (e.g., parental) polynucleotide or polypeptide, respectively, but retains the necessary properties. A typical variant of a polynucleotide differs in nucleic acid sequence from a reference polynucleotide. Nucleotide changes may or may not alter the amino acid sequence of the polypeptide encoded by the reference polynucleotide. Nucleotide changes can result in amino acid substitutions, additions, deletions, or truncations in the polypeptide encoded by the reference polynucleotide. A typical variant of a polypeptide differs in amino acid sequence from a reference polypeptide. Typically, this difference is limited such that the sequences of the reference and variant polypeptides are generally very similar and identical in many regions. The amino acid sequences of the variant polypeptide and the reference polypeptide may differ by any combination of one or more of substitutions, additions, deletions, or truncations. A substituted or inserted amino acid residue may or may not be an amino acid residue encoded by the genetic code. Variants of a polynucleotide or polypeptide may be naturally occurring (such as allelic variants), or may be non-naturally occurring. Non-naturally occurring variants of polynucleotides and polypeptides can be prepared by mutagenesis techniques, by direct synthesis, or by other recombinant methods known to those of skill in the art.

As used herein, the term "wild-type" has the meaning commonly understood by those skilled in the art and means the typical form of an organism, strain, gene or trait. It can be isolated from resources in nature and has not been deliberately decorated.

As used herein, the terms "non-naturally occurring" and "engineered" are used interchangeably and refer to artificial involvement. When these terms are used to describe a nucleic acid molecule or polypeptide, it is meant that the nucleic acid molecule or polypeptide is at least substantially free of at least one other component with which it is naturally associated or occurs in nature.

In some embodiments, the Cas12i variant is isolated. In some embodiments, the Cas12i variant is engineered or non-naturally occurring. In some embodiments, the Cas12i variant is artificially synthesized. In some embodiments, the Cas12i variant has one or more amino acid mutations (e.g., insertions, deletions, or substitutions) in one or more domains relative to a reference Cas12i protein (e.g., the parental Cas12i protein), such as PI domain, Helical domain, RuvC domain, WED domain, Nuc domain, etc.

In some embodiments, the Cas12i variant is a variant relative to SiCas12i (SEQ ID NO: 1). This means that the Cas12i variant (e.g., a variant of Si2Cas12i) in its original sequence (e.g., Si2Cas12i, SEQ ID NO: 2) and the original SiCas12i (SEQ ID NO: 1) can be aligned, and the one or more positions with amino acid mutations (such as insertions, deletions or substitutions) can be identified. In some embodiments, the Cas12i variant is an engineered SiCas12i.

In some embodiments, the Cas12i variant (e.g., a SiCas12i variant) has a higher spacer-specific endonuclease cleavage activity against a target sequence of a target DNA that is complementary to the guide sequence, compared to the corresponding reference Cas12i protein (e.g., Cas12i protein comprising any of SEQ ID NOs: 1-10), such as at least about 1.2-fold (e.g., at least about any of 1.3, 1.4, 1.5, 1.6, 1.7, 1.8, 1.9, 2, 2.5, 3, 3.5, 4, 5, 10, 20, 50-fold, or higher) higher than the corresponding reference Cas12i protein.

In some embodiments, the original reference Cas12i protein (e.g., Cas12i protein comprising any of SEQ ID NOs: 1-10) has a higher spacer-specific endonuclease cleavage activity against a target sequence of a target DNA that is complementary to the guide sequence, compared to the corresponding Cas12i variant (e.g., SiCas12i variant), such as at least about 1.2-fold (e.g., at least about any of 1.3, 1.4, 1.5, 1.6, 1.7, 1.8, 1.9, 2, 2.5, 3, 3.5, 4, 5, 10, 20, 50-fold, or higher) higher than the Cas12i variant.

In some embodiments, the spacer-specific endonuclease cleavage activity of the Cas12i variant (e.g., a SiCas12i variant) against a target sequence of a target DNA that is complementary to a guide sequence is the same as or not significantly different from (e.g., within about 1.2-fold) that of the corresponding original Cas12i protein (e.g., Cas12i protein comprising any of SEQ ID NOs: 1-10). For example, in some embodiments, the Cas12i variant has the same spacer-specific endonuclease cleavage activity against the target sequence of the target DNA that is complementary to the guide sequence as the corresponding original Cas12i protein. In some embodiments, the Cas12i variant has a spacer-specific endonuclease cleavage activity against a target sequence of a target DNA that is complementary to a guide sequence of no more than about 1.2-fold higher than the corresponding original Cas12i protein (e.g., less than or equal to about any of 1.2, 1.19, 1.15, 1.1, 1.01, 1.001-fold, etc.). In some embodiments, the spacer-specific endonuclease cleavage activity of the original Cas12i protein against a target sequence of a target DNA that is complementary to the guide sequence is no more than about 1.2-fold higher than that of the corresponding Cas12i variant (e.g., less than or equal to about any of 1.2, 1.19, 1.15, 1.1, 1.01, 1.001-fold, etc.).

Cas12i Proteins Substantially Lacking Catalytic Activity (dCas12i)

The present invention also provides dead Cas12i (dCas12i) proteins lacking or substantially lacking catalytic activity. For example, in some embodiments, the dCas12i protein retains less than about 50% (e.g., less than about any of 40%, 35%, 30%, 27.5%, 25%, 22.5%, 20%, 17.5%, 15%, 12.5%, 10%, 7.5%, 5%, 4%, 3%, 2.5%, 2%, 1% or less) spacer-specific endonuclease cleavage activity of the corresponding parental Cas12i protein (e.g., Cas12i protein comprising any of SEQ ID NOs: 1-10) for a target sequence of a target DNA that is complementary to a guide sequence. In some embodiments, the dCas12i protein comprises one or more amino acid substitutions in the RuvC domain (e.g., RuvC domain of a Cas12i protein comprising any of SEQ ID NOs: 1-10), resulting in substantial lack of catalytic activity. In some embodiments, the DNA cleavage activity of dCas12i is zero or negligible compared to the non-mutated Cas12i form. In some embodiments, the dCas12i is a Cas12i protein without catalytic activity, which contains mutation (s) in the RuvC domain that allow for formation of a CRISPR complex and successful binding to a target nucleic acid while not allowing for successful nuclease activity (catalytic/cleavage activity).

In some embodiments, the dCas12i is a dSiCas12i substantial lacking catalytic activity. In some embodiments, the dSiCas12i comprises one or more substitutions at amino acid residues 650, 700, 875, and/or 1049 relative to SEQ ID NO: 1. In some embodiments, the dSiCas12i comprises one or more substitutions selected from the group consisting of D700A, D700V, D650A, D650V, E875A, E875V, D1049A, and D1049V relative to SEQ ID NO: 1. In one embodiment, the dSiCas12i comprises the amino acid sequence of any of SEQ ID NOs: 79-82, named dSiCas12i(D700A), dSiCas12i (D650A), dSiCas12i(E857A), and dSiCas12i(D1049A), respectively. In some embodiments, the dSiCas12i comprises one or more substitutions selected from the group consisting of D650A, D700A, E875A, D1049A, D650A+D700A, D700A+E875A, D700A+D1049A, D650A+E875A, D650A+D1049A, E875A+D1049A, D650A+D700A+E875A, D650A+D700A+D1049A, D650A+E875A+D1049A, D700A+E875A+D1049A, and D650A+D700A+E875A+D1049A, relative to SEQ ID NO: 1.

In addition, the dCas12i may contain mutations other than those previously described that do not substantially affect (e.g., affect no more than about any of 5%, 4%, 3%, 2%, 1%, or smaller) the catalytic activity or nucleic acid binding function of the dCas12i protein. The dCas12i protein, which substantially lacks catalytic activity, can be used as a DNA-binding protein.

In some embodiments, the dCas12i described herein (e.g., dSiCas12i comprising the sequence of any of SEQ ID NOs: 79-82) can be fused with an adenosine deaminase (ADA) or a cytidine deaminase (CDA), or a catalytic domain thereof, to achieve single-base editing. In some embodiments, the single-base editing efficiency of a fusion protein comprising any of the dCas12i proteins described herein and an ADA or a CDA (or catalytic domain thereof) is at least about 10% higher (e.g., at least about any of 20%, 30%, 40%, 50%, 60%, 70%, 80% 90%, 100%, 120%, 150%, 200%, 500%, 1000%, or higher) than that of a fusion protein comprising a dCas12i not from present invention and a sane ADA or CDA (or catalytic domain thereof).

The number of amino acids in a full-length sequence of any of the Cas12i or dCas12i proteins described above is remarkably less than that of Cas12 proteins of other types, and their smaller molecular size facilitates the subsequent assembly and delivery of the Cas system in vivo.

In some embodiments, the adenosine deaminase is TadA8e, such as TadA8e comprising the sequence of SEQ ID NO: 182.

In some embodiments, the C' terminus of a deaminase, such as adenosine deaminase, is fused to the N' terminus of a dCas12i via an optional peptide linker, such as a peptide linker comprising SEQ ID NO: 183. In some embodiments, the N' terminus of a deaminase, such as adenosine deaminase, is fused to the C' terminus of a dCas12i via an optional peptide linker, such as a peptide linker comprising SEQ ID NO: 183. In some embodiments, there is provided a fusion protein comprising dSiCas12i and an adenosine deaminase (e.g., TadA8e), such as fusion protein TadA8e-dSiCas12i (D1049A) set forth in SEQ ID NO: 85, or fusion protein TadA8e-dSiCas12i(E875A) set forth in SEQ ID NO: 184.

Unless otherwise specified, "Cas12i," or "Cas12i protein" described herein include any Cas12i protein described in the present invention and its variants (such as mutants), derivatives (such as Cas12i fusion proteins), as well as dCas12i proteins substantially lacking catalytic activity and derivatives thereof (such as dCas12i fusion proteins, such as dCas12i-TadA). The present invention also provides nucleotide sequences encoding any of the Cas12i proteins and variants and derivatives thereof, such as the polynucleotide sequences of any of SEQ ID NOs: 11-20 and 37-46.

CRISPR (crRNA)

Typically, crRNAs described herein comprise, consist essentially of, or consist of a direct repeat (DR) and a spacer. In some embodiments, the crRNA comprises, consists essentially of, or consists of a DR linked to a spacer. In some embodiments, the crRNA comprises a DR, a spacer, and a DR (DR-spacer-DR). This is a typical configuration of a pre-crRNA. In some embodiments, the crRNA comprises a DR, a spacer, a DR, and a spacer (DR-spacer-DR-spacer). In some embodiments, the crRNA comprises two or more DRs and two or more spacers. In some embodiments, the crRNA comprises a truncated DR, and a spacer. This is typical for processed or mature crRNAs. In some embodiments, the CRISPR-Cas12i effector protein forms a complex with the crRNA, and the spacer directs the complex to a target nucleic acid that is complementary to the spacer for sequence-specific binding.

In some embodiments, the CRISPR-Cas12i system described herein comprises one or more crRNAs (e.g., 1, 2, 3, 4, 5, 10, 15, or more), or nucleic acids encoding thereof. In some embodiments, the two or more crRNAs target different target sites, e.g., 2 target sites of the same target DNA or gene, or 2 target sites of 2 different target DNA or genes.

The sequences and lengths of the crRNAs described herein can be optimized. In some embodiments, the optimal length of the crRNA can be determined by identifying the processed form of the crRNA or by empirical length studies of the crRNA. In some embodiments, the crRNA comprises base modifications.

Direct Repeat (DR)

Figure 11:
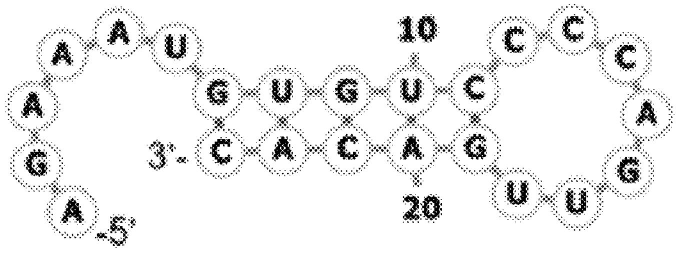
FIG. 11 shows comparison of cleavage activity of SiCas12i mediated by crRNAs with different direct repeat (DR) variants. DR-P is the parental DR.
Figure 11:
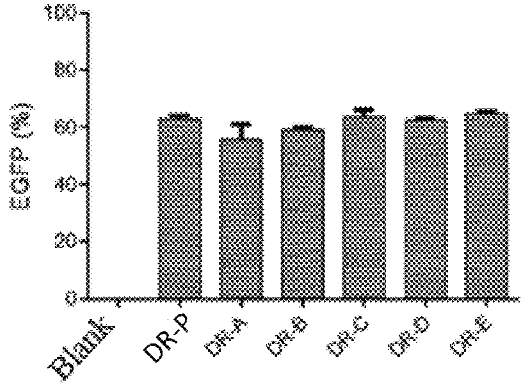

Table A exemplifies DR sequences of corresponding Cas12i protein of the present invention. For example, the DR sequence corresponding to SiCas12i (or a variant or derivative thereof, or dSiCas12i or a fusion protein thereof) may comprise the nucleotide sequence set forth in SEQ ID NO: 21 or a functional variant thereof. Any DR sequence that can mediate the binding of the Cas12i protein described herein to the corresponding crRNA can be used in the present invention. In some embodiments, the DR comprises the RNA sequence of any one of SEQ ID NOs: 21-30 and 101. In some embodiments, the DR comprises the sequence set forth in SEQ ID NO: 21 or 101. In some embodiments, the DR is a "functional variant" of any of the RNA sequences of SEQ ID NOs: 21-30 and 101, such as a "functionally truncated version," "functionally extended version," or "functionally replacement version." For example, DR sequence of SEQ ID NO: 101 is a part of SEQ ID NO: 21 (truncated version), it still has DR function, as demonstrated in Example 8, and is therefore a functional variant, or a functionally truncated DR variant. A "functional variant" of a DR is a 5' and/or 3' extended (functionally extended version) or truncated (functionally truncated version) variant of a reference DR (e.g., a parental DR), or comprises one or more insertions, deletions, and/or substitutions (functional replacement version) of one or more nucleotides relative to the reference DR (e.g., a parental DR), while still retaining at least about 20% (such as at least about any of 30%, 40%, 50%, 60%, 60%, 70%, 80%, 90%, 95%, or higher) functionality of the reference DR, i.e., the function to mediate the binding of a Cas12i protein to the corresponding crRNA. DR functional variants typically retain stem-loop-like secondary structure or portions thereof available for Cas12i protein binding. As shown in FIG. 11, DR-P (SEQ ID NO: 101) is one of the functionally truncated versions of the DR shown in SEQ ID NO: 21. In some embodiments, the DR or functional variant thereof comprises a stem-loop-like secondary structure or portion thereof available for binding by the Cas12i protein. In some embodiments, the DR or functional variant thereof comprises at least two (e.g., 2, 3, 4, 5 or more) stem-loop-like secondary structures or portions thereof available for binding by the Cas12i protein.

In some embodiments, the DR or functional variant thereof comprises at least about 16 nucleotides (nt), such as 16, 17, 18, 19, 20, 21, 22, 23, 24, 25, 26, 27, 28, 29, 30, 31, 32, 33, 34, 35, 36, 37, 38, 39, 40 or more nucleotides. In some embodiments, the DR comprises about 20 nt to about 40 nt, such as about 20 nt to about 30 nt, about 22 nt to about 40 nt, about 23 nt to about 38 nt, about 23 nt to about 36 nt, or about 30 nt to about 40 nt. In some embodiments, the DR comprises 22 nt, 23 nt, or 24 nt. In some embodiments, the DR comprises 35 nt, 36 nt, or 37 nt.

In some embodiments, the DR sequence comprises a stem-loop structure near the 3' end (immediately adjacent to the spacer sequence). "Stem-loop structure" refers to a nucleic acid having a secondary structure that includes regions of nucleotides known or predicted to form a double-strand (stem) portion and connected at one end by a linking region (loop) of substantially single-stranded nucleotides. The term "hairpin" structure is also used herein to refer to stem-loop structures. Such structures are well known in the art, and these terms are used in accordance with their commonly known meanings in the art. Stem-loop structures do not require precise base pairing. Thus, the stem may comprise one or more base mismatches. Alternatively, base pairing may be exact, i.e., not including any mismatches.

The crRNA of the present invention comprises a DR comprising a stem-loop structure near the 3' end of the DR sequence. The DR stem-loop structure of SiCas12i is exemplified in FIG. 11. In some embodiments, the stem contained in the DR consists of 5 pairs of complementary bases that hybridize to each other, and the loop length is 6, 7, 8, or 9 nucleotides. In some embodiments, the loop length is 7 nucleotides. In some embodiments, the stem can comprise at least 2, at least 3, at least 4, or at least 5 base pairs. In some embodiments, the DR comprises two complementary stretches of nucleotides about 5 nucleotides in length separated by about 7 nucleotides. In some embodiments, the stem-loop structure comprises a first stem nucleotide chain of 5 nucleotides in length; a second stem nucleotide chain of 5 nucleotides in length, wherein the first and the second stem nucleotide chains can hybridize to each other; and a cyclic nucleotide chain arranged between the first and second stem nucleotide chains, wherein the cyclic nucleotide chain comprises 6, 7 or 8 nucleotides.

As used herein, the secondary structure of two or more crRNAs are substantially identical or not substantially different means that these crRNAs contain stems and/or loops differing by no more than 1, 2, or 3 nucleotides in length; in terms of nucleotide type (A, U, G, or C), the nucleotide sequences of these crRNAs when compared by sequence alignment differ by no more than 1, 2, 3, 4, 5, 6, 7 or 8 nucleotides. In some embodiments, the secondary structure of two or more crRNAs are substantially identical or not substantially different means that the crRNAs contain stems that differ by at most one pair of complementary bases, and/or loops that differ by at most one nucleotide in length, and/or contain stems with same length but with mismatched bases. In some embodiments, the stem-loop structure comprises 5'-$X_1X_2X_3X_4X_5$NNNnNNN$X_6X_7X_8X_9X_{10}$-3', wherein $X_1$, $X_2$, $X_3$, $X_4$, $X_5$, $X_6$, $X_7$, $X_8$, $X_9$, and $X_{10}$ can be any base, n can be any base or deletion, and N can be any base; wherein $X_1X_2X_3X_4X_5$ and $X_6X_7X_8X_9X_{10}$ can hybridize to each other to form a stem and make NNNnNNN form a loop. In some embodiments, the stem-loop structure comprises the sequence of any one of SEQ ID NOs: 114-123.

In some embodiments, the DR sequence that can direct any of the Cas12i of the invention to the target site comprises one or more nucleotide changes selected from the group consisting of nucleotide additions, insertions, deletions, and substitutions that do not result in substantial differences in secondary structure compared to DR sequence set forth in any of SEQ ID NOs: 21-30 and 101 or functionally truncated version thereof.

Spacer

In some embodiments, the length of the spacer sequence is at least about 16 nucleotides, preferably about 16 to about 100 nucleotides, more preferably about 16 to about 50 nucleotides (e.g., about any of 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides). In some embodiments, the spacer is about 16 to about 27 nucleotides, such as any of about 17 to about 24 nucleotides, about 18 to about 24 nucleotides, or about 18 to about 22 nucleotides.

In some embodiments, the spacer is at least about 70% (e.g., at least about any of 75%, 80%, 85%, 90%, 90%, 91%, 92%, 93%, 94%, 95%, 96%, 97%, 98%, 99% or 100%) complementary to the target sequence. In some embodiments, there are at least about 15 (e.g., at least about any of 16, 17, 18, 19, 20, 21, 22, 23, 24, 25, 26, 27, 28, 29, 30, 35, 40, 45, 50 or more) between the spacer sequence and the target sequence of the target nucleic acid (e.g., DNA).

Complete complementarity is not required for spacers, provided that there is sufficient complementarity for the crRNA to function (i.e., directing Cas12i protein to the target site). The cleavage efficiency by Cas12i mediated by the crRNA can be adjusted by introducing one or more mismatches (e.g., 1 or 2 mismatches between the spacer sequence and the target sequence, including the positions along the mismatches of the spacer/target sequence). Mismatches, such as double mismatches, have greater impact on cleavage efficiency when they are located more central to the spacer (i.e., not at the 3' or 5' end of the spacer). Thus, by choosing the position of mismatches along the spacer sequence, the cleavage efficiency of Cas12i can be tuned. For example, if less than 100% cleavage of the target sequence is desired (e.g., in a population of cells), 1 or 2 mismatches between the spacer sequence and the target sequence can be introduced into the spacer sequence.

PAM

In some embodiments, the Cas12i protein of the present invention can recognize PAM (protospacer adjacent motif, protospacer adjacent motif) to act on the target sequence. In some embodiments, the PAM comprises or consists of 5'-TTN-3' (wherein N is A, T, G, or C) or 5'-NTN-3' (wherein N is A, T, G or C). In some embodiments, the PAM comprises or consists of 5'-TTC-3', 5'-TTA-3', 5'-TTT-3', 5'-TTG-3', 5'-ATA-3', or 5'-ATG-3'. In some embodiments, the PAM comprises or consists of 5'-TTC-3'.

The invention provides the following embodiments:

1. A Cas12i protein comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identity to the amino acid sequence as set forth in any one of SEQ ID NOs: 1-10 (preferably, SEQ ID NOs: 1-3 and 6, and more preferably, SEQ ID NO: 1).

The Cas12i protein may also contain amino acid mutations that do not substantially affect the catalytic activity (endonuclease cleavage activity) or nucleic acid binding function of Cas12i.

2. The Cas12i protein according to any one of the preceding embodiments, wherein the Cas12i protein substantially lacks (e.g., retains less than 50%, 40%, 35%, 30%, 27.5%, 25%, 22.5%, 20%, 17.5%, 15%, 12.5%, 10%, 7.5%, 5%, 4%, 3%, 2.5%, 2%, 1% or less) spacer-specific endonuclease cleavage activity of the corresponding parental Cas12i protein (e.g., Cas12i protein comprising any of SEQ ID NOs: 1-10) for a target sequence of a target DNA complementary to a guide sequence.

In one embodiment, the Cas12i substantially lacks (e.g., retains less than 50%, 40%, 35%, 30%, 27.5%, 25%, 22.5%, 20%, 17.5%, 15%, 12.5%, 10%, 7.5%, 5%, 4%, 3%, 2.5%, 2%, 1%, or less) spacer-specific endonuclease cleavage activity or spacer non-specific collateral activity of the corresponding parental Cas12i protein (e.g., Cas12i protein comprising any of SEQ ID NOs: 1-10).

3. The Cas12i protein according to any one of the preceding embodiments, wherein the Cas12i protein comprises one or more amino acid variations in its RuvC domain such that the Cas12i protein substantially lacks (e.g., retains less than 50%, 40%, 35%, 30%, 27.5%, 25%, 22.5%, 20%, 17.5%, 15%, 12.5%, 10%, 7.5%, 5%, 4%, 3%, 2.5%, 2%, 1% or less) spacer-specific endonuclease cleavage activity of the corresponding parental Cas12i protein (e.g., Cas12i protein comprising any of SEQ ID NOs: 1-10) for a target sequence of a target DNA complementary to a guide sequence.

4. The Cas12i protein according to any one of the preceding embodiments, wherein the amino acid variation is selected from the group consisting of amino acid additions, insertions, deletions, and substitutions.

5. The Cas12i protein according to any one of the preceding embodiments, wherein the Cas12i protein comprises an amino acid substitution at one or more positions corresponding to positions 700 (D700), 650 (D650), 875 (E875) or 1049 (D1049) of the sequence as set forth in SEQ ID NO: 1.

The amino acid at the above amino acid site (D700, D650, E875 or D1049) may be mutated to another amino acid different from the corresponding amino acid on the parental sequence (e.g., parental Cas12i protein comprising any of SEQ ID NOs: 1-10) to substantially lose endonuclease cleavage activity.

The Cas12i protein may also contain other mutations that have no substantial effect on the catalytic activity or nucleic acid binding function of the Cas12i.

6. The Cas12i protein according to any one of the preceding embodiments, wherein the amino acid substitution is selected from the group consisting of D700A/V, D650A/V, E875A/V, and D1049A/V.

7. The Cas12i protein according to any one of the preceding embodiments, wherein the amino acid substitution is selected from the group consisting of D700A, D650A, E875A, and D1049A.

8. The Cas12i protein according to any one of the preceding embodiments, wherein the amino acid substitution is selected from the group consisting of D700A, D650A, E875A, D1049A, D700A+D650A, D700A+E875A, D700A+D1049A, D650A+E875A, D650A+D1049A, E875A+D1049A, D700A+D650A+E875A, D700A+D650A+D1049A, D650A+E875A+D1049A, and D700A+D650A+E875A+D1049A.

9. The Cas12i protein according to any one of the preceding embodiments, wherein the Cas12i protein comprises the amino acid sequence as set forth in any one of SEQ ID NOs: 79-82.

10. The Cas12i protein according to any one of the preceding embodiments, wherein the Cas12i protein is linked to one or more functional domains.

11. The Cas12i protein according to any one of the preceding embodiments, wherein the functional domain is linked to the N-terminus and/or C-terminus of the Cas12i protein.

The linking may be a direct linking or an indirect linking through a linker.

12. The Cas12i protein according to any one of the preceding embodiments, wherein the functional domain is selected from the group consisting of a nuclear localization signal (NLS), nuclear export signal (NES), deaminase (e.g., adenosine deaminase or cytidine deaminase) catalytic domain, a DNA methylation catalytic domain, a DNA demethylation catalytic domain, a histone residue modification domain, a nuclease catalytic domain, a fluorescent protein, a transcription modification factor (e.g., a transcription activation catalytic domain, a transcription inhibition catalytic domain), a light gating factor, a chemical inducible factor, a chromatin visualization factor, a targeting polypeptide for providing binding to a cell surface portion on a target cell or a target cell type.

13. The Cas12i protein according to any one of the preceding embodiments, wherein the functional domain exhibits activity to modify a target DNA, selected from the group consisting of nuclease activity, methylation activity, demethylation activity, DNA repair activity, DNA damage activity, deamination activity, dismutase activity, alkylation activity, depurination activity, oxidation activity, pyrimidine dimer formation activity, integrase activity, transposase activity, recombinase activity, polymerase activity, ligase activity, helicase activity, photolyase activity, glycosylase activity, acetyl transferase activity, deacetylase activity, kinase activity, phosphatase activity, ubiquitin ligase activity, deubiquitination activity, adenylation activity, deadenylation activity, SUMOylation activity, deSUMOylation activity, ribosylation activity, deribosylation activity, myristoylation activity, demyristoylation activity, glycosylation activity (e.g., from O-GlcNAc transferase), deglycosylation activity, transcription inhibition activity, transcription activation activity.

14. The Cas12i protein according to any one of the preceding embodiments, wherein the functional domain is selected from an adenosine deaminase catalytic domain or a cytidine deaminase catalytic domain.

15. The Cas12i protein according to any one of the preceding embodiments, wherein the functional domain is a full length or functional fragment of TadA8e.

16. The Cas12i protein according to any one of the preceding embodiments, wherein the Cas12i protein comprises the amino acid sequence as set forth in SEQ ID NO: 85.

17. The Cas12i protein according to any one of the preceding embodiments, wherein the Cas12i protein is modified to reduce or eliminate spacer non-specific endonuclease collateral activity.

18. A polynucleotide encoding the Cas12i protein according to any one of the preceding embodiments.

19. The polynucleotide according to any one of the preceding embodiments, wherein the polynucleotide is codon optimized for expression in eukaryotic cells.

20. The polynucleotide according to any one of the preceding embodiments, wherein the polynucleotide comprises a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identity to the nucleotide sequence as set forth in any one of SEQ ID NOs: 11-20 and SEQ ID NOs: 37-46.

21. A vector comprising the polynucleotide according to any one of the preceding embodiments.

22. The vector according to any one of the preceding embodiments, wherein the polynucleotide is operably linked to a promoter.

23. The vector according to any one of the preceding embodiments, wherein the promoter is a constitutive promoter, an inducible promoter, a ubiquitous promoter, a cell type specific promoter, or a tissue specific promoter.

24. The vector according to any one of the preceding embodiments, wherein the vector is a plasmid.

25. The vector according to any one of the preceding embodiments, wherein the vector is a retroviral vector, a phage vector, an adenovirus vector, a herpes simplex virus (HSV) vector, an adeno-associated virus (AAV) vector, or a lentiviral vector.

26. The vector according to any one of the preceding embodiments, wherein the AAV vector is selected from the group consisting of recombinant AAV vectors of serotypes AAV1, AAV2, AAV4, AAV5, AAV6, AAV7, AAVrh74, AAV8, AAV9, AAV10, AAV11, AAV12, and AAV13.

27. A delivery system comprising (1) a delivery medium; and (2) the Cas12i protein, polynucleotide or vector according to any one of the preceding embodiments.

28. The delivery system according to any one of the preceding embodiments, wherein the delivery medium is nanoparticle, liposome, exosome, microvesicle, or gene gun.

29. An engineered, non-naturally occurring CRISPR-Cas system comprising:

(1) the Cas12i protein or a polynucleotide encoding the Cas12i protein according to any one of the preceding embodiments; and (2) a CRISPR RNA (crRNA) or a polynucleotide encoding the crRNA, the crRNA comprising:

(i) a spacer capable of hybridizing to a target sequence of a target DNA, and (ii) a Direct Repeat (DR) linked to the spacer and capable of guiding the Cas12i protein to bind to the crRNA to form a CRISPR-Cas complex targeting the target sequence.

The Cas12i protein is capable of binding to the crRNA and targeting the target sequence, wherein the target sequence is a single-stranded or double-stranded DNA or RNA.

30. A CRISPR-Cas system comprising one or more vectors, wherein the one or more vectors comprise:

(1) a first regulatory element operably linked to a nucleotide sequence encoding the Cas12i protein according to any one of the preceding embodiments; and (2) a second regulatory element operably linked to a polynucleotide encoding a CRISPR RNA (crRNA), the crRNA comprising:

(i) a spacer capable of hybridizing to a target sequence of a target DNA, and (ii) a Direct Repeat (DR) linked to the spacer that is capable of guiding the Cas12i protein to bind to the crRNA to form a CRISPR-Cas complex targeting the target sequence;

wherein the first regulatory element and the second regulatory element are located on the same or different vectors of the CRISPR-Cas vector system.

31. An engineered, non-naturally occurring CRISPR-Cas complex comprising:

(1) the Cas12i protein according to any one of the above embodiments; and (2) a CRISPR RNA (crRNA), the crRNA comprising:

(i) a spacer capable of hybridizing to a target sequence of a target DNA, and (ii) a Direct Repeat (DR) linked to the spacer; the DR guides the Cas12i protein to bind to the crRNA.

32. The CRISPR-Cas system or complex according to any one of the preceding embodiments, wherein the spacer is greater than 16 nucleotides in length, preferably 16 to 100 nucleotides, more preferably 16 to 50 nucleotides (e.g., 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides), more preferably 16 to 27 nucleotides, more preferably 17 to 24 nucleotides, more preferably 18 to 24 nucleotides, and most preferably 18 to 22 nucleotides.

33. The CRISPR-Cas system or complex according to any one of the preceding embodiments, wherein the DR has a secondary structure substantially identical to the secondary structure of the DR as set forth in any one of SEQ ID NOs: 21-30.

34. The CRISPR-Cas system or complex according to any one of the preceding embodiments, wherein the DR has nucleotide additions, insertions, deletions or substitutions without causing substantial differences in the secondary structure as compared to the DR as set forth in any one of SEQ ID NOs: 21-30.

35. The CRISPR-Cas system or complex according to any one of the preceding embodiments, wherein the DR comprises a stem-loop structure near the 3' end of the DR, wherein the stem-loop structure comprises 5'-$X_1X_2X_3X_4X_5$NNNnNNN$X_6X_7X_8X_9X_{10}$-3' ($X_1$, $X_2$, $X_3$, $X_4$, $X_5$, $X_6$, $X_7$, $X_8$, $X_9$, $X_{10}$ are any base, n is any nucleobase or deletion, N is any nucleobase); wherein $X_1X_2X_3X_4X_5$ and $X_6X_7X_8X_9X_{10}$ can hybridize to each other.

36. The CRISPR-Cas system or complex according to any one of the preceding embodiments, wherein the DR comprises a stem-loop structure selected from any one of the following:

5'-CUCCCNNNNNNUGGGAG-3' (SEQ ID NO: 114) near the 3' end of the DR, wherein N is any nucleobase;

5'-CUCCUNNNNNNUGGGAG-3' (SEQ ID NO: 115) near the 3' end of the DR, wherein N is any nucleobase;

5'-GUCCCNNNNNNUGGGAC-3' (SEQ ID NO: 116) near the 3' end of the DR, wherein N is any nucleobase;

5'-GUGUCNNNNNNUGACAC-3' (SEQ ID NO: 117) near the 3' end of the DR, wherein N is any nucleobase;

5'-GUGCCNNNNNNUGGCAC-3' (SEQ ID NO: 118) near the 3' end of the DR, wherein N is any nucleobase;

5'-UGUGUNNNNNNUCACAC-3' (SEQ ID NO: 119) near the 3' end of the DR, wherein N is any nucleobase;

5'-CCGUCNNNNNNUGACGG-3' (SEQ ID NO: 120) near the 3' end of the DR, where N is any nucleobase;

5'-GUUUCNNNNNNUGAAAC-3' (SEQ ID NO: 121) near the 3' end of the DR, where N is any nucleobase;

5'-GUGUUNNNNNNUAACAC-3' (SEQ ID NO: 122) near the 3' end of the DR, where N is any nucleobase; and 5'-UUGUCNNNNNNUGACAA-3' (SEQ ID NO: 123) near the 3' end of the DR, where N is any nucleobase.

37. The CRISPR-Cas system or complex according to any one of the preceding embodiments, further comprising a target DNA capable of hybridizing to the spacer.

38. The CRISPR-Cas system or complex according to any one of the preceding embodiments, wherein the target DNA is a eukaryotic DNA.

39. The CRISPR-Cas system or complex according to any one of the preceding embodiments, wherein the target DNA is in cells; preferably the cells are selected from the group consisting of prokaryotic cells, eukaryotic cells, animal cells, plant cells, fungal cells, vertebrate cells, invertebrate cells, rodent cells, mammalian cells, primate cells, non-human primate cells, and human cells.

40. The CRISPR-Cas system or complex according to any one of the preceding embodiments, wherein the crRNA hybridizes to and forms a complex with the target sequence of the target DNA, causing the Cas12i protein to cleave the target sequence.

41. The CRISPR-Cas system or complex according to any one of the preceding embodiments, wherein the target sequence is at the 3' end of a protospacer adjacent motif (PAM).

42. The CRISPR-Cas system or complex according to any one of the preceding embodiments, wherein the PAM comprises a 5'-T-rich motif.

43. The CRISPR-Cas system or complex according to any one of the preceding embodiments, wherein the PAM is 5'-TTA, 5'-TTT, 5'-TTG, 5'-TTC, 5'-ATA or 5'-ATG.

44. The CRISPR-Cas system or complex according to any one of the preceding embodiments, wherein the one or more vectors comprise one or more retroviral vectors, phage vectors, adenoviral vectors, herpes simplex virus (HSV) vectors, adeno-associated virus (AAV) vectors, or lentiviral vectors.

45. The CRISPR-Cas system or complex according to any one of the preceding embodiments, wherein the AAV vector is selected from the group consisting of recombinant AAV vectors of serotypes AAV1, AAV2, AAV4, AAV5, AAV6, AAV7, AAVrh74, AAV8, AAV9, AAV10, AAV11, AAV12, and AAV13.

46. The CRISPR-Cas system or complex according to any one of the preceding embodiments, wherein the regulatory element comprises a promoter.

47. The CRISPR-Cas system or complex according to any one of the preceding embodiments, wherein the promoter is selected from the group consisting of a constitutive promoter, an inducible promoter, a ubiquitous promoter, a cell type specific promoter, or a tissue specific promoter.

48. The CRISPR-Cas system or complex according to any one of the preceding embodiments, wherein the promoter is functional in eukaryotic cells.

49. The CRISPR-Cas system or complex according to any one of the preceding embodiments, wherein the eukaryotic cells include animal cells, plant cells, fungal cells, vertebrate cells, invertebrate cells, rodent cells, mammalian cells, primate cells, non-human primate cells, and human cells.

50. The CRISPR-Cas system or complex according to any one of the preceding embodiments, further comprising a DNA donor template optionally inserted at a locus of interest by homology-directed repair (HDR).

51. A cell or descendant thereof comprising the Cas12i protein, polynucleotide, vector, delivery system, CRISPR-Cas system or complex according to any one of the preceding embodiments, wherein preferably, the cell is selected from the group consisting of prokaryotic cells, eukaryotic cells, animal cells, plant cells, fungal cells, vertebrate cells, invertebrate cells, rodent cells, mammalian cells, primate cells, non-human primate cells, and human cells.

52. A non-human multicellular organism, comprising the cell or descendant thereof according to any one of the preceding embodiments; preferably, the non-human multicellular organism is an animal (e.g., rodent or non-human primate) model for human gene related diseases.

53. A method of modifying a target DNA, comprising contacting a target DNA with the CRISPR-Cas system or complex according to any one of the preceding embodiments, the contacting resulting in modification of the target DNA by the Cas12i protein.

54. The method according to any one of the preceding embodiments, wherein the modification occurs outside cells in vitro.

55. The method according to any one of the preceding embodiments, wherein the modification occurs inside cells in vitro.

56. The method according to any one of the preceding embodiments, wherein the modification occurs inside cells in vivo.

57. The method according to any one of the preceding embodiments, wherein the cell is a eukaryotic cell.

58. The method according to any one of the preceding embodiments, wherein the eukaryotic cell is selected from the group consisting of animal cells, plant cells, fungal cells, vertebrate cells, invertebrate cells, rodent cells, mammalian cells, primate cells, non-human primate cells, and human cells.

59. The method according to any one of the preceding embodiments, wherein the modification is cleavage of the target DNA.

Optionally, the cleavage is performed in a manner of cleaving a single-stranded DNA, or optionally, in a manner of sequentially cleaving the same site or different sites of a double-stranded DNA.

60. The method according to any one of the preceding embodiments, wherein the cleavage results in deletion of a nucleotide sequence and/or insertion of a nucleotide sequence.

61. The method according to any one of the preceding embodiments, wherein the cleavage comprises cleaving the target nucleic acid at two sites resulting in deletion or inversion of a sequence between the two sites.

62. The method according to any one of the preceding embodiments, wherein the modification is a base variation, preferably A→G or C→T base variation.

63. A cell or descendant thereof from the method according to any one of the preceding embodiments, comprising the modification absent in a cell not subjected to the method.

64. The cell or descendant thereof according to any one of the preceding embodiments, wherein a cell not subjected to the method comprises abnormalities and the abnormalities in the cell from the method have been resolved or corrected.

65. A cell product from the cell or descendant thereof according to any one of the preceding embodiments, wherein the product is modified relative to the nature or quantity of a cell product from a cell not subjected to the method.

66. The cell product according to any one of the preceding embodiments, wherein cells not subjected to the method comprise abnormalities and the cell product reflects that the abnormalities have been resolved or corrected by the method.

67. A method of non-specifically cleaving a non-target DNA, comprising contacting the target DNA with the CRISPR-Cas system or complex according to any one of the preceding embodiments, whereby hybridization of the spacer to the target sequence of the target DNA and cleavage of the target sequence by the Cas12i protein make the Cas12i protein cleave the non-target DNA by spacer non-specific endonuclease collateral activity.

68. A method of detecting a target DNA in a sample, comprising:

(1) contacting the sample with the CRISPR-Cas system or complex according to any one of the preceding embodiments and a reporter nucleic acid capable of releasing a detectable signal after being cleaved, whereby hybridization of the spacer to the target sequence of the target DNA and cleavage of the target sequence by the Cas12i protein make the Cas12i protein cleave the reporter nucleic acid by spacer non-specific endonuclease collateral activity; and (2) measuring a detectable signal generated by cleavage of the reporter nucleic acid, thereby detecting the presence of the target DNA in the sample.

69. The method according to any one of the preceding embodiments, further comprising comparing the level of the detectable signal to the level of a reference signal and determining the level of the target DNA in the sample based on the level of the detectable signal.

70. The method according to any one of the preceding embodiments, wherein the measurement is performed using gold nanoparticle detection, fluorescence polarization, colloidal phase change/dispersion, electrochemical detection, or semiconductor-based sensing.

71. The method according to any one of the preceding embodiments, wherein the reporter nucleic acid comprises a fluorescence emission dye pair, a fluorescence resonance energy transfer (FRET) pair, or a quencher/fluorophore pair, and cleavage of the reporter nucleic acid by the Cas12i protein results in an increase or decrease in the level of the detectable signal produced by cleavage of the reporter nucleic acid.

72. A method of treating a condition or disease in a subject in need thereof, comprising administering to the subject the CRISPR-Cas system according to any one of the preceding embodiments.

73. The method according to any one of the preceding embodiments, wherein the condition or disease is a cancer or infectious disease or neurological disease, optionally, the cancer is selected from the group consisting of:

Wilms' tumor, Ewing's sarcoma, neuroendocrine tumor, glioblastoma, neuroblastoma, melanoma, skin cancer, breast cancer, colon cancer, rectal cancer, prostate cancer, liver cancer, kidney cancer, pancreatic cancer, lung cancer, biliary cancer, cervical cancer, endometrial cancer, esophageal cancer, gastric cancer, head and neck cancer, thyroid myeloid cancer, ovarian cancer, glioma, lymphoma, leukemia, myeloma, acute lymphocytic leukemia, acute myeloid leukemia, chronic lymphocytic leukemia, chronic myelocytic leukemia, Hodgkin's lymphoma, non-Hodgkin's lymphoma and urinary bladder cancer;

optionally, the infectious disease is caused by:

human immunodeficiency virus (HIV), herpes simplex virus-1 (HSV1) and herpes simplex virus-2 (HSV2);

optionally, the neurological disorder is selected from the group consisting of:

glaucoma, age-related loss of RGC, optic nerve injury, retinal ischemia, Leber's hereditary optic neuropathy, neurological diseases associated with RGC neuronal degeneration, neurological diseases associated with functional neuronal degeneration in the striatum of subjects in need, Parkinson's disease, Alzheimer's disease, Huntington's disease, schizophrenia, depression, drug addiction, dyskinesia such as chorea, choreoathetosis and dyskinesia, bipolar affective disorder, autism spectrum disorder (ASD) or dysfunction.

74. The method according to any one of the preceding embodiments, wherein the condition or disease is selected from the group consisting of cystic fibrosis, progressive pseudohypertrophic muscular dystrophy, Becker muscular dystrophy, alpha-1-antitrypsin deficiency, Pompe disease, myotonic dystrophy, Huntington's disease, fragile X syndrome, Friedreich ataxia, amyotrophic lateral sclerosis, frontotemporal dementia, hereditary chronic kidney disease, hyperlipidemia, hypercholesterolemia, Leber congenital amaurosis, sickle cell disease, and beta thalassemia.

75. The method according to any one of the preceding embodiments, wherein the condition or disease is caused by the presence of a pathogenic point mutation.

76. A kit comprising the CRISPR-Cas system according to any one of the preceding embodiments; preferably the components of the system are in the same container or in separate containers.

77. A sterile container comprising the CRISPR-Cas system according to any one of the preceding embodiments; preferably the sterile container is a syringe.

78. An implantable device comprising the CRISPR-Cas system according to any one of the preceding embodiments; preferably the CRISPR-Cas system is stored in a reservoir.

Collateral Activity

The Cas12i protein may have collateral activity, that is, under certain conditions, the activated Cas12i protein remains active after binding to the target sequence and continues to non-specifically cleave non-target oligonucleotides. This collateral activity enables detection of the presence of specific target oligonucleotides using the Cas12i system. In one embodiment, the Cas12i system is engineered to non-specifically cleave ssDNA or transcript. In certain embodiments, Cas12i is transiently or stably provided or expressed in an in vitro system or cell and is targeted or triggered to non-specifically cleave cellular nucleic acids, such as ssDNA, such as viral ssDNA. In some embodiments, the Cas12i protein described herein is modified to reduce (e.g., reduce at least about any of 10%, 20%, 30%, 40%, 50%, 60%, 70%, 80%, 90%, 95%, or higher) or eliminate spacer non-specific endonuclease cleavage activity. In some embodiments, the Cas12i protein described herein substantially lacks (e.g., lacks at lease about any of 50%, 60%, 70%, 80%, 90%, 95%, or 100%) spacer non-specific endonuclease collateral activity of the parental/reference Cas12i protein (e.g., Cas12i protein of any of SEQ ID NOs: 1-10) against a non-target DNA.

The collateral activity has recently been used in a highly sensitive and specific nucleic acid detection platform known as SHERLOCK which can be used in many clinical diagnostics (Gootenberg, J. S. et al., Nucleic acid detection with CRISPR-Cas13a/C2c2. Science 356, 438-442 (2017)).

Reporter Nucleic Acid

A "reporter nucleic acid" refers to a molecule that can be cleaved or otherwise deactivated by the activated CRISPR system protein as described herein. The reporter nucleic acid comprises a nucleic acid element cleavable by the CRISPR protein. Cleavage of the nucleic acid element releases an agent or produces a conformational change allowing for the generation of a detectable signal. The reporter nucleic acid prevents the generation or detection of a positive detectable signal prior to cleavage or when the reporter nucleic acid is in an "active" state. It will be appreciated that in certain exemplary embodiments, minimal background signals may be generated in the presence of the active reporter nucleic acid. The positive detectable signal may be any signal that may be detected using optical, fluorescent, chemiluminescent, electrochemical or other detection methods known in the art. For example, in certain embodiments, a first signal (i.e., a negative detectable signal) may be detected when a reporter nucleic acid is present, and then it is converted to a second signal (e.g., a positive detectable signal) when the target molecule is detected and the reporter nucleic acid is cleaved or deactivated by the activated CRISPR protein.

Functional Domains

Functional domains are used in their broadest sense and include proteins such as enzymes or factors themselves or specific functional fragments (domains) thereof.

A Cas12i protein (e.g., dCas12i) is associated with one or more functional domains selected from the group consisting of a deaminase (e.g., adenosine deaminase or cytidine deaminase) catalytic domain, a DNA methylation catalytic domain, a DNA demethylation catalytic domain, a histone residue modification domain, a nuclease catalytic domain, a fluorescent protein, a transcription modification factor (e.g., a transcription activation catalytic domain, a transcription inhibition catalytic domain), a nuclear localization signal (NLS), nuclear export signal (NES), a light gating factor, a chemical inducible factor, or a chromatin visualization factor; preferably, the functional domain is selected from the group consisting of an adenosine deaminase catalytic domain or cytidine deaminase catalytic domain.

In some embodiments, the functional domain may be a transcription activation domain. In some embodiments, the functional domain is a transcription repression domain. In some embodiments, the functional domain is an epigenetic modification domain such that an epigenetic modification enzyme is provided. In some embodiments, the functional domain is an activation domain. In some embodiments, the Cas12i protein is associated with one or more functional domains; and the Cas12i protein contains one or more mutations within the RuvC domain, and the resulting CRISPR complex can deliver epigenetic modifiers, or transcript or translate activation or repression signals.

In some embodiments, the functional domain exhibits activity to modify a target DNA or proteins associated with the target DNA, wherein the activity is one or more selected from the group consisting of nuclease activity (e.g., HNH nuclease, RuvC nuclease, Trex1 nuclease, Trex2 nuclease), methylation activity, demethylation activity, DNA repair activity, DNA damage activity, deamination activity, dismutase activity, alkylation activity, depurination activity, oxidation activity, pyrimidine dimer formation activity, integrase activity, transposase activity, recombinase activity, polymerase activity, ligase activity, helicase activity, photolyase activity, glycosylase activity, acetyl transferase activity, deacetylase activity, kinase activity, phosphatase activity, ubiquitin ligase activity, deubiquitination activity, adenylation activity, deadenylation activity, SUMOylation activity, deSUMOylation activity, ribosylation activity, deribosylation activity, myristoylation activity, demyristoylation activity, glycosylation activity (e.g., from O-GlcNAc transferase), deglycosylation activity, transcription inhibition activity, and transcription activation activity. Target DNA associated proteins include, but not limited to, proteins that can bind to target DNA, or proteins that can bind to proteins bound to target DNA, such as histones, transcription factors, Mediator, etc.

The functional domain may be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., photo-inducible). When more than one functional domain is included, the functional domains may be the same or different.

Base Editing

In certain exemplary embodiments, Cas12i (e.g., dCas12i) may be fused to adenosine deaminase or cytidine deaminase for base editing purposes.

Adenosine Deaminase

As used herein, the term "adenosine deaminase" or "adenosine deaminase protein" refers to a protein, polypeptide, or one or more functional domains of a protein or polypeptide that can catalyze hydrolytic deamination reaction to convert adenine (or the adenine portion of a molecule) to hypoxanthine (or the hypoxanthine portion of a molecule), as shown below. In some embodiments, the adenine-containing molecule is adenosine (A) and the hypoxanthine-containing molecule is inosine (I). The adenine-containing molecule may be deoxyribonucleic acid (DNA) or ribonucleic acid (RNA).

According to the present disclosure, adenosine deaminases that can be used in combination with the present disclosure include, but are not limited to, enzyme family members referred to as adenosine deaminase acting on RNA (ADAR), enzyme family members referred to as adenosine deaminase acting on tRNA (ADAT), and other family members comprising adenosine deaminase domain (ADAD). According to the present disclosure, the adenosine deaminase is capable of targeting adenine in RNA/DNA and RNA duplexes. In fact, Zheng et al. (Nucleic Acids Res. 2017, 45 (6): 3369-3377) demonstrated that ADAR can edit adenosine to inosine in RNA/DNA and RNA/RNA duplexes. In specific embodiments, adenosine deaminase has been modified to increase its ability to edit DNA in the RNA/DNA heteroduplex of the RNA duplex, as described in detail below.

In some embodiments, the adenosine deaminase is derived from one or more metazoan species, including but not limited to mammals, birds, frogs, squid, fish, flies, and worms. In some embodiments, the adenosine deaminase is human, squid, or *drosophila* adenosine deaminase.

In some embodiments, the adenosine deaminase is human ADAR, including hADAR1, hADAR2, and hADAR3. In some embodiments, the adenosine deaminase is *Caenorhabditis elegans* ADAR protein, including ADR-1 and ADR-2. In some embodiments, the adenosine deaminase is *drosophila* ADAR protein, including dAdar. In some embodiments, the adenosine deaminase is squid (*Loligo pealeii*) ADAR protein, including sqADAR2a and sqADAR2b. In some embodiments, adenosine deaminase is human ADAT protein. In some embodiments, the adenosine deaminase is *drosophila* ADAT protein. In some embodiments, the adenosine deaminase is human ADAD protein, including TENR (hADAD1) and TENRL (hADAD2).

In some embodiments, the adenosine deaminase is TadA protein, such as *E. coli* TadA. See Kim et al., Biochemistry 45: 6407-6416 (2006); Wolf et al., EMBO J. 21: 3841-3851 (2002). In some embodiments, the adenosine deaminase is mouse ADA. See Grunebaum et al., Curr. Opin. Allergy Clin. Immunol. 13: 630-638 (2013). In some embodiments, the adenosine deaminase is human ADAT2. See Fukui et al., J. Nucleic Acids 2010: 260512 (2010). In some embodiments, the deaminase (e.g., adenosine or cytidine deaminase) is one or more of those described in: Cox et al., Science. Nov. 24, 2017; 358(6366): 1019-1027; Komore et al., Nature. May 19, 2016; 533 (7603): 420-4; and Gaudelli et al., Nature. Nov. 23, 2017; 551 (7681): 464-471.

In some embodiments, the adenosine deaminase protein recognizes one or more target adenosine residues in a double-stranded nucleic acid substrate and converts them to inosine residues. In some embodiments, the double-stranded nucleic acid substrate is an RNA-DNA heteroduplex. In some embodiments, the adenosine deaminase protein recognizes a binding window on a double-stranded substrate. In some embodiments, the binding window comprises at least one target adenosine residue. In some embodiments, the binding window is in the range of about 3 bp to about 100 bp. In some embodiments, the binding window is in the range of about 5 bp to about 50 bp. In some embodiments, the binding window is in the range of about 10 bp to about 30 bp. In some embodiments, the binding window is about 1 bp, 2 bp, 3 bp, 5 bp, 7 bp, 10 bp, 15 bp, 20 bp, 25 bp, 30 bp, 40 bp, 45 bp, 50 bp, 55 bp, 60 bp, 65 bp, 70 bp, 75 bp, 80 bp, 85 bp, 90 bp, 95 by or 100 bp.

In some embodiments, the adenosine deaminase protein comprises one or more deaminase domains. Without wishing to be bound by a particular theory, it is contemplated that the deaminase domain is used to recognize one or more target adenosine (A) residues contained in a double-stranded nucleic acid substrate and convert them to inosine (I) residues. In some embodiments, the deaminase domain comprises an active center. In some embodiments, the active center comprises zinc ions. In some embodiments, during A-I editing, the base pair at the target adenosine residue is destroyed and the target adenosine residue is "flipped" out of the double helix to become accessible by the adenosine deaminase. In some embodiments, amino acid residues in or near the active center interact with one or more nucleotides 5' of the target adenosine residue. In some embodiments, amino acid residues in or near the active center interact with one or more nucleotides 3' of the target adenosine residue. In some embodiments, amino acid residues in or near the active center further interact with nucleotides complementary to the target adenosine residues on the opposite chain. In some embodiments, the amino acid residue forms a hydrogen bond with the 2' hydroxyl group of the nucleotide.

In some embodiments, the adenosine deaminase comprises human ADAR2 whole protein (hADAR2) or deaminase domain (hADAR2-D) thereof. In some embodiments, the adenosine deaminase is a member of the ADAR family homologous to hADAR2 or hADAR2-D.

In particular, in some embodiments, the homologous ADAR protein is human ADAR1 (hADAR1) or deaminase domain (hADAR1-D) thereof. In some embodiments, glycine 1007 of hADAR1-D corresponds to glycine 487hADAR2-D, and glutamic acid 1008 of hADAR1-D corresponds to glutamic acid 488 of hADAR2-D.

In some embodiments, the adenosine deaminase comprises the wild-type amino acid sequence of hADAR2-D. In some embodiments, the adenosine deaminase comprises one or more mutations in the hADAR2-D sequence such that the editing efficiency and/or substrate editing preference of hADAR2-D are changed as desired.

In some embodiments, the adenosine deaminase is TadA8e, such as TadA8e comprising the sequence of SEQ ID NO: 182. In some embodiments, the Cas12i protein described herein (e.g., dCas12i) is fused to TadA8e or functional fragment thereof (i.e., capable of A-to-I single base editing).

Cytidine Deaminase

In some embodiments, the deaminase is cytidine deaminase. As used herein, the term "cytidine deaminase" or "cytidine deaminase protein" refers to a protein, polypeptide, or one or more functional domains of a protein or polypeptide that can catalyze hydrolytic deamination reaction to convert cytosine (or the cytosine portion of a molecule) to uracil (or the uracil portion of a molecule), as shown below. In some embodiments, the cytosine-containing molecule is cytidine (C) and the uracil-containing molecule is uridine (U). The cytosine-containing molecule may be deoxyribonucleic acid (DNA) or ribonucleic acid (RNA).

According to the present disclosure, cytidine deaminases that can be used in combination with the present disclosure include, but are not limited to, members of an enzyme family known as apolipoprotein B mRNA editing complex (APOBEC) family deaminases, activation-induced deaminase (AID), or cytidine deaminase 1 (CDA1), and in specific embodiments, the deaminase in APOBEC1 deaminases, APOBEC2 deaminases, APOBEC3A deaminases, APOBEC3B deaminases, APOBEC3C deaminases and APOBEC3D deaminases, APOBEC3E deaminases, APOBEC3F deaminases, APOBEC3G deaminases, APOBEC3H deaminases or APOBEC4 deaminases.

In the methods and systems of the invention, the cytidine deaminase is capable of targeting cytosines in a DNA single strand. In certain exemplary embodiments, the cytidine deaminase can edit on a single strand present outside of the binding component, e.g., bind to Cas13. In other exemplary embodiments, the cytidine deaminase may edit at localized bubbles, such as those formed at target editing sites but with guide sequence mismatching. In certain exemplary embodiments, the cytidine deaminase may comprise mutations that contribute to focus activity, such as those described in Kim et al., Nature Biotechnology (2017) 35 (4): 371-377 (doi: 10.1038/nbt.3803).

In some embodiments, the cytidine deaminase is derived from one or more metazoan species, including but not limited to mammals, birds, frogs, squid, fish, flies, and worms. In some embodiments, the cytidine deaminase is human, primate, bovine, canine, rat, or mouse cytidine deaminase.

In some embodiments, the cytidine deaminase is human APOBEC, including hAPOBEC1 or hAPOBEC3. In some embodiments, the cytidine deaminase is human AID.

In some embodiments, the cytidine deaminase protein recognizes one or more target cytosine residues in a single-stranded bubble of a RNA duplex and converts them to uracil residues. In some embodiments, the cytidine deaminase protein recognizes a binding window on a single-stranded bubble of an RNA duplex. In some embodiments, the binding window comprises at least one target cytosine residue. In some embodiments, the binding window is in the range of about 3 bp to about 100 bp. In some embodiments, the binding window is in the range of about 5 bp to about 50 bp. In some embodiments, the binding window is in the range of about 10 bp to about 30 bp. In some embodiments, the binding window is about 1 bp, 2 bp, 3 bp, 5 bp, 7 bp, 10 bp, 15 bp, 20 bp, 25 bp, 30 bp, 40 bp, 45 bp, 50 bp, 55 bp, 60 bp, 65 bp, 70 bp, 75 bp, 80 bp, 85 bp, 90 bp, 95 by or 100 bp.

In some embodiments, the cytidine deaminase protein comprises one or more deaminase domains. Without wishing to be bound by theory, it is contemplated that deaminase domains are used to recognize one or more target cytosine (C) residues contained in a single-stranded bubble of a RNA duplex and convert them to uracil (U) residues. In some embodiments, the deaminase domain comprises an active center. In some embodiments, the active center comprises zinc ions. In some embodiments, amino acid residues in or near the active center interact with one or more nucleotides at 5' of the target cytosine residue. In some embodiments, amino acid residues in or near the active center interact with one or more nucleotides at 3' of the target cytosine residue.

In some embodiments, the cytidine deaminase comprises human APOBEC1 whole protein (hAPOBEC1) or its deaminase domain (hAPOBEC1-D) or its C-terminal truncated form (hAPOBEC-T). In some embodiments, the cytidine deaminase is a member of the APOBEC family homologous to hAPOBEC1, hAPOBEC-D, or hAPOBEC-T. In some embodiments, the cytidine deaminase comprises human AID1 whole protein (hAID) or its deaminase domain (hAID-D) or its C-terminal truncated form (hAID-T). In some embodiments, the cytidine deaminase is a member of the AID family homologous to hAID, hAID-D, or hAID-T. In some embodiments, hAID-T is hAID with the C-terminus truncated by about 20 amino acids.

In some embodiments, the cytidine deaminase comprises the wild-type amino acid sequence of cytosine deaminase. In some embodiments, the cytidine deaminase comprises one or more mutations in the cytosine deaminase sequence such that the editing efficiency and/or substrate editing preference of the cytosine deaminase are changed as desired.

As used herein, "associated" is used in its broadest sense and encompasses both the case where two functional modules form a fusion protein directly or indirectly (via a linker)

and the case where two functional modules are each independently bonded together by covalent bonds (e.g., disulfide bond) or non-covalent bonds.

The term "vector" refers to a nucleic acid molecule capable of transporting another nucleic acid attached thereto. It is a replicon, such as a plasmid, phage, or cosmid, into which another DNA segment can be inserted to effect replication of the inserted segment. Typically, the vector is capable of replication when combined with suitable control elements.

In some cases, the vector system comprises a single vector. Alternatively, the vector system comprises a plurality of vectors. The vector may be a viral vector.

The vector includes, but are not limited to, a single-stranded, double-stranded or partially double-stranded nucleic acid molecule; a nucleic acid molecule comprising one or more free ends, or without a free end (e. g., circular); a nucleic acid molecule comprising DNA, RNA or both; and other polynucleotide variants known in the art. One type of vector is "plasmid", which refers to a circular double-stranded DNA ring into which other DNA segments can be inserted, for example by standard molecular cloning techniques. Another type of vector is viral vector in which a viral-derived DNA or RNA sequence is present for packaging into a virus (e.g., retrovirus, replication-defective retrovirus, adenovirus, replication-defective adenovirus, and adeno-associated virus). The viral vector also comprises a polynucleotide carried by the virus for transfection into a host cell. Certain vectors are capable of autonomous replication in the host cells into which they are introduced (e.g., bacterial vectors having origins of bacterial replication and episomal mammalian vectors). After these vectors are introduced into the host cells, other vectors (e.g., non-episomal mammalian vectors) are integrated into the genomes of the host cells for replication with the host genomes. In addition, certain vectors are capable of guiding expression of genes operably linked thereto. Such vectors are referred to herein as "expression vectors". Vectors expressed in eukaryotic cells and vectors resulting in expression in eukaryotic cells may be referred to herein as "eukaryotic expression vectors". Common expression vectors useful in recombinant DNA techniques are usually in the forms of plasmids.

The recombinant expression vector may comprise the nucleic acid of the invention in a form suitable for expression in a host cell, which means that the recombinant expression vector comprises one or more regulatory elements that can be selected according to the host cell to be used for expression, and the nucleic acid is operably linked to a nucleic acid sequence to be expressed. Within recombinant expression vectors, "operably linked" is intended to mean that the nucleotide sequence of interest is linked to a regulatory element in a manner that allows expression of the nucleotide sequence (e.g., in an in vitro transcription/translation system or in a host cell when the vector is introduced into the host cell). Advantageous vectors include lentiviruses and adeno-associated viruses, and the type of these vectors may also be selected to target specific types of cells.

The term "regulatory element" is intended to include promoters, enhancers, internal ribosome entry sites (IRES), and other expression control elements (e.g., transcription termination signals such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif.(1990) (1990). Regulatory elements include those that guide constitutive expression of nucleotide sequences in many types of host cells and those that guide expression of nucleotide sequences only in certain host cells (e.g., tissue-specific regulatory sequences). Tissue-specific promoters may guide expression primarily in desired target tissues such as muscle, neuron, bone, skin, blood, particular organs (e. g., liver, pancreas) or particular cell types (e.g., lymphocytes). Regulatory elements may also guide expression in a time-dependent manner, e.g., in a cell cycle dependent or developmental stage dependent manner, which may or may not be tissue or cell type specific.

In some embodiments, the vector encodes a Cas12i protein comprising one or more nuclear localization sequences (NLSs), e.g., about or greater than about 1, 2, 3, 4, 5, 6, 7, 8, 9, 10 or more NLSs. More specifically, the vector comprises one or more NLSs that are not naturally occurring in the Cas12i protein. Most particularly, the NLS is present in 5' and/or 3' of the vector for the Cas12i protein sequence. In some embodiments, the protein targeting RNA comprises about or greater than about 1, 2, 3, 4, 5, 6, 7, 8, 9, 10 or more NLSs at or near the amino terminus and about or greater than about 1, 2, 3, 4, 5, 6, 7, 8, 9, 10 or more NLSs at or near the carboxyl terminus, or a combination of these (e.g., 0 or at least one or more NLSs at the amino terminus and 0 or one or more NLSs at the carboxyl terminus). When more than one NLSs are present, each of them may be selected independently of the others such that a single NLS may be present in more than one copies and/or in combination with one or more other NLSs in one or more copies. In some embodiments, NLS is considered to be near the N-terminus or C-terminus when its nearest amino acid is within about 1, 2, 3, 4, 5, 10, 15, 20, 25, 30, 40, 50, or more amino acids along the polypeptide chain from the N-terminus or C-terminus.

"Codon optimization" refers to a method of modifying a nucleic acid sequence in a target host cell to enhance expression by replacing at least one codon (e.g., about or greater than about 1, 2, 3, 4, 5, 10, 15, 20, 25, 50, or more codons) of a natural sequence with a codon that is more frequently or most frequently used in the gene of the host cell while maintaining the natural amino acid sequence. A variety of species show particular bias towards certain codons for particular amino acids. Codon bias (the difference in codon usage among organisms) is generally related to the translation efficiency of messenger RNA (mRNA), which in turn is thought to depend, inter alia, on the characteristics of the translated codons and the availability of specific transfer RNA (tRNA) molecules. The dominance of the selected tRNA in the cell generally reflects the codons most commonly used in peptide synthesis. Thus, genes can be tailored to optimize gene expression in a given organism based on codon optimization. Codon usage tables are readily available, for example, in the "codon usage database" in kazusa.or.jp/codon, and may be modified in a number of ways. See Nakamura, Y., et al. "Codon usage tabulated from the international DNA Sequence databases: status for the year 2000" Nucl. Acids Res. 28: 292 (2000). Computerized algorithms for codon optimization of specific sequences for expression in specific host cells are also available, such as Gene Forge (Aptagen; Jacobus, Pa.). In some embodiments, one or more codons (e.g., 1, 2, 3, 4, 5, 10, 15, 20, 25, 50 or more or all codons) in a sequence encoding the Cas protein targeting DNA/RNA correspond to the codons most commonly used for particular amino acids. For codon usage in yeast, reference can be made to the online *saccharomyces* genome database available from yeastgenome.org/community/codon_usage, or Codon selection in yeast, Bennetzen and Hall, J Biol Chem. Mar. 25, 1982; 257(6): 3026-31. For codon usage in plants including algae, see Codon usage in higher plants, green algae, and cyanobacteria, Campbell and Gowri, Plant Physiol., January 1990; 92(1): 1-11; and Codon usage in plant genes, Murray et al., Nucleic Acids Res. Jan. 25, 1989; 17(2): 477-98; or Selection on the codon bias of chloroplast and cyanelle genes in different plant and algal lineages, Morton BR, J Mol Evol. April 1998; 46(4): 449-59.

Delivery System

In some embodiments, the components of the CRISPR-Cas system may be delivered in various forms, such as a combination of DNA/RNA or RNA/RNA or protein RNA. For example, the Cas12i protein may be delivered as a polynucleotide encoding DNA or a polynucleotide encoding RNA or as a protein. The guide may be delivered as a polynucleotide encoding DNA or RNA. All possible combinations are contemplated, including mixed delivery forms.

In some aspects, the invention provides a method for delivering one or more polynucleotides, such as one or more vectors, one or more transcripts thereof, and/or one or more proteins transcribed therefrom as described herein, to host cells.

In some embodiments, one or more vectors that drive expression of one or more elements of the nucleic acid targeting system are introduced into host cells such that expression of elements of the nucleic acid targeting system guides formation of the nucleic acid targeting complex at one or more target sites. For example, the nucleic acid encoding effector enzymes and the nucleic acid encoding guide RNAs may each be operably linked to separate regulatory elements on separate vectors. The RNA of the nucleic acid targeting system can be delivered to a transgenic nucleic acid targeting effector protein animal or mammal, e.g., an animal or mammal that constitutively or inductively or conditionally expresses the nucleic acid targeting effector protein; or an animal or mammal that otherwise expresses the nucleic acid targeting effector protein or has cells containing the nucleic acid targeting effector protein, for example, by administering thereto one or more vectors encoding and expressing the in vivo nucleic acid targeting effector protein in advance. Alternatively, two or more elements regulated by the same or different regulatory elements may be combined in a single vector, while one or more additional vectors provide any components of the nucleic acid targeting system not contained in the first vector. The elements of the nucleic acid targeting system combined in the single vector may be arranged in any suitable orientation, for example, one element is positioned 5' ("upstream") relative to the second element or 3' ("downstream") relative to the second element. The coding sequence of one element may be on the same or opposite chain of the coding sequence of the second element and oriented in the same or opposite direction. In some embodiments, a single promoter drives the expression of transcripts encoding the nucleic acid targeting effector protein and the nucleic acid targeting guide RNA, and the transcripts are embedded into one or more intron sequences (e.g., each in a separate intron, two or more in at least one intron, or all in a single intron). In some embodiments, the nucleic acid targeting effector protein and the nucleic acid targeting guide RNA may be operably linked to the same promoter and expressed from the same promoter. Delivery vehicles, vectors, particles, nanoparticles, formulations and components thereof for expressing one or more elements of the nucleic acid targeting system are as used in the previous documents such as WO 2014/093622 (PCT/US2013/074667; the content of which is incorporated herein by reference in its entirety). In some embodiments, the vector comprises one or more insertion sites, such as a restriction endonuclease recognition sequence (also referred to as a "cloning site"). In some embodiments, one or more insertion sites (e.g., about or greater than about 1, 2, 3, 4, 5, 6, 7, 8, 9, 10 or more insertion sites) are located upstream and/or downstream of one or more sequence elements of one or more vectors. When a plurality of different guide sequences are used, a single expression construct may be used to target nucleic acids to various corresponding target sequences within active target cells. For example, a single vector may comprise about or greater than about 1, 2, 3, 4, 5, 6, 7, 8, 9, 10, 15, 20 or more guide sequences. In some embodiments, about or greater than about 1, 2, 3, 4, 5, 6, 7, 8, 9, 10 or more such vectors containing guide sequences may be provided and optionally delivered to the cells. In some embodiments, the vector comprises a regulatory element operably linked to an enzyme coding sequence encoding the nucleic acid targeting effector protein. The nucleic acid targeting effector protein or one or more nucleic acid targeting guide RNAs may be delivered separately; and advantageously at least one of these is delivered via a particle complex. The nucleic acid targeting effector protein mRNA may be delivered prior to the nucleic acid targeting guide RNA to allow time for expression of the nucleic acid targeting effector protein. The nucleic acid targeting effector protein mRNA may be administered 1-12 h (preferably about 2-6 h) prior to administration of the nucleic acid targeting guide RNA. Alternatively, the nucleic acid targeting effector protein mRNA and the nucleic acid targeting guide RNA may be administered together. Advantageously, the second boosted dose of guide RNA may be administered 1-12 h (preferably about 2-6 h) after the initial administration of the nucleic acid targeting effector protein mRNA+guide RNA. The additional administration of the nucleic acid targeting effector protein mRNA and/or guide RNA may be useful to achieve the most effective level of genomic modification.

Conventional viral and non-viral based gene transfer methods can be used to introduce nucleic acids into mammalian cells or target tissues. Such methods can be used to administer nucleic acids encoding the components of a nucleic acid targeting system to cells in culture or in a host organism. A non-viral vector delivery system comprises DNA plasmids, RNA (e.g., transcripts of vectors as described herein), naked nucleic acids, and nucleic acids complexed with a delivery vehicle such as liposome. Viral vector delivery systems comprise DNA and RNA viruses that have episomal or integrated genomes upon delivery to cells. For a review of gene therapy procedures, see Anderson, Science 256: 808-813 (1992); Nabel and Felgner, TIBTECH 11: 211-217 (1993); Mitani and Caskey, TIBTECH 11: 162-166 (1993); Dillon, TIBTECH 11:167-175 (1993); Miller, Nature 357: 455-460 (1992); Van Brunt, Biotechnology 6 (10): 1149-1154 (1988); Vigne, Restorative Neurology and Neuroscience 8: 35-36 (1995); Kremer and Perricaudet, British Medical Bulletin 51 (1): 31-44 (1995); Haddada et al., Current Topics in Microbiology and Immunology, Doerfler and Bohm (eds.) (1995); and Yu et al., Gene Therapy 1:13-26 (1994).

Non-viral delivery methods for nucleic acids include lipid transfection, nuclear transfection, microinjection, biolistics, virosomes, liposomes, immunoliposomes, polycations or lipids: nucleic acid conjugates, naked DNA, artificial virosomes, and reagent-enhanced DNA uptake. Lipid transfection is described, for example, in U.S. Pat. Nos. 5,049,386, 4,946,787; and 4,897,355, and lipid transfection reagents are commercially available (e.g., Transfectam™ and Lipofectin™). Cationic and neutral lipids suitable for effective receptor recognition lipid transfection for polynucleotides include those in Felgner, WO 91/17424; WO 91/16024, which can be delivered to cells (e.g., in vitro or ex vivo administration) or target tissues (e.g., in vivo administration).

Plasmid delivery involves cloning the guide RNA into a plasmid expressing the CRISPR-Cas protein and transfecting DNA in cell culture. The plasmid backbone is commercially available and does not require specific equipment. Advantageously, they are modularized, and can carry CRISPR-Cas coding sequences of different sizes, including sequences encoding larger-sized protein, as well as selection markers. Also, plasmids are advantageous in that they ensure transient but continuous expression. However, the delivery of plasmids is not direct, usually leading to low in vivo efficiency. Continuous expression may also be disadvantageous in that it can increase off-target editing. In addition, excessive accumulation of CRISPR-Cas proteins may be toxic to cells. Finally, plasmids always have the risk of random integration of dsDNA into the host genome, more particularly considering the risk of double-stranded breakage (on-target and off-target).

The preparation of lipid: nucleic acid complexes (including targeting liposomes, such as immunolipid complexes) are well known to those skilled in the art (see, for example, Crystal, Science 270: 404-410 (1995); Blaese et al., Cancer Gene Ther. 2: 291-297 (1995); Behr et al., Bioconjugate Chem. 5: 382-389 (1994); Remy et al., Bioconjugate Chem. 5: 647-654 (1994); Gao et al., Gene Therapy 2: 710-722 (1995); Ahmad et al., Cancer Res. 52: 4817-4820 (1992); U.S. Pat. Nos. 4,186,183, 4,217,344, 4,235,871, 4,261,975, 4,485,054, 4,501,728, 4,774,085, 4,837,028 and 4,946,787), as will be discussed in more detail below.

The use of RNA or DNA virus-based systems to deliver nucleic acids takes advantage of a highly evolved process of targeting viruses to specific cells in vivo and transporting viral payloads to the nuclei. The viral vectors may be administered directly to a patient (in vivo) or they may be used to treat cells in vitro, and the modified cells may optionally be administered to a patient (ex vivo). Conventional virus-based systems may include retrovirus, lentivirus, adenovirus, adeno-associated virus and herpes simplex virus vectors for gene transfer. Integration into the host genome by retroviral, lentiviral and adeno-associated virus gene transfer methods often results in long-term expression of the inserted transgene. In addition, high transduction efficiency has been observed in many different cell types and target tissues.

The tropism of a retrovirus can be altered by incorporation of a foreign envelope protein to expand the potential target population of target cells. Lentiviral vectors are retroviral vectors that can transduce or infect non-dividing cells and generally produce high viral titers. Therefore, the choice of a retroviral gene transfer system will depend on the target tissue. Retroviral vectors consist of cis-acting long terminal repeats with a packaging capacity up to 6-10 kb of foreign sequences. The minimal cis-acting LTR is sufficient to replicate and package the vector, which is then used to integrate therapeutic genes into target cells to provide permanent transgene expression. Widely used retroviral vectors include vectors based on murine leukemia virus (MuLV), gibbon ape leukemia virus (GaLV), simian immunodeficiency virus (SIV), human immunodeficiency virus (HIV), and combinations thereof (see, e.g., Buchscher et al., J. Virol. 66: 2731-2739 (1992); Johann et al., J. Virol. 66: 1635-1640 (1992); Sommnerfelt et al., Virol. 176: 58-59 (1990); Wilson et al., J. Virol. 63: 2374-2378 (1989); Miller et al., J. Virol. 65: 2220-2224 (1991); PCT/US94/05700).

In applications where transient expression is preferred, adenovirus-based systems may be used. Adenovirus-based vectors provide high transduction efficiency in many cell types and do not require cell division. With such vectors, high titers and expression levels have been achieved. The vector can be mass produced in a relatively simple system. Adeno-associated virus ("AAV") vectors can also be used to transduce cells with target nucleic acids, e.g., in the in vitro production of nucleic acids and peptides, as well as in in vivo and ex vivo gene therapy procedures (see, e.g., West et al., Virology 160: 38-47 (1987); U.S. Pat. No. 4,797,368; WO 93/24641; Kotin, Human Gene Therapy 5: 793-801 (1994); Muzyczka, J. Clin. Invest. 94: 1351 (1994)). Construction of recombinant AAV vectors is described in numerous publications, including U.S. Pat. No. 5,173,414; Tratschin et al., Mol. Cell. Biol. 5: 3251-3260 (1985); Tratschin et al., Mol. Cell. Biol. 4: 2072-2081 (1984); Hermonat and Muzyczka, PNAS 81: 6466-6470 (1984); and Samulski et al., J. Virol. 63: 03822-3828 (1989).

The invention provides AAV comprising or consisting essentially of an exogenous nucleic acid molecule encoding a CRISPR system, e.g., a plurality of cassettes comprising or consisting of a first cassette comprising or consisting essentially of a promoter, a nucleic acid molecule encoding a CRISPR associated (Cas) protein (putative nuclease or helicase protein), e.g., Cas12i and a terminator, and one or more, advantageously up to the packaging size limit of the vector, for example five cassettes in total (including the first cassette) comprising or consisting essentially of a promoter, a nucleic acid molecule encoding guide RNA (gRNA) and a terminator (for example, each cassette is schematically represented as promoter-gRNA1-terminator, promoter-gRNA2-terminator . . . promoter-gRNA(N)-terminator, where N is the upper limit of the package size limits of the insertable vectors), or two or more individual rAAVs, wherein each rAAV contains one or more cassettes of the CRISPR system, for example, a first rAAV contains a first cassette comprising or consisting essentially of a promoter, a Cas-encoding nucleic acid molecule such as Cas (Cas12i) and a terminator, and a second rAAV contains one or more cassettes, each cassette comprising or consisting essentially of a promoter, a nucleic acid molecule encoding guide RNA (gRNA) and a terminator (e.g., each cassette is schematically represented as promoter-gRNA1-terminator, promoter-gRNA2-terminator . . . promoter-gRNA(N)-terminator, where N is the upper limit of the package size limits of the insertable vectors). Alternatively, a single crRNA/gRNA array can be used for multiplex gene editing, since Cas12i can process its own crRNA/gRNA. Thus, rather than comprising a plurality of cassettes to deliver gRNA, rAAV can contain a single cassette comprising or consisting essentially of a promoter, a plurality of crRNA/gRNA, and a terminator (e.g., schematically represented as promoter-gRNA1-gRNA2 . . . gRNA(N)-terminator, where N is the upper limit of the package size limits of the insertable vector). See Zetsche et al., Nature Biotechnology 35, 31-34 (2017), which is incorporated herein by reference in its entirety. Since rAAV is a DNA virus, the nucleic acid molecule in the discussion herein with respect to AAV or rAAV is advantageously DNA. In some embodiments, the promoter is advantageously human synaptophysin I promoter (hSyn). Other methods for delivering nucleic acids to cells are known to those skilled in the art. See, for example, US20030087817, which is incorporate herein by reference.

In another embodiment, cocal vesiculovirus enveloped pseudoretrovirus vector particles are considered (see, for example, U.S. Patent Publication No. 20120164118 assigned to Fred Hutchinson Cancer Research Center). Cocal virus belongs to the genus vesiculovirus and is the pathogen of vesicular stomatitis in mammals. The cocal virus was originally isolated from mites in Trinidad (Jonkers et al., Am. J. Vet. Res. 25: 236-242 (1964)), and cocal virus infections have been identified in insects, cattle, and horses in Trinidad, Brazil, and Argentina. Many vesicular viruses that infect mammals have been isolated from naturally infected arthropods, suggesting that they are vector-borne. Antibodies to vesicular viruses are widely available in rural areas where the viruses are obtained locally and in laboratories; their infections in humans usually cause flu-like symptoms. The envelope glycoprotein of cocal virus shares 71.5% identity to VSV-G Indiana at the amino acid level, and phylogenetic comparison of the vesicular virus envelope gene shows that cocal virus is serologically distinct from, but most closely related to, the VSV-G Indiana strain of vesicular virus. Jonkers et al., Am. J. Vet. Res. 25: 236-242 (1964) and Travassos da Rosa et al., AM. J. Tropical Med. & Hygiene 33: 999-1006 (1984). Cocal vesicular virus envelope pseudoretrovirus vector particles may include, for example, lentivirus, alpha retrovirus, beta retrovirus, gamma retrovirus, delta retrovirus and epsilon retrovirus vector particles, which may comprise retrovirus Gag, Pol and/or one or more helper proteins and cocal vesicular virus envelope proteins. In certain aspects of these embodiments, the Gag, Pol and helper proteins are lentiviruses and/or gamma retroviruses.

In some embodiments, host cells are transiently or non-transiently transfected with one or more vectors described herein. In some embodiments, when the cells are naturally present in the subject, the cells are transfected, and optionally reintroduced therein. In some embodiments, the transfected cells are taken from a subject. In some embodiments, the cells are derived from cells from a subject, such as cell lines. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelium, BALB/3T3 mouse embryonic fibroblasts, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cell, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cell, K562 cell, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell line, Peer, PNT-1A/PNT 2, RenCa, RIN-5F, RMA/RMAS, Saos-2 cell, Sf-9, SkBr3, T2, T-47D, T84, THP1 cell line, U373, U87, U937, VCaP, Vero cell, WM39, WT-49, X63, YAC-1, YAR and transgenic varieties thereof. Cell lines may be obtained from a variety of sources known to those skilled in the art (see, for example, the American Type Culture Collection (ATCC) (Manassas, Va.)).

In particular embodiments, the transient expression and/or presence of one or more components of an AD-functionalized CRISPR system may be of interest, for example, to reduce off-target effects. In some embodiments, cells transfected with one or more vectors described herein are used to establish novel cell lines comprising one or more vector derived sequences. In some embodiments, cells transiently transfected (e.g., transiently transfected with one or more vectors, or transfected with RNA) with components of the AD-functionalized CRISPR system as described herein and modified by the activity of the CRISPR complex are used to establish new cell lines comprising cells containing the modifications but lacking any other exogenous sequence. In some embodiments, cells transiently or non-transiently transfected with one or more vectors described herein, or cell lines derived from such cells, are used to evaluate one or more test compounds.

In some embodiments, direct introduction of RNA and/or protein into host cells is contemplated. For example, the CRISPR-Cas protein may be delivered as encoded mRNA along with guide RNA from in vitro transcription. Such methods may reduce and ensure the action time of the CRISPR-Cas protein and further prevent long-term expression of the components of the CRISPR system.

In some embodiments, the RNA molecules of the invention are delivered as liposomes or lipofectin formulations and the like, and may be prepared by methods well known to those skilled in the art. Such methods are described, for example, in U.S. Pat. Nos. 5,593,972, 5,589,466 and 5,580,859, which are incorporated herein by reference in their entirety. Delivery systems specifically designed to enhance and improve the delivery of siRNA into mammalian cells have been developed (see, e.g., Shen et al., FEBS Let. 2003, 539: 111-114; Xia et al., Nat. Biotech. 2002, 20: 1006-1010; Reich et al., Mol. Vision. 2003, 9: 210-216; Sorensen et al., J. Mol. Biol. 2003, 327: 761-766; Lewis et al., Nat. Gen. 2002, 32: 107-108; and Simeoni et al., NAR 2003, 31, 11: 2717-2724) and may be applied to the invention. siRNA have recently been successfully used to inhibit gene expression in primates (see, for example, Tolentino et al., Retina 24 (4): 660), which can also be applied to the invention.

In fact, RNA delivery is a useful method of delivery in vivo. Cas12i, adenosine deaminase, and guide RNA may be delivered to cells using liposomes or particles. Thus, the delivery of CRISPR-Cas proteins (e.g., Cas12i), the delivery of adenosine deaminase (which may be fused to CRISPR-Cas proteins or adaptor proteins) and/or the delivery of RNA of the invention may be in the form of RNA and via microvesicles, liposomes or particles or nanoparticles. For example, Cas12i mRNA, adenosine deaminase mRNA, and guide RNA may be packaged into liposome particles for delivery in vivo. Liposome transfection reagents, such as lipofectamine from Life Technologies and other reagents on the market, can efficiently deliver RNA molecules into the liver. In some embodiments, the lipid nanoparticle (LNP) comprises ALC-0315:Cholesterol:PEG-DMG:DOPE at a molar ratio of 50 mM:50 mM:10 mM:20 mM. In some embodiments, the LNP encapsulates both Cas12i and its corresponding crRNA (e.g., SiCas12i:crRNA with a weight ratio of 1:1), or nucleic acid(s) encoding thereof. In some embodiments, the LNP comprising Cas12i and/or crRNA (or nucleic acid(s) encoding thereof) is administered to an individual (e.g., human) by intravenous infusion.

Delivery of RNA also preferably includes RNA delivery via particles (Cho, S., Goldberg, M., Son, S., Xu, Q., Yang, F., Mei, Y., Bogatyrev, S., Langer, R., and Anderson, D., Lipid-like nanoparticles for small interfering RNA delivery to endothelial cells, Advanced Functional Materials, 19: 3112-3118, 2010) or via exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). In fact, exosomes have been shown to be particularly useful in delivering siRNA, and this system is somewhat similar to the CRISPR system. For example, El-Andaloussi S et al. ("Exosome-mediated delivery of siRNA in vitro and in vivo." Nat Protoc. December 2012; 7 (12): 2112-26. doi: 10.1038/nprot.2012.131. Electronically published on Nov. 15, 2012) describes how exosomes can become promising tools for drug delivery across different biological barriers and for in vitro and in vivo delivery of siRNA. Their method involves generating targeting exosomes by transfecting an expression vector comprising an exosome protein fused to a peptide ligand. The exosome is then purified and characterized from the transfected cell supernatant, and the RNA is loaded into the exosome. Delivery or administration according to the invention may be performed using exosomes, particularly (but not limited to) the brain. Vitamin E (α-tocopherol) can be conjugated with CRISPR Cas and delivered to the brain along with high-density lipoprotein (HDL), for example, in a manner similar to that of Uno et al. (HUMAN GENE THERAPY 22: 711-719 (June 2011)) for delivery of short interfering RNA (siRNA) to the brain. Infusion to mice is performed via an Osmotic micro-pump (Model 1007D; Alzet, Cupertino, Calif.) filled with phosphate buffered saline (PBS) or free TocsiBACE or TocsiBACE/HDL and connected to brain infusion kit 3 (Alzet). A brain infusion cannula is placed approximately 0.5 mm posterior to the anterior fontanel at the midline for infusion into the dorsal side of the third ventricle. Uno et al. found that Toc-siRNA containing HDL as low as 3 nmol could induce the target reduction considerably by the same ICV infusion method. In the invention, for humans, similar doses of CRISPR Cas conjugated to α-tocopherol and co-administered with brain-targeted HDL may be considered, for example, about 3 nmol to about 3 μmol of brain-targeted CRISPR Cas may be considered. Zou et al. (HUMAN GENE THERAPY 22: 465-475 (April 2011)) describes a lentivirus-mediated delivery method of short hairpin RNA targeting PKCγ for in vivo gene silencing in the spinal cords of rats. Zou et al. administered approximately 10 μl of recombinant lentivirus through an intrathecal catheter with a titer of $1\times10^9$ transducing units (TU)/ml. In the invention, for humans, a similar dose of CRISPR Cas expressed in a brain-targeted lentivirus vector may be considered, for example, about 10-50 ml of brain-targeted CRISPR Cas in a lentivirus with a titer of $1\times10^9$ transduced units (TU)/ml may be considered.

Other suitable modifications and variations of the methods of the invention described herein will be apparent to those skilled in the art and may be made using suitable equivalents without departing from the scope of the invention or the embodiments disclosed herein.

EXEMPLARY EMBODIMENTS

Embodiment 1. A Cas12i protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identity to an amino acid sequence as set forth in any one of SEQ ID NOs: 1-10 (preferably, SEQ ID NOs: 1-3 and 6, and more preferably, SEQ ID NO: 1).

Embodiment 2. The Cas12i protein according to any one of the preceding embodiments, wherein the Cas12i protein substantially lacks (e.g., retains less than 50%, 40%, 35%, 30%, 27.5%, 25%, 22.5%, 20%, 17.5%, 15%, 12.5%, 10%, 7.5%, 5%, 4%, 3%, 2.5%, 2%, 1% or less) spacer-specific endonuclease cleavage activity of the corresponding parental Cas12i protein (e.g., Cas12i protein comprising any of SEQ ID NOs: 1-10) for a target sequence of a target DNA complementary to a guide sequence.

Embodiment 3. The Cas12i protein according to any one of the preceding embodiments, wherein the Cas12i protein comprises one or more amino acid variations in its RuvC domain such that the Cas12i protein substantially lacks (e.g., retains less than 50%, 40%, 35%, 30%, 27.5%, 25%, 22.5%, 20%, 17.5%, 15%, 12.5%, 10%, 7.5%, 5%, 4%, 3%, 2.5%, 2%, 1% or less) spacer-specific endonuclease cleavage activity of the corresponding parental Cas12i protein (e.g., Cas12i protein comprising any of SEQ ID NOs: 1-10) for a target sequence of a target DNA complementary to a guide sequence.

Embodiment 4. The Cas12i protein according to any one of the preceding embodiments, wherein the amino acid variation is selected from the group consisting of amino acid additions, insertions, deletions, and substitutions.

Embodiment 5. The Cas12i protein according to any one of the preceding embodiments, wherein the Cas12i protein comprises an amino acid substitution at one or more positions corresponding to positions 700 (D700), 650 (D650), 875 (E875) or 1049 (D1049) of the sequence as set forth in SEQ ID NO: 1.

Embodiment 6. The Cas12i protein according to any one of the preceding embodiments, wherein the amino acid substitution is selected from the group consisting of D700A/V, D650A/V, E875A/V, and D1049A/V.

Embodiment 7. The Cas12i protein according to any one of the preceding embodiments, wherein the amino acid substitution is selected from the group consisting of D700A, D650A, E875A, and D1049A.

Embodiment 8. The Cas12i protein according to any one of the preceding embodiments, wherein the amino acid substitution is selected from the group consisting of D700A, D650A, E875A, D1049A, D700A+D650A, D700A+E875A, D700A+D1049A, D650A+E875A, D650A+D1049A, E875A+D1049A, D700A+D650A+E875A, D700A+D650A+D1049A, D650A+E875A+D1049A, and D700A+D650A+E875A+D1049A.

Embodiment 9. The Cas12i protein according to any one of the preceding embodiments, wherein the Cas12i protein comprises the amino acid sequence as set forth in any one of SEQ ID NOs: 79-82.

Embodiment 10. The Cas12i protein according to any one of the preceding embodiments, wherein the Cas12i protein is linked to one or more functional domains.

Embodiment 11. The Cas12i protein according to any one of the preceding embodiments, wherein the functional domain is linked to the N-terminus and/or C-terminus of the Cas12i protein.

Embodiment 12. The Cas12i protein according to any one of the preceding embodiments, wherein the functional domain is selected from the group consisting of a nuclear localization signal (NLS), a nuclear export signal (NES), a deaminase (e.g., adenosine deaminase or cytidine deaminase) catalytic domain, a DNA methylation catalytic domain, a histone residue modification domain, a nuclease catalytic domain, a fluorescent protein, a transcription modification factor, a light gating factor, a chemical inducible factor, a chromatin visualization factor, a targeting polypeptide for providing binding to a cell surface portion on a target cell or a target cell type.

Embodiment 13. The Cas12i protein according to any one of the preceding embodiments, wherein the functional domain exhibits activity to modify a target DNA, selected from the group consisting of nuclease activity, methylation activity, demethylation activity, DNA repair activity, DNA damage activity, deamination activity, dismutase activity, alkylation activity, depurination activity, oxidation activity, pyrimidine dimer formation activity, integrase activity, transposase activity, recombinase activity, polymerase activity, ligase activity, helicase activity, photolyase activity, glycosylase activity, acetyl transferase activity, deacetylase activity, kinase activity, phosphatase activity, ubiquitin ligase activity, deubiquitination activity, adenylation activity, deadenylation activity, SUMOylation activity, deSUMOylation activity, ribosylation activity, deribosylation activity, myristoylation activity, demyristoylation activity, glycosylation activity (e.g., from O-GlcNAc transferase), deglycosylation activity, transcription inhibition activity, transcription activation activity.

Embodiment 14. The Cas12i protein according to any one of the preceding embodiments, wherein the functional domain is selected from an adenosine deaminase catalytic domain or a cytidine deaminase catalytic domain.

Embodiment 15. The Cas12i protein according to any one of the preceding embodiments, wherein the functional domain is a full length or functional fragment of TadA8e.

Embodiment 16. The Cas12i protein according to any one of the preceding embodiments, wherein the Cas12i protein comprises the amino acid sequence as set forth in SEQ ID NO: 85.

Embodiment 17. The Cas12i protein according to any one of the preceding embodiments, wherein the Cas12i protein is modified to reduce or eliminate spacer non-specific endonuclease collateral activity.

Embodiment 18. A polynucleotide encoding the Cas12i protein according to any one of the preceding embodiments.

Embodiment 19. The polynucleotide according to any one of the preceding embodiments, wherein the polynucleotide is codon optimized for expression in eukaryotic cells.

Embodiment 20. The polynucleotide according to any one of the preceding embodiments, comprising a nucleotide sequence having at least 80%, 81%, 82%, 83%, 84%, 85%, 86%, 87%, 88%, 89%, 90%, 91%, 92%, 93%, 94%, 95%, 96%, 97%, 98%, 99%, 99%, 99.5% or 100% identity to any one of the nucleotide sequences as set forth in SEQ ID NOs: 11-20 and SEQ ID NOs: 37-46.

Embodiment 21. A vector comprising the polynucleotide according to any one of the preceding embodiments.

Embodiment 22. The vector according to any one of the preceding embodiments, wherein the polynucleotide is operably linked to a promoter.

Embodiment 23. The vector according to any one of the preceding embodiments, wherein the promoter is a constitutive promoter, an inducible promoter, a ubiquitous promoter, a cell type specific promoter, or a tissue specific promoter.

Embodiment 24. The vector according to any one of the preceding embodiments, wherein the vector is a plasmid.

Embodiment 25. The vector according to any one of the preceding embodiments, wherein the vector is a retroviral vector, a phage vector, an adenovirus vector, a herpes simplex virus (HSV) vector, an adeno-associated virus (AAV) vector, or a lentiviral vector.

Embodiment 26. The vector according to any one of the preceding embodiments, wherein the AAV vector is selected from the group consisting of recombinant AAV vectors of serotypes AAV1, AAV2, AAV4, AAV5, AAV6, AAV7, AAVrh74, AAV8, AAV9, AAV10, AAV11, AAV12, and AAV13.

Embodiment 27. A delivery system comprising (1) a delivery medium; and (2) the Cas12i protein, polynucleotide or vector according to any one of the preceding embodiments.

Embodiment 28. The delivery system according to any one of the preceding embodiments, wherein the delivery medium is nanoparticle, liposome, exosome, microvesicle, or gene gun.

Embodiment 29. An engineered, non-naturally occurring CRISPR-Cas system comprising:

(1) the Cas12i protein or a polynucleotide encoding the Cas12i protein according to any one of the preceding embodiments; and (2) a CRISPR RNA (crRNA) or a polynucleotide encoding the crRNA, the crRNA comprising:

(i) a spacer capable of hybridizing to a target sequence of a target DNA, and (ii) a Direct Repeat (DR) linked to the spacer and capable of guiding the Cas12i protein to bind to the crRNA to form a CRISPR-Cas complex targeting the target sequence.

Embodiment 30. A CRISPR-Cas system comprising one or more vectors, wherein the one or more vectors comprise:

(1) a first regulatory element operably linked to a nucleotide sequence encoding the Cas12i protein according to any one of the preceding embodiments; and (2) a second regulatory element operably linked to a polynucleotide encoding a CRISPR RNA (crRNA), the crRNA comprising:

(i) a spacer capable of hybridizing to a target sequence of a target DNA, and (ii) a Direct Repeat (DR) linked to the spacer and capable of guiding the Cas12i protein to bind to the crRNA to form a CRISPR-Cas complex targeting the target sequence;

wherein the first regulatory element and the second regulatory element are located on the same or different vectors of the CRISPR-Cas vector system.

Embodiment 31. An engineered, non-naturally occurring CRISPR-Cas complex comprising:

(1) the Cas12i protein according to any one of the preceding embodiments; and (2) a CRISPR RNA (crRNA), the crRNA comprising:

(i) a spacer capable of hybridizing to a target sequence of a target DNA, and (ii) a Direct Repeat (DR) linked to the spacer; the DR guides the Cas12i protein to bind to the crRNA.

Embodiment 32. The CRISPR-Cas system or complex according to any one of the preceding embodiments, wherein the spacer is greater than 16 nucleotides in length, preferably 16 to 100 nucleotides, more preferably 16 to 50 nucleotides, more preferably 16 to 27 nucleotides, more preferably 17 to 24 nucleotides, more preferably 18 to 24 nucleotides, and most preferably 18 to 22 nucleotides.

Embodiment 33. The CRISPR-Cas system or complex according to any one of the preceding embodiments, wherein the DR has a secondary structure substantially identical to the secondary structure of the DR as set forth in any one of SEQ ID NOs: 21-30.

Embodiment 34. The CRISPR-Cas system or complex according to any one of the preceding embodiments, wherein the DR has nucleotide additions, insertions, deletions or substitutions without causing substantial differences in the secondary structure as compared to the DR as set forth in any one of SEQ ID NOs: 21-30.

Embodiment 35. The CRISPR-Cas system or complex according to any one of the preceding embodiments, wherein the DR comprises a stem-loop structure near the 3' end of the DR,
wherein the stem-loop structure comprises 5'-$X_1X_2X_3X_4X_5$NNNnNNN$X_6X_7X_8X_9X_{10}$-3' ($X_1$, $X_2$, $X_3$, $X_4$, $X_5$, $X_6$, $X_7$, $X_8$, $X_9$, $X_{10}$ are any base, n is any nucleobase or deletion, N is any nucleobase); wherein $X_1X_2X_3X_4X_5$ and $X_6X_7X_8X_9X_{10}$ can hybridize to each other.

Embodiment 36. The CRISPR-Cas system or complex according to any one of the preceding embodiments, wherein the DR comprises a stem-loop structure selected from any one of the following:
5' CUCCCNNNNNNUGGGAG 3' near the 3' end of the DR, wherein N is any nucleobase;
5' CUCCUNNNNNNUGGGAG 3' near the 3' end of the DR, wherein N is any nucleobase;
5' GUCCCNNNNNNUGGGAC 3' near the 3' end of the DR, wherein N is any nucleobase;
5' GUGUCNNNNNNUGACAC 3' near the 3' end of the DR, wherein N is any nucleobase;
5' GUGCCNNNNNNUGGCAC 3' near the 3' end of the DR, wherein N is any nucleobase;
5' UGUGUNNNNNNUCACAC 3' near the 3' end of the DR, wherein N is any nucleobase; and
5' CCGUCNNNNNNUGACGG 3' near the 3' end of the DR, where N is any nucleobase;
5' GTTTCNNNNNNUGAAAC 3' near the 3' end of the DR, where N is any nucleobase;
5' GTGTTNNNNNNUAACAC 3' near the 3' end of the DR, where N is any nucleobase;
5' TTGTCNNNNNNUGACAA 3' near the 3' end of the DR, where N is any nucleobase.

Embodiment 37. The CRISPR-Cas system or complex according to any one of the preceding embodiments, further comprising a target DNA capable of hybridizing to the spacer.

Embodiment 38. The CRISPR-Cas system or complex according to any one of the preceding embodiments, wherein the target DNA is a eukaryotic DNA.

Embodiment 39. The CRISPR-Cas system or complex according to any one of the preceding embodiments, wherein the target DNA is in cells; preferably the cells are selected from the group consisting of prokaryotic cells, eukaryotic cells, animal cells, plant cells, fungal cells, vertebrate cells, invertebrate cells, rodent cells, mammalian cells, primate cells, non-human primate cells, and human cells.

Embodiment 40. The CRISPR-Cas system or complex according to any one of the preceding embodiments, wherein the crRNA hybridizes to and forms a complex with the target sequence of the target DNA, causing the Cas12i protein to cleave the target sequence.

Embodiment 41. The CRISPR-Cas system or complex according to any one of the preceding embodiments, wherein the target sequence is at the 3' end of a protospacer adjacent motif (PAM).

Embodiment 42. The CRISPR-Cas system or complex according to any one of the preceding embodiments, wherein the PAM comprises a 5'-T-rich motif.

Embodiment 43. The CRISPR-Cas system or complex according to any one of the preceding embodiments, wherein the PAM is 5'-TTA, 5'-TTT, 5'-TTG, 5'-TTC, 5'-ATA or 5'-ATG.

Embodiment 44. The CRISPR-Cas system or complex according to any one of the preceding embodiments, wherein the one or more vectors comprise one or more retroviral vectors, phage vectors, adenovirus vectors, herpes simplex virus (HSV) vectors, adeno-associated virus (AAV) vectors, or lentiviral vectors.

Embodiment 45. The CRISPR-Cas system or complex according to any one of the preceding embodiments, wherein the AAV vector is selected from the group consisting of recombinant AAV vectors of serotypes AAV1, AAV2, AAV4, AAV5, AAV6, AAV7, AAVrh74, AAV8, AAV9, AAV10, AAV11, AAV12, and AAV13.

Embodiment 46. The CRISPR-Cas system or complex according to any one of the preceding embodiments, wherein the regulatory element comprises a promoter.

Embodiment 47. The CRISPR-Cas system or complex according to any one of the preceding embodiments, wherein the promoter is selected from the group consisting of a constitutive promoter, an inducible promoter, a ubiquitous promoter, a cell type specific promoter, or a tissue specific promoter.

Embodiment 48. The CRISPR-Cas system or complex according to any one of the preceding embodiments, wherein the promoter is functional in eukaryotic cells.

Embodiment 49. The CRISPR-Cas system or complex according to any one of the preceding embodiments, wherein the eukaryotic cells include animal cells, plant cells, fungal cells, vertebrate cells, invertebrate cells, rodent cells, mammalian cells, primate cells, non-human primate cells, and human cells.

Embodiment 50. The CRISPR-Cas system or complex according to any one of the preceding embodiments, further comprising a DNA donor template optionally inserted at a locus of interest by homology-directed repair (HDR).

Embodiment 51. A cell or descendant thereof, comprising the Cas12i protein, polynucleotide, vector, delivery system, CRISPR-Cas system or complex according to any one of the preceding embodiments, wherein preferably, the cell is selected from the group consisting of prokaryotic cells, eukaryotic cells, animal cells, plant cells, fungal cells, vertebrate cells, invertebrate cells, rodent cells, mammalian cells, primate cells, non-human primate cells, and human cells.

Embodiment 52. A non-human multicellular organism, comprising the cell or descendant thereof according to any one of the preceding embodiments; preferably, the non-human multicellular organism is an animal (e.g., rodent or non-human primate) model for human gene related diseases.

Embodiment 53. A method of modifying a target DNA, comprising contacting a target DNA with the CRISPR-Cas system or complex according to any one of the preceding embodiments, the contacting resulting in modification of the target DNA by the Cas12i protein.

Embodiment 54. The method according to any one of the preceding embodiments, wherein the modification occurs outside cells in vitro.

Embodiment 55. The method according to any one of the preceding embodiments, wherein the modification occurs inside cells in vitro.

Embodiment 56. The method according to any one of the preceding embodiments, wherein the modification occurs inside cells in vivo.

Embodiment 57. The method according to any one of the preceding embodiments, wherein the cell is a eukaryotic cell.

Embodiment 58. The method according to any one of the preceding embodiments, wherein the eukaryotic cell is selected from the group consisting of animal cells, plant cells, fungal cells, vertebrate cells, invertebrate cells, rodent cells, mammalian cells, primate cells, non-human primate cells, and human cells.

Embodiment 59. The method according to any one of the preceding embodiments, wherein the modification is cleavage of the target DNA.

Embodiment 60. The method according to any one of the preceding embodiments, wherein the cleavage results in deletion of a nucleotide sequence and/or insertion of a nucleotide sequence.

Embodiment 61. The method according to any one of the preceding embodiments, wherein the cleavage comprises cleaving the target nucleic acid at two sites resulting in deletion or inversion of a sequence between the two sites.

Embodiment 62. The method according to any one of the preceding embodiments, wherein the modification is a base variation, preferably A→G or C→T base variation.

Embodiment 63. A cell or descendant thereof from the method according to any one of the preceding embodiments, comprising the modification absent in a cell not subjected to the method.

Embodiment 64. The cell or descendant thereof according to any one of the preceding embodiments, wherein a cell not subjected to the method comprises abnormalities and the abnormalities in the cell from the method have been resolved or corrected.

Embodiment 65. A cell product from the cell or descendant thereof according to any one of the preceding embodiments, wherein the product is modified relative to the nature or quantity of a cell product from a cell not subjected to the method.

Embodiment 66. The cell product according to any one of the preceding embodiments, wherein cells not subjected to the method comprise abnormalities and the cell product reflects that the abnormalities have been resolved or corrected by the method.

Embodiment 67. A method of non-specifically cleaving a non-target DNA, comprising contacting the target DNA with the CRISPR-Cas system or complex according to any one of the preceding embodiments, whereby hybridization of the spacer to the target sequence of the target DNA and cleavage of the target sequence by the Cas12i protein make the Cas12i protein cleave the non-target DNA by spacer non-specific endonuclease collateral activity.

Embodiment 68. A method of detecting a target DNA in a sample, comprising:

(1) contacting the sample with the CRISPR-Cas system or complex according to any one of the preceding embodiments and a reporter nucleic acid capable of releasing a detectable signal after being cleaved, whereby hybridization of the spacer to the target sequence of the target DNA and cleavage of the target sequence by the Cas12i protein make the Cas12i protein cleave the reporter nucleic acid by spacer non-specific endonuclease collateral activity; and (2) measuring a detectable signal generated by cleavage of the reporter nucleic acid, thereby detecting the presence of the target DNA in the sample.

Embodiment 69. The method according to any one of the preceding embodiments, further comprising comparing the level of the detectable signal to the level of a reference signal and determining the content of the target DNA in the sample based on the level of the detectable signal.

Embodiment 70. The method according to any one of the preceding embodiments, wherein the measurement is performed using gold nanoparticle detection, fluorescence polarization, colloidal phase change/dispersion, electrochemical detection, or semiconductor-based sensing.

Embodiment 71. The method according to any one of the preceding embodiments, wherein the reporter nucleic acid comprises a fluorescence emission dye pair, a fluorescence resonance energy transfer (FRET) pair, or a quencher/fluorophore pair, and cleavage of the reporter nucleic acid by the Cas12i protein results in an increase or decrease in the level of the detectable signal produced by cleavage of the reporter nucleic acid.

Embodiment 72. A method of treating a condition or disease in a subject in need thereof, comprising administering to the subject the CRISPR-Cas system according to any one of the preceding embodiments.

Embodiment 73. The method according to any one of the preceding embodiments, wherein the condition or disease is a cancer or infectious disease or neurological disease, optionally, the cancer is selected from the group consisting of:

Wilms' tumor, Ewing's sarcoma, neuroendocrine tumor, glioblastoma, neuroblastoma, melanoma, skin cancer, breast cancer, colon cancer, rectal cancer, prostate cancer, liver cancer, kidney cancer, pancreatic cancer, lung cancer, biliary cancer, cervical cancer, endometrial cancer, esophageal cancer, gastric cancer, head and neck cancer, thyroid myeloid cancer, ovarian cancer, glioma, lymphoma, leukemia, myeloma, acute lymphocytic leukemia, acute myeloid leukemia, chronic lymphocytic leukemia, chronic myelocytic leukemia, Hodgkin's lymphoma, non-Hodgkin's lymphoma and urinary bladder cancer;

optionally, the infectious disease is caused by:

human immunodeficiency virus (HIV), herpes simplex virus-1 (HSV1) and herpes simplex virus-2 (HSV2);

optionally, the neurological disease is selected from the group consisting of:

glaucoma, age-related loss of RGC, optic nerve injury, retinal ischemia, Leber's hereditary optic neuropathy, neurological diseases associated with RGC neuronal degeneration, neurological diseases associated with functional neuronal degeneration in the striatum of subjects in need, Parkinson's disease, Alzheimer's disease, Huntington's disease, schizophrenia, depression, drug addiction, dyskinesia such as chorea, choreoathetosis and dyskinesia, bipolar affective disorder, autism spectrum disorder (ASD) or dysfunction.

Embodiment 74. The method according to any one of the preceding embodiments, wherein the condition or disease is selected from the group consisting of cystic fibrosis, progressive pseudohypertrophic muscular dystrophy, Becker muscular dystrophy, alpha-1-antitrypsin deficiency, Pompe disease, myotonic dystrophy, Huntington's disease, fragile X syndrome, Friedreich ataxia, amyotrophic lateral sclerosis, frontotemporal dementia, hereditary chronic kidney disease, hyperlipidemia, hypercholesterolemia, Leber congenital amaurosis, sickle cell disease, and beta thalassemia.

Embodiment 75. The method according to any one of the preceding embodiments, wherein the condition or disease is caused by the presence of a pathogenic point mutation.

Embodiment 76. A kit comprising the CRISPR-Cas system according to any one of the preceding embodiments; preferably the components of the system are in the same container or in separate containers.

Embodiment 77. A sterile container comprising the CRISPR-Cas system according to any one of the preceding embodiments; preferably the sterile container is a syringe.

Embodiment 78. An implantable device comprising the CRISPR-Cas system according to any one of the preceding embodiments; preferably the CRISPR-Cas system is stored in a reservoir.

EXAMPLES

Hereinafter, the invention will be described in detail by examples. The examples provided herein, however, are for illustrative purposes only and are not intended to limit the invention.

The experimental methods used in the following examples are conventional methods unless otherwise specified.

The materials, reagents, etc. used in the following examples are commercially available unless otherwise specified.

Example 1: Identification of Cas12i Proteins

A total of 16 TB of high-quality data were obtained by downloading the metagenomic database from the Joint Genome Institute (JGI) (jgi.doe.gov). More than 6,000 metagenomic data were aligned locally using TBLASTN (blast.ncbi.nlm.nih.gov). Among them, 10 new Cas12i proteins were found in four groups of samples of different origins, which were respectively named as SiCas12i, Si2Cas12i, WiCas12i, Wi2Cas12i, Wi3Cas12i, SaCas12i, Sa2Cas12i, Sa3Cas12i, WaCas12i and Wa2Cas12i according to the different origins of the samples (Singapore, Wisconsin, San Francisco, Washington). SiCas12i is 287 amino acids and 193 amino acids smaller than SpCas9 and LbCas12a, respectively.

The amino acid sequences, nucleotide encoding sequences, codon-optimized nucleic acid encoding sequences are shown in Table A. Four Cas12i-containing samples were annotated with CRISPR loci by using PILERCR, and the DR corresponding to each Cas12i was obtained, shown in Table A.

Example 2: Comparison of Cleavage Activity of Cas12i with Three Controls SpCas9, LbCas12a, and Cas12i.3 Using Fluorescence Reporting System To sensitively detect the cleavage activity of the CRISPR/Cas system, a reporter vector for transcription of BFP-P2A-GFxFP mRNA (BFP-P2A-GFxFP reporter vector, SEQ ID NO: 31, FIG. 1) was constructed. BFP expresses the coding sequence of the blue fluorescent protein, and indicates the successful transfection of the reporter vector into the host cells through blue fluorescence. The GF and FP sequences in GFxFP are 561 nt sequence at the N-terminus and 609 nt sequence at the C-terminus of gene EGFP encoding the green fluorescent protein, respectively, and the two sequences share an overlap of 450 nt. Intermediate the GFxFP is an insert (SEQ ID NO: 32) containing the target sequence (SEQ ID NO: 33) targeted by the CRISPR/Cas system.

At present, most of the known Cas12i proteins recognize the 5'-T-rich PAM in double-stranded DNA, while Cas9 recognizes the 3'-G-rich PAM in double-stranded DNA. In order to simultaneously compare the cleavage activity of SpCas9 (SEQ ID NO: 34), LbCas12a (SEQ ID NO: 35), Cas12i.3 (SEQ ID NO: 36) and the 10 Cas12i as described above, a PAM having sequence TTC was designed at the external 5' end of the target sequence, and a PAM having sequence GGG was designed at the external 3' end of the target sequence. The target sequence with PAMs of 5'-TTC and 3'-GGG at the two external ends is suitable for use for both the CRISPR/Cas12i system and the CRISPR/Cas9 system.

TABLE A

Sequences of Cas12i proteins

| Cas12i protein | Cas12i amino acid sequence | Cas12i nucleic acid sequence | DR sequence | Codon-optimized Cas12i encoding sequences |
|---|---|---|---|---|
| SiCas12i | SEQ ID NO: 1 | SEQ ID NO: 11 | SEQ ID NO: 21 | SEQ ID NO: 37 |
| Si2Cas12i | SEQ ID NO: 2 | SEQ ID NO: 12 | SEQ ID NO: 22 | SEQ ID NO: 38 |
| WiCas12i | SEQ ID NO: 3 | SEQ ID NO: 13 | SEQ ID NO: 23 | SEQ ID NO: 39 |
| Wi2Cas12i | SEQ ID NO: 4 | SEQ ID NO: 14 | SEQ ID NO: 24 | SEQ ID NO: 40 |
| Wi3Cas12i | SEQ ID NO: 5 | SEQ ID NO: 15 | SEQ ID NO: 25 | SEQ ID NO: 41 |
| SaCas12i | SEQ ID NO: 6 | SEQ ID NO: 16 | SEQ ID NO: 26 | SEQ ID NO: 42 |
| Sa2Cas12i | SEQ ID NO: 7 | SEQ ID NO: 17 | SEQ ID NO: 27 | SEQ ID NO: 43 |
| Sa3Cas12i | SEQ ID NO: 8 | SEQ ID NO: 18 | SEQ ID NO: 28 | SEQ ID NO: 44 |
| WaCas12i | SEQ ID NO: 9 | SEQ ID NO: 19 | SEQ ID NO: 29 | SEQ ID NO: 45 |
| Wa2Cas12i | SEQ ID NO: 10 | SEQ ID NO: 20 | SEQ ID NO: 30 | SEQ ID NO: 46 |

TABLE B

| Sequences of control Cas proteins | | | |
|---|---|---|---|
| Control Cas protein | Control Cas amino acid sequence | Codon-optimized control Cas encoding sequences | Corresponding gRNA/crRNA of control Cas |
| SpCas9 | SEQ ID NO: 34 | SEQ ID NO: 57 | SEQ ID NO: 60 |
| LbCas12a | SEQ ID NO: 35 | SEQ ID NO: 58 | SEQ ID NO: 61 |
| Cas12i.3 | SEQ ID NO: 36 | SEQ ID NO: 59 | SEQ ID NO: 62 |

Figure 2:
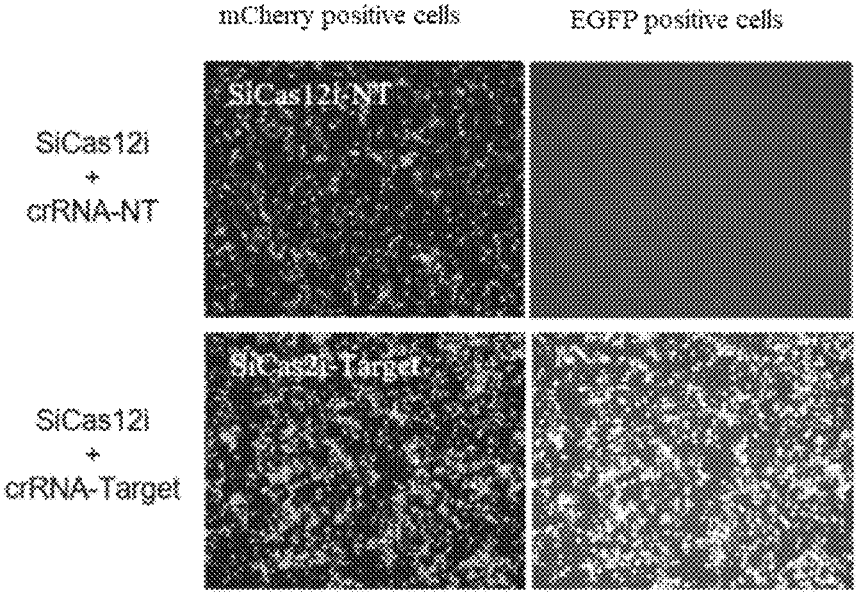
FIG. 2 shows fluorescent microscopic pictures of cells co-transfected with SiCas12i-mCherry expression vector (red fluorescence) and crRNA-target-BFP-P2A-GFxFP or crRNA-non-target (NT)-BFP-P2A-GFxFP reporter vector (blue fluorescence). Cells with target sequence cleaved by the CRISPR-SiCas12i system show green fluorescence (GFP).

A TAG premature terminator is located in the middle of the target sequence, and when it is cleaved, the GFxFP produces the correct GFP coding frame using the recombination mechanism (e.g., single strand annealing, SSA) to express GFP, thus changing the cell from having no green fluorescence to having green fluorescence (FIG. 2 show results of exemplary Cas12i protein SiCas12i).

The nucleotide coding sequences of the ten Cas12i proteins were codon optimized for mammalian, namely, SEQ ID NOs: 37-46 (Table A), and they were constructed on an expression vector expressing mCherry red fluorescent protein. Cas12i expression was driven by a CAG promoter, and the successful transfection of the expression vector into host cells was indicated by red fluorescence (FIG. 2).

The nucleic acids encoding the crRNAs of the Cas12i proteins that target the BFP-P2A-GFxFP target sequence (SEQ ID NOs: 47-56; Table C) were respectively designed to contain a DR+Spacer structure, wherein the spacer was 20 nt in length (SEQ ID NO: 185), and constructed on the BFP-P2A-GFxFP reporter vector together with a U6 promoter for driving crRNA transcription, and the successful transfection of the reporter vector into host cells was indicated by blue fluorescence. DNA sequence encoding the crRNA spacer sequence is identical to the target DNA sequence SEQ ID NO: 33. crRNA sequences of corresponding Cas12i proteins are provided in Table C. For example, crRNA of SEQ ID NO: 47 consists of 5' to 3': DR of SEQ ID NO: 21 and spacer of SEQ ID NO: 226.

inserted into an expression vector expressing mCherry red fluorescent protein, Cas expression was driven by a CAG promoter, and successful transfection of the expression vector into host cells was indicated by red fluorescence. Similarly, the corresponding reporter vectors for the transcription of the respective crRNA/sgRNA (SpCas9-sgRNA of SEQ ID NO: 60, LbCas12a-crRNA of SEQ ID NO: 61, and Cas12i.3-crRNA of SEQ ID NO: 62) and BFP-P2A-GFxFP mRNA were constructed, and the successful transfection of the reporter vector into host cells was indicated by blue fluorescence.

As a negative control ("NT"), crRNA-NT or sgRNA-NT against non-target sequence (NT; SEQ ID NO: 186) for corresponding Cas12i proteins and controls SpCas9, LbCas12a, and Cas12i.3 were constructed, which were identical to the corresponding crRNAs or sgRNAs described above except for the spacer sequence against NT (spacer-NT; SEQ ID NO: 187). crRNA-NT or sgRNA-NT encoding sequences were inserted into the BFP-P2A-GFxFP reporter vector and under transcription control of U6. Successful transfection of the reporter vector into host cells was indicated by blue fluorescence. Such non-target sequence is not present on the BFP-P2A-GFxFP reporter vector. For example, the crRNA-NT for SiCas12i (SiCas12i crRNA-NT) consists of from 5' to 3': DR of SiCas12i (SEQ ID NO: 21) and spacer-NT (SEQ ID NO: 187), and comprises the sequence of SEQ ID NO: 188.

TABLE C

| crRNAs corresponding to Cas12i proteins | | | |
|---|---|---|---|
| Cas12i protein | DR sequence | Spacer sequence | crRNA sequence |
| SiCas12i | SEQ ID NO: 21 | SEQ ID NO: 226 | SEQ ID NO: 47 |
| Si2Cas12i | SEQ ID NO: 22 | SEQ ID NO: 226 | SEQ ID NO: 48 |
| WiCas12i | SEQ ID NO: 23 | SEQ ID NO: 226 | SEQ ID NO: 49 |
| Wi2Cas12i | SEQ ID NO: 24 | SEQ ID NO: 226 | SEQ ID NO: 50 |
| Wi3Cas12i | SEQ ID NO: 25 | SEQ ID NO: 226 | SEQ ID NO: 51 |
| SaCas12i | SEQ ID NO: 26 | SEQ ID NO: 226 | SEQ ID NO: 52 |
| Sa2Cas12i | SEQ ID NO: 27 | SEQ ID NO: 226 | SEQ ID NO: 53 |
| Sa3Cas12i | SEQ ID NO: 28 | SEQ ID NO: 226 | SEQ ID NO: 54 |
| WaCas12i | SEQ ID NO: 29 | SEQ ID NO: 226 | SEQ ID NO: 55 |
| Wa2Cas12i | SEQ ID NO: 30 | SEQ ID NO: 226 | SEQ ID NO: 56 |

Similarly, the mammalian codon-optimized nucleotide coding sequences of SpCas9 (SEQ ID NO: 57), LbCas12a (SEQ ID NO: 58) and Cas12i.3 (SEQ ID NO: 59) were The expression vector (red fluorescence) expressing Cas12i/LbCas12a/SpCas9 and the reporter vector (blue fluorescence) transcribing BFP-P2A-GFxFP mRNA and crRNA/sgRNA, respectively, were co-transferred into the HEK293 cell line by PEI transfection. Control groups were similarly double transfected. After 48 hours of culture, transfection double positive (both red and blue fluorescence) cells were obtained by flow cytometry sorting. A "blank" control group was also set up, and only the reporter vector encoding BFP-P2A-GFxFP (only blue fluorescence) was transfected, no Cas expression vector was introduced.

Figure 3:
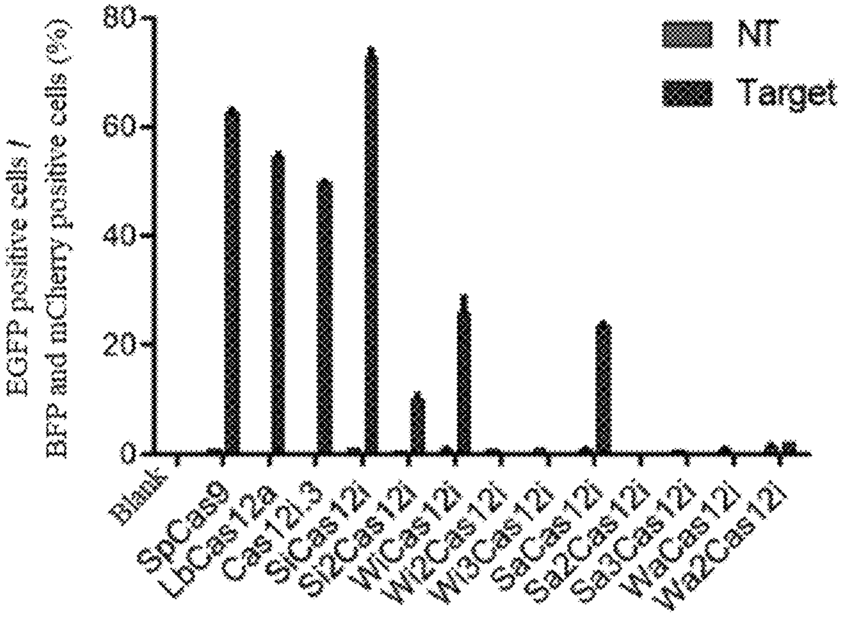
FIG. 3 shows comparison of cleavage activity (shown as % of GFP positive signal) among 10 Cas12 is described herein, and positive controls SpCas9, LbCas12i, and Cas12i.3. NT is non-target control.

For each test group and control group, green fluorescent cell numbers were counted, then divided by the total number of cells co-expressing red and blue fluorescence, to calculate target sequence cleavage activity (FIG. 3).

Through analysis, we found that SiCas12i, Si2Cas12i, WiCas12i and SaCas12i had significant cleavage activity (characterized by green fluorescence intensity). Among them, SiCas12i had the highest cleavage activity (with the highest green fluorescence intensity), which was even significantly higher than that of SpCas9, LbCas12a and Cas12i.3 (FIG. 3). Negative control group (transfected with crRNA-NT or sgRNA-NT) and blank control group showed no or only background level cleavage activity (FIGS. 2 and 3).

Example 3: Test of Identification of PAM of SiCas12i and Effective Target Sequence Length To test the PAM identification of SiCas12i, a target sequence (SEQ ID NO: 33) having 5'-TTN or 5'-NTN (where N is A, T, G, or C) was designed and inserted into the aforementioned BFP-P2A-GFxFP reporter vector, respectively, to replace original PAM and target sequence in Example 2. The reporter vector also carried the aforementioned corresponding crRNA for SiCas12i (SEQ ID NO: 47) and the U6 promoter for driving crRNA transcription.

As negative control, similarly as described in Example 2, nucleic acid sequence encoding SiCas12i crRNA-NT (SEQ ID NO: 188) against non-target sequence (NT; SEQ ID NO: 186) was constructed into the BFP-P2A-GFxFP reporter vector (5' PAM of TTC, target sequence SEQ ID NO: 33) under transcription control of U6. Blue fluorescence indicates successful transfection.

The aforementioned SiCas12i expression vector and the BFP-P2A-GFxFP reporter vector with different PAMs were co-transferred into the HEK293 cell line by PEI transfection. Control group was similarly double transfected. A "blank" control group was also set up, and only the reporter vector encoding BFP-P2A-GFxFP (only blue fluorescence) was transfected, no Cas expression vector was introduced. After 48 hours of culture, transfection double positive (both red and blue fluorescence) cells were obtained by flow cytometry sorting.

Figure 4:
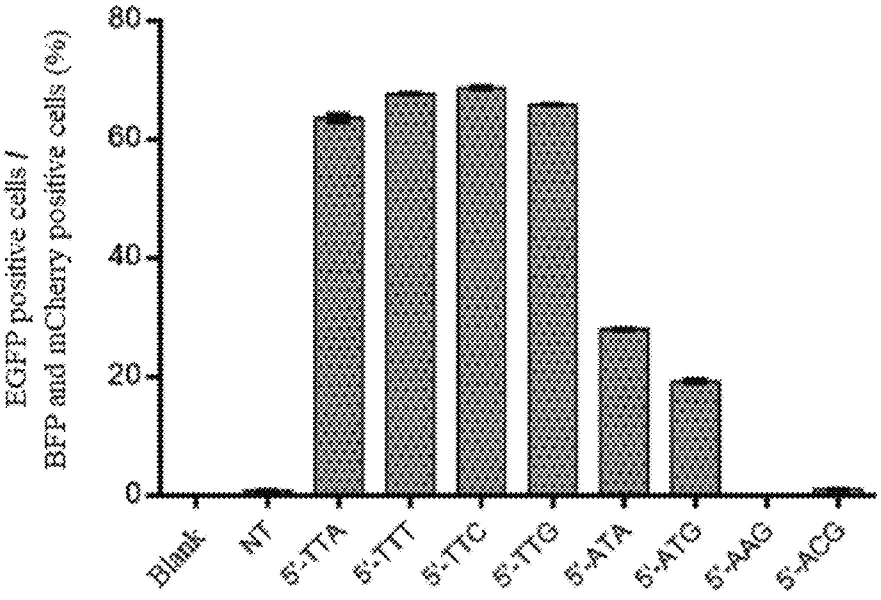
FIG. 4 shows test for applicable PAMs for SiCas12i. NT is non-target control.

For each test group and control group, green fluorescent cell numbers were counted, then divided by the total number of cells co-expressing red and blue fluorescence, to calculate target sequence cleavage activity. Through analysis, SiCas12i was found to have a high cleavage activity when PAM was 5'-TTN (where N is A, T, G, or C) and a low but still significant cleavage activity when PAM was 5'-ATA or ATG (FIG. 4).

To test the effective spacer length on the crRNA corresponding to SiCas12i, spacers of different lengths ranging from 10 to 50 nt were designed (corresponding to the target sequences of different lengths in Table 1), and the coding sequence of the crRNA containing the spacer and the U6 promoter for driving crRNA transcription were constructed together on the BFP-P2A-GFxFP reporter vector in Example 2 (5' PAM of TTC). The DNA coding sequence of the 20-nt spacer is the aforementioned SEQ ID NO: 33 itself in Example 2. The DNA coding sequence of the spacer shorter than 20-nt in length is a truncated version of SEQ ID NO: 33. The portion of the DNA coding sequence of the spacer longer than 20-nt beyond SEQ ID NO: 33 is the 5' portion of the nucleotide coding sequence of the FP segment of the GFxFP immediately adjacent to the C-terminus of x, i.e., the nucleotide sequence extending continuously in the 3' direction from SEQ ID NO: 33.

As negative control, nucleic acid encoding SiCas12i crRNA-NT (SEQ ID NO: 188) against non-target sequence (NT; SEQ ID NO: 186) was constructed into the BFP-P2A-GFxFP reporter vector (5' PAM of TTC) under transcription control of U6. Blue fluorescence indicates successful transfection.

Figure 5:
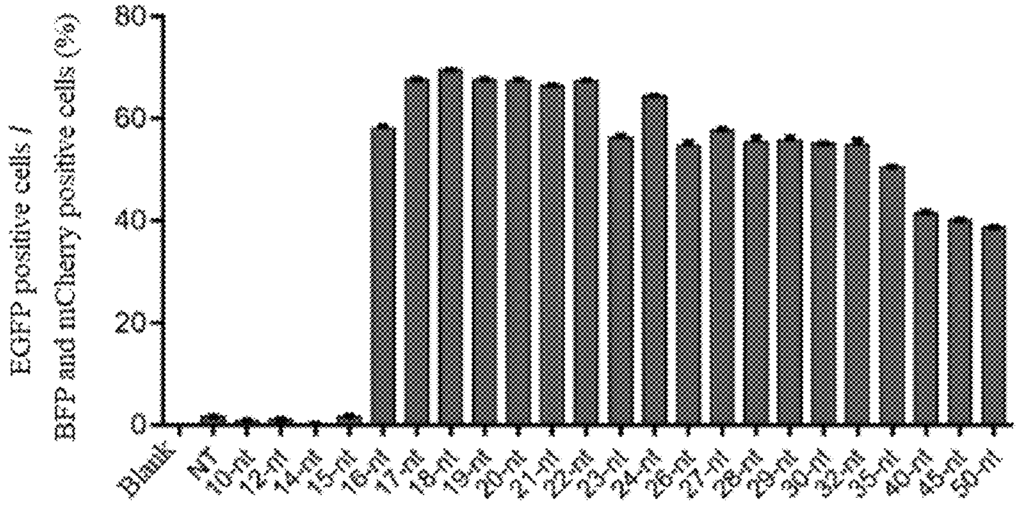
FIG. 5 shows test for applicable spacer lengths for SiCas12i. NT is non-target control.

The aforementioned SiCas12i expression vector and the BFP-P2A-GFxFP reporter vector with different DNA coding sequences of spacers were co-transferred into the HEK293 cell line by PEI transfection. Control group was similarly double transfected. A "blank" control group was also set up, and only the Example 2 reporter vector encoding BFP-P2A-GFxFP (only blue fluorescence) was transfected, no Cas expression vector was introduced. After 48 hours of culture, transfection double positive (both red and blue fluorescence) cells were obtained by flow cytometry sorting. For each test group and control group, green fluorescent cell numbers were counted, then divided by the total number of cells co-expressing red and blue fluorescence, to calculate target sequence cleavage activity. It was found that when the spacer length is greater than 15 nt (not including 15 nt), SiCas12i has high-efficiency cleavage activity in cells (FIG. 5).

TABLE 1

DNA nucleotide coding sequences of spacers/target sequences of different lengths

| | DNA nucleotide coding sequence of spacer/target sequence |
|---|---|
| 10-nt | CCATTACAGT (SEQ ID NO: 124) |
| 12-nt | CCATTACAGTAG (SEQ ID NO: 125) |
| 14-nt | CCATTACAGTAGGA (SEQ ID NO: 126) |
| 15-nt | CCATTACAGTAGGAG (SEQ ID NO: 127) |
| 16-nt | CCATTACAGTAGGAGC (SEQ ID NO: 128) |
| 17-nt | CCATTACAGTAGGAGCA (SEQ ID NO: 129) |
| 18-nt | CCATTACAGTAGGAGCAT (SEQ ID NO: 130) |

TABLE 1-continued

| DNA nucleotide coding sequences of spacers/target sequences of different lengths | |
|---|---|
| | DNA nucleotide coding sequence of spacer/target sequence |
| 19-nt | CCATTACAGTAGGAGCATA (SEQ ID NO: 131) |
| 20-nt | CCATTACAGTAGGAGCATAC (SEQ ID NO: 33) |
| 21-nt | CCATTACAGTAGGAGCATACG (SEQ ID NO: 132) |
| 22-nt | CCATTACAGTAGGAGCATACGG (SEQ ID NO: 133) |
| 23-nt | CCATTACAGTAGGAGCATACGGG (SEQ ID NO: 134) |
| 24-nt | CCATTACAGTAGGAGCATACGGGA (SEQ ID NO: 135) |
| 26-nt | CCATTACAGTAGGAGCATACGGGAGA (SEQ ID NO: 136) |
| 27-nt | CCATTACAGTAGGAGCATACGGGAGAC (SEQ ID NO: 137) |
| 28-nt | CCATTACAGTAGGAGCATACGGGAGACA (SEQ ID NO: 138) |
| 30-nt | CCATTACAGTAGGAGCATACGGGAGACAAG (SEQ ID NO: 139) |
| 32-nt | CCATTACAGTAGGAGCATACGGGAGACAAGCT (SEQ ID NO: 140) |
| 35-nt | CCATTACAGTAGGAGCATACGGGAGACAAGCTTTG (SEQ ID NO: 141) |
| 40-nt | CCATTACAGTAGGAGCATACGGGAGACAAGCTTTGGCCAC (SEQ ID NO: 142) |
| 45-nt | CCATTACAGTAGGAGCATACGGGAGACAAGCTTTGGCCACCTACG (SEQ ID NO: 143) |
| 50-nt | CCATTACAGTAGGAGCATACGGGAGACAAGCTTTGGCCACCTACGGCAAG (SEQ ID NO: 144) |

Example 4: Cleavage of the TTR Gene by SiCas12i in Mammalian Cells

In order to test the cleavage activity of SiCas12i for endogenous genes, 14 crRNAs and 6 crRNAs were designed for mouse TTR gene (mTTR) and human TTR gene (hTTR), respectively, against target sequences with different 5'-TTN as PAMs (Table 2). DR comprises the sequence of SEQ ID NO: 21. The crRNA-mTTR and the crRNA-hTTR encoding nucleic acid sequences were constructed on an mCherry red fluorescent protein expression vector capable of expressing SiCas12i protein in mammalian cells ("SiCas12i/crRNA-mTTR expression vector" and "SiCas12i/crRNA-hTTR expression vector," respectively), that is, a single vector was used for crRNA transcription and SiCas12i protein expression, and the successful transfection of the vector into the host cells was indicated by red fluorescence. As negative control, nucleic acid encoding SiCas12i crRNA-NT (SEQ ID NO: 188) against non-target sequence (NT; SEQ ID NO: 186) was constructed into the mCherry/SiCas12i expression vector ("SiCas12i/crRNA-NT").

The SiCas12i/crRNA-mTTR and SiCas12i/crRNA-hTTR expression vectors were transfected into mouse N2A cell line and human HEK293 cell line by PEI transfection, respectively. Control group was similarly transfected. After 48 hours of culture, mCherry red fluorescence-positive cells were obtained by flow cytometry sorting.

PCR amplification was performed on the TTR gene target sites of the transfection positive cells. As shown by deep sequencing and alignment analysis on the PCR products, the CRISPR-SiCas12i system of the invention has a cleavage activity of up to 91.77% at the TTR gene of mouse N2A cell line (Table 2) and up to 99.85% at the TTR gene of human HEK293 cell line (Table 3). Cleavage activity was expressed as the ratio of the number of target sequences containing indels (insertion/deletions) divided by the total number of target sequences. Since cleavage at any one or more of the indicated target sites of the TTR gene can result in inactivation of the TTR gene, the highest cleavage activity at any of the indicated sites can be considered as the highest efficiency in inactivating the TTR gene as a whole. In other words, SiCas12i can achieve a gene inactivation efficiency of up to 91.77% for mouse TTR gene and up to 99.85% for human TTR gene.

TABLE 2

Editing efficiency of SiCas12i at different target sites of mouse TTR gene (first three bases as PAM sequence)

| | PAM + target sequence | Indel | Total | Percentage (%) |
|---|---|---|---|---|
| mTTR-1 | **TTG**CCTCGCTGGACTGGTATTTG (SEQ ID NO: 145) | 36,250 | 71,553 | 50.66 |
| mTTR-2 | **TTG**TGTCTGAAGCTGGCCCCGCG (SEQ ID NO: 146) | 60,837 | 73,708 | 82.53 |

TABLE 2-continued

Editing efficiency of SiCas12i at different target sites of mouse TTR gene (first three bases as PAM sequence)

| | PAM + target sequence | Indel | Total | Percentage (%) |
|---|---|---|---|---|
| mTTR-3 | **TTC**CCTTCGACTCTTCCTCCTTT (SEQ ID NO: 147) | 63,024 | 78,418 | 80.37 |
| mTTR-4 | **TTC**CTCCTTTGCCTCGCTGGACT (SEQ ID NO: 148) | 39,196 | 107,179 | 36.57 |
| mTTR-5 | **TTG**ACCATCAGAGGACATTTGGA (SEQ ID NO: 149) | 83,346 | 120,336 | 69.26 |
| mTTR-6 | **TTG**GATTCTCCAGCACCCTGGGC (SEQ ID NO: 150) | 57,889 | 315,351 | 18.36 |
| mTTR-7 | **TTA**CAGCCACGTCTACAGCAGGG (SEQ ID NO: 151) | 79,919 | 117,015 | 68.30 |
| mTTR-8 | **TTC**AAAAAGACCTCTGAGGGATC (SEQ ID NO: 152) | 89,744 | 148,541 | 60.42 |
| mTTR-9 | **TTG**AACACTTTTACAGCCACGTC (SEQ ID NO: 153) | 20,802 | 136,682 | 15.22 |
| mTTR-10 | **TTG**GTGTCCAGTTCTACTCTGTA (SEQ ID NO: 154) | 96,448 | 105,094 | 91.77 |
| mTTR-11 | **TTC**TCATCTGTGGTGAGCCCGTG (SEQ ID NO: 155) | 20,548 | 99,368 | 20.68 |
| mTTR-12 | **TTG**TAGAAGGAGTGTACAGAGTA (SEQ ID NO: 156) | 26,791 | 35,925 | 74.57 |
| mTTR-13 | **TTC**TACAAACTTCTCATCTGTGG (SEQ ID NO: 157) | 43,757 | 116,430 | 37.58 |
| mTTR-14 | **TTT**CACAGCCAACGACTCTGGCC (SEQ ID NO: 158) | 26,290 | 106,510 | 24.68 |

TABLE 3

Editing efficiency of SiCas12i at different target sites in the human TTR gene (first three bases as PAM sequence)

| | PAM + target sequence | Indel | Total | Percentage (%) |
|---|---|---|---|---|
| hTTR-1 | **TTG**ACCATCAGAGGACACTTGGA (SEQ ID NO: 159) | 18,383 | 159,005 | 11.56 |
| hTTR-2 | **TTC**AGAAAGGCTGCTGATGACAC (SEQ ID NO: 160) | 116,017 | 292,247 | 39.70 |
| hTTR-3 | **TTG**TAGAAGGGATATACAAAGTG (SEQ ID NO: 161) | 647,858 | 673,470 | 96.20 |
| hTTR-4 | **TTG**GCATCTCCCCATTCCATGAG (SEQ ID NO: 162) | 1,085,294 | 1,086,931 | 99.85 |
| hTTR-5 | **TTC**CAGTAAGATTTGGTGTCTAT (SEQ ID NO: 163) | 711,892 | 768,861 | 92.59 |
| hTTR-6 | **TTC**CACCACGGCTGTCGTCACCA (SEQ ID NO: 164) | 233,948 | 504,804 | 46.34 |

Example 5: Comparison of Cleavage Activity of SiCas12i with Controls SpCas9, LbCas12a and Cas12i.3 in Mammalian Cells To compare the cleavage activity of SiCas12i with the controls SpCas9, LbCas12a and Cas12i.3 at different endogenous gene sites, total four target sites in human DNA Methyltransferase 1 (DNMT1), TTR and Proprotein convertase subtilisin/kexin type 9 (PCSK9; 2 target sites were selected for PCSK9) genes with both 5'-TTN and 3'-NGG (N is any of A, T, G, or C) PAMs were selected for test, and these four sites were applicable to both Cas12i and Cas9. The corresponding guide RNAs (crRNA for Cas12i and sgRNA for Cas9) for SiCas12i, SpCas9, LbCas12a and Cas12i.3 were designed for these four sites, respectively (SEQ ID NOs: 63-78). The nucleic acids encoding the guide RNAs were accordingly constructed on an mCherry red fluorescent protein expression vector capable of expressing SiCas12i, SpCas9, LbCas12a or Cas12i.3 proteins in mammalian cells, i.e., a single vector was used for transcription of the guide RNA and expression of the Cas protein, and the successful transfection of the vector into the host cells was indicated by red fluorescence. As negative control, nucleic acid encoding SiCas12i crRNA-NT (SEQ ID NO: 188) against non-target sequence (NT; SEQ ID NO: 186) was constructed into the mCherry/SiCas12i expression vector ("SiCas12i/crRNA-NT"). The SiCas12i/crRNA, SpCas9/sgRNA, LbCas12a/crRNA and Cas12i.3/crRNA expression vectors were respectively transfected into the human HEK293 cell line by PEI transfection. After 48 hours of culture, mCherry red fluorescence-positive cells were obtained by flow cytometry sorting. Negative control group was similarly transfected and sorted.

Figure 6:
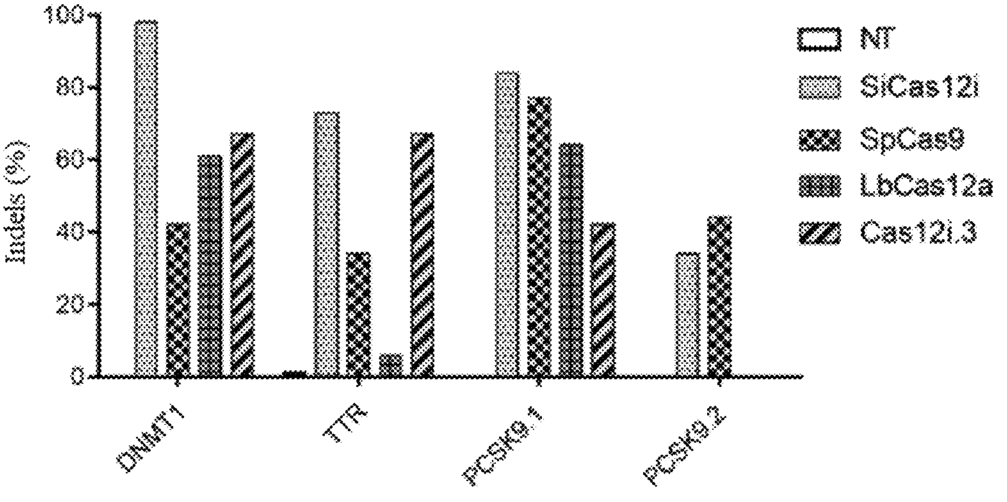
FIG. 6 shows comparison of cleavage activity for DNMT1 gene, TTR gene, and PCSK9 gene (PCSK9.1 and PCSK9.2 are 2 different targets of PCSK9) in human HEK293 cell line by SiCas12i, and controls SpCas9, LbCas12i, and Cas12i.3. NT is non-target control. indel % is insert/deletion frequency, indicating cleavage activity at the target site.

PCR primers were designed for above 4 target sites. PCR amplification was performed on the target sites of transfection positive cells. Cleavage activity was expressed as the ratio of the number of target sequences containing indels (insertion/deletions) divided by the total number of target sequences. Deep sequencing and alignment analysis of the PCR products showed that SiCas12i had the highest cleavage activity at three sites (DNMT1, TTR, and PCSK9.1), and the cleavage activity at each of the four sites was higher than that of Cas12i.3 and LbCas12a (FIG. 6).

Example 6: Comparison of Cleavage Activity in Endogenous Genes Between SiCas12i and Control Cas12i.3

To further compare the cleavage activity in endogenous genes between SiCas12i and the control Cas12i.3, 11 target sequences with different 5'-TTNs (N is any of A, T, G, or C) as PAMs were selected from TTR and PCSK9 genes and tested. The respective crRNAs of SiCas12i and Cas12i.3 were designed for these 11 sites, respectively (Table 4). DR sequence for SiCas12i was SEQ ID NO: 21. DR sequence for Cas12i.3 was SEQ ID NO: 189. Nucleic acid encoding the spacer had the same sequence as the target sequence.

The nucleic acid encoding crRNA was constructed on the mCherry red fluorescent protein expression vector capable of expressing SiCas12i or Cas12i.3 proteins in mammalian cells, that is, a single vector was used for transcription of the crRNA and expression of the Cas protein, and the successful transfection of the vector into the host cells was indicated by red fluorescence. As negative control, spacer encoding sequences of above constructs were replaced with a non-target sequence (NT; SEQ ID NO: 186). The SiCas12i/crRNA and Cas12i.3/crRNA expression vectors were transfected into human HEK293 cell line by PEI transfection. After 48 hours of culture, mCherry red fluorescence-positive cells were obtained by flow cytometry sorting. Negative control group was similarly transfected and sorted.

Figure 7:
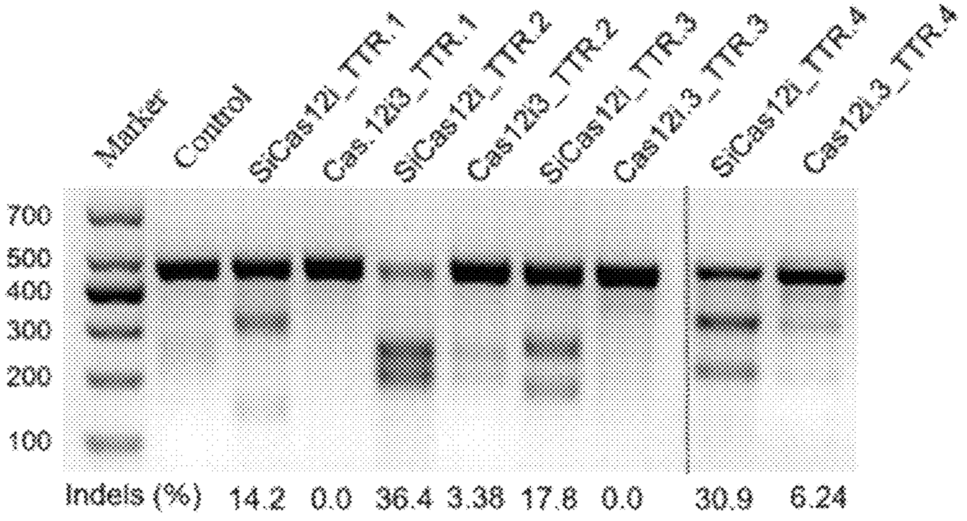
FIG. 7 shows comparison of cleavage activity at 4 different target sites of the TTR gene in human HEK293 cell line by SiCas12i and control Cas12i.3. indel % is insert/deletion frequency, indicating cleavage activity at the target site.
Figure 8:
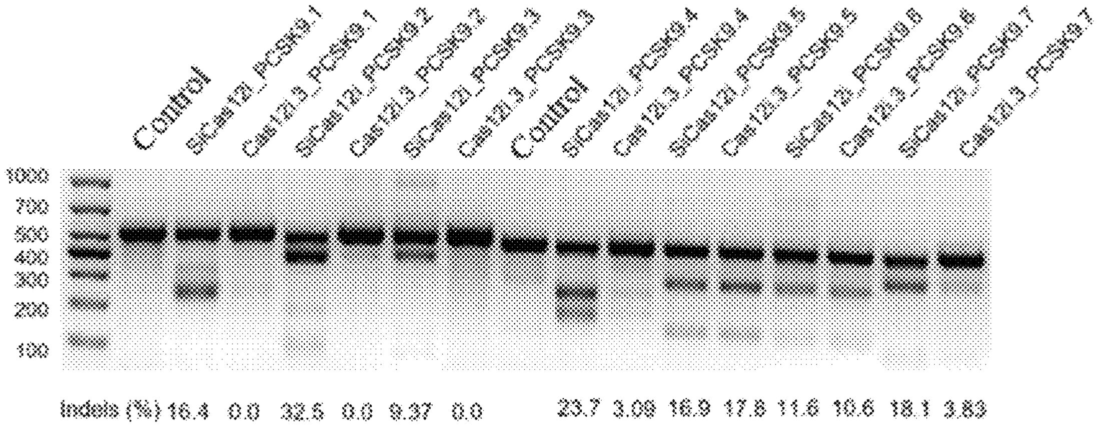
FIG. 8 shows comparison of cleavage activity at 7 different target sites of PCSK9 gene in human HEK293 cell line by SiCas12i and control Cas12i.3. indel % is insert/deletion frequency, indicating cleavage activity at the target site.

PCR primers were designed for above 11 target sites. PCR amplification was performed on the target sites of transfection positive cells. T7E1 enzyme treatment and gel electrophoresis were performed, and cleavage efficiency (indel %) at target sites were calculated. Cleavage activity of SiCas12i was higher or equivalent to that of Cas12i.3 at all the sites; even at target sites incapable of being cleaved by Cas12i.3 (indel % of 0% or close to 0%; e.g., TTR-1, TTR-3, PCSK9-1, PCSK9-3), SiCas12i still exhibited excellent cleavage efficiency (FIGS. 7-8).

TABLE 4

Human TTR and PCSK9 gene target sequences with different PAMs

| | Target sequence | 5'-PAM |
|---|---|---|
| TTR-1 | AATCCAAGTGTCCTCTGATGGT (SEQ ID NO: 165) | TTG |
| TTR-2 | AATGTGGCCGTGCATGTGTTCA (SEQ ID NO: 166) | TTC |
| TTR-3 | TAGATGCTGTCCGAGGCAGTCC (SEQ ID NO: 167) | TTC |
| TTR-4 | CACCACGGCTGTCGTCACCAAT (SEQ ID NO: 168) | TTC |
| PCSK9-1 | TTCCTGGCTTCCTGGTGAAG (SEQ ID NO: 169) | TTC |
| PCSK9-2 | CTGGTGAAGATGAGTGGCGA (SEQ ID NO: 170) | TTC |
| PCSK9-3 | AAGTTGCCCCATGTCGACTA (SEQID NO: 171) | TTG |
| PCSK9-4 | CCCAGAGCATCCCGTGGAAC (SEQ ID NO: 172) | TTG |
| PCSK9-5 | GCCCAGAGCATCCCGTGGAA (SEQ ID NO: 173) | TTT |
| PCSK9-6 | CCCCTCCACGGTACCGGGCG (SEQ ID NO: 174) | TTA |
| PCSK9-7 | ATCCGCCCGGTACCGTGGAG (SEQ ID NO: 175) | TTA |

Example 7: Application of dSiCas12i in Single Base Editing (A→I)

To obtain a dSiCas12i version with lost cleavage activity, dSiCal2i proteins with D700A, D650A, E875A, or D1049A single-point mutations were constructed: dSiCas12i (D700A) (SEQ ID NO: 79), dSiCas12i(D650A) (SEQ ID NO: 80), dSiCas12i(E875A) (SEQ ID NO: 81), and dSiCas12i(D1049A) (SEQ ID NO: 82). All mutation sites were within SiCas12i RuvC domain.

TadA8e (SEQ ID NO: 182) is a variant of transfer RNA adenosine deaminase (TadA), can act on single-stranded DNA (ssDNA) to replace A to I (A-to-I). After DNA repair and replication, base I will be eventually replaced to base G. Hence TadA8e can be considered as A-to-G base editing enzyme.

To construct CRISPR-Cas12i system capable of performing A-to-I (or A-to-G) single base DNA editing, above four dSiCas12i proteins were separately fused with TadA8e to construct fusion protein TadA8e-dSiCas12i, in which N' TadA8e and C' dSiCas12i were connected by a linker peptide (SEQ ID NO: 183).

To investigate DNA cleavage activity of the 4 dSiCas12i proteins, spacers with two lengths of 20 nt (SEQ ID No: 83) and 23 nt (SEQ ID NO: 84) were designed for the human KLF4 gene. dSiCas12i DR sequence was SEQ ID NO: 21. Nucleic acid sequences encoding the two crRNAs with the aforementioned spacers were constructed on the mCherry red fluorescent protein expression vector capable of expressing the four TadA8e-dSiCas12i proteins in mammalian cells, namely, a single vector was used for transcription of the crRNA and expression of the TadA8e-dSiCas12i protein, and the successful transfection of the vector into the host cells was indicated by red fluorescence.

As positive control, dLbCas12a(D832A) (LbCas12a variant with lost DNA cleavage activity) was fused to the C-terminus of TadA8e with the same linker peptide (SEQ ID NO: 183), to obtain the fusion protein TadA8e-dLbCas12a (D832A). crRNA corresponding to dLbCas12a(D832A) was also constructed, with the same spacer sequence as the 23 nt dSiCas12i spacer sequence, and with same DR sequence as used in Example 2. Nucleic acid sequence encoding the control crRNA was constructed on an mCherry red fluorescent protein expression vector capable of expressing TadA8e-dLbCas12a(D832A) in mammalian cells.

The TadA8e-dSiCas12i/crRNA expression vector was transfected into human HEK293 cell line by PEI transfection. After 48 hours of culture, mCherry red fluorescence-positive cells were obtained by flow cytometry sorting. Positive control group was similarly transfected and sorted.

Figure 9:
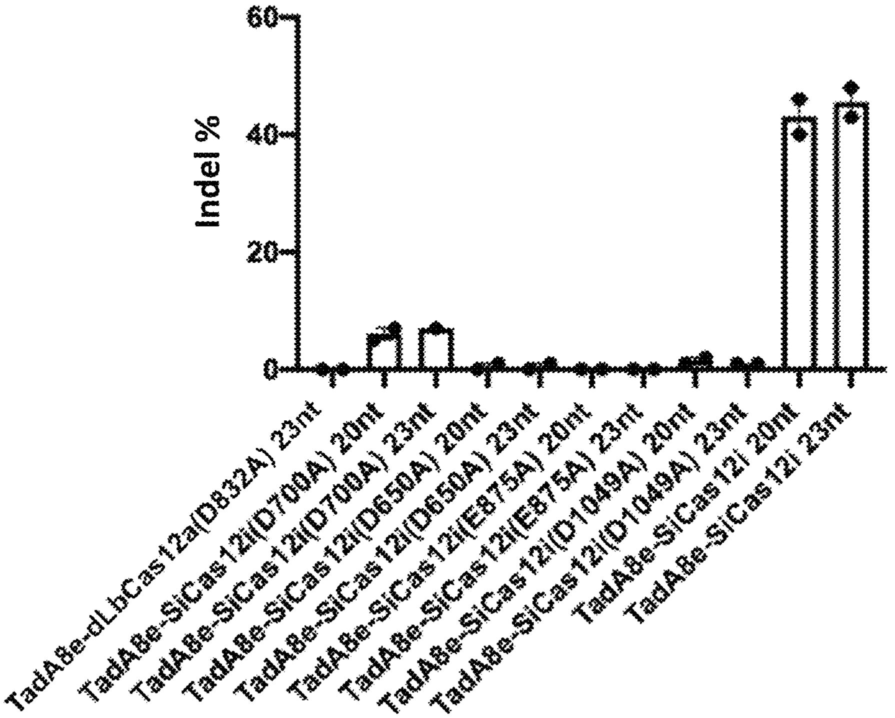
FIG. 9 shows comparison of cleavage activity by 4 dSiCas12i mutants with different single point mutations (D700A, D650A, E875A, and D1049A; with reduced or eliminated cleavage activity) at human KLF4 gene in human HEK293 cell line. For each dSiCas12i mutant, 20 nt and 23 nt spacer length do not affect cleavage activity. dLbCas12a (D832A) with no cleavage activity and parental SiCas12i (SEQ ID NO: 1) served as controls. A TadA8e portion was fused to each Cas protein, but had no impact on Cas protein's cleavage activity.

PCR amplification was performed on the KLF4 sites of transfection positive cells. TadA8e fusion domain should not have had impact on DNA cleavage efficiency of dSiCas12i or dLbCas12a(D832A). Hence, the cleavage efficiency detected from TadA8-dSiCas12i or TadA8-dLbCas12a (D832A) could be considered as that of dSiCas12i or dLbCas12a(D832A), respectively. As indicated by sequencing analysis, the D700A point mutation in dSiCas12i (D700A) resulted in a decrease in cleavage activity of approximately 84% compared to its parental counterpart SiCas12i (SEQ ID NO: 1), while D650A in dSiCas12i (D650A) caused a decrease in cleavage activity of about 99% compared to parental SiCas12i (SEQ ID NO: 1), E875A in dSiCas12i(E875A) caused a decrease in cleavage activity of about 100% compared to parental SiCas12i (SEQ ID NO: 1), and the D1049A point mutation in dSiCas12i (D1049A) caused a decrease in cleavage activity of about 98% compared to parental SiCas12i (SEQ ID NO: 1). The difference in spacer lengths between 20 nt and 23 nt had no significant effect on the cleavage activity of dSiCas12i proteins (FIG. 9). Positive control dLbCas12a(D832A) had no cleavage activity at KLF4 target site.

To investigate the A-to-I (or A-to-G) single base editing activity of TadA8e-dSiCas12i, dSiCas12i (D1049A) was selected to form a fusion protein with TadA8e (TadA8e-dSiCas12i(D1049A); SEQ ID NO: 85), with TadA8e at the N-terminus, dSiCas12i(D1049A) at the C-terminus, and connected by a linker peptide (SEQ ID NO: 183). As positive control, dCas12i.3(D641A) (Cas12i.3 variant with lost DNA cleavage activity) was fused to the C-terminus of TadA8e with linker peptide (SEQ ID NO: 183) in between to construct a fusion protein (TadA8e-dCas12i.3(D641A); SEQ ID NO: 86). Corresponding crRNAs (SEQ ID NOs: 87 and 88, respectively) for TadA8e-dSiCas12i(D1049A) and TadA8e-dCas12i.3(D641A) were designed for the human KLF4 target site. Nucleic acids encoding the crRNAs were respectively constructed on mCherry red fluorescent protein expression vectors capable of expressing TadA8e-dSiCas12i (D1049A) or TadA8e-dCas12i.3(D641A) proteins in mammalian cells, that is, a single vector was used for transcription of the crRNA and expression of the Cas protein, and the successful transfection of the vector into the host cells was indicated by red fluorescence. TadA8e-dSiCas12i(D1049A)/crRNA and TadA8e-dCas12i.3(D641A)/crRNA expression vectors were respectively transfected into human HEK293 cell line by PEI transfection. After 48 hours of culture, mCherry red fluorescence-positive cells were obtained by flow cytometry sorting.

Figure 10:
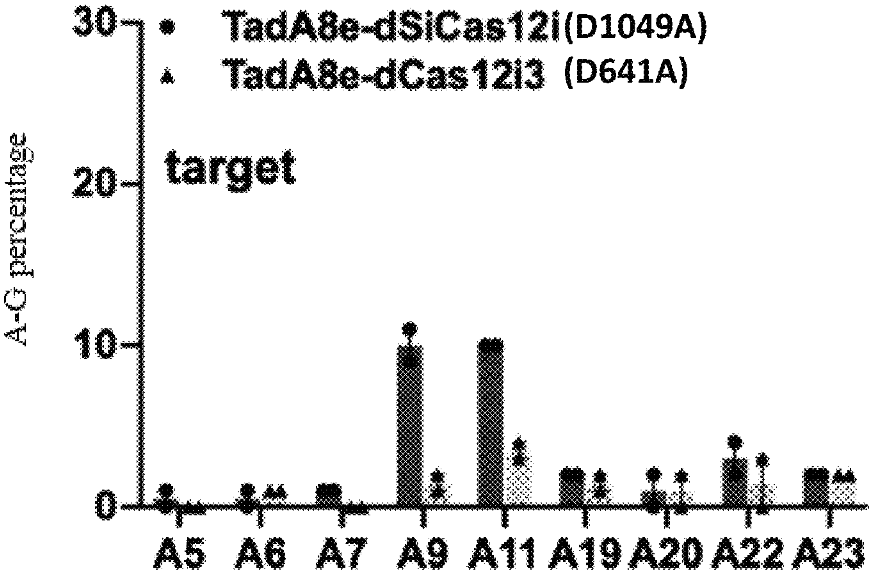
FIG. 10 shows single base editing (A→I or A→G) activity by TadA8e-dSiCas12i (D1049A). TadA8e-dCas12i.3 (D641A) served as control.

PCR amplification was performed on the KLF4 sites of transfection positive cells. A5, A6, and A23 etc. in FIG. 10 indicate base A at positions 5, 6, and 23, etc. of the target sequence, respectively. Sequencing analysis revealed that TadA8e-dSiCas12i(D1049A) had an A-to-G single-base editing activity of more than 10% in mammalian cells, and much higher A-to-G single-base editing activity at almost every As within the target sequence compared to TadA8e-dCas12i.3(D641A) (FIG. 10).

Example 8: Effect of the DR Sequence on SiCas12i Cleavage Activity

To test whether the DR of SiCas12i could tolerate mutations, a series of mismatches or deletions were designed at different positions in the parental SiCas12i DR sequence ("DR-P"; RNA sequence SEQ ID NO: 101, DNA coding sequence SEQ ID NO: 113). DR-P used herein is a functionally truncated version of SiCas12i DR of SEQ ID NO: 21. A total of 5 different DR variants (DR-A, DR-B, DR-C, DR-D, DR-E; for their DNA coding sequences, refer to the upper panel in FIG. 11) containing 5% to 30% mutations in the stem-loop regions were designed without destroying the secondary structures (i.e. secondary structures of the DR variants were substantially the same as that of parental DR ("DR-P")). The target sequence (SEQ ID NO: 33) was designed on the aforementioned BFP-P2A-GFxFP reporter vector (see Example 2), and the coding sequences (SEQ ID NO: 89-94) of the six corresponding crRNAs (SEQ ID NOs: 95-100) were constructed under the U6 promoter for driving crRNA transcription on the reporter vector.

The aforementioned SiCas12i mCherry red fluorescent expression vector and the BFP-P2A-GFxFP reporter vector described herein were co-transfected into the human HEK293 cell line by PEI transfection, respectively. After 48 hours of culture, transfection double positive (both red and blue fluorescence) cells were obtained by flow cytometry sorting. A "blank" control group was also set up, and only the reporter vector encoding BFP-P2A-GFxFP and crRNA with DR-P (only blue fluorescence) was transfected, no Cas expression vector was introduced. The control group was similarly transfected. For each test group and control group, green fluorescent cell numbers were counted, then divided by the total number of cells co-expressing red and blue fluorescence, to calculate target sequence cleavage activity, see bottom panel of FIG. 11.

Through analysis, SiCas12i was found to have a high cleavage activity (characterized by green fluorescence intensity) mediated by crRNAs with different DR variants, comparable to crRNA with DR-P (the bottom panel in FIG. 11). It can be seen that under the condition that the secondary structure of DR is maintained (i.e., the secondary structures of DR variants are substantially the same as that of DR-P), the CRISPR-SiCas12i system can tolerate mismatching or deletion on DR without loss of cleavage activity, and has wide adaptability to variations in DR. These data also demonstrated that functionally truncated version of SiCas12i DR of SEQ ID NO: 21 (36 nt), i.e., DR-P (SEQ ID NO: 101, 23 nt), could still mediate high cleavage activity of SiCas12i.

Example 9: Cleavage of the TTR Gene in Mice by Lipid Nanoparticle-Delivered SiCas12i-crRNA System In order to test whether the SiCas12i-crRNA system described herein can efficiently and specifically knock out the mouse TTR gene in mouse liver cells, the mTTR-10 target site (SEQ ID NO: 154 comprising PAM+target sequence), which showed the highest cleavage efficiency in the mouse N2a cell line by SiCas12i-crRNA in Example 4, was selected as the target site for in vivo mTTR gene cleavage efficiency test.

SiCas12i-encoding mRNA (5'UTR-SiCas12i-3'UTR-PolyA; SEQ ID NO: 176) with 5' UTR and 3' UTR and PolyA was obtained by in vitro transcription. A short gRNA (SEQ ID NO: 177) and a long gRNA (SEQ ID NO: 178) with terminal modifications and HPLC purification was prepared by GenScript. The two gRNAs both had 2' methoxyl modifications (marked with "m" on the base, representing "methoxyl") on the 3 bases at the 5' end and the 3' end. Both gRNAs were complementary to the antisense strand of the mTTR-10 target site. The short gRNA had a 5' to 3' DR-spacer sequence, while the long gRNA had a 5' to 3' DR-spacer-DR-spacer sequence.

SiCas12i-encoding mRNA and short gRNA mixture, or SiCas12i-encoding mRNA and long gRNA mixture, was loaded into lipid nanoparticles (four lipids ALC-0315:Cholesterol:PEG-DMG:DOPE mixed in a molar ratio of 50 mM:50 mM:10 mM:20 mM), respectively, to obtain the LNP1 package and the LNP2 package (the mass ratio of SiCas12i:gRNA was 1:1). Ai9 mice were then administered with the LNP1 package or the LNP2 package by tail vein injection. The specific injection information is shown in Table 5.

TABLE 5

Mice dosing scheme

| Mice | LNP | Dosage (mg/kg; MPK) | RNA mixture in the LNP |
|---|---|---|---|
| Ai9-1 | LNP1 | 3 | SiCas12i mRNA + short gRNA |
| Ai9-2 | LNP1 | 1 | SiCas12i mRNA + short gRNA |
| Ai9-3 | LNP2 | 3 | SiCas12i mRNA + long gRNA |
| Ai9-4 | LNP2 | 1 | SiCas12i mRNA + long gRNA |

Figure 12:
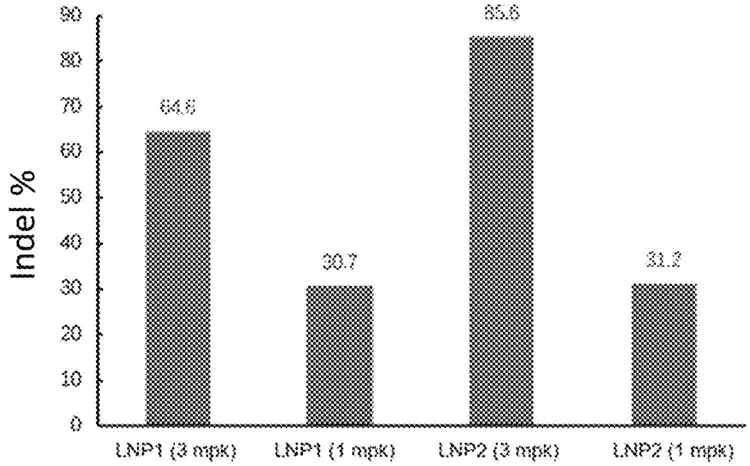
FIG. 12 shows comparison of cleavage activity of a mixture of SiCas12i-encoding mRNA and gRNA delivered using lipid nanoparticles (LNPs) on the liver TTR gene in mice. LNP1 and LNP2 deliver CRISPR-SiCas12i systems using short and long gRNAs, respectively.

Mice liver tissue was harvested 7 days after LNP injection. PCR primers were designed from upstream and downstream of the mTTR-10 target site, and PCR products were sequenced. Frequency of indels (insertion/deletion) at the mTTR-10 target site was determined by analyzing the sequencing data. The cleavage frequency of the two SiCas12i-gRNA systems targeting the liver TTR gene in mice delivered by LNPs is shown in FIG. 12, with the highest cleavage frequency of 85.6%. As shown in FIG. 12, both SiCas12i-gRNA systems exhibited dose-dependent cleavage activity. The SiCas12i-gRNA system with long gRNA achieved better cleavage activity at higher doses than the SiCas12i-gRNA system with short gRNA.

Mis-folding and aggregation of transthyretin (TTR) is associated with amyloid diseases, including transthyretin-related wild-type amyloidosis (ATTRwt), transthyretin-related hereditary amyloidosis (ATTRm), familial amyloid polyneuropathy (FAP), and familial amyloid cardiomyopathy (FAC). Gene silencing of TTR to reduce TTR protein production may have therapeutic effects in TTR-associated amyloid diseases. The high-efficiency cleavage of TTR target sites in mice in this example demonstrates that the SiCas12i-crRNA system of the present invention has very promising prospects for the treatment of TTR-related amyloid diseases, such as ATTR (e.g., ATTRwt or ATTRm).

SEQUENCE LISTING

```
SEQ ID NO: 1        >SiCas12i protein
                    MSSDVVRPYNTKLLPDNRKHNMFLQTFKRLNSISLNHFDLLICLYAAITNKKAEEYKSEKEAHVTADSLCAINW
                    FRPMSKRYSKYATTTFNMLELFKEYSGHEPDAYSKNYLMSNIDSDRFVWVDCRKFAKDFAYQMELGFHEFTVL
                    AETLLANSILVLNESTKANWAWGTVSALYGGGDKEDSTLKSKILLAFVDALNNHELKTKREILNQVCESLKYQ
                    SYQDMYVDFRSVVDENGNKKSPNGSMPIVTKFETDDLISDNQRKAMISNFTKNAAAKAAKKPIPYLDRLKEH
                    MVSLCDEYNVYAWAAAITNSNADVTARNTRNLTFIGEQNSRRKELSVLQTTTNEKAKDILNKINDNLIQEVRYT
                    PAPKHLGRDLANLFDTLKEKDINNIENEEEKQNVINDCIEQYVDDCRSLNRNPIAALLKHISRYYEDFSAKNFLD
                    GAKLNVLTEVVNRQKAHPTIWSEKAYTWISKFDKNRRQANSSLVGWVVPPEEVHKEKIAGQQSMMWVTLTLL
                    DDGKWVKHHIPFSDSRYYSEVYAYNPNLPYLDGGIPRQSKFGNKPTTNLTAESQALLANSKYKKANKSFLRAK
                    ENATHNVRVSPNTSLCIRLLKDSAGNQMFDKIGNVLFGMQINHKITVGKPNYKIEVGDRFLGFDQNQSENHTY
                    AVLQRVSESSHDTHHFNGWDVKVLEKGKVTSDVIVRDEVYDQLSYEGVPYDSSKFAEWRDKRRRFVLENLSI
                    QLEEGKTFLTEFDKLNKDSLYRWNMNYLKLLRKAIRAGGKEFAKIAKTEIFELAVERFGPINLGSLSQISLKMIAS
                    FKGVVQSYFSVSGCVDDASKKAHDSMLFTFMCAAEEKRTNKREEKTNRAASFILQKAYLHGCKMIVCEDDLP
                    VADGKTGKAQNADRMDWCARALAKKVNDGCVAMSICYRAIPAYMSSHQDPFVHMQDKKTSVLRPRFMEVN
                    KDSIRDYHVAGLRRMLNSKSDAGTSVYYRQAALHFCEALGVSPELVKNKKTHAAELGKHMGSAMLMPWRG
                    GRVYIASKKLTSDAKSVKYCGEDMWQYHADEIAAVNIAMYEVCCQTGAFGKKQKKSDELPG

SEQ ID NO: 2        >Si2Cas12i protein
                    MSSDVVRPYNTKLLPDNRKYNMFLQTFKRLNLISSNHFDLLVCLYAAITNKKAEEYKSEKEDHVTADSLCAIN
                    WFRPMSKRYIKYATTTFKMLELFKEYSGHEPDTYSKNYLMSNIVSDRFVWVDCRKFAKDFANQMELSFHEFTT
                    LSETLLANSILVLNESTKANWAWGAVSALYGGGDKEDSTLKSKILLAFVDALNNPELKTRREILNHVCESLKYQ
                    SYQDMYVDFRSVVDDKGNKKSPNGSMPIVTKFESDDLIGDNQRKTMISSFTKNAAAKASKKPIPYLDILKDHM
                    ISLCEEYNVYAWAAAITNSNADVTARNTRNLTFIGEQNTRRKELSVLQTSTNEKAKDILNKINDNLIPEVRYTPAP
                    KHLGRDLANLFEMFKEKDINQIGNEEEKQNVINDCIEQYVDDCRSLNRNPVAALLKHISGYYEDFSAKNFLDG
                    AKLNVLTEVVNRQKAHPTICSEKAYTWISKIDKNRRQANSSLVGWVVPPEEVHKEKIAGQQSMMWVTLTLLD
                    DGKWVKHHIPFADSRYYSEVYAYNPNLPYLEGGIPRQSKFGNKPTTNLTAESQALLANSKHKKANKTFLRAKE
                    NITHNVRVSPNTSLCIRPLKDSAGNQMFDNIGNMLFGMQINHRITVGKPNYKIEVGDRFLGFDQNQSENHTYAV
                    LQRVSESSHGTHHFNGWDVKVIEKGKVTSDVVVRDEVYDQLSYEGVPYDSPKFTEWREKRRKFVLENMSIQIE
                    EGKTFLTEFDKLNKDSLYRWNMNYMKLLRKAIRAGGKEFAKITKAEIFELGVMRFGPMNLGSLSQVSLKMIAA
                    FKGVIQSYFSVSGCIDDASKKAHDSMLFAFLCSADEKRTNKREEKTNRAASFILQKAYSHGCKMIVCEDDLPIA
```

-continued

SEQUENCE LISTING

DGKVGKAQNADRMDWCARSLAKKVNDGCVAMSICYRAIPAYMSSHQDPFTHMQDKKTSVLRPRFMEVGKD
SIRDHHVAGLRRMLNSKGNTGTSVYYREAALRFCEALGVLPELVKNKKTHASELGKHMGSAMLMPWRGGRI
YVASKKLTSDAKSIKYCGEDMWQYHADEIAAINIAMYEV

SEQ ID NO: 3 >WiCas12i protein
MGISISRPYGTKLRPDARKKEMLDKFFTTLAKGQRVFADLGLCIYGSLTLEMVKRLEPESDSELVCAIGWFRLV
DKVTWSENEIKQENLVRQYETYSGKEASEVIKTYLSSPSSDKYVWIDCRQKFLRFQRDLGTRNLSEDFECMLFE
QYLRLTKGELDGHTAMSNMFGTKTKEDRATKLRYAARMKEWLEANEEITWEQYHQALQDKLDANTLEEAVD
NYKGKAGGSNPFFSYTLLNRGQIDKKTHEQQLKKFNKVLKTKSKNLNFPNKEKLKQYLETAIGIPVDAQVYGQ
MFNNGVSEVQPKTTRNMSFSMEKLELLNELKSLNKTDGFERANEVLNGFFDSELHTTEDKFNITSRYLGGDRN
NRLPKLYELWKKEGVDREEGIQQFSQAIQDKMGQIPVKNVLRYIWEFRETVSAEDFEAAAKANQLEEKITRTK
AHPVVISNRYWTFGSSALVGNIMPADKMHKDQYAGQSFKMWLEAELHYDGKKVKHHLPFYNARFFEEVYCY
HPSVAEVTPFKTKQFGYAIGKDIPADVSVVLKDNPYKKATKRFLRAISNPVANTVDVNKPTVCSFMIKRENDEY
KLVINRKIGVDRPKRIKVGRKVMGYDRNQTASDTYWIGELVPHGTTGAYRIGEWSVQYIKSGPVLSSTQGVND
STTDQLIYNGMPSSSERFKAWKKSRMSFIRKLIRQLNAEGLESKGQDYVPENPSSFDVRGETLYVFNSNYMKAL
VSKHRKAKKPVEGILEEIEALTSKAKDSCSLMRLSSLSDAAMQGIASLKSLINSYFNKNGCKTIEDKEKFNPDLY
VKLVEVEQKRTNKRKEKVGRIAGSLEQLALLNGVDVVIGEADLGEVKKGKSKKQNSRNMDWCAKQVAERLE
YKLTFHCIGYFGVNPMYTSHQDPFEHRRVADHLVMRARFEEVNVSNVSEWHMRNFSNYLRADSGTGLYYKQA
TLDFLKHYDLEEHADDLEKQNIKFYDFRKILEDKQLTSVIVPKRGGRIYMATNPVTSDSTPVTYAGKTYNRCNA
DEVAAANIAISVLAPHSKKEEKEDKIPIISKKPKSKNTPKARKNLKTSQLPQK SEQ ID NO: 4 >Wi2Cas12i protein
MASKHVVRPFNGKVTATGKRLAYLEETFHYLEKAAGGVSTLFAALGSYLDATTISNLINKNQDLAVVIFRYHVV
PKGEAHTLPVGTDMVSRFVADYGMEPNEFQRAYLDSPIDQEKYCWQDNRDVGCWLGEQLGVSEADMRAIAV
TFYNNQMLYDCVKGTGSGNAVSLLFGSGKKSDYSMKGVIAGKAASVLAKYRPATYQDARKMILEANGFTSVK
DLVTSYGITGRSSALQIFMEGIESGPISSKTLDARIKKFTEDSERNGRKNLVPHAGAIRNWLIEQAGSSVENYQM
AWCEVYGNVSADWNAKVESNFNFVAEKVKALTELSNIQKSTPDLGKALKLFEEYLTTCQDEFAIAPYHFSVME
EVRMEMATGREFNDAYDDALNSLDMESKQPIQPLCKFLIERGGSISFDTFKSAAKYLKTQSKIAGRYPHPFVKG
NQGFTFGSKNIWAAINDPMMEYADGRIAGGSAMMWVTATLLDGKKWVRHHIPFANTRYFEEVYASKKGLPVL
PCARDGKHSFKLGNNLSVERVEKVKEGGRTKATKAQERILSNLTHNVQFDSSTTFIIRRQEESFVICVNHRHPAP
LMKKEMEVGDKIIGIDQNVTAPTTYAIVERVASGGIERNGKQYKVTAMGAISSVQKTRGGEVDVLSYMGVELS
DSKNGFQSLWNKCLDFVTKHGTENDVKYYNNTAVWANKLYVWHKMYFRLLKQLMRRAKDLKPFRDHLQHL
LFHPNLSPLQRHSLSLTSLEATKIVRNCIHSYFSLLGLKTLDERKAADINLLEVLEKLYAGLVERRKERTKLTAGL
LVRLCNEHGISFAAIEGDLPVVGEGKSKAANNTQQDWTARELEKRLSEMAEVVGIKVIAVLPHYTSHQDPFVYS
KNTKKMRCRWNWRTTKTFTDRDALSIRRILSKPETGTNLYYQKGLKAFAEKHGLDLAEMKKRKDAQWYLERI
QDKNFLVPMNGGRVYLSSVKLAGKETIDMGGEILYLNDADQVAALNVLLVKI SEQ ID NO: 5 >Wi3Cas12i protein
MAKKEHIIRPFKGTLPLRGDRLRYLQDTMKYMKKVEDTITELCAAVIAYAKPTIIQQILGEEIETTSTFCSFRLVGI
HENFTMPLTTNMIKHFQKTFNINPSEKQAIYLSSGFDSDKYRWQDTSEVSRNFANKCRLTNQEFQEFAEQALLN
MCFIGCSGSPGATNAVSQIFGTGEKSDYQRKSQIAKIAADTLENHKPSTYESARLMVLNTLGHKTIEDCVNDYG
AIGAKSAFRLFMESKEIGPITSEQLTTKIKKFREDHKKNSIKKQLPHVEKVRNALLSQFKEQYLPSAWAEAWCNI
MGEFNSKLSNNNNFIDQKTKMVNDCDNIKKSNPQLDKAVNMLDEWKYKNWDDNSAIHPYHIGDLKKLMAIF
NINNEGTFDERFSASWEQFSTSLEYGEKPPVRDLLAHIIKNMNDLTYTDVINAAKFLKLQDNIRNKYPHPFVMP
NKGCTFGKDNLWGEINDPTAKIKSTEEVAGQRPMMWLTAKLLDNGKWVEHHIPFASSRYFAEVYYTNPALPTL
PIARDGKHSYKLTKTIDANTAKTLVNNPRDKAAKLIARTKANTTHNVKWIKPTYRIQKENNQFVITINHRHPCIT
PPKEIILGDRILSFDQNETAPTAFSILEKTTKGTEFCGHHIKVLKTGMLEAKIKTSKKSIDAFTYMGPMEDDHASG
FPTLLNICEKFISENGDEKDKSFSSRKLPFKRSLYFFHGSHFDLLKKMIRKAKNDPKKLKLVRIHINEILFNSNLSP
IKLHSLSIHSMENTKKVIAAISCYMNVHEWKTIDEQKNADITLYNAKEKLYNNLVNRRKERVKVTAGMLIRLAR
ENNCRFMVGEAELPTQQQGKSKKNNNSKQDWCARDIAQRCEDMCEVVGIKWNGVTPHNTSHQNPFIYKNTS
GQQMRCRYSLVKKSEMTDKMAEKIRNILHAEPVGTTAYYREGILEFAKHHGLDLGMMKKRRDAKYYDNLPD
EFLLPTRGGRIYLSENQLGGNETIVINGKKYFVNQADQVAAVNIGLLYLLPKKNQS SEQ ID NO: 6 >SaCas12i protein
MSEKKFHIRPYRCSISPNARKADMLKATISYLDSLTSVFRSGFTALLAGIDPSTVSRLAPSGAVGSPDLWSAVNW
FRIVPLAEAGDARVGQASLKNLFRGYAGHEPDEEASIYMESRVDDKRHAWVDCRAMFRAMALECGLEEAQLA
SDVFALASREVIVFKDGEINGWGIASLLFGEGEKADSQKKVALLRSVRLALEGDYATYEELSGLMLAKTGASSG
SDLLDEYKRSEKGGSSGGRHPFFDEVFRRGGRVKQEERERLLKSCDTAIQKQGQALPLSHVASWRQWFLRRVT
LLRNRRQESFAVCITNALMDLQPKNLRNVHYVTNPKSEKDKGVLELRVDVKNNEGPDVAGAQAVFDAYMARL
APDLRFSVMPRHLGSLKDLYALWAKLGRDEAIEEYLEGYEGPFSKRPIAGILQIIHAHRGKVGHDSLLRAARLN
RAMDRLERKRAHACAAGNKGYVYGKSSMVGRINPQSLEVGGRKSGRSPMMWVTLDLVDGDRFAQHHLPFQ
SARFFSEVYCHGDGLPATRVPGMVRNRRNGLAIGNGLGEGGLSALRAGSDRRKRANKRTLRALENITHNVEID
PSTSFTLREDGIIISHRIEKIEPKLVAFGDRALGFDLNQTGAHTFAVLQKVDSGGLDVGHSRVSIVLTGTVRSICKG
NQASGGRDYDLLSYDGPERDDGAFTAWRSDRQAFLMSAIRELPTPAEGEKDYKADLLSQMASLDHYRRLYAY
NRKCLGIYIGALRRATRRQAVAAFKDEILSIANHRCGPLMRGSLSVNGMESLANLKGLATAYLSKFKDSKSEDL
LSKDEEMADLYRACARRMTGKRKERYRRAASEIVRLANEHGCLFVFGEKELPTTSKGNKSKQNQRNTDWSAR
AIVKAVKEACEGCGLGFKPVWKEYSSLTDPFERDGDGRPALRCRFAKVAAPDSELPPRLTKAVGSYVKNALKA
DKAEKKQTCYQRGAIEFCSRHGIDVRKATDKAIRKAVRGSSDLLVPFDGGRTFLLSTRLSPESRKVEWAGRTLY
EFPSDMVAAINIACRGLEPRKA SEQ ID NO: 7 >Sa2Cas12i protein
MDEQAVVSSGSDKTLKIVRPYRAKVTATGIRLEGIKNTLNYLKRTEICLSRLNAACGAFLTPAIVEQICKDDPALV
CAIARFQLVPVGSEATLSDSGLMRHFKAALGELTPLQEAYLNSSYNDELYAWQDTLVLARQIIAETGLTEDQFRA
FAHACFKNGNIIGCAGGPGASNAISGIFGEGIKSDYSLRSEMTAAVAKVFEEKRPITYEEARALALEATGHASVQ
SFVEAFGKQGRKGTLILFMEDTKTGAFPSNEFDYKLKKLKEDAERVGRKGIIPHRDVIASYLRNQTGADIEYNS
KAWCESYCCAVSEYNSKMSNNVRFATEKSLDLTKLDETIRETPKISEAMLVFENYMARIDADLRFIVSKHHLGN
LAKFRQTMMHVSASEFEEAFKAMWADYLAGLEYGEKPAICELVRYVLTHGNDLPVEAFYAACKFLSLDDKIK -continued

| SEQUENCE LISTING | |
|---|---|
| | NRYPHPFVPGNKGYTFGAKNLWAEINDPFKPIRQGNPEVAGQRPMMWATADLLDNNKWVLHHIPFASSRYFEE<br>VYYTDPSLPTAQKARDGKHGYRLGKVLDEAARERLKANNRQRKAAKAIERIKANCEHNVAWDPTTTFMLQL<br>DSEGNVKMTINHRHIAYRAPKEIGVGDRVIGIDQNETAPTTYAILERTENPRDLEYNGKYYRVVKMGSVTSPNV<br>SKYRTVDALTYDGVSLSDDASGAVNFVVLCREFFAAHGDDEGRKYLERTLGWSSSLYSFHGNYFKCLTQMMR<br>RSARSGGDLTVYRAHLQQILFQHNLSPLRMHSLSLRSMESTMKVISCMKSYMSLCGWKTDADRIANDRSLFEA<br>ARKLYTSLVNRRTERVRVTAGILMRLCLEHNVRFIHMEDELPVAETGKSKKSNGAKMHWCARELAVRLSQMA<br>EVTSVKFTGVSPHYTSHQDPFVHSKTSKVMRARWSWRNRADFTDKDAERIRTILGGDDAGTKAYYRSALAEF<br>ASRYGLDMEQMRKRRDAQWYQERLPETFIIPQRGGRVYLSSHDLGSGQKVDGIYGGRAFVNHADEVAALNVA<br>LVRL |
| SEQ ID NO: 8 | >Sa3Cas12i protein<br>MKTETLIRPYPGKLNLQPRRAQFLEDSIQYHQKMTEFFYQFLQAVGGATTHQNISDFIDNKATDEHQATLLFQV<br>VSKDSTTPECPAEELLARFAQYTGKQPNEAVTHYLTSRINTDKYRWQDNRLLAQNIASQLNISETQFQEIAHAIL<br>SNNLYIGQTASNAAANFISQVTGTGQKAPKAARLDVLFQTNQALAKTQPTTFGQLQQIIVQACGESTTDAVLAK<br>FGNKGAATSLQLALKTDPNTTLDQKKYEALQKKFAEDETKYRNKVDIPHKTQLRNLILNTSNQFCNWHTKPAI<br>EAFKCAIADIQSKVSNNLRIMQEKAKLYEAFRNVDPQVQIAVQALENHMNTLEEPYAPYAHSFGSVKDFYEDL<br>NNGSNLDEAIQTIVHDSDNFNRKPDPNWLRIIAPLHSSHSASQIMEAVKYLSSKQDYELRKPFPFVATNLPATYG<br>KFNIPGTLNPPTDSLHGRLNGSHSNMWLTALLLDGRDWKNHHLCFASSRYFEEVYFTNPSLPTTDKVRSPKCGF<br>TLKSVLDSEAKDRIRNAPKSRTKAVKAIERIKANSTHNVAWNPETSFQMQKRNDEFYITINHRIEMEKIPGQKKT<br>DDGFTIHPKGLFAILKEGDRILSQDLNQTAATHCAVYEVAKPDQNTFNHHGIHLKLIATEELKMPLKTKKSTIPD<br>ALSYQGIHAHDRENGLQQLKDACGAFISPRLDPKQKATWDNSVSKKENLYPFITAYMKLLKKVMKAGRQELK<br>LFRTHLDHILFKHNLSPLKLHGVSMIGLESSRATKSVINSFFNLQNAKTEQQQIALDRPLFEAGKTLINNQTRRR<br>QERVRLETSLTMRLAHKYNAKAIIIEGELPHSSTGTSQYQNNVRLDWSAKKSAKLKTESANCAGIAICQIDPCHT<br>SHQNPFRHTPTNPDLRPRFAQVKKGKMFQYQLNGLQRLLNPRSKSSTAIYYRQAVQSFCAHHNLTERDITSAKF<br>PSDLEKKIKDDTYLIPQRGGRIYISSFPVTSCARPCTSNHYFGGGQFECNADAVAAVNIMLKVHP |
| SEQ ID NO: 9 | >WaCas12i protein<br>MPIRGYKCTVVPNVRKKKLLEKTYSYLQEGSDVFFDLFLSLYGGIAPKMIPQDLGINEQVICAANWFKIVEKTK<br>DCIADDALLNQFAQYYGEKPNEKVVQFLTASYNKDKYVWVDCRQKFYTLQKDLGVQNLENDLECLIREDLLP<br>VGSDKEVNGWHSISKLFGCGEKEDRTIKAKILNGLWERIEKEDILTEEDARNELLHSAGVLTPKEFRKVYKGAA<br>GGRDCYHTLLVDGRNFTFNLKTLIKQTKDKLKEKSVDVEIPNKEALRLYLEKRIGRSFEQKPWSEMYKTALSAV<br>MPKNTLNYCFAIDRHAQYTKIQTLKQPYDSAITALNGFFESECFTGSDVFVISPSHLGKTLKKLYNYKDVESGIS<br>EIVEDEDNSLRSGVNVNLLRYIFTLKDMFSAEDFIKAAEYNVVFERYNRQKVHPTVKGNQSFTFGNSALSGKVI<br>PPSKCLSNLPGQMWLAINLLDQGEWKEHHIPFHSARFYEEIYATSDNQNNPVDLRTKRFGCSLNKTFSAADIEK<br>VKESAKKKHGKAAKRILRAKNTNTAVNWVDCGFMLEKTEVNFKITVNYKLPDQKLGKFEPIVGTKILAYDQN<br>QTAPDAYAILEICDDSEAFDYKGYKIKCLSTGDLASKSLTKQTEVDQLAYKGVDKTSNFYKKWKQQRRLFVKS<br>LNIPDALKSFENINKEYLYGFNNSYLKLLKQILRGKFGPILVDIRPELIEMCQGIGSIMRLSSLNHDSLDAIQSLKS<br>LLHSYFDLKVKEEIKTEELREKADKEVFKLLQQVIQKQKNKRKEKVNRTVDAILTLAADEQVQVIVGEGDLCV<br>STKGTKKRQNNRTIDWCARAVVEKLEKACKLHGLHFKEIPPHYTSHQDCFEHNKDIENPKEVMKCRFNSSENV<br>APWMIKKFANYLKCETKYYVQGMQDFLEHYGLVEYKDHIKKGKISIGDFQKLIKLALEKVGEKEIVFPCKGGR<br>IYLSTYCLTNESKPIVFNGRRCYVNNADHVAAINVGICLLNFNARAKVAEKTP |
| SEQ ID NO: 10 | >Wa2Cas12i protein<br>MAKKDFIARPYNSFLLPNDRKLAYLEETWTAYKSIKTVLHRFLIAAYGAIPFQTFAKTIENTQEDELQLAYAVRM<br>FRLVPKDFSKNENNIPPDMLISKLASYTNINQSPTNVLSYVNSNYDPEKYKWIDSRNEAISLSKEIGIKLDELADY<br>ATTMLWEDWLPLNKDTVNGWGTTSGLFGAGKKEDRTQKVQMLNALLLGLKNNPPKDYKQYSTILLKAFDAK<br>SWEEAVKIYKGECSGRTSSYLTEKHGDISPETLEKLIQSIQRDIADKQHPINLPKREEIKAYLEKQSGTPYNLNLW<br>SQALHNAMSSIKKTDTRNFNSTLEKYEKEIQLKECLQDGDDVELLGNKFFSSPYHKTNDVFVICSEHIGTNRKY<br>NVVEQMYQLASEHADFETVFTLLKDEYEEKGIKTPIKNILEYIWNNKNVPVGTWGRIAKYNQLKDRLAGIKAN<br>PTVECNRGMTFGNSAMVGEVMRSNRISTSTKNKGQILAQMHNDRPVGSNNMIWLEMTLLNNGKWQKHHIPT<br>HNNKFFEEVHAFNPELKQSVNVRNRMYRSQNYSQLPTSLTDGLQGNPKAKIFKRQYRALNNMTANVIDPKLSF<br>IVNKKDGRFEISIIHNVEVIRARRDVLVGDYLVGMDQNQTASNTYAVMQVVQPNTPDSHEFRNQWVKFIESGKI<br>ESSTLNSRGEYIDQLSHDGVDLQEIKDSEWIPAAEKFLNKLGAINKDGTPISISNTSKRAYTFNSIYFKILLNYLRA<br>NDVDLNLVREEILRIANGRFSPMRLGSLSWTTLKMLGNFRNLIHSYFDHCGFKEMPERESKDKTMYDLLMHTI<br>TKLTNKRAERTSRIAGSLMNVAHKYKIGTSVVHVVVEGSLSKTDKSSSKGNNRNTTDWCSRAVVKKLEDMCV<br>FYGFNLKAVSAHYTSHQDPLVHRADYDDPKLALRCRYSSYSRADFEKWGEKSFAAVIRWATDKKSNTCYKVG<br>AVEFFKNYKIPEDKITKKLTIKEFLEIMCAESHYPNEYDDILIPRRGGRIYLTTKKLLSDSTHQRESVHSHTAVVK<br>MNGKEYYSSDADEVAAINICLHDWVVPLNWTNHCLPAGWCSDHLKECVQCHTPDPVRISM |
| SEQ ID NO: 11 | >SiCas12i gene<br>ATGTCTAGTGATGTCGTTCGTCCATATAACACCAAACTGCTTCCAGATAATCGCAAACACAATATGTTTTTGC<br>AAACTTTCAAGCGACTTAATTCTATTTCTCTTAATCATTTTGATCTCTTAATTTGTCTTTATGCTGCCATTACCA<br>ACAAGAAGGCAGAAGAATATAAGTCTGAAAAAGAAGCTCATGTAACCGCTGATAGCCTTTGTGCTATCAAT<br>TGGTTCCGTCCTATGTCCAAGCGTTACAGCAAATACGCAACTACAACTTTCAATATGCTTGAATTGTTCAAA<br>GAATACTCTGGGCATGAACCAGATGCTTATTCCAAGAATTATCTTATGTCCAATATTGACTCAGACAGGTTTG<br>TCTGGGTTGATTGCCGTAAATTTGCCAAAGATTTTGCGTATCAAATGGAACTTGGTTTCCATGAATTTACAGT<br>CTTGGCAGAAACCTTGTTGGCAAATAGTATTCTTGTACTCAACGAATCAACTAAGGCAAATTGGGCATGGG<br>GCACCGTTTCTGCACTTTACGGTGGAGGCGATAAGGAAGATTCTACGCTGAAGTCGAAAATCCTTTTGGCTT<br>TTGTTGATGCACTCAATAACCACGAACTTAAAACTAAGCGTGAAATTCTCAATCAAGTTTGTGAATCACTAA<br>AATATCAATCATACCAAGACATGTATGTTGATTTCCGTTCTGTTGTTGACGAAAATGGAAACAAGAAGTCTC<br>CCAATGGCTCAATGCCAATCGTCACCAAGTTTGAAACAGATGATTTGATTTCTGATAATCAACGCAAAGCAA<br>TGATTTCTAATTTCACAAAGAATGCTGCTGCTAAAGCGGCTAAAAAACCTATTCCCTACCTAGACAGACTCA<br>AGGAACATATGGTTTCCTTGTGCGATGAATATAATGTTTATGCTTGGGCAGCAGCTATCACTAACTCTAATGC<br>CGATGTAACAGCTAGGAATACTCGCAATTTAACATTCATCGGGGAACAAAATTCTCGAAGGAAAGAACTATC<br>GGTTTTACAAACTACAACAAACGAAAAAGCAAAAGATATCTTGAATAAGATTAATGACAATCTTATTCAAGA<br>AGTAAGGTATACCCCTGCCCCCAAGCACTTGGGGCGTGATCTTGCCAATCTTTTTGATACTCTGAAAGAAAA<br>AGATATCAATAATATTGAAAACGAAGAAGAGAAGCAGAATGTAATTAATGATTGCATTGAGCAATATGTTGA |

-continued

SEQUENCE LISTING

TGATTGCCGTTCACTGAACCGCAATCCCATTGCTGCTTTGCTCAAGCACATTAGCCGATACTATGAAGATTTT
TCAGCCAAGAATTTCTTGGATGGTGCCAAGTTGAATGTCTTGACTGAAGTTGTAAATCGTCAAAAGGCACA
TCCAACTATTTGGTCTGAAAAGGCTTATACTTGGATTTCCAAGTTTGACAAGAATAGGCGACAAGCAAACTC
TTCTTTGGTTGGATGGGTTGTTCCACCAGAAGAAGTCCATAAAGAGAAGATTGCTGGTCAACAAAGCATGA
TGTGGGTCACTTTGACTCTGCTTGATGATGGCAAGTGGGTAAAGCACCATATTCCTTTTTCAGATTCCAGATA
TTATTCTGAAGTCTATGCCTACAATCCAAATTTGCCATATCTTGATGGTGGTATTCCACGCCAGTCAAAGTTT
GGCAATAAACCAACCACTAATCTGACTGCTGAAAGTCAAGCGTTACTTGCAAACAGCAAGTATAAAAAGGC
AAATAAGTCATTTCTCCGTGCCAAGGAAAATGCTACTCACAATGTCCGTGTTAGTCCAAACACTTCCTTGTG
CATTCGTTTGCTCAAGGATAGTGCTGGTAATCAAATGTTTGATAAGATTGGCAATGTTCTGTTTGGAATGCAG
ATCAACCATAAAATCACCGTTGGCAAGCCCAACTACAAGATCGAAGTTGGTGATAGGTTCCTTGGTTTCGAC
CAGAACCAAAGTGAAAACCACACTTATGCTGTCTTGCAACGAGTCTCTGAAAGCTCTCATGACACTCATCA
TTTTAATGGATGGGATGTCAAGGTTCTTGAAAAGGGCAAAGTAACAAGTGATGTCATCGTTAGAGATGAGG
TCTATGACCAACTTAGCTATGAGGGCGTTCCTTATGATTCTTCAAAGTTTGCAGAATGGAGAGACAAGAGGA
GAAGGTTTGTTTTGGAAAACTTGTCTATCCAGTTGGAAGAAGGCAAAACATTCTTGACTGAATTCGACAAA
TTAAATAAAGATTCTCTTTATCGTTGGAATATGAATTATCTGAAACTGCTCAGGAAAGCTATTCGTGCCGGTG
GCAAGGAATTTGCCAAGATTGCTAAGACTGAGATTTTTGAATTGGCAGTTGAAAGGTTTGGACCAATCAAC
CTTGGTAGTTTGTCACAAATTAGCTTGAAGATGATTGCATCTTTCAAGGGAGTGGTTCAGTCTTACTTTTCTG
TATCTGGTTGTGTTGATGACGCATCCAAGAAGGCACATGATTCCATGCTCTTCACTTTCATGTGTGCAGCAG
AAGAAAAAAGGACAAACAAAAGAGAAGAAAAGACTAATCGTGCAGCATCTTTTATCTTGCAGAAAGCATA
TTTGCATGGCTGCAAGATGATTGTTTGCGAAGACGATCTTCCTGTTGCTGATGGAAAAACAGGCAAGGCAC
AAAATGCGGATCGTATGGACTGGTGTGCCCGTGCTTTGGCAAAGAAAGTCAACGATGGTTGTGTGGCAATG
TCTATCTGCTATCGTGCCATTCCAGCTTATATGTCTAGCCACCAAGATCCATTTGTTCACATGCAAGACAAAA
AGACTTCTGTTTTGCGTCCAAGGTTCATGGAAGTTAACAAGGATAGCATCAGGGATTATCATGTTGCTGGTT
TGCGGAGAATGCTGAACAGCAAGAGTGATGCAGGCACTTCCGTTTACTATCGTCAGGCAGCTTTGCATTTCT
GCGAAGCGTTGGGCGTGTCTCCAGAATTAGTCAAGAACAAAAAGACTCATGCTGCCGAATTAGGAAAGCA
TATGGGTTCTGCCATGTTGATGCCTTGGCGGGGTGGCAGGGTTTATATTGCCAGCAAGAAGTTGACTTCGGA
TGCTAAAAGTGTAAAATACTGTGGAGAAGATATGTGGCAGTATCATGCTGATGAGATTGCTGCTGTCAATAT
CGCAATGTATGAAGTTTGCTGCCAGACAGGTGCGTTTGGCAAGAAGCAAAAGAAGAGTGATGAACTACCG
GGATAA

SEQ ID NO: 12

>Si2Cas12i gene
CATGTCTAGTGATGTTGTTCGTCCATATAACACTAAGCTGCTTCCTGATAATCGCAAATACAATATGTTTTTGC
AAACTTTCAAAAGACTCAATTTGATTTCATCAAATCATTTTGATCTCTTGGTTTGTCTTTATGCTGCTATCACC
AACAAAAAAGCTGAAGAATATAAGTCAGAAAAAGAAGATCATGTAACCGCTGATAGCCTTTGCGCCATCAA
TTGGTTCCGTCCTATGTCCAAGCGTTATATCAAATACGCAACCACTACTTTTAAGATGCTTGAATTGTTTAAG
GAGTACTCTGGTCATGAACCAGATACTTATTCCAAGAATTATCTCATGTCCAATATCGTCTCAGATAGGTTTG
TTTGGGTTGATTGCCGCAAATTTGCCAAAGATTTTGCCAATCAAATGGAACTTAGTTTCCACGAATTTACCA
CTTTGTCAGAGACTTTGTTGGCAAATAGTATCCTTGTACTCAATGAGTCAACCAAGGCAAATTGGGCATGGG
GTGCTGTTTCAGCACTTTATGGTGGAGGCGACAAAGAAGATTCTACGCTGAAGTCCAAAATCCTTTTGGCTT
TTGTTGATGCTCTCAATAATCCTGAACTTAAAACTAGGCGGGAAATTCTCAATCATGTTTGTGAATCACTAAA
ATATCAATCATACCAAGATATGTATGTTGATTTTCGATCTGTCGTTGATGATAAGGGAAACAAGAAGTCTCCC
AATGGCTCAATGCCAATCGTCACTAAGTTTGAATCAGATGATTTGATTGGTGACAATCAACGCAAAACTATG
ATTTCTAGTTTCACAAAAAACGCCGCTGCCAAAGCGTCTAAGAAGCCCATTCCATATCTAGACATTCTAAAA
GACCACATGATTTCCTTGTGCGAGGAATACAATGTCTATGCTTGGGCAGCAGCTATTACCAATTCCAATGCTG
ATGTAACTGCTAGAAACACTCGCAATCTGACATTCATCGGGGAACAAAATACCCGAAGGAAAGAACTATCG
GTTTTACAAACTTCTACAAACGAAAAAGCAAAAGATATCTTAAATAAGATTAACGACAATCTTATTCCAGAA
GTAAGGTACACCCCTGCTCCCAAGCACTTGGGGCGTGATCTTGCCAATCTTTTTGAAATGTTCAAAGAAAA
AGATATAAATCAGATTGGAAATGAAGAAGAAAAGCAAAATGTGATCAATGATTGCATTGAGCAATATGTCGA
TGATTGCCGTTCATTGAACCGCAATCCTGTTGCAGCTTTGCTCAAGCATATTAGCGGATATTATGAAGATTTT
TCAGCCAAGAATTTCTTGGATGGTGCCAAGTTGAATGTCTTGACGGAAGTTGTCAATCGTCAAAAGGCACA
TCCAACTATTTGTTCTGAAAAGGCTTATACTTGGATTTCCAAGATTGACAAGAATAGGCGACAAGCAAACTC
TTCTTTGGTTGGATGGGTTGTTCCACCGGAGGAAGTCCATAAGGAAAAAATTGCCGGTCAACAAAGCATGA
TGTGGGTCACTTTGACTTTGCTTGATGACGGCAAGTGGGTAAAGCATCATATTCCTTTTGCAGACTCAAGAT
ATTATTCTGAAGTCTATGCCTATAATCCAAATTTGCCATATCTTGAAGGTGGTATTCCACGACAATCAAAGTTT
GGCAATAAACCAACAACTAATTTGACCGCTGAAAGCCAAGCATTACTTGCCAACAGTAAGCACAAGAAAG
CCAACAAGACATTTCTCCGTGCCAAGGAGAATATCACTCACAATGTTCGTGTTAGTCCAAATACTTCATTGT
GCATTCGTCCCCTCAAGGATAGTGCTGGTAATCAAATGTTTGACAACATTGGTAATATGTTGTTTGGAATGCA
GATCAATCACAGAATTACTGTCGGCAAGCCAAACTACAAGATCGAAGTTGGTGATCGGTTCCTTGGTTTTGA
CCAGAACCAAAGCGAAAACCACACCTATGCAGTTCTTCAACGAGTATCCGAAAGCTCTCATGGCACTCATC
ATTTCAATGGTTGGGATGTCAAAGTGATTGAGAAGGGCAAGGTGACAAGTGATGTCGTCGTCAGAGATGAA
GTCTATGATCAATTAAGCTACGAGGGTGTCCCTTACGATTCTCCAAAGTTTACAGAATGGAGAGAGAAGAG
GCGAAAGTTTGTCTTGGAAAATATGTCAATCCAGATTGAAGAAGGCAAAACATTCTTGACTGAATTTGACA
AGTTAAACAAAGACTCTTTGTATCGTTGGAACATGAATTACATGAAATTGCTTAGGAAGGCAATTCGTGCTG
GTGGCAAGGAATTTGCCAAGATTACAAAGGCTGAGATTTTTGAACTAGGAGTTATGAGATTTGGACCAATG
AACTTGGGCAGCTTGTCGCAAGTCAGCTTGAAGATGATTGCTGCTTTTAAGGGAGTTATTCAGTCTTACTTT
TCCGTATCTGGTTGCATTGATGACGCATCCAAGAAAGCTCATGATTCGATGTTATTCGCTTTCTTGTGTTCAG
CAGATGAGAAAAGGACAAACAAGAGGGAAGAAAAGACAAATCGTGCAGCATCTTTCATATTGCAGAAAGC
ATACTCGCATGGTTGCAAGATGATTGTTTGCGAGGATGATCTTCCCATTGCCGATGGCAAGGTGGGCAAGGC
ACAAAATGCGGATCGCATGGACTGGTGCGCCCGTTCATTGGCAAAGAAAGTCAACGATGGTTGTGTGGCTA
TGTCCATATGTTATCGTGCCATTCCAGCATATATGTCAAGCCATCAAGATCCATTTACTCATATGCAAGATAAA
AAGACTTCTGTTTTGCGTCCAAGGTTCATGGAAGTCGGCAAGGATAGCATTAGGGATCATCATGTTGCTGGT
CTGCGGAGAATGCTGAACAGTAAAGGTAATACTGGCACTTCTGTTTACTATCGTGAGGCAGCTTTGCGTTTC
TGCGAAGCGTTGGGTGTGCTTCCCGAATTAGTCAAGAACAAAAAGACTCATGCTTCGGAATTAGGAAAGCA
TATGGGTTCTGCCATGTTGATGCCTTGGCGGGGTGGCAGGATCTATGTCGCCAGCAAGAAATTGACTTCGGA
TGCCAAGAGTATAAAATATTGTGGAGAAGATATGTGGCAATATCATGCTGATGAGATTGCTGCTATCAATATC
GCAATGTATGAGGTCTGCTGTCAGACAGGTGCTTTTGGCAAAAAACAAAAGAAGAGTGATGAACTACCGG
GATAA -continued

| SEQUENCE LISTING | |
|---|---|
| SEQ ID NO: 13 | >WiCas12i gene<br>ATGGGTATTAGCATTTCACGTCCGTACGGTACAAAGTTGCGTCCTGATGCTCGTAAGAAGGAAATGTTGGAT<br>AAGTTTTTCACCACGCTAGCAAAAGGTCAGCGTGTTTTTGCGGATCTGGGACTGTGCATTTACGGCAGCCTT<br>ACTTTAGAAATGGTAAAGCGGCTTGAGCCAGAATCCGATTCTGAACTTGTCTGTGCAATTGGTTGGTTTCGT<br>CTTGTAGATAAGGTAACTTGGTCTGAGAATGAAATTAAACAAGAGAACCTGGTTAGACAATATGAGACGTAT<br>TCAGGAAAAGAAGCGTCTGAGGTTATCAAGACTTACCTAAGCTCTCCAAGTTCAGACAAGTATGTGTGGAT<br>AGACTGCCGACAAAAGTTTCTTAGGTTTCAAAGGGATCTGGGAACACGTAATCTGTCTGAAGACTTTGAGT<br>GCATGCTTTTTGAACAGTACCTCAGACTCACAAAGGGAGAGCTTGATGGGCATACCGCTATGTCCAACATGT<br>TTGGAACAAAAACAAAGAAGATCGCGCCACAAAACTGAGATATGCCGCAAGGATGAAAGAATGGCTCGA<br>GGCTAACGAAGAAATTACTTGGGAACAATATCACCAAGCGTTGCAAGATAAATTAGACGCCAATACTTTAGA<br>GGAGGCTGTTGATAATTACAAAGGCAAAGCGGGAGGCTCTAATCCATTTTTTAGTTACACGCTTTTAAACAG<br>AGGTCAGATTGATAAAAAAACTCACGAGCAGCAATTAAAGAAATTCAACAAAGTTCTAAAAACCAAATCC<br>AAAAATTTAAATTTTCCAAACAAAGAGAAGTTAAAACAATATTTAGAAACAGCAATTGGTATTCCTGTTGAT<br>GCTCAGGTCTACGGTCAGATGTTTAATAACGGCGTTTCTGAAGTTCAACCAAAGACAACGCGCAACATGTC<br>TTTTTCTATGGAGAAGCTTGAGCTTTAAACGAGTTGAAAAGTCTCAACAAGACTGACGGTTTTGAACGCG<br>CTAATGAAGTCTTGAATGGTTTCTTTGATTCTGAACTTCACACTACTGAAGACAAGTTCAACATCACTTCCA<br>GGTATTTGGGTGGAGACAGAAACAATCGGCTACCAAAGCTGTACGAGCTTTGGAAAAAGGAAGGAGTAGA<br>TCGTGAGGAAGGTATCCAGCAATTCAGCCAAGCAATCCAAGATAAGATGGGTCAGATACCTGTTAAGAATG<br>TCCTTAGGTATATTTGGGAATTTCGTGAGACTGTTTCTGCCGAAGACTTTGAAGCGGCAGCGAAAGCGAATC<br>AGTTGGAAGAAAAAATCACGCGTACCAAAGCGCACCCCGTTGTTATATCTAACAGGTATTGGACATTTGGCT<br>CTTCGGCTCTTGTTGGTAATATCATGCCAGCAGACAAGATGCACAAAGACCAGTACGCAGGTCAAAGTTTC<br>AAGATGTGGCTTGAAGCCGAACTGCACTACGACGGTAAGAAAGTCAAACATCACTTGCCGTTCTACAACGC<br>CAGGTTCTTTGAAGAGGTCTACTGCTATCACCCGAGCGTAGCTGAAGTTACACCATTCAAAACCAAGCAGT<br>TTGGTTATGCAATTGGAAAAGATATTCCAGCTGACGTTTCGGTTGTACTGAAAGACAATCCTTATAAAAAGG<br>CAACCAAGCGCTTCCTTCGGGCTATCAGCAATCCAGTCGCCAACACAGTGGATGTAAACAAGCCTACAGTT<br>TGCTCATTCATGATTAAACGAGAAAATGACGAATACAAACTAGTCATTAATCGAAAGATCGGTGTTGATCGC<br>CCAAAGCGTATTAAAGTAGGTAGGAAGGTCATGGGCTATGACCGTAACCAAACTGCTTCTGATACTTACTGG<br>ATTGGAGAGCTTGTTCCACATGGAACAACCGGAGCGTACCGTATTGGAGAATGGAGCGTCCAGTATATCAA<br>GAGCGGTCCCGTGTTGTCTTCTACGCAAGGCGTAAATGACAGTACTACGGATCAACTTATATACAACGGAAT<br>GCCGAGCTCCAGCGAACGTTTTAAAGCTTGGAAGAAATCTAGGATGTCTTTCATTCGTAAGTTGATACGCCA<br>ACTGAACGCCGAAGGCTTGGAAAGTAAAGGACAGGACTATGTTCCTGAAAATCCAAGTAGCTTTGATGTTA<br>GGGGCGAAACACTTTACGTATTCAACAGCAACTATATGAAAGCTTTGGTGTCTAAGCATCGAAAAGCCAAG<br>AAACCTGTTGAAGGTATTCTTGAAGAAATAGAAGCCTTGACAAGCAAAGCTAAAGATTCTTGTTCGTTGAT<br>GCGTTTGAGTTCTTTGTCTGATGCGGCTATGCAAGGTATTGCTTCGTTGAAGAGTTTGATCAACTCATACTTC<br>AACAAGAATGGTTGCAAAACAATTGAAGACAAAGAAAAGTTTAACCCAGATCTGTATGTGAAACTTGTTGA<br>AGTTGAGCAAAAGAGAACTAACAAGAGAAAAGAAAAAGTTGGTCGAATCGCCGGTTCTCTTGAACAGTTA<br>GCTTTGCTTAACGGTGTTGACGTTGTTATCGGTGAAGCTGATCTTGGCGAAGTCAAGAAAGGCAAATCCAA<br>AAAACAAAATAGTCGAAACATGGACTGGTGTGCCAAGCAAGTCGCTGAGCGGCTTGAGTACAAGCTGACC<br>TTCCATTGTATTGGTTATTTTGGTGTCAACCCGATGTATACGTCTCATCAAGATCCATTTGAACATCGTCGCGT<br>TGCTGACCACCTAGTAATGCGTGCGAGGTTTGAAGAAGTGAATGTAAGTAATGTTTCGGAATGGCACATGC<br>GAAACTTCTCAAACTATCTGCGTGCGGACTCAGGTACTGGTTTGTATTACAAACAAGCTACCTTGGATTTCC<br>TCAAGCATTATGATTTGGAAGAGCACGCCGATGATTTGGAAAAGCAGAATATCAAATTCTATGACTTCAGGA<br>AAATTCTTGAAGACAAACAATTGACTTCTGTTATTGTTCCAAAACGTGGCGGTCGCATTTACATGGCGACTA<br>ACCCGGTAACTTCCGATAGTACGCCTGTCACTTATGCCGGTAAAACTTACAACCGGTGTAATGCTGACGAAG<br>TGGCTGCGGCTAACATCGCTATCAGCGTCTTAGCTCCTCACTCTAAGAAAGAAGAAAAGGAAGATAAGATC<br>CCGATTATTTCTAAGAAGCCTAAGTCTAAGAATACTCCCAAGGCCCGGAAGAATTTAAAGACTTCTCAACTT<br>CCTCAGAAA |
| SEQ ID NO: 14 | >Wi2Cas12i gene<br>ATGGCTAGCAAACATGTAGTGCGTCCCTTTAATGGCAAAGTAACAGCTACTGGCAAGCGTTTGGCATACTTG<br>GAAGAAACTTTTCATTATTTGGAAAAAGCTGCTGGTGGTGTTAGTACTTTGTTTGCTGCCCTTGGTTCTTATC<br>TTGATGCAACCACAATAAGCAATTTAATTAATAAAAATCAAGATTTAGCCGTTGTAATATTTCGTTATCATGTG<br>GTTCCCAAAGGTGAGGCTCATACTTTACCTGTAGGTACAGACATGGTTAGTCGTTTTGTTGCCGACTATGGT<br>ATGGAGCCGAATGAGTTTCAGAGAGCTTATTTGGACAGTCCGATTGACCAAGAAAAGTATTGTTGGCAGGA<br>TAATAGGGATGTTGGTTGTTGGTTGGGTGAGCAATTGGGTGTTAGCGAAGCGGACATGCGGGCAATAGCAG<br>TAACTTTTTATAACAATCAGATGCTTTATGATTGTGTAAAAGGTACTGGGAGTGGTAATGCTGTGAGTCTTTT<br>GTTTGGCAGTGGTAAAAAGTCTGATTACAGTATGAAGGGCGTTATAGCAGGTAAGGCTGCTTCAGTACTGG<br>CAAAATATCGCCCAGCTACCTATCAAGATGCCCGAAAGATGATTTTGGAAGCTAATGGTTTCACCTCAGTAA<br>AAGATTTGGTTACTTCTTATGGAATAACTGGAAGGTCTAGTGCTTTGCAGATATTTATGGAAGGGATTGAAA<br>GTGGTCCTATTAGCAGCAAGACATTAGATGCTCGTATTAAGAAGTTCACAGAGGATTCGGAGCGCAATGGC<br>AGGAAGAATCTAGTCCCTCATGCTGGGGCTATACGAAATTGGCTGATTGAGCAAGCTGGTAGTAGTGTAGA<br>AAACTATCAGATGGCATGGTGCGAGGTTTACGGTAATGTGTCTGCCGACTGGAATGCCAAAGTAGAAAGTA<br>ATTTCAATTTCGTAGCGGAGAAAGTAAAGGCATTAACAGAATTATCCAACATTCAGAAATCGACTCCTGATT<br>TGGGTAAGGCTTTGAAATTATTTGAAGAATATTTGACTACTTGTCAGGATGAATTTGCTATTGCGCCTTATCAT<br>TTTAGCGTCATGGAAGAGGTGCGAATGGAAATGGCAACAGGCAGGGAATTCAATGATGCTTATGATGACGC<br>CCTAAATAGCTTGGACATGGAGTCTAAGCAGCCCATTCAGCCTTTGTGTAAGTTTTTGATTGAGCGTGGAGG<br>TAGTATCAGTTTTGATACTTTCAAGAGTGCAGCCAAGTATTTGAAAACACAGAGCAAGATTGCTGGTCGATA<br>TCCACATCCATTTGTAAAAGGTAATCAGGGATTTACTTTTGGTTCCAAAAACATTTGGGCAGCCATCAACGA<br>TCCTATGATGGAGTATGCAGATGGTCGTATTGCTGGTGGTTCTGCAATGATGTGGGTGACGGCTACATTGTTG<br>GATGGGAAAAAGTGGGTTCGCCATCATATCCCATTTGCCAATACTCGATACTTTGAGGAGGTTTATGCTAGC<br>AAGAAAGGGTTGCCTGTATTGCCTTGTGCTAGAGATGGCAAACACTCATTTAAATTGGGCAATAATTTGAGT<br>GTAGAGAGAGTTGAAAAGGTCAAAGAAGGCGGTAGAACTAAAGCAACCAAGGCACAAGAGCGTATTTTA<br>AGCAACTTGACTCACAATGTGCAGTTTGACAGTTCGACAACTTTTATTATTCGTCGTCAGGAAGAAAGTTTT<br>GTAATTTGCGTGAATCATCGACATCCAGCTCCGCTCATGAAGAAGGAGATGGAAGTTGGCGACAAAATCAT<br>TGGTATCGACCAGAATGTGACGGCACCCACAACCTATGCCATAGTTGAGCGTGTGGCTTCTGGCGGCATTG<br>AGCGTAACGGCAAGCAGTACAAAGTGACGGCGATGGGAGCCATTTCCAGCGTTCAGAAGACCAGAGGCG |

-continued

SEQUENCE LISTING

GTGAGGTGGATGTTTTGAGTTATATGGGGGTTGAACTTTCTGACAGCAAAAATGGATTTCAAAGCTTGTGGA
ATAAATGTTTGGACTTTGTTACCAAACATGGCACTGAAAATGATGTTAAATATTATAACAACACTGCTGTCTG
GGCCAACAAGCTGTATGTGTGGCACAAGATGTATTTCCGGCTTTTGAAGCAGTTGATGCGTCGGGCAAAGG
ACTTGAAACCTTTCAGGGACCATTTACAGCATCTATTATTCCATCCTAATCTTAGTCCCTTGCAACGCCATAG
CTTGTCCTTAACAAGTCTGGAAGCAACTAAGATAGTGCGGAATTGCATTCATTCGTATTTCAGTCTATTGGGG
TTGAAGACCTTGGATGAACGCAAAGCCGCTGACATCAATTTATTGGAAGTTTTGGAAAAGCTGTATGCTGG
TTTGGTTGAGAGGCGAAAAGAAAGAACCAAACTAACCGCTGGGCTATTGGTTCGCTTATGTAATGAGCATG
GGATTTCTTTTGCAGCTATTGAGGGTGATTTGCCGGTCGTTGGAGAGGGCAAATCTAAAGCTGCCAACAATA
CACAACAGGATTGGACAGCCAGAGAGTTAGAGAAGCGATTATCTGAGATGGCGGAGGTGGTTGGCATCAA
GGTAATAGCTGTTTTGCCCCACTATACCAGTCATCAGGACCCATTTGTTTATAGTAAAAATACCAAGAAAATG
AGATGTCGTTGGAACTGGAGGACCACCAAGACCTTCACTGATCGTGATGCTTTGAGTATACGCAGGATATTA
AGCAAGCCTGAGACGGGTACAAATTTGTATTATCAGAAGGGCTTGAAAGCATTTGCTGAAAAGCATGGTCT
GGATTTGGCAGAGATGAAGAAGCGCAAGGATGCTCAATGGTATCTTGAGCGCATTCAAGACAAGAATTTTT
TGGTGCCAATGAATGGTGGTAGAGTTTATTTGAGTTCTGTCAAATTAGCCGGGAAAGAAACAATTGACATG
GGTGGCGAAATTTTATATCTTAACGATGCCGATCAAGTCGCAGCGTTGAATGTTTTGTTAGTGAAGATTTGA

SEQ ID NO: 15

>Wi3Cas12i gene
ATGGCTAAGAAAGAACATATTATAAGACCATTCAAAGGAACACTACCACTTCGTGGTGATAGACTAAGGTAT
CTTCAAGATACCATGAAATATATGAAAAAGGTTGAAGATACTATCACAGAACTCTGCGCCGCTGTTATCGCC
TATGCCAAACCCACCATCATTCAACAAATACTTGGCGAAGAAATTGAAACCACCAGCACATTTTGTAGCTTC
CGCTTAGTAGGCATTCATGAAAACTTTACCATGCCACTAACCACAAATATGATAAAACACTTCCAGAAAACC
TTTAACATAAACCCATCAGAAAAACAAGCAATCTATCTCTCCAGTGGATTCGATTCAGATAAATATCGCTGGC
AAGATACTTCCGAAGTATCCAGAAACTTCGCCAACAAATGCCGACTTACTAATCAAGAATTCCAAGAATTTG
CCGAACAAGCACTACTCAATATGTGCTTCATAGGTTGCTCTGGTAGCCCCGGTGCAACTAATGCCGTCTCAC
AAATCTTTGGCACAGGCGAAAAAAGCGATTACCAACGCAAAAGCCAAATCGCTAAAATTGCTGCTGATACC
CTCGAAAACCACAAACCTAGCACCTATGAGTCTGCTAGATTAATGGTTCTTAATACACTTGGACACAAAACA
ATAGAAGATTGTGTCAATGACTATGGCGCAATAGGAGCCAAATCCGCCTTCCGACTATTCATGGAATCAAAA
GAAATAGGACCAATTACATCTGAACAACTCACAACCAAAATTAAGAAGTTCAGAGAAGATCATAAAAAGA
ACTCCATCAAGAAACAACTTCCACATGTAGAAAAAGTTCGTAACGCTTTGCTATCACAATTCAAAGAACAA
TACCTGCCCTCAGCATGGGCAGAAGCATGGTGCAATATCATGGGCGAATTTAACTCCAAATTATCAAATAATA
ATAACTTCATCGACCaaaaaacaaaaaTGGTCAATGACTGCGATAATATTAAAAAATCTAATCCACAACTAGACAA
AGCTGTTAATATGCTCGATGAATGGAAATATAAAAACTGGGATGATAATTCTGCTATACACCCATATCATATTG
GCGATCTTAAAAAACTCATGGCAATATTCAATATCAATAACGAAGGAACCTTCGACGAAAGATTTTCAGCTA
GCTGGGAACAATTCTCCACATCACTAGAATACGGGGAGAAACCACCCGTTCGTGATCTACTAGCCCATATCA
TCAAAAATATGAATGACCTCACCTACACAGACGTAATCAACGCCGCAAAATTTCTCAAACTTCAAGATAATA
TAAGAAATAAATACCCACACCCTTTCGTTATGCCAAATAAAGGATGTACCTTTGGTAAAGATAACCTTTGGG
GCGAAATTAATGACCCCACAGCCAAAATCAAATCAACAGAAGAAGTTGCTGGACAAAGACCTATGATGTG
GCTGACAGCCAAACTTCTCGATAATGGAAAATGGGTAGAACACCACATCCCTTTCGCCTCCAGTAGATACTT
TGCCGAAGTTTATTATACCAATCCAGCACTCCCCACTCTACCAATAGCTAGAGATGGAAAACATTCATACAA
ATTAACAAAAACTATAGATGCCAATACTGCAAAAACTCTAGTAAATAATCCTAGAGATAAAGCAGCTAAACT
AATCGCACGAACTAAAGCCAATACTACACACAATGTAAAATGGATTAAACCTACATACAGAATCCAAAAAG
AAAATAACCAATTCGTTATTACTATCAATCATCGACACCCATGCATAACACCACCAAAGGAAATCATACTCGG
AGATCGTATCCTATCCTTCGACCAAAACGAAACAGCCCCCACAGCATTCTCCATTCTCGAAAAAACAACCA
AAGGTACAGAATTCTGTGGCCACCACATTAAAGTGCTAAAGACTGGTATGCTAGAAGCTAAAATTAAAACC
AGTAAGAAATCAATAGATGCATTCACATACATGGGACCAATGGAAGATGATCATGCGTCTGGCTTCCCAACA
CTACTCAACATATGTGAAAAATTCATATCAGAGAATGGAGATGAAAAAGACAAAAGTTTCTCTTCTCGTAAA
TTGCCCTTTAAAAGGTCTTTGTACTTCTTTCATGGCTCACACTTCGATTTACTAAAGAAAATGATCAGAAAG
GCCAAAAATGACCCCAAGAAATTGAAGTTAGTAAGAATTCATATCAATGAAATTCTATTCAATTCCAATTTGT
CACCAATAAAACTACACAGTCTGTCTATTCACAGCATGGAAAATACCAAAAAAGTTATAGCTGCTATTAGCT
GCTATATGAATGTTCATGAATGGAAAACTATCGATGAACAAAAGAATGCTGATATAACATTGTATAATGCTAA
AGAAAAACTATACAACAACCTTGTTAACCGCCGTAAAGAAAGAGTAAAAGTAACTGCAGGTATGTTGATTC
GATTAGCTAGAGAAAACAATTGCAGATTCATGGTCGGGGAAGCAGAATTACCCACCCAACAACAAGGCAA
ATCAAAAAAGAACAATAACTCCAAACAGGATTGGTGCGCCAGAGATATAGCACAACGATGTGAAGATATGT
GCGAAGTCGTAGGTATAAAATGGAATGGCGTTACTCCGCATAATACCAGCCATCAAAACCCATTCATCTATAA
AAATACTAGTGGACAACAAATGCGATGCCGTTATAGTCTCGTAAAGAAGTCAGAAATGACAGACAAGATGG
CAGAAAAAATTAGAAATATTTTACACGCTGAACCTGTAGGCACTACAGCATACTACCGTGAAGGCATTTTGG
AATTCGCCAAACATCATGGATTAGATCTGGGAATGATGAAAAAACGAAGAGATGCTAAGTATTATGATAATC
TTCCAGATGAGTTTCTGCTTCCTACTAGAGGTGGTAGAATCTATCTGTCCGAAAATCAACTAGGCGGAAACG
AAACCATTGTTATTAATGGGAAAAAATATTTGTCAATCAGGCAGATCAAGTCGCTGCCGTAAATATTGGCCT
GCTTTATCTTCTGCCGAAGAAAAACCAGAGTTAAG

SEQ ID NO: 16

>SaCas12i gene
ATGTCCGAGAAGAAGTTCCACATCAGGCCCTACCGCTGCTCGATAAGCCCGAACGCCCGCAAGGCCGATAT
GCTCAAGGCGACGATCTCCTACCTTGACTCCCTGACCTCCGTGTTCAGGTCGGGATTCACCGCACTACTTGC
GGGCATAGACCCGTCGACGGTGAGCCGCCTGGCGCCTTCGGGGGCCGTCGGCAGCCCGGACCTGTGGAGC
GCCGTCAACTGGTTCCGCATCGTGCCGCTCGCAGAGGCCGGCGACGCCCGAGTCGGCCAGGCATCGCTCA
AGAACCTCTTCCGTGGCTACGCAGGCCACGAGCCCGACGAAGAGGCGTCGATCTATATGGAGTCGAGAGT
GGACGATAAGAGGCACGCGTGGGTGGACTGCCGTGCCATGTTCAGGGCGATGGCGCTCGAGTGCGGGCTG
GAGGAGGCCCAGCTCGCCTCCGACGTGTTCGCCCTCGCCTCAAGGGAGGTCATAGTCTTCAAGGACGGCG
AGATCAACGGCTGGGGCATAGCCTCCCTGCTGTTCGGCGAGGGCGAGAAGGCCGACTCGCAAAAGAAGGT
CGCCCTGCTCCGCTCCGTGAGGCTGGCCCTTGAGGGGGACTACGCGACCTACGAGGAACTCTCCGGGCTC
ATGCTGGCCAAGACCGGAGCCTCCAGCGGCTCCGACCTCCTTGACGAGTACAAGAGGAGCGAGAAGGGC
GGCAGCAGCGGCGGCAGGCACCCCTTCTTCGACGAGGTCTTCCGGAGGGGCGGCAGGGTCAAGCAGGAG
GAGCGCGAGAGGCTGCTGAAGAGCTGCGACACAGCGATCCAGAAGCAGGGGCAGGCGCTGCCGCTGTCG
CACGTCGCATCTTGGAGGCAATGGTTCCTGCGCAGGGTCACGCTGCTGCGCAACCGCAGGCAAGAGTCGT
TCGCAGTCTGCATCACCAACGCCCTCATGGACCTACAGCCCAAGAACCTACGCAACGTCCACTACGTGACG
AACCCCAAGAGCGAGAAGGACAAGGGCGTGCTCGAGCTGCGCGTCGACGTCAAGAACAACGAGGGGCCG -continued

SEQUENCE LISTING

GACGTGGCGGGCGCGCAGGCGGTCTTCGACGCCTACATGGCGAGGCTGGCACCCGACCTGCGCTTCTCCG
TGATGCCACGGCACCTCGGCTCCCTCAAGGACCTCTACGCCCTTTGGGCCAAGCTCGGGCGGGACGAGGC
CATCGAGGAGTACCTCGAGGGCTACGAGGGACCATTCAGCAAGAGGCCCATCGCAGGCATTCTACAAATCA
TCCACGCACACCGTGGCAAGGTGGGCTACGATAGCCTGTTGCGTGCGGCGAGGCTCAACAGGGCGATGGA
CAGGCTGGAGAGGAAGAGGGCCCACGCCTGCGCAGCCGGCAACAAGGGTTACGTCTACGGCAAGAGCTC
GATGGTCGGCCGCATCAACCCGCAGAGCCTCGAGGTCGGCGGCCGCAAGTCGGGCCGAAGCCCGATGATG
TGGGTGACCCTCGACCTGGTGGACGGCGACAGGTTCGCGCAGCACCACCTTCCCTTCCAGAGCGCCCGCT
TCTTCTCCGAGGTCTACTGCCACGGCGACGGGCTCCCGGCCACCCGTGTCCCCGGCATGGTCAGGAACCGT
CGCAACGGGCTGGCGATAGGGAACGGGCTCGGGGAGGGTGGACTCTCAGCGCTGCGCGCAGGCAGCGAC
AGGAGGAAGAGGGCCAACAAGAGGACGCTGCGCGCCCTCGAGAACATCACGCACAACGTGGAGATCGAC
CCCAGCACCTCCTTCACGCTGCGGGAGGACGGGATAATCATTTCGCACAGGATCGAGAAGATTGAGCCGAA
GCTTGTCGCCTTCGGGGACAGGGCGCTCGGCTTCGACCTCAACCAGACAGGGGCTCATACGTTTGCGGTGC
TCCAGAAGGTGGACTCGGGCGGCCTAGACGTCGGCCACTCTCGCGTGTCGATCGTGCTCACCGGCACTGTT
CGCAGCATCTGCAAGGGCAACCAGGCGAGCGGCGGACGGGACTACGACCTGCTTTCCTACGACGGCCCCG
AGCGCGACGACGGGGCGTTCACGGCATGGAGGTCGGACAGGCAGGCCTTCCTGATGTCTGCCATACGGGA
GCTGCCCACGCCCGCCGAGGGGGAAAAGGACTACAAGGCAGACCTCCTCTCCCAGATGGCGAGCCTTGAC
CACTACAGGCGACTGTACGCGTACAACAGGAAGTGCCTCGGCATCTACATCGGGGCCTTGAGACGCGCGA
CCAGGAGGCAGGCCGTGGCCGCATTCAAGGACGAGATACTCTCGATCGCGAATCACCGCTGCGGGCCTCTC
ATGCGTGGGAGCCTTTCGGTGAACGGCATGGAGTCCCTCGCGAACCTCAAGGGCCTAGCCACGGCATACCT
GAGCAAGTTCAAGGACAGCAAGTCCGAGGACCTGCTGTCGAAGGACGAGGAGATGGCCGACCTGTACAG
GGCTTGCGCGCGCAGAATGACTGGCAAGCGCAAGGAGAGGTACAGGAGGGCGGCTAGCGAGATCGTCCG
GCTGGCCAACGAGCACGGCTGCCTGTTCGTCTTCGGCGAGAAAGAGCTGCCCACCACCAGCAAGGGCAAC
AAGAGCAAGCAGAACCAGAGGAACACCGACTGGTCGGCCCGTGCCATAGTGAAGGCGGTCAAGGAGGCC
TGCGAGGGCTGCGGTCTCGGCTTCAAGCCCGTGTGGAAGGAGTACTCGAGCCTCACGGACCCGTTCGAGA
GGGACGGGGACGGAAGGCCTGCCCTCCGCTGCCGGTTCGCCAAGGTGGCCGCACCCGACTCCGAACTCCC
GCCTCGCCTGACGAAGGCCGTCGGCTCCTATGTGAAGAACGCCCTCAAGGCCGACAAGGCGGAGAAGAA
GCAGACCTGCTACCAGCGTGGCGCCATCGAGTTCTGCTCAAGGCACGGCATCGACGTCCGGAAGGCGACC
GACAAGGCCATTCGCAAGGCAGTCCGTGGCTCCTCCGACCTGCTTGTGCCGTTCGACGGGGGGAGGACCT
TCCTGCTCTCGACGAGGCTGTCCCCGGAGTCGCGAAAGGTGGAGTGGGCCGGGCGCACCCTGTACGAGTT
CCCCAGCGACATGGTCGCCGCAATCAACATCGCCTGCAGGGGCCTAGAGCCACGCAAGGCCTAG

SEQ ID NO: 17

>Sa2Cas12i gene
ATGGACGAGCAAGCTGTTGTTTCCTCTGGTTCCGACAAGACCCTCAAGATCGTACGCCCTTACAGGGCAAA
AGTAACCGCTACTGGAATTCGCCTTGAGGGAATTAAAAATACCCTGAATTACCTGAAGCGTACAGAAATTTG
TCTGTCACGCCTGAATGCAGCTTGTGGAGCTTTTCTCACTCCTGCCATCGTGGAGCAGATCTGTAAGGACG
ATCCTGCCCTAGTTTGTGCCATTGCTCGCTTTCAATTGGTTCCGGTTGGTAGTGAAGCCACTTTGTCCGACA
GTGGGCTAATGCGTCATTTTAAGGCTGCTCTCGGTGAATTGACCCCGCTACAAGAAGCCTACCTGAATAGCA
GCTATAACGACGAATTGTACGCATGGCAGGATACTCTTGTCTTAGCGCGACAGATTATTGCTGAAACCGGAT
TGACTGAAGATCAATTCCGCGCCTTTGCTCATGCCTGTTTCAAGAACGGCAATATTATCGGGTGCGCTGGTG
GTCCCGGTGCCAGCAACGCCATCTCTGGCATTTTTGGCGAGGGAATTAAATCCGATTATTCACTCCGAAGTG
AAATGACCGCTGCCGTTGCAAAGGTGTTTGAAGAGAAACGTCCTATCACTTACGAAGAAGCTCGGGCTCTC
GCTCTGGAAGCAACTGGACACGCCAGCGTTCAGTCTTTCGTGGAAGCATTTGGTAAACAGGGGCGTAAAG
GCACTCTGATTCTTTTCATGGAAGATACCAAGACAGGCGCATTCCCAAGCAATGAATTCGATTACAAGCTCA
AGAAACTGAAGGAGGATGCAGAGCGTGTCGGGCGTAAGGGTATCATCCCGCACCGCGATGTGATTGCTTCT
TATCTCCGCAATCAGACTGGTGCTGATATTGAATACAACTCCAAGGCATGGTGCGAGTCCTACTGTTGTGCC
GTGAGCGAATACAACTCAAAGATGAGCAACAATGTTCGATTTGCCACGGAAAAAAGTCTTGATTTGACCAA
GCTTGATGAAACGATCAGGGAAACGCCCAAGATCAGTGAAGCCATGCTTGTTTTTGAAAACTACATGGCGC
GAATTGATGCCGATCTCCGGTTCATTGTGAGCAAGCATCATCTCGGCAATCTCGCCAAATTCCGTCAGACCA
TGATGCATGTCTCTGCATCAGAATTTGAAGAGGCTTTTAAGGCGATGTGGGCTGATTACTTGGCTGGTCTGG
AATACGGTGAAAAACCCGCGATCTGTGAACTGGTGCGGTATGTCCTGACCCATGGCAACGATTTGCCTGTC
GAAGCGTTTTACGCTGCGTGCAAGTTCCTTAGCTTGGATGACAAGATCAAGAATCGTTACCCTCACCCATTT
GTTCCGGGTAACAAAGGCTACACCTTTGGCGCGAAAAACTTGTGGGCAGAAATCAATGATCCCTTCAAGCC
CATCCGTCAAGGCAACCCAGAGGTTGCTGGTCAACGCCCCATGATGTGGGCTACCGCCGACCTTCTGGACA
ACAACAAATGGGTCTTGCATCACATCCCCTTTGCCTCCAGCAGGTATTTCGAGGAAGTGTACTACACCGATC
CCTCGCTTCCTACGGCTCAAAAGGCGCGAGACGGCAAGCATGGCTATCGGTTGGGCAAAGTGCTGGATGA
GGCTGCTCGGGAGCGTTTAAAAGCAAATAATCGCCAGCGCAAGGCAGCTAAAGCCATCGAGCGGATCAAA
GCCAACTGTGAGCACAATGTGGCTTGGGATCCGACCACCACCTTCATGCTTCAGTTGGATTCTGAGGGTAAT
GTGAAAATGACGATCAATCATCGTCACATTGCCTATCGCGCACCCAAGGAAATTGGTGTTGGGGACAGGGT
GATTGGCATCGACCAAAACGAGACTGCTCCTACAACCTACGCCATTCTTGAGCGCACGGAAAATCCTCGCG
ATCTTGAATACAACGGCAAGTATTACCGTGTAGTCAAGATGGGTAGTGTGACTTCACCGAATGTCAGCAAGT
ATCGCACGGTGGACGCTTTGACTTACGATGGCGTGTCCTTGTCGGATGATGCTTCTGGTGCTGTGAACTTTG
TGGTATTGTGTCGCGAGTTTTTTGCAGCACATGGCGACGATGAGGGTCGCAAGTACCTTGAGAGGACTTTG
GGGTGGAGTTCAAGCCTGTATTCCTTCCATGGAAACTATTTCAAGTGCCTTACGCAGATGATGCGTCGATCC
GCTCGTTCTGGTGGTGATTTGACGGTCTATCGCGCCCATTTGCAGCAGATCCTGTTCCAACACAATCTGTCG
CCCTTGAGGATGCACAGCTTGTCTTTAAGGAGCATGGAATCGACGATGAAGGTCATCAGTTGCATGAAGAG
CTACATGTCTCTTTGTGGCTGGAAGACCGACGCGGATCGGATTGCCAATGATAGGTCGCTGTTTGAGGCTGC
TCGTAAGCTTTACACCAGTTTGGTAAATCGTCGGACGGAGCGGGTTCGTGTGACTGCTGGCATTCTGATGCG
TCTGTGCTTGGAGCACAACGTTAGGTTTATTCACATGGAGGATGAACTTCCTGTGGCTGAAACGGGCAAAA
GCAAGAAAAGCAATGGCGCGAAGATGCATTGGTGTGCCCGGGAGCTTGCCGTTCGTTTGTCCCAGATGGCA
GAGGTGACGAGCGTCAAGTTCACAGGTGTGTCACCGCATTACACTAGCCATCAAGACCCATTTGTGCATTC
CAAGACTAGTAAGGTAATGCGTGCCCGTTGGAGTTGGCGGAATCGTGCCGATTTCACGGACAAGGATGCGG
AGCGTATTCGGACGATTCTGGGTGGTGATGACGCAGGGACGAAGGCTTATTATCGCTCGGCGTTGGCTGAAT
TTGCCTCGCGCTATGGTCTGGACATGGAGCAGATGCGGAAGAGGCGCGATGCTCAGTGGTATCAAGAGAGA
CTGCCAGAAACCTTTATTATTCCTCAGCGGGGTGGTAGAGTGTACTTGTCTTCTCACGATCTGGGATCAGGT
CAAAAAGTTGACGGGATTTATGGTGGTCGTGCTTTCGTGAATCACGCTGACGAGGTTGCTGCGCTGAATGT
GGCGTTGGTCAGGCTGTGA -continued

SEQUENCE LISTING

SEQ ID NO: 18

>Sa3Cas12i gene
ATGAAGACTGAAACTCTTATCCGTCCCTACCCCGGCAAACTCAACCTCCAACCCCGTCGAGCACAATTCCT
CGAAGACTCCATTCAATATCACCAGAAAATGACGGAATTTTTCTACCAATTCCTCCAAGCAGTCGGCGGTGC
CACCACGCACCAAAACATCAGCGATTTCATCGACAATAAAGCCACCGATGAACACCAAGCCACTCTCCTCT
TCCAAGTAGTCTCCAAAGACAGCACAACACCAGAATGCCCCGCAGAAGAACTCCTAGCCCGATTTGCCCA
ATACACCGGCAAACAACCCAATGAGGCTGTCACCCACTACCTGACCAGCAGAATCAATACAGATAAATACC
GCTGGCAGGACAATCGACTCCTCGCCCAAAACATCGCTTCACAACTGAACATCTCCGAAACTCAATTCCAA
GAGATCGCTCACGCAATCCTGTCCAACAACCTATACATCGGTCAAACTGCATCCAACGCAGCAGCCAACTT
CATCAGCCAAGTCACAGGCACAGGCCAGAAAGCCCCCAAGGCAGCACGGCTCGATGTCCTGTTCCAGACC
AACCAAGCCCTCGCCAAAACACAACCCACAACCTTCGGCCAACTCCAACAGATCATCGTACAAGCCTGCG
GTGAATCCACCACCGATGCAGTCCTCGCCAAATTCGGCAACAAAGGCGCTGCAACCAGCCTTCAACTGGCC
CTTAAAACCGACCCCAACACAACGCTGGATCAGAAGAAGTACGAAGCCCTGCAAAAGAAATTTGCAGAGG
ACGAAACCAAATATCGCAACAAGGTCGATATCCCCCACAAGACCCAACTGCGCAACCTCATCCTCAACACC
TCAAACCAATTCTGCAACTGGCACACCAAGCCAGCCATCGAAGCCTTTAAGTGCGCCATCGCTGACATCCA
GTCCAAAGTCAGCAACAACCTCCGCATCATGCAGGAAAAGGCCAAACTCTACGAGGCATTCAGAAATGTC
GATCCACAAGTCCAGATCGCCGTCCAAGCTCTTGAAAACCACATGAACACACTTGAGGAACCCTACGCACC
CTACGCCCACTCGTTCGGCAGCGTCAAAGACTTCTACGAAGACCTCAACAACGGCTCCAACTTAGATGAGG
CCATTCAAACCATCGTCCACGATTCCGACAACTTCAACAGGAAGCCAGACCCCAACTGGCTCCGCATCATC
GCACCTCTCCACTCATCCCATTCCGCAAGCCAAATCATGGAGGCAGTAAAATACCTGTCCAGCAAACAGGA
TTACGAACTCCGTAAACCCTTCCCATTCGTCGCCACTAACCTGCCAGCAACCTACGGGAAATTTAACATTCC
CGGCACCCTCAACCCACCCACCGACAGCCTTCACGGCAGACTGAACGGTAGCCACTCCAATATGTGGCTCA
CAGCCCTGCTCCTCGACGGCAGGGATTGGAAAAACCACCACCTTTGCTTCGCCTCAAGCCGCTACTTCGAG
GAGGTCTACTTCACAAACCCCAGCCTGCCCACTACAGACAAAGTCCGTAGCCCCAAATGCGGCTTCACACT
CAAGAGCGTGCTCGACTCCGAAGCCAAAGACAGGATTCGCAACGCTCCCAAATCCCGCACCAAGGCCGTG
AAAGCCATCGAACGCATCAAGGCCAACTCCACCCACAATGTGGCGTGGAACCCCGAAACCTCTTTCCAGAT
GCAGAAAAGAAACGATGAGTTCTACATCACCATCAACCACCGCATCGAAATGGAAAAAATCCCCGGTCAG
AAAAAGACCGATGACGGTTTCACAATCCACCCCAAAGGTCTCTTCGCCATCCTCAAGGAAGGCGACAGAA
TCCTGTCACAAGACCTCAACCAGACCGCAGCCACACATTGCGCCGTCTATGAAGTCGCCAAACCCGACCA
GAACACCTTCAACCACCACGGCATTCACCTCAAGCTGATTGCCACAGAAGAACTCAAAATGCCCCTCAAG
ACCAAAAAGTCCACAATCCCAGATGCCCTCTCCTACCAAGGCATCCACGCCCACGACCGTGAAAACGGCTT
ACAACAACTCAAAGATGCCTGCGGAGCTTTCATCAGCCCCAGACTCGATCCCAAACAAAAGGCTACTTGG
GACAACTCCGTCTCCAAGAAGGAGAATCTCTATCCATTCATCACCGCCTACATGAAACTCCTCAAGAAGGT
CATGAAGGCAGGTCGTCAAGAACTGAAACTTTTCAGGACACACCTTGACCACATCCTCTTTAAACACAACC
TCAGCCCCCTCAAGCTGCACGGTGTGTCCATGATCGGTCTGGAATCATCCAGAGCAACCAAATCCGTCATC
AACAGCTTCTTCAACCTTCAGAACGCCAAGACGGAACAGCAGCAGATCGCCCTCGACCGACCCCTGTTTG
AGGCCGGTAAAACCCTCATCAACAACCAAACCCGCCGACGACAGGAAAGGGTCAGGTTAGAAACCAGTCT
CACCATGAGACTGGCACACAAATACAACGCCAAGGCAATCATCATCGAGGGTGAACTGCCACACTCCAGC
ACCGGAACCTCGCAGTACCAGAACAATGTCCGTCTGGACTGGTCTGCCAAGAAATCCGCAAAGCTGAAAA
CCGAATCAGCCAACTGTGCAGGCATTGCCATATGCCAGATCGATCCGTGCCACACAAGCCACCAAAATCCC
TTCCGGCACACTCCAACTAACCCAGACCTCAGACCACGATTTGCGCAAGTCAAAAAGGGCAAAATGTTCC
AGTATCAACTCAATGGACTACAGAGGCTGCTCAACCCCAGAAGCAAATCCTCAACTGCCATCTACTACAGG
CAGGCAGTCCAAAGTTTCTGCGCCCACCACAACCTGACGGAGAGGGACATCACCTCTGCCAAATTCCCCA
GCGATCTGGAGaaaaaaaTCAAGGATGACACCTATCTGATTCCCCAGAGAGGTGGTAGAATATACATCAGCAGC
TTCCCCGTCACTAGCTGCGCCCGTCCCTGCACCAGCAACCATTATTTCGGGGGTGGACAATTCGAGTGCAAT
GCTGACGCTGTCGCAGCCGTCAACATCATGCTGAAGGTTCACCCGTAA

SEQ ID NO: 19

>WaCas12i gene
ATGCCCATTCGCGGATATAAATGCACTGTTGTCCCAAACGTACGCAAAAAGAAACTCTTGGAAAAAAACCTA
TAGCTACTTACAAGAGGGTTCTGATGTATTTTTTGATCTTTTCTTGAGTCTGTATGGTGGGATCGCCCCAAAA
ATGATTCCACAAGACCTGGGGATCAATGAACAAGTAATTTGTGCTGCCAATTGGTTCAAAATTGTTGAAAA
AACGAAAGATTGCATCGCTGATGATGCGTTGTTGAATCAATTTGCTCAATATTATGGGGAAAAACCCAATGA
AAAGGTTGTTCAATTTTTGACGGCATCTTACAATAAAGACAAATATGTTTGGGTCGATTGTCGTCAAAAATT
TTACACTCTGCAAAAGGATTTGGGAGTCCAAAACCTAGAAAACGACCTGGAGTGTTTGATTCGAGAAGATT
TGTTGCCCGTAGGAAGCGACAAAGAAGTTAATGGATGGCACTCGATATCAAAATTGTTTGGTTGTGGAGAA
AAAGAAGACAGAACAATTAAGGCTAAAATTCTGAATGGCCTATGGGAAAGAATTGAGAAAGAAGATATTCT
AACAGAAGAAGACGCAAGAAATGAACTATTGCACTCTGCTGGGGTGTTGACTCCAAAAGAATTTAGAAAA
GTATATAAAGGGGCTGCTGGTGGGCGTGATTGTTATCACACGTTGCTGGTAGATGGGAGAAACTTCACTTTT
AACCTTAAAACACTCATTAAGCAGACCAAGGATAAATTAAAAGAAAAGTCTGTTGATGTTGAAATCCCCAA
TAAAGAAGCATTGCGTCTATATCTCGAAAAACGAATTGGACGGTCTTTCGAGCAAAAGCCATGGAGCGAAA
TGTATAAAACGGCCCTCTCAGCCGTTATGCCAAAAAATACGCTAAATTATTGTTTCGCCATTGATAGGCACGC
CCAATATACAAAAATTCAAACACTAAAGCAGCCATATGATTCGGCAATTACTGCCCTAAATGGGTTTTTTGA
GTCTGAATGCTTTACAGGCTCAGATGTTTTTGTTATTTCTCCCTCCCATTTGGGGAAAACTCTTAAAAAACTT
TATAATTACAAAGATGTTGAATCTGGCATTAGCGAAATTGTTGAAGATGAAGACAATAGTTTGCGATCTGGG
GTAAATGTAAATTTACTTAGATATATTTTTACTCTTAAAGATATGTTTTCTGCTGAGGATTTCATCAAAGCGGC
AGAATATAATGTTGTATTTGAACGCTACAACAGGCAAAAAGTCCACCCTACAGTAAAAGGGAATCAATCGTT
CACTTTCGGCAATTCCGCATTGAGCGGTAAAGTTATTCCTCCATCAAAATGCTTGTCCAATTTGCCTGGACA
AATGTGGCTGGCCATTAATCTACTTGACCAGGGCGAATGGAAAGAACATCACATTCCTTTTCACAGTGCAA
GATTCTATGAAGAAATCTATGCAACAAGTGACAATCAAAATAATCCCGTAGATTTGCGAACTAAACGTTTTG
GCTGCTCTCTTAACAAGACTTTTTCTGCTGCTGACATCGAAAAGGTGAAAGAAAGTGCCAAGAAAAAACA
TGGCAAAGCAGCTAAACGTATTTTGAGAGCCAAAAACACCAATACAGCCGTAAATTGGGTTGATTGCGGTT
TTATGTTGGAAAAAACAGAGGTTAACTTTAAAATTACTGTTAACTACAAACTTCCAGACCAAAAGTTGGGA
AAATTTGAACCAATTGTTGGGACGAAGATTTTGGCTTATGACCAAAATCAAACCGCTCCTGATGCTTATGCG
ATTCTTGAAATTTGCGATGATAGCGAAGCTTTTGATTACAAGGGATATAAAATCAAATGTTTGTCTACTGGTG
ATTTGGCTTCAAAGTCATTGACCAAACAAACAGAAGTTGATCAGCTAGCTTATAAGGGTGTGGACAAAACT
AGCAATTTTTACAAAAAGTGGAAACAGCAACGAAGGCTTTTTGTCAAAAGTCTTAACATTCCAGATGCCCT
AAAGAGTTTTGAAAACATCAATAAAGAATATCTTTATGGGTTCAACAATTCGTATCTGAAGTTGCTTAAACA
AATTTTACGGGGCAAATTTGGACCAATTCTTGTTGATATTCGACCAGAACTTATTGAAATGTGTCAGGGAATT -continued

SEQUENCE LISTING

GGCTCTATCATGCGATTGTCTAGTCTAAACCATGATAGTTTGGACGCAATTCAATCTCTCAAATCCTTGCTTC
ACTCCTATTTTGATCTCAAAGTAAAGGAAGAAATCAAAACAGAAGAATTGAGAGAAAAAGCAGATAAAGA
GGTTTTTAAGTTGCTTCAACAAGTGATTCAAAAACAAAAGAATAAACGCAAAGAAAAAGTTAATAGAACT
GTTGATGCCATTTTGACTTTGGCGGCTGATGAGCAAGTACAAGTCATTGTAGGAGAGGGAGATCTTTGTGTT
TCCACCAAAGGAACAAAAAAGAGACAAAACAACAGAACCATTGATTGGTGTGCCAGAGCAGTTGTGGAA
AAACTAGAAAAAGCATGCAAACTACATGGGTTGCATTTTAAGGAAATTCCACCACATTACACTTCACATCAA
GATTGTTTTGAACACAACAAGGATATTGAAAATCCAAAAGAAGTCATGAAGTGTCGTTTCAATAGCAGCGA
AAATGTAGCTCCTTGGATGATCAAGAAATTCGCAAATTATCTTAAATGCGAAACAAAATATTATGTTCAAGG
AATGCAAGATTTTCTAGAGCATTATGGTCTAGTAGAATACAAAGATCACATCAAAAAGGGAAAAATCTCAAT
TGGGGATTTTCAAAAACTTATCAAACTTGCTCTTGAGAAAGTTGGAGAAAAAGAGATTGTTTTTCCATGTAA
AGGTGGTAGAATCTATTTGTCAACCTATTGCTTAACAAATGAGTCTAAACCCATTGTTTTCAATGGCAGAAG
ATGCTATGTTAATAATGCAGACCATGTTGCTGCGATTAATGTTGGCATTTGTCTTTTGAATTTTAATGCGAGAG
CCAAGGTGGCGGAAAAAACCCCTTGA

SEQ ID NO: 20

>Wa2Cas12i gene
ATGGCTAAGAAGGATTTTATCGCTCGTCCCTACAATTCATTCCTGCTCCCCAACGACAGAAAGCTTGCTTATC
TGGAAGAAACTTGGACTGCCTACAAGTCAATCAAAACAGTACTGCACCGTTTCCTCATCGCAGCATACGGC
GCTATTCCCTTCCAGACCTTTGCAAAAACCATCGAAAACACACAAGAAGACGAATTGCAATTGGCATATGC
CGTTAGAATGTTCAGACTAGTTCCAAAAGACTTCTCCAAGAATGAAAACAACATACCCCCCGATATGCTCAT
TAGCAAGCTTGCTAGCTATACAAATATAAATCAATCACCAACCAATGTCTTGAGCTATGTAAACAGCAACTAC
GATCCAGAAAAGTATAAGTGGATCGACTCACGCAACGAAGCCATCTCATTGTCCAAAGAAATCGGCATCAA
ACTCGATGAGTTGGCAGACTACGCTACCACCATGCTTTGGGAGGACTGGCTTCCACTTAACAAAGACACAG
TCAACGGTTGGGGCACCACTAGCGGCCTATTCGGCGCAGGaaaaaaaGAGGATCGTACCCAAAAGGTACAAAT
GCTCAACGCATTGCTTTTGGGGCTTAAAAACAACCCTCCCAAGGACTACAAACAGTATTCGACCATCCTTCT
CAAGGCATTTGATGCCAAATCATGGGAAGAGGCTGTTAAAATTTATAAAGGCGAATGCTCAGGTAGAACCA
GTAGCTACCTGACAGAAAAGCATGGAGACATTTCCCCAGAAACTTTGGAAAAACTAATTCAAAGTATTCAG
AGAGATATTGCTGACAAACAACACCCCATCAATCTACCTAAAAGAGAAGAAATTAAGGCATACTTGGAAAA
GCAGAGTGGTACTCCATACAATCTCAATCTCTGGTCACAAGCCCTACACAACGCTATGTCTTCTATCAAGAA
GACAGATACTCGCAATTTCAATAGCACACTAGAAAAATATGAAAAAGAAATTCAACTCAAGGAGTGCTTGC
AAGATGGTGATGATGTAGAATTACTTGGCAACAAATTCTTTTCATCTCCATATCATAAGACCAACGATGTCTT
TGTCATTTGCTCTGAGCATATCGGCACCAATCGCAAATACAATGTCGTTGAGCAGATGTACCAACTCGCTAG
CGAACATGCCGATTTTGAAACAGTGTTCACTCTCCTCAAAGATGAATACGAAGAAAAAGGTATCAAAACCC
CAATCAAAAACATTCTTGAATACATTTGGAACAACAAGAATGTGCCTGTAGGCACTTGGGGTAGAATTGCC
AAATACAATCAGCTGAAAGATAGATTGGCTGGAATCAAAGCCAATCCTACCGTTGAATGCAACCGTGGCAT
GACATTTGGCAATTCTGCGATGGTTGGCGAAGTTATGCGATCCAATCGCATTTCGACCAGCACGAAGAATAA
AGGCCAGATTTTGGCCCAAATGCACAACGATAGGCCCGTTGGGTCAAACAACATGATCTGGCTGGAAATGA
CGCTTTTAAACAACGGGAAATGGCAAAAACACCACATCCCGACCCACAATAATAAGTTCTTTGAAGAAGTC
CATGCTTTCAATCCAGAACTGAAGCAATCCGTGAATGTGCGAAATAGAATGTATCGTTCTCAAAACTATTCG
CAACTTCCAACATCTCTGACCGATGGGCTGCAAGGCAACCCAAAAGCCAAGATTTTCAAGCGTCAATATCG
TGCGCTCAATAACATGACGGCAAACGTGATTGATCCAAAGTTGAGTTTTATTGTTAACAAAAAGGATGGCA
GATTCGAAATTAGCATCATTCACAATGTTGAAGTGATCAGGGCCAGACGAGATGTTCTGGTCGGGGATTACT
TGGTCGGCATGGATCAAAACCAGACTGCCAGCAACACTTACGCTGTCATGCAGGTGGTTCAGCCAAACACT
CCTGACTCCCATGAATTTCGCAACCAATGGGTGAAGTTTATTGAGAGTGGCAAGATTGAATCTTCTACTCTC
AATTCTAGAGGCGAATACATTGACCAGTTGAGTCATGATGGCGTGGATTTGCAAGAAATCAAGGATTCTGAA
TGGATTCCAGCTGCTGAGAAATTCTTAAACAAGTTGGGAGCAATCAACAAGGACGGCACTCCAATCAGCAT
CTCTAATACTTCAAAGAGGGCTTACACCTTCAACTCCATATATTTCAAAATCTTATTGAATTATCTTCGTGCTA
ATGATGTTGATCTGAATTTGGTGAGAGAGGAGATTCTGCGTATTGCCAACGGCAGGTTTTCGCCCATGCGTC
TGGGTAGTCTGTCGTGGACTACTCTTAAGATGTTGGGCAACTTTAGAAATTTGATTCATAGTTATTTCGATCA
CTGTGGTTTCAAGGAAATGCCTGAAAGGGAATCTAAAGACAAAACCATGTACGATCTGTTGATGCATACCAT
CACAAAGCTGACAAACAAGCGTGCCGAAAGAACGAGTAGGATTGCTGGTTCTTTGATGAATGTAGCCCATA
AGTATAAAATTGGCACAAGCGTTGTGCATGTTGTCGTTGAAGGCAGTCTAAGCAAGACCGACAAATCCAGC
AGCAAGGGTAATAACCGAAATACCACTGATTGGTGCTCAAGGGCTGTAGTCAAAAAGCTGGAAGACATGT
GCGTCTTTTATGGGTTCAATTTGAAAGCAGTTTCGGCGCATTACACTAGTCACCAAGACCCATTGGTTCATC
GGGCTGATTATGATGATCCCAAGCTTGCTTTGCGGTGTCGATATTCGTCGTATAGTCGGGCTGATTTTGAAAA
GTGGGGTGAGAAGTCGTTTGCTGCTGTGATTCGTTGGGCTACCGACAAAAAGAGCAATACTTGTTACAAGG
TTGGGGCTGTGGAGTTCTTTAAAAATTATAAAATCCCAGAGGACAAGATCACCAAGAAGCTGACCATAAAG
GAATTCCTTGAGATAATGTGTGCAGAGTCACACTATCCGAATGAGTATGACGATATTTTGATTCCTCGCCGTG
GAGGCAGGATTTATCTGACAACGAAGAAGTTGCTAAGTGATTCGACCCACCAAAGAGAAAGTGTGCATAGT
CACACGGCTGTTGTCAAAATGAACGGGAAAGAGTATTATTCCTCAGATGCAGATGAGGTGGCTGCGATCAA
CATCTGCCTACATGACTGGGTTGTCCCACTGAATTGGACCAATCACTGCCTACCTGCTGGCTGGTGCTCTGA
CCACCTGAAAGAATGTGTGCAATGTCACACTCCAGACCCAGTACGAATATCCATGTAA

SEQ ID NO: 21

>SiCas12i Direct Repeat
CUAGCAAUGACUCAGAAAUGUGUCCCCAGUUGACAC

SEQ ID NO: 22

>Si2Cas12i Direct Repeat
AUCGCAACAUCUUAGAAAUCCGUCCUUAGUUGACGG

SEQ ID NO: 23

>WiCas12i Direct Repeat
UCUCAACGAUAGUCAGACAUGUGUCCCCAGUGACAC

SEQ ID NO: 24

>Wi2Cas12i Direct Repeat
CUCAAAGUGUCAAAAGAAUGUCCCUGCUAAUGGGAC

SEQ ID NO: 25

>Wi3Cas12i Direct Repeat
UCCCAAAGUGGCAAAAGAAUCUCCCUGUUAAUGGGAG

-continued

SEQUENCE LISTING

SEQ ID NO: 26
>SaCas12i Direct Repeat
GUCUAACUGCCAUAGAAUCGUGCCUGCAAUUGGCAC

SEQ ID NO: 27
>Sa2Cas12i Direct Repeat
UCGGGGCACCAAAAUAAUCUCCUUGGUAAUGGGAG

SEQ ID NO: 28
>Sa3Cas12i Direct Repeat
CCACAACAACCAAAAGAAUGUCCCUGAAAGUGGGAC

SEQ ID NO: 29
>WaCas12i Direct Repeat
GUAACAGUGGCUAAGUAAUGUGUCUUCCAAUGACAC

SEQ ID NO: 30
>Wa2Cas12i Direct Repeat
GAGAGAAUGUGUGCAAAGUCACAC

SEQ ID NO: 31
>BFP-TTTC_Target_GGG_GFxFP
ATGAGCGAGCTGATTAAGGAGAACATGCACATGAAGCTGTAtATGGAGGGCACCGTGGACAACCATCACTT
CAAGTGCACATCCGAGGGCGAAGGCAAGCCCTACGAGGGCACCCAGACCATGAGAATCAAGGTGGTCGA
GGGCGGCCCTCTCCCCTTCGCCTTCGACATCCTGGCTACTAGCTTCCTCTACGGCAGCAAGACCTTCATCAA
CCACACCCAGGGCATCCCCGACTTCTTCAAGCAGTCCTTCCCTGAGGGCTTCACATGGGAGAGAGTCACCA
CATACGAgGACGGGGGCGTGCTGACCGCTACCCAGGACACCAGCCTCCAGGACGGCTGCCTCATCTACAAC
GTCAAGATCAGAGGGGTGAACTTCACATCCAACGGCCCTGTGATGCAGAAGAAAACACTCGGCTGGGAGG
CCTTCACCGAGACaCTGTACCCCGCTGACGGCGGCCTGGAAGGCAGAAACGACATGGCCCTGAAGCTCGT
GGGCGGGAGCCATCTGATCGCAAACATCAAGACCACATATAGATCCAAGAAACCCGCTAAGAACCTCAAGA
TGCCTGGCGTCTACTATGTGGACTACAGACTGGAAAGAATCAAGGAGGCCAACAACGAGACaTACGTCGAG
CAGCACGAGGTGGCAGTGGCCAGATACTGCGACCTCCCTAGCAAACTGGGGCACAAGCTgAATGAATTCG
AGGGCAGGGGCAGCCTGCTGACCTGCGGCGACGTGGAGGAGAACCCCGGCCCCatggtgagcaagggcgaggagctgtt
caccggggtggtgcccatcctggtcgagctggacggcgacgtaaacggccacaagttcagcgtgtccggcgagggcgagg
gcgatgccacctacggcaagctgaccctgaagttcatctgcaccaccggcaagctgcccgtgccctggcccaccctcgtg
accaccctgacctacggcgtgcagtgcttcagccgctaccccgaccacatgaagcagcacgacttcttcaagtccgccat
gcccgaaggctacgtccaggagcgcaccatcttcttcaaggacgacggcaactacaagacccgcgccgaggtgaagttcg
agggcgacaccctggtgaaccgcatcgagctgaagggcatcgacttcaaggaggacggcaacatcctggggcacaagctg
gagtacaactacaacagccacaacgtctatatcatggccgacaagcagaagaacggcatcaaggtgaacttcaagatccg
ccacaacatcgaggacggcagcgtgcagctcgccgaccactaccagcagaacaccGGATCCGtGTCTTTcCCATTACAGT
AGGAGCATACGGGaGACAAGCTTtGgccacctacggcaagctgaccctgaagttcatctgcaccaccggcaagctgcccg
tgccctggcccaccctcgtgaccaccctgacctacggcgtgcagtgcttcagccgctaccccgaccacatgaagcagcac
gacttcttcaagtccgccatgcccgaaggctacgtccaggagcgcaccatcttcttcaaggacgacggcaactacaagac
ccgcgccgaggtgaagttcgagggcgacaccctggtgaaccgcatcgagctgaagggcatcgacttcaaggaggacggca
acatcctggggcacaagctggagtacaactacaacagccacaacgtctatatcatggccgacaagcagaagaacggcatc
aaggtgaacttcaagatccgccacaacatcgaggacggcagcgtgcagctcgccgaccactaccagcagaacacccccat
cggcgacggccccgtgctgctgcccgacaaccactacctgagcacccagtccgccctgagcaaagaccccaacgagaagc
gcgatcacatggtcctgctggagttcgtgaccgccgccgggatcactctcggcatggacgagctgtacaagtaa SEQ ID NO: 32
>Insert-seq
GGATCCGtGTCTTTcCCATTACAGTAGGAGCATACGGGaGACAAGCTTtG SEQ ID NO: 33
>Target
CCATTACAGTAGGAGCATAC SEQ ID NO: 34
>SpCas9 protein
MDKKYSIGLDIGTNSVGWAVITDEYKVPSKKFKVLGNTDRHSIKKNLIGALLFDSGETAEATRLKRTARRRYTR
RKNRICYLQEIFSNEMAKVDDSFFHRLEESFLVEEDKKHERHPIFGNIVDEVAYHEKYPTIYHLRKKLVDSTDKA
DLRLIYLALAHMIKFRGHFLIEGDLNPDNSDVDKLFIQLVQTYNQLFEENPINASGVDAKAILSARLSKSRRLEN
LIAQLPGEKKNGLFGNLIALSLGLTPNFKSNFDLAEDAKLQLSKDTYDDDLDNLLAQIGDQYADLFLAAKNLSD
AILLSDILRVNTEITKAPLSASMIKRYDEHHQDLTLLKALVRQQLPEKYKEIFFDQSKNGYAGYIDGGASQEEFY
KFIKPILEKMDGTEELLVKLNREDLLRKQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDKNLPNEKVLPKHSLLYEYFTVYNE
LTKVKYVTEGMRKPAFLSGEQKKAIVDLLFKTNRKVTVKQLKEDYFKKIECFDSVEISGVEDRFNASLGTYHD
LLKIIKDKDFLDNEENEDILEDIVLTLTLFEDREMIEERLKTYAHLFDDKVMKQLKRRRYTGWGRLSRKLINGIR
DKQSGKTILDFLKSDGFANRNFMQLIHDDSLTFKEDIQKAQVSGQGDSLHEHIANLAGSPAIKKGILQTVKVVD
ELVKVMGRHKPENIVIEMARENQTTQKGQKNSRERMKRIEEGIKELGSQILKEHPVENTQLQNEKLYLYYLQN
GRDMYVDQELDINRLSDYDVDHIVPQSFLKDDSIDNKVLTRSDKNRGKSDNVPSEEVVKKMKNYWRQLLNA
KLITQRKFDNLTKAERGGLSELDKAGFIKRQLVETRQITKHVAQILDSRMNTKYDENDKLIREVKVITLKSKLVS
DFRKDFQFYKVREINNYHHAHDAYLNAVVGTALIKKYPKLESEFVYGDYKVYDVRKMIAKSEQEIGKATAKYF
FYSNIMNFFKTEITLANGEIRKRPLIETNGETGEIVWDKGRDFATVRKVLSMPQVNIVKKTEVQTGGFSKESILP
KRNSDKLIARKKDWDPKKYGGFDSPTVAYSVLVVAKVEKGKSKKLKSVKELLGITIMERSSFEKNPIDFLEAKG
YKEVKKDLIIKLPKYSLFELENGRKRMLASAGELQKGNELALPSKYVNFLYLASHYEKLKGSPEDNEQKQLFV
EQHKHYLDEIIEQISEFSKRVILADANLDKVLSAYNKHRDKPIREQAENIIHLFTLTNLGAPAAFKYFDTTIDRKR
YTSTKEVLDATLIHQSITGLYETRIDLSQLGGD SEQ ID NO: 35
>LbCas12a protein
MAIPVGKTQENIDNKRLLVEDEKRAEDYKGVKKLLDRYYLSFINDVLHSIKLKNLNNYISLFRKKTRTEKENKE
LENLEINLRKEIAKAFKGNEGYKSLFKKDIIETILPEFLDDKDEIALVNSFNGFTTAFTGFFDNRENMFSEEAKSTS
IAFRCINENLTRYISNMDIFEKVDAIFDKHEVQEIKEKILNSDYDVEDFFEGEFFNFVLTQEGIDVYNAIIGGFVTE
SGEKIKGLNEYINLYNQKTKQKLPKFKPLYKQVLSDRESLSFYGEGYTSDEEVLEVFRNTLNKNSEIFSSIKKLE
KLFKNFDEYSSAGIFVKNGPAISTISKDIFGEWNVIRDKWNAEYDDIHLKKKAVVTEKYEDDRRKSFKKIGSFSL
EQLQEYADADLSVVEKLKEIIIQKVDEIYKVYGSSEKLFDADFVLEKSLKKNDAVVAIMKDLLDSVKSFENYIK -continued

SEQUENCE LISTING

AFFGEGKETNRDESFYGDFVLAYDILLKVDHIYDAIRNYVTQKPYSKDKFKLYFQNPQFMGGWDKDKETDYR
ATILRYGSKYYLAIMDKKYAKCLQKIDKDDVNGNYEKINYKLLPGPNKMLPKVFFSKKWMAYYNPSEDIQKIY
KNGTFKKGDMFNLNDCHKLIDFFKDSISRYPKWSNAYDFNFSETEKYKDIAGFYREVEEQGYKVSFESASKKE
VDKLVEEGKLYMFQIYNKDFSDKSHGTPNLHTMYFKLLFDENNHGQIRLSGGAELFMRRASLKKEELVVHPAN
SPIANKNPDNPKKTTTLSYDVYKDKRFSEDQYELHIPIAINKCPKNIFKINTEVRVLLKHDDNPYVIGIDRGERNL
LYIVVVDGKGNIVEQYSLNEIINNFNGIRIKTDYHSLLDKKEKERFEARQNWTSIENIKELKAGYISQVVHKICEL
VEKYDAVIALEDLNSGFKNSRVKVEKQVYQKFEKMLIDKLNYMVDKKSNPCATGGALKGYQITNKFESFKSM
STQNGFIFYIPAWLTSKIDPSTGFVNLLKTKYTSIADSKKFISSFDRIMYVPEEDLFEFALDYKNFSRTDADYIKKW
KLYSYGNRIRIFRNPKKNNVFDWEEVCLTSAYKELFNKYGINYQQGDIRALLCEQSDKAFYSSFMALMSLMLQ
MRNSITGRTDVDFLISPVKNSDGIFYDSRNYEAQENAILPKNADANGAYNIARKVLWAIGQFKKAEDEKLDKV
KIAISNKEWLEYAQTSVKH

SEQ ID NO: 36

>Cas12i.3 protein
MKKVEVSRPYQSLLLPNHRKFKYLDETWNAYKSVKSLLHRFLVCAYGAVPFNKFVEVVEKVDNDQLVLAFAV
RLFRLVPVESTSFAKVDKANLAKSLANHLPVGTAIPANVQSYFDSNFDPKKYMWIDCAWEADRLAREMGLSAS
QFSEYATTMLWEDWLPLNKDDVNGWGSVSGLFGEGKKEDRQQKVKMLNNLLNGIKKNPPKDYTQYLKILLN
AFDAKSHKEAVKNYKGDSTGRTASYLSEKSGEITELMLEQLMSNIQRDIGDKQKEISLPKKDVVKKYLESESGV
PYDQNLWSQAYRNAASSIKKTDTRNFNSTLEKFKNEVELRGLLSEGDDVEILRSKFFSSEFHKTPDKFVIKPEHI
GFNNKYNVVAELYKLKAEATDFESAFATVKDEFEEKGIKHPIKNILEYIWNNEVPVEKWGRVARFNQSEEKLLRI
KANPTVECNQGMTFGNSAMVGEVLRSNYVSKKGALVSGEHGGRLIGQNNMIWLEMRLLNKGKWETHHVPT
HNMKFFEEVHAYNPSLADSVNVRNRLYRSEDYTQLPSSITDGLKGNPKAKLLKRQHCALNNMTANVLNPKLS
FTINKKNDDYTVIIVHSVEVSKPRREVLVGDYLVGMDQNQTASNTYAVMQVVKPKSTDAIPFRNMWVRFVESG
SIESRTLNSRGEYVDQLNHDGVDLFEIGDTEWVDSARKFFNKLGVKHKDGTLVDLSTAPRKAYAFNNFYFKTM
LNHLRSNEVDLTLLRNEILRVANGRFSPMRLGSLSWTTLKALGSFKSLVLSYFDRLGAKEMVDKEAKDKSLFDL
LVAINNKRSNKREERTSRIASSLMTVAQKYKVDNAVVHVVVEGNLSSTDRSASKAHNRNTMDWCSRAVVKKL
EDMCNLYGFNIKGVPAFYTSHQDPLVHRADYDDPKPALRCRYSSYSRADFSKWGQNALAAVVRWASNKKSNT
CYKVGAVEFLKQHGLFADKKLTVEQFLSKVKDEEILIPRRGGRVFLTTHRLLAESTFVYLNGVKYHSCNADEVA
AVNICLNDWVIPCKKKMKEESSASGGSGS

SEQ ID NO: 37

>SiCas12i Codon Optimized
ATGAGTTCTGATGTGGTGCGGCCTTATAACACAAAGCTGCTCCCAGATAACAGAAAGCACAATATGTTCCTG
CAGACCTTCAAGCGGCTGAACAGCATCTCTCTGAACCACTTCGACCTGCTGATCTGCCTGTACGCTGCAAT
CACCAACAAGAAGGCCGAGGAATACAAGTCTGAAAAGGAAGCCCACGTGACCGCCGATAGCCTGTGTGCC
ATCAATTGGTTCAGACCCATGAGCAAGAGATACAGCAAATACGCCACCACCACCTTCAACATGTTAGAACT
GTTTAAGGAGTACAGCGGCCACGAGCCTGATGCCTATTCCAAGAACTACCTGATGAGCAATATCGACAGCG
ACAGATTCGTGTGGGTGGATTGTAGGAAGTTCGCTAAGGACTTTGCCTATCAGATGGAACTGGGTTTCCAC
GAGTTCACCGTGTTGGCCGAAACCCTGCTGGCTAATTCTATCCTGGTGCTGAACGAGAGCACCAAGGCCAA
TTGGGCTTGGGGAACCGTGTCTGCCCTGTACGGCGGCGGAGATAAGGAGGACAGCACACTGAAGAGCAAG
ATTCTGCTGGCCTTCGTGGACGCCCTGAACAACCACGAGCTGAAAACAAAGAGAGAAATCTTGAATCAAG
TGTGTGAATCTCTGAAATACCAGAGCTACCAGGACATGTACGTGGATTTTAGAAGCGTGGTTGACGAAAAC
GGCAACAAGAAGTCTCCTAACGGCTCTATGCCTATCGTGACCAAGTTCGAGACAGACGACCTGATCAGCGA
CAACCAAAGAAAGGCCATGATCAGCAACTTCACTAAGAACGCCGCTGCCAAGGCAGCTAAGAAACCTATC
CCTTACTTGGACCGCCTGAAGGAGCACATGGTGTCCCTGTGCGACGAGTACAATGTGTATGCCTGGGCCGC
GGCCATCACAAACAGCAACGCCGACGTGACCGCCCGGAATACCAGAAACCTGACATTCATCGGCGAACAG
AACAGCAGACGAAAGGAACTGAGCGTGCTGCAGACAACAACCAACGAGAAGGCTAAGGACATCCTGAAC
AAGATCAACGACAACCTGATTCAGGAGGTGCGGTACACCCCTGCCCCTAAGCACCTGGGCAGAGATCTGG
CCAACCTGTTTGATACACTGAAGGAAAAGGACATCAACAACATCGAGAACGAAGAAGAGAAACAGAACG
TGATCAATGACTGTATCGAGCAGTACGTGGACGATTGCAGAAGCCTCAACCGGAACCCCATCGCAGCCCTC
CTGAAGCACATCTCTAGGTACTACGAGGATTTCAGCGCCAAGAATTTCCTGGACGGCGCCAAGCTGAACGT
GCTGACTGAGGTGGTGAACCGGCAGAAGGCCCACCCCACCATCTGGAGCGAGAAGGCTTACACCTGGATC
AGCAAGTTCGACAAGAACCGGAGACAGGCCAACAGCAGCCTGGTCGGATGGGTTGTGCCCCCCGAGGAG
GTGCACAAGGAGAAAATCGCCGGACAGCAGAGCATGATGTGGGTGACCCTCACCCTGCTGGACGACGGCA
AGTGGGTCAAACATCACATCCCCTTCAGCGACAGCAGATACTACAGCGAAGTGTACGCCTACAACCCTAAT
CTGCCTTATCTGGACGGAGGCATCCCAAGACAGAGCAAGTTCGGCAACAAACCAACAACCAACCTGACAG
CCGAGTCCCAGGCCCTCCTGGCTAATTCTAAGTACAAGAAAGCCAACAAGAGCTTCCTGCGGGCTAAAGA
GAATGCCACACACAACGTGCGGGTGTCCCCTAACACCTCTCTGTGCATTAGACTGCTGAAGGACAGCGCCG
GAAACCAGATGTTCGACAAAATCGGCAACGTGCTCTTCGGCATGCAGATCAACCACAAGATCACCGTGGG
AAAACCTAACTACAAGATCGAGGTGGGCGACAGATTCCTGGGCTTCGATCAGAACCAGAGCGAGAACCAC
ACCTACGCCGTGCTGCAGAGAGTGTCCGAGAGCAGTCACGACACCCACCACTTTAACGGCTGGGACGTGA
AGGTGCTGGAAAAGGGCAAAGTGACCAGCGATGTGATCGTGCGGGACGAGGTCTACGACCAACTGTCTTA
CGAGGGCGTCCCCTACGATAGCAGCAAGTTCGCCGAGTGGCGGGACAAGCGCAGAAGATTTGTGCTTGAG
AACCTGAGCATCCAGCTGGAAGAGGGCAAGACCTTCCTGACAGAGTTCGACAAGCTGAATAAGGACAGCC
TGTACCGCTGGAACATGAACTACCTGAAACTGCTGAGAAAGGCCATCCGGGCCGGAGGCAAAGAGTTCGC
CAAGATCGCTAAGACAGAGATCTTCGAGCTGGCGGTGGAAAGATTCGGCCCTATTAACCTGGGCAGCCTGT
CCCAGATCAGCCTTAAGATGATTGCCTCCTTTAAGGGCGTGGTCCAGTCCTACTTCTCCGTGAGCGGCTGCG
TGGATGATGCCTCCAAAAAGGCCCATGATTCTATGCTGTTCACATTTATGTGCGCCGCCGAAGAAAAGCGGA
CCAACAAGAGAGAAGAAAAGACCAACAGAGCCGCCAGCTTTATCCTGCAAAAAGCCTACCTGCATGGCTG
CAAGATGATCGTGTGCGAGGACGACCTTCCTGTGGCCGACGGCAAGACAGGCAAAGCCCAGAATGCCGAC
CGGATGGACTGGTGCGCCAGAGCCCTGGCCAAGAAGGTGAACGACGGCTGTGTTGCCATGAGCATCTGCT
ACAGAGCTATCCCTGCCTACATGAGCAGCCACCAGGACCCCTTTGTGCACATGCAGGATAAGAAAACCAGC
GTGCTGCGGCCTAGATTCATGGAAGTTAATAAGGATAGCATCAGAGACTACCACGTGGCGGGCCTGAGAAG
AATGCTGAACAGCAAGAGTGACGCTGGCACCAGTGTTTATTACCGGCAAGCTGCCCTGCATTTCTGCGAAG
CCCTGGGCGTGAGCCCTGAACTGGTGAAAAACAAGAAAACCCACGCCGCCGAACTGGGCAAGCACATGG
GCAGCGCTATGCTGATGCCCTGGAGAGGCGGTAGAGTGTACATCGCCAGCAAAAAGCTGACCTCCGATGCC
AAATCAGTGAAGTACTGCGGCGAGGATATGTGGCAGTACCACGCCGATGAGATCGCCGCTGTTAACATCGC
CATGTATGAGGTGTGCTGCCAGACCGGCGCTTTCGGAAAGAAACAGAAAAAATCGGACGAGCTGCCTGGA -continued

SEQUENCE LISTING

SEQ ID NO: 38

>Si2Cas12i Codon Optimized
ATGAGCTCTGACGTGGTGCGGCCTTACAATACCAAGCTGCTGCCAGACAACCGGAAGTACAACATGTTTCT
GCAGACCTTCAAGAGACTGAACCTGATCTCCAGCAACCACTTCGACCTGCTGGTGTGCCTGTACGCCGCTA
TCACCAACAAGAAAGCTGAGGAATACAAGAGCGAAAAAGAGGATCACGTTACAGCCGACAGCCTGTGTG
CCATCAACTGGTTCCGGCCTATGTCTAAGCGGTACATCAAGTACGCTACAACCACCTTTAAGATGCTGGAAC
TGTTCAAGGAGTACAGCGGCCACGAGCCTGACACCTACAGCAAGAACTACCTGATGTCTAATATCGTGAGC
GATAGGTTCGTGTGGGTGGACTGCCGGAAATTCGCTAAGGACTTCGCCAATCAAATGGAACTGTCCTTCCA
CGAGTTCACCACCCTGAGTGAAACCCTGCTGGCTAACAGCATCCTGGTGCTAAATGAGTCTACAAAGGCCA
ACTGGGCCTGGGGCGCCGTGAGTGCTCTGTACGGCGGCGGCGACAAAGAGGACTCTACACTGAAAAGCA
AGATCCTTCTGGCCTTTGTGGACGCCCTGAACAACCCTGAACTGAAAACACGTAGAGAAATTCTGAACCAC
GTGTGCGAATCTCTGAAGTATCAGAGCTACCAGGACATGTACGTCGATTTCAGAAGCGTGGTCGATGATAA
GGGCAACAAGAAGAGCCCAAACGGCAGCATGCCTATCGTGACCAAGTTCGAGAGCGATGATCTGATCGGC
GATAACCAGAGAAAGACAATGATCTCTAGCTTTACGAAGAACGCCGCCGCCAAGGCCAGCAAGAAGCCCA
TCCCATACCTGGACATCCTCAAGGACCACATGATCAGCCTGTGTGAAGAGTACAACGTGTATGCCTGGGCC
GCTGCCATCACCAACAGCAACGCCGACGTGACAGCCCGCAACACCAGAAACCTGACATTCATCGGAGAAC
AGAACACCCGGAGGAAGGAACTGAGCGTGCTGCAGACAAGCACCAACGAGAAGGCTAAAGACATCCTGA
ACAAAATCAACGACAACCTGATCCCTGAGGTGCGGTACACACCTGCCCCTAAGCACCTGGGTCGGGACCT
GGCCAATCTGTTCGAGATGTTCAAGGAAAAGGACATCAACCAGATCGGCAACGAGGAGGAGAAGCAGAA
CGTGATCAACGACTGCATCGAACAGTACGTGGACGACTGTAGAAGCCTGAACAGAAACCCAGTGGCCGCC
CTGCTAAAGCACATCAGCGGATACTACGAGGATTTCAGCGCCAAAAATTTCCTGGACGGCGCCAAGCTGAA
TGTGCTGACCGAAGTGGTCAACAGACAGAAGGCTCATCCTACAATCTGCAGCGAAAAGGCCTACACCTGG
ATTAGCAAGATCGATAAGAACCGGCGGCAGGCCAATTCCTCCCTGGTCGGATGGGTGGTGCCCCCCGAGGA
AGTGCACAAGGAAAAGATTGCCGGCCAGCAGAGCATGATGTGGGTGACACTGACACTGCTGGACGACGGC
AAGTGGGTTAAGCACCACATCCCCTTCGCCGATTCTAGATACTACAGCGAGGTGTATGCCTATAATCCTAACC
TGCCTTATCTCGAGGGCGGCATCCCCAGACAGTCTAAGTTTGGCAACAAACCTACCACCAACCTGACCGCC
GAATCTCAGGCCCTGTTGGCCAACTCCAAGCACAAAAAAGCCAACAAGACCTTCCTGAGGGCCAAAGAGA
ACATCACCCACAACGTGAGAGTGTCTCCTAATACCAGCCTGTGCATCAGACCACTGAAGGACTCTGCTGGC
AATCAAATGTTCGACAACATCGGCAACATGCTGTTCGGTATGCAGATCAACCATAGAATCACCGTAGGAAA
ACCCAACTACAAGATAGAGGTGGGCGATAGATTTCTCGGATTCGACCAGAATCAGAGCGAGAACCACACCT
ACGCAGTGCTGCAAAGAGTATCTGAGAGCAGCCACGGCACACACCACTTTAACGGCTGGGACGTGAAAGT
GATCGAGAAGGGCAAGGTGACCAGCGACGTGGTGGTGCGGGACGAGGTGTACGATCAGCTGTCCTACGAA
GGCGTTCCTTACGACTCCCCTAAGTTTACCGAATGGCGGGAAAAACGGAGAAAGTTCGTGCTGGAAAACAT
GAGCATCCAGATCGAGGAGGGCAAGACTTTTCTGACCGAGTTCGATAAGCTGAATAAAGACAGCCTGTATA
GATGGAACATGAACTACATGAAACTGCTGAGGAAGGCCATCAGAGCCGGCGGAAAAGAGTTCGCCAAGAT
CACCAAGGCCGAGATCTTCGAACTGGGCGTGATGAGATTCGGGCCTATGAACCTGGGCAGCCTGAGCCAA
GTGAGTCTCAAGATGATCGCCGCCTTCAAGGGAGTGATCCAGAGCTACTTCTCTGTGTCTGGCTGCATCGAT
GATGCTTCCAAGAAGGCCCACGACAGCATGCTGTTCGCCTTCCTGTGTAGCGCCGATGAAAAGCGGACCAA
CAAGCGGGAAGAAAAGACCAATCGGGCCGCCAGCTTCATCCTTCAAAAGGCCTACTCCCACGGCTGTAAA
ATGATTGTGTGCGAGGACGACCTTCCTATCGCCGATGGCAAAGTGGGAAAGGCCCAGAACGCCGACAGAA
TGGACTGGTGCGCCCGGAGCCTGGCTAAGAAAGTGAACGATGGCTGCGTGGCCATGTCCATCTGCTACAGA
GCCATCCCCGCCTACATGAGCTCCCACCAGGACCCCTTCACCCATATGCAGGATAAGAAAACCAGCGTGCT
GCGGCCTAGATTTATGGAAGTTGGCAAGGACAGCATCCGGGACCACCACGTGGCTGGCCTGAGACGGATG
CTGAATAGCAAGGGCAACACAGGCACCAGCGTGTACTACAGAGAGGCCGCACTGCGCTTCTGCGAGGCCC
TGGGCGTGCTGCCTGAGCTGGTGAAGAATAAGAAAACACACGCCAGCGAGCTGGGAAAGCATATGGGCAG
CGCAATGCTGATGCCTTGGAGAGGCGGCAGAATCTACGTGGCCAGCAAGAAACTGACAAGCGACGCCAAA
TCTATCAAGTACTGCGGCGAGGATATGTGGCAGTACCACGCCGACGAGATCGCTGCTATCAACATCGCCATG
TACGAGGTC

SEQ ID NO: 39

>WiCas12i Codon Optimized
ATGGGCATCTCTATCAGCAGACCTTACGGCACCAAACTGCGGCCTGATGCCAGAAAGAAAGAAATGCTGGA
TAAATTCTTCACCACCCTGGCCAAAGGCCAGAGAGTGTTCGCCGACCTGGGCCTGTGCATCTACGGCAGCC
TGACACTGGAGATGGTGAAAAGACTGGAGCCTGAGAGCGACAGCGAGCTGGTGTGCGCCATCGGCTGGTT
CCGGCTGGTGGATAAAGTGACCTGGAGCGAAAACGAGATCAAGCAGGAAAACCTGGTGCGGCAGTACGA
AACCTACTCTGGCAAGGAAGCCAGCGAGGTGATCAAGACCTATCTGAGCAGTCCCTCTTCTGATAAGTACG
TGTGGATAGATTGCAGACAGAAGTTTCTGCGGTTCCAGCGGGACCTGGGCACAAGAAACCTGTCCGAGGA
TTTCGAGTGCATGCTGTTCGAGCAGTATCTGAGACTGACTAAGGGCGAGCTGGATGGACACACCGCCATGA
GCAATATGTTCGGCACCAAGACAAAGGAGGATAGAGCCACCAAGCTGCGATACGCCGCCAGAATGAAGGA
GTGGCTGGAAGCTAATGAGGAGATCACCTGGGAACAGTACCACCAGGCCCTGCAGGATAAGCTCGACGCG
AACACTCTGGAGGAAGCCGTGGATAACTACAAGGGCAAGGCTGGCGGAAGCAACCCTTTCTTTAGCTACA
CCCTGCTGAACCGAGGACAGATCGACAAGAAAACCCACGAGCAGCAGCTGAAGAAGTTCAACAAGGTGC
TGAAAACCAAGTCTAAGAACCTGAACTTCCCTAACAAAGAGAAGCTAAAGCAGTACCTCGAGACAGCGAT
CGGAATCCCCGTGGACGCTCAGGTGTACGGCCAGATGTTTAACAACGGCGTGTCTGAGGTTCAACCTAAGA
CAACCAGAAACATGTCCTTTAGCATGGAAAAGCTGGAGCTCCTGAACGAACTGAAGAGCCTGAACAAGAC
CGACGGATTCGAGAGAGCCAACGAGGTGCTCAATGGCTTCTTCGACAGCGAACTGCACACAACAGAGGAC
AAATTCAATATCACAAGCAGATACCTGGGCGGCGACAGAAACAACCGGCTCCCTAAGCTGTATGAGTTGTG
GAAGAAGGAGGGCGTGGACAGAGAGGAGGGCATCCAGCAATTTTCCCAAGCCATCCAGGACAAGATGGG
CCAAATCCCTGTTAAGAACGTGCTCCGCTACATCTGGGAGTTCCGGGAAACCGTGAGCGCAGAAGATTTCG
AGGCTGCTGCCAAGGCCAACCAGCTGGAGGAAAAGATCACCCGGACCAAAGCCCACCCCGTCGTGATCAG
CAACAGATACTGGACCTTCGGGTCCAGCGCCCTGGTGGGCAACATCATGCCTGCCGACAAGATGCACAAG
GACCAGTACGCCGGCCAGAGCTTTAAGATGTGGCTGGAAGCTGAGCTGCACTACGACGGCAAgAAGGTGA
AGCACCACCTGCCCTTCTACAATGCCAGATTCTTCGAGGAGGTGTACTGCTACCACCCATCAGTGGCCGAA
GTGACCCCTTTTAAGACCAAGCAGTTCGGATATGCCATCGGCAAGGACATCCCAGCTGACGTGTCTGTGGT
GCTGAAAGATAACCCCTACAAGAAGGCCACCAAGAGATTTCTGAGGGCCATCAGCAATCCAGTCGCCAAC
ACTGTGGACGTGAACAAGCCTACAGTGTGTAGCTTCATGATCAAGCGGGAAAACGACGAGTACAAGCTGG
TGATCAACAGAAAgATCGGAGTGGACAGACCCAAGAGAATCAAGGTGGGCAGAAAAGTGATGGGCTACGA
CAGAAACCAGACCGCCAGCGACACATATTGGATCGGCGAGCTGGTTCCTCATGGGACCACAGGCGCCTAC
AGAATCGGAGAATGGAGCGTGCAATACATTAAAAGCGGCCCTGTGCTTTCTTCTACACAGGGCGTGAACGA -continued

SEQUENCE LISTING

TTCTACCACCGATCAGCTGATCTACAACGGAATGCCCAGCAGCAGCGAGCGGTTCAAGGCCTGGAAGAAG
TCCAGAATGAGCTTCATCCGGAAGCTGATCAGACAGCTGAATGCCGAAGGCCTGGAAAGCAAAGGACAGG
ACTACGTGCCCGAGAACCCTAGCAGCTTCGACGTCAGAGGAGAAACACTGTACGTGTTTAACAGCAACTA
CATGAAAGCCCTGGTGTCCAAGCACAGGAAGGCCAAgAAGCCCGTGGAAGGCATCCTGGAAGAAATCGAG
GCTCTGACCTCCAAAGCCAAGGACAGCTGCAGCCTGATGCGCCTGAGCTCTCTGAGCGACGCCGCCATGC
AGGGCATCGCCAGCCTGAAGTCCCTGATCAACTCTTATTTCAACAAGAATGGCTGTAAAACCATCGAGGAC
AAGGAAAAGTTCAACCCCGACCTGTACGTGAAGCTGGTCGAGGTCGAACAGAAAAGAACCAACAAGCGG
AAGGAGAAGGTGGGCCGGATCGCCGGCAGCCTGGAACAGCTCGCCCTGCTGAATGGTGTTGACGTGGTGA
TCGGCGAGGCCGATCTGGGGGAAGTCAAGAAAGGCAAGTCTAAgAAGCAGAATAGCAGAAACATGGACTG
GTGCGCCAAGCAGGTCGCTGAGCGCCTGGAATACAAACTGACCTTCCACTGTATCGGCTACTTCGGCGTGA
ACCCTATGTACACAAGCCACCAAGATCCTTTTGAACACCGGAGAGTGGCCGACCACCTGGTGATGAGAGCT
AGGTTCGAAGAGGTGAACGTTAGCAACGTAAGCGAATGGCACATGAGAAACTTCAGCAATTACCTGCGGG
CCGACAGCGGCACAGGTCTGTACTACAAGCAAGCCACCCTGGACTTTCTGAAACATTACGACCTGGAGGA
GCACGCCGACGACCTGGAGAAACAGAATATCAAGTTCTACGATTTCAGAAAGATCCTGGAGGACAAGCAG
CTGACATCTGTTATAGTGCCTAAGCGGGGCGGCAGAATCTACATGGCCACAAACCCCGTGACATCAGACAG
CACCCCTGTGACCTACGCCGGCAAGACCTACAATAGATGCAACGCCGATGAGGTGGCTGCCGCTAATATCG
CTATTTCTGTGCTGGCCCCTCACAGCAAGAAGGAAGAgAAAGAGGATAAGATCCCTATCATCAGCAAGAAG
CCTAAGTCCAAGAACACCCCAAAGGCTAGAAAGAACCTGAAAACAAGCCAGCTGCCTCAGAAG

SEQ ID NO: 40

>Wi2Cas12i Codon Optimized
ATGGCCAGCAAACACGTGGTGCGGCCTTTTAACGGCAAAGTGACCGCTACCGGCAAGCGGCTGGCCTACC
TGGAGGAAACCTTTCATTACCTGGAGAAGGCCGCCGGCGGCGTGTCTACCCTGTTCGCCGCTCTGGGCAGC
TACCTCGACGCCACAACCATCAGCAACCTGATCAACAAgAACCAGGACTTGGCTGTCGTGATCTTCCGGTA
CCACGTGGTGCCTAAGGGCGAAGCCCACACACTGCCCGTGGGCACCGACATGGTGTCAAGGTTCGTGGCC
GACTACGGCATGGAGCCTAATGAGTTCCAAAGAGCCTACCTGGATAGCCCCATCGATCAGGAGAAGTACTG
CTGGCAGGACAATCGGGACGTGGGATGTTGGCTGGGCGAACAGCTGGGTGTTTCTGAGGCCGACATGCGG
GCTATCGCCGTGACTTTTTACAACAACCAGATGCTGTACGACTGTGTGAAGGGAACTGGCAGCGGCAATGC
CGTCTCTCTGCTGTTTGGCAGCGGCAAgAAGTCCGACTACAGCATGAAGGGAGTCATTGCCGGCAAGGCTG
CCTCAGTGCTGGCTAAGTATAGACCTGCCACCTACCAGGATGCCAGAAAGATGATCCTGGAAGCTAATGGC
TTCACCAGCGTGAAAGATCTGGTCACATCTTACGGCATCACCGGCAGAAGCAGCGCCCTGCAAATCTTCAT
GGAAGGCATTGAAAGCGGACCTATCTCCTCCAAAACATTGGACGCCAGAATCAAGAAGTTCACGGAAGAT
AGTGAGCGGAACGGCCGCAAGAACCTGGTCCCCCACGCCGGCGCCATTAGAAATTGGCTGATCGAGCAGG
CCGGTTCTTCTGTGGAAAACTACCAAATGGCCTGGTGCGAGGTTTACGGCAACGTGAGCGCTGACTGGAA
CGCCAAGGTGGAAAGCAACTTCAACTTCGTGGCCGAGAAGGTGAAAGCCCTGACCGAGCTGAGCAATATC
CAGAAGAGCACCCCTGATCTGGGCAAGGCTCTGAAACTGTTTGAGGAGTACCTGACCACATGCCAGGACG
AGTTCGCCATCGCCCCATACCACTTCAGCGTGATGGAAGAGGTGCGGATGGAAATGGCCACAGGCAGAGA
GTTTAACGATGCATACGACGACGCTCTGAACAGCCTGGACATGGAAAGCAAGCAGCCTATCCAGCCTCTGT
GTAAATTCCTGATCGAGCGGGGCGGAAGCATCAGCTTCGACACCTTCAAGAGCGCCGCCAAATACCTGAAA
ACCCAGAGCAAGATTGCCGGCAGATACCCTCATCCATTCGTGAAGGGAAACCAGGGCTTCACATTCGGCTC
CAAgAACATCTGGGCCGCCATAAACGACCCCATGATGGAGTACGCCGACGGCCGGATCGCCGGCGGCTCTG
CCATGATGTGGGTCACCGCTACCCTGCTGGACGGCAAGAAGTGGGTGAGACACCACATCCCCTTCGCCAAC
ACAAGATACTTCGAGGAGGTTTACGCCAGCAAGAAGGGCCTGCCTGTCCTGCCGTGCGCCAGAGATGGCA
AGCACAGCTTTAAGCTGGGTAACAACCTGAGCGTGGAGAGAGTGGAAAAGGTGAAGGAAGGCGGCAGAA
CAAAGGCCACAAAGGCTCAGGAGAGAATCCTGAGCAACCTGACACACAACGTGCAGTTCGACAGCAGCA
CCACCTTCATCATCCGGAGACAGGAGGAATCCTTTGTGATCTGCGTGAACCACAGACACCCCGCCCCTCTG
ATGAAgAAGGAGATGGAAGTGGGCGACAAGATCATCGGCATCGACCAGAACGTGACCGCCCCTACCACCT
ACGCCATCGTGGAGAGGGTGGCCAGCGGAGGCATCGAGCGGAACGGCAAACAGTACAAGGTGACAGCCA
TGGGCGCCATCTCCTCTGTGCAGAAAACCAGAGGCGGAGAGGTGGACGTGCTGAGCTACATGGGTGTGGA
GCTGTCCGACTCGAAGAACGGATTCCAGAGCCTGTGGAACAAGTGTCTGGACTTCGTGACCAAGCACGGC
ACAGAGAACGACGTGAAGTACTACAACAACACAGCCGTGTGGGCCAACAAGCTTTACGTGTGGCACAAGA
TGTACTTCAGACTGCTCAAGCAACTGATGAGAAGAGCCAAGGACCTGAAGCCTTTCAGAGATCACCTGCA
ACACCTGCTGTTCCACCCTAACCTGTCTCCTCTGCAGCGGCATAGCCTGTCTCTTACAAGCCTGGAGGCTAC
CAAGATCGTGCGCAATTGCATCCACAGCTATTTCAGCCTTCTCGGGCTGAAAACCCTGGATGAGAGAAAGG
CAGCCGACATCAACCTGCTCGAGGTGCTGGAAAAGCTGTATGCCGGCCTTGTGGAAAGAAGGAAGGAGAG
AACCAAGCTGACAGCCGGCCTGCTGGTCAGACTGTGCAACGAGCACGGAATTAGCTTTGCCGCCATCGAA
GGCGACCTGCCTGTGGTGGGCGAAGGCAAGAGCAAGGCCGCTAACAACACCCAGCAGGACTGGACCGCC
CGGGAACTGGAGAAGAGACTGAGCGAAATGGCTGAGGTGGTGGGCATCAAGGTGATCGCTGTTCTACCAC
ACTACACCAGCCACCAGGACCCTTTCGTTTACTCCAAGAATACCAAGAAAATGCGGTGCAGATGGAATTGG
CGGACCACCAAGACCTTCACCGATAGAGATGCCCTGAGCATCCGGAGAATCCTGAGCAAGCCCGAAACCG
GAACCAACCTGTATTACCAGAAGGGACTGAAGGCCTTCGCCGAGAAGCACGGCCTGGATCTGGCCGAAAT
GAAGAAGCGGAAGGACGCCCAGTGGTACCTGGAAAGAATCCAGGATAAGAACTTCCTGGTGCCCATGAAC
GGCGGAAGAGTGTACCTGAGCAGCGTGAAGCTGGCCGGCAAAGAGACAATCGACATGGGCGGCGAGATT
CTGTACCTGAACGACGCCGATCAGGTGGCCGCCCTCAACGTGCTGCTGGTGAAGATC

SEQ ID NO: 41

>Wi3Cas12i Codon Optimized
ATGGCCAAAAAGGAACACATTATCAGACCTTTCAAGGGCACCCTGCCACTGCGGGGGGACAGACTGAGAT
ACCTGCAGGACACCATGAAGTACATGAAGAAGGTTGAGGACACCATCACCGAGCTGTGCGCCGCCGTGAT
CGCCTACGCCAAGCCTACAATCATCCAGCAGATTCTGGGAGAAGAAATCGAGACTACCTCCACCTTCTGCA
GCTTCAGACTGGTTGGGATTCATGAGAACTTCACTATGCCCCTGACAACCAATATGATCAAGCACTTCCAGA
AAACCTTCAACATCAATCCTTCTGAGAAGCAGGCCATCTATCTGAGCAGCGGATTTGATAGCGACAAATACA
GATGGCAGGATACAAGCGAGGTGTCTAGAAATTTCGCTAATAAGTGCCGCCTGACCAACCAGGAGTTCCAG
GAGTTCGCCGAGCAAGCTCTGTTAAACATGTGCTTTATCGGCTGTAGCGGATCTCCTGGCGCCACAAACGC
CGTGTCCCAGATCTTCGGCACCGGCGAAAAGTCTGATTACCAGCGGAAGTCTCAGATCGCCAAGATCGCCG
CTGATACCCTCGAGAACCACAAACCTAGCACATACGAGTCTGCTAGGCTGATGGTGCTGAACACACTGGGA
CACAAGACGATCGAAGATTGCGTGAACGACTACGGCGCTATTGGAGCCAAGTCCGCCTTCCGGCTGTTTAT
GGAAAGTAAAGAAATCGGCCCAATCACCAGCGAACAACTGACCACAAAAATCAAGAAATTCAGAGAGGA
CCACAAGAAGAACAGCATCAAGAAGCAGCTGCCTCATGTGGAAAAGGTGCGGAACGCACTACTGAGCCA -continued

| SEQUENCE LISTING | |
|---|---|
| | GTTCAAGGAGCAGTACCTGCCAAGCGCCTGGGCCGAGGCCTGGTGTAACATCATGGGAGAGTTCAATAGC<br>AAGCTGTCCAACAACAACAATTTCATCGACCAAAAAACCAAGATGGTCAACGACTGCGACAACATCAAAA<br>AATCTAACCCCCAGCTGGATAAGGCCGTGAATATGCTGGACGAATGGAAGTACAAGAATTGGGACGACAAT<br>TCTGCCATCCACCCCTACCACATCGGCGATCTGAAAAAGCTGATGGCCATCTTCAACATCAACAATGAGGGC<br>ACCTTCGACGAGAGATTCAGCGCCAGCTGGGAGCAGTTTTCTACCAGCCTGGAGTACGGCGAGAAGCCCC<br>CCGTGCGGGACCTGCTGGCCCACATCATCAAGAACATGAACGACCTGACTTACACCGACGTGATCAATGCC<br>GCTAAGTTCCTGAAGCTGCAAGATAATATCAGAAACAAGTATCCTCACCCTTTTGTGATGCCTAACAAGGGA<br>TGTACCTTCGGCAAGGATAACCTGTGGGGCGAGATCAATGATCCTACAGCTAAGATCAAGTCCACAGAGGA<br>AGTGGCCGGCCAGCGGCCTATGATGTGGCTGACCGCCAAGCTCCTGGACAACGGCAAATGGGTCGAGCAC<br>CATATCCCCTTCGCCTCTAGCAGATACTTCGCCGAAGTGTACTACACCAACCCCGCCCTGCCTACCTTACCCA<br>TCGCCCGCGACGGCAAGCACAGCTACAAGCTGACCAAGACCATCGACGCCAACACCGCCAAAACCCTGGT<br>GAACAACCCTAGAGACAAGGCCGCCAAGCTCATTGCCAGAACAAAGGCGAACACCACCCACAACGTGAA<br>GTGGATCAAACCTACATACAGAATCCAGAAAGAGAACAACCAGTTCGTGATCACCATCAATCACAGACACC<br>CATGTATCACCCCTCCTAAGGAAATCATCTTGGGCGATAGAATCCTGTCATTCGACCAAAACGAGACAGCCC<br>CTACCGCCTTTAGCATCCTGGAAAAGACCACCAAGGGCACAGAGTTCTGCGGCCACCACATCAAAGTGCT<br>GAAAACCGGCATGCTGGAAGCCAAGATCAAGACATCGAAGAAATCCATCGACGCCTTCACCTACATGGGCC<br>CTATGGAGGACGACCACGCCAGCGGTTTCCCCACCCTGCTGAACATCTGTGAAAAGTTCATCAGCGAGAAC<br>GGCGACGAGAAGGACAAGAGCTTCAGCAGCAGAAAGCTGCCTTTTAAGAGAAGCCTGTATTTTTTCCACG<br>GCAGCCACTTCGACCTGCTGAAGAAGATGATCCGGAAGGCTAAAAATGACCCTAAGAAACTGAAGCTGGT<br>GAGAATCCACATCAACGAGATCCTATTCAACAGCAACCTGTCCCCTATCAAGCTGCACAGCCTGAGCATCC<br>ACTCTATGGAGAACACAAAAAAGGTGATCGCTGCCATCTCTTGCTACATGAACGTACACGAGTGGAAAACC<br>ATCGATGAGCAAAAAAACGCCGACATCACACTGTACAACGCCAAGGAAAAGCTGTACAACAACCTGGTTA<br>ATAGAAGAAAGGAAAGAGTGAAGGTGACCGCTGGCATGCTGATCCGGCTGGCCCGGGAAAACAACTGCA<br>GATTCATGGTGGGCGAAGCCGAACTGCCAACACAGCAGCAGGGCAAGAGCAAGAAGAACAACAACAGCA<br>AGCAGGACTGGTGCGCCAGAGACATCGCACAGAGATGCGAGGATATGTGCGAGGTGGTGGGCATCAAATG<br>GAACGGCGTGACACCTCACAACACCAGCCACCAGAATCCATTCATCTACAAGAACACCTCCGGCCAGCAG<br>ATGCGGTGCAGATACAGCCTGGTCAAAAAGTCTGAGATGACCGATAAGATGGCTGAGAAGATCCGGAACAT<br>TCTGCACGCCGAGCCTGTGGGCACAACCGCTTATTACAGAGAGGGCATCCTGGAGTTTGCCAAGCACCACG<br>GACTGGACCTGGGCATGATGAAGAAAAGAAGAGATGCCAAGTATTACGACAACCTGCCCGACGAATTTCT<br>GCTGCCGACAAGAGGCGGAAGAATATACCTGTCGGAAAACCAGCTGGGCGGCAACGAGACAATCGTGATC<br>AACGGCAAGAAATACTTCGTGAATCAGGCCGACCAGGTGGCCGCCGTGAACATAGGGCTGCTGTACCTGCT<br>GCCTAAGAAGAACCAGAGC |
| SEQ ID NO: 42 | >SaCas12i Codon Optimized<br>ATGAGCGAGAAGAAATTCCACATCAGACCCTACAGATGCAGCATCTCCCCTAACGCCCGGAAGGCCGACAT<br>GCTGAAGGCTACCATCTCCTACCTGGACAGCCTGACCTCTGTGTTCAGAAGCGGGTTTACCGCCCTGCTGG<br>CTGGAATCGATCCTAGCACCGTGTCCAGGCTGGCTCCTAGCGGCGCCGTGGGCAGCCCCGACCTGTGGAGC<br>GCCGTGAACTGGTTCAGAATCGTGCCCCTGGCCGAAGCCGGCGATGCCAGAGTCGGCCAGGCAAGCCTGA<br>AAAACCTGTTTAGAGGCTACGCCGGGCACGAACCTGACGAGGAAGCCAGCATCTACATGGAAAGCAGAGT<br>GGACGACAAACGGCACGCCTGGGTCGACTGCAGGGCCATGTTCAGAGCTATGGCCCTCGAGTGCGGCCTG<br>GAGGAAGCCCAGCTGGCTTCCGACGTGTTCGCCCTGGCCAGCAGAGAGGTGATCGTGTTCAAGGACGGCG<br>AAATCAACGGCTGGGGCATCGCCAGTCTGCTGTTCGGCGAAGGAGAGAAGGCTGATTCTCAGAAAAAGGT<br>GGCCCTGCTGAGAAGCGTGAGACTGGCCCTCGAGGGCGATTACGCTACCTACGAGGAGCTGTCTGGCCTG<br>ATGCTGGCCAAGACCGGCGCCAGCTCTGGCTCCGATCTGCTGGACGAGTACAAACGGTCCGAAAAAGGTG<br>GCTCTTCTGGAGGCAGACATCCTTTCTTTGACGAGGTGTTTCGGAGAGGCGGCAGAGTTAAACAGGAGGA<br>AAGAGAGAGACTCCTGAAAAGCTGCGACACCGCAATCCAGAAGCAGGGACAGGCCCTGCCTCTGTCTCAC<br>GTGGCCAGCTGGCGGCAGTGGTTCCTGAGAAGAGTGACCCTGCTGAGGAATAGACGGCAGGAGAGCTTCG<br>CTGTGTGCATCACAAACGCCCTGATGGACCTGCAACCCAAGAACCTGAGAAATGTGCACTACGTGACCAA<br>CCCCAAGAGCGAGAAGGATAAGGGGGTTCTGGAACTGCGGGTGGACGTCAAAAACAACGAGGGCCCTGA<br>TGTGGCTGGCGCCCAAGCCGTGTTTGACGCCTACATGGCCAGACTTGCCCCAGATCTGAGATTCAGCGTGA<br>TGCCTAGACATCTGGGCTCACTGAAGGACCTGTACGCCTTGTGGGCCAAGCTGGGAAGAGATGAGGCGAT<br>CGAGGAGTACCTGGAAGGCTATGAGGGCCCTTTCAGCAAAAGACCAATCGCCGGCATCCTGCAGATCATCC<br>ACGCCCATCGGGGCAAGGTGGGGCACGACAGCCTGTTGAGAGCCGCCAGACTTAACAGAGCTATGGATAG<br>ACTGGAGAGAAAAAGAGCCCACGCCTGTGCCGCCGGCAACAAGGGATATGTGTACGGCAAGAGCAGCATG<br>GTGGGCCGGATCAACCCTCAGAGCCTTGAAGTGGGCGGACGGAAGTCTGGCCGGAGCCCCATGATGTGGG<br>TGACACTGGACCTGGTCGACGGCGACAGATTCGCCCAGCACCACCTGCCCTTTCAATCTGCCCGGTTCTTC<br>AGCGAAGTGTACTGCCACGGAGACGGCCTGCCCGCCACCAGAGTGCCAGGCATGGTCAGAAACCGGAGA<br>AATGGCCTGGCCATCGGAAATGGCCTGGGCGAGGGAGGACTGAGTGCTCTGAGAGCCGGAAGCGACCGG<br>AGAAAGCGGGCTAACAAGAGAACACTGAGAGCCCTGGAGAATATCACCCACAACGTGGAAATCGATCCTA<br>GCACATCCTTCACACTGAGAGAGGACGGCATCATCATCAGCCACAGAATCGAGAAGATCGAGCCTAAGCTG<br>GTGGCTTTTGGAGACAGAGCTCTGGGCTTCGACCTGAACCAGACCGGCGCCCACACCTTTGCCGTGCTGC<br>AGAAGGTGGACAGCGGCGGGCTGGATGTGGGTCACAGCCGGGTCAGCATTGTGCTGACCGGCACCGTGCG<br>GAGCATCTGCAAGGGCAATCAGGCCAGCGGGGGCCGGGACTACGACCTGCTGTCTTACGACGGCCCCGAG<br>AGAGATGATGGCGCTTTTACCGCCTGGAGGTCTGACAGACAGGCCTTTCTGATGAGCGCCATTCGGGAACT<br>GCCTACCCCTGCCGAGGGCGAGAAAGATTACAAGGCCGACCTGCTGTCCCAGATGGCCAGCCTGGACCAC<br>TACCGGAGGCTGTACGCCTACAACAGAAAGTGCCTGGGCATCTACATCGGTGCCCTGCGGCGCGCCACAAG<br>ACGGCAGGCCGTTGCCGCCTTCAAGGACGAGATTCTGTCCATCGCCAACCACAGATGCGGCCCCCTGATGA<br>GAGGCTCCCTGAGCGTCAACGGCATGGAAAGCCTGGCCAACCTGAAGGGCCTGGCAACCGCTTATCTGTC<br>TAAGTTCAAGGACAGCAAGTCCGAGGACCTGCTGAGTAAGGACGAAGAAATGGCCGACCTGTACAGAGCT<br>TGCGCCAGACGCATGACCGGAAAAAGAAAGGAACGGTACCGGCGTGCTGCCAGCGAAATCGTGAGACTG<br>GCTAACGAGCACGGCTGTCTGTTCGTGTTCGGCGAGAAGGAACTGCCTACAACCAGCAAGGGCAACAAGT<br>CTAAACAGAACCAGCGGAACACCGACTGGTCGGCCCGGGCCATCGTGAAGGCCGTGAAGGAGGCCTGCG<br>AGGGATGTGGCCTGGGCTTCAAGCCGGTGTGGAAGGAATACTCTAGCTTGACCGACCCCTTCGAGAGGGA<br>CGGCGATGGCCGGCCTGCTCTGAGATGTAGATTCGCCAAGGTGGCTGCTCCCGACAGCGAGCTCCCACCTA<br>GACTGACAAAGGCCGTGGGAAGCTATGTGAAGAACGCCCTAAAGGCCGATAAGGCCGAGAAGAAACAAA<br>CATGTTACCAGAGAGGAGCCATCGAGTTCTGCAGCAGGCACGGCATCGACGTCCGGAAAGCTACAGATAA<br>GGCCATTCGGAAAGCTGTGCGGGGTAGCAGTGACCTATTAGTGCCTTTCGATGGAGGCAGAACCTTCCTGC |

-continued

SEQUENCE LISTING

TATCAACAAGACTGAGCCCTGAGAGCAGAAAGGTGGAATGGGCCGGAAGAACACTGTACGAGTTCCCTTC
TGATATGGTGGCCGCCATCAACATCGCCTGCCGGGGCCTGGAACCTAGAAAGGCA

SEQ ID NO: 43

>Sa2Cas12i Codon Optimized
ATGGACGAGCAGGCCGTGGTGAGCAGCGGCTCTGATAAGACCCTGAAGATCGTGAGGCCCTACAGAGCTA
AGGTGACCGCTACTGGAATCAGATTGGAAGGGATCAAAAACACCCTGAATTACCTGAAGAGAACAGAGAT
TTGTCTGTCCAGACTGAACGCCGCTTGCGGCGCCTTTCTGACCCCTGCCATCGTGGAGCAGATCTGTAAAG
ACGATCCCGCCCTGGTGTGCGCCATAGCTAGATTCCAGCTGGTGCCTGTGGGCAGCGAAGCTACCCTGAGC
GATAGCGGACTGATGCGGCACTTCAAGGCGGCGCTGGGCGAACTGACCCCTCTGCAGGAAGCCTACCTGA
ACAGCAGTTATAACGATGAGCTGTACGCCTGGCAGGATACCCTGGTGCTGGCCAGACAGATCATCGCGGAA
ACCGGCCTGACCGAGGACCAGTTCCGGGCATTTGCCCACGCCTGCTTCAAGAACGGTAATATCATCGGTTG
TGCCGGAGGCCCTGGCGCAAGCAATGCCATTAGCGGCATCTTCGGCGAGGGAATCAAGAGCGACTACAGC
CTCCGCAGCGAGATGACAGCCGCTGTGGCTAAGGTGTTCGAGGAAAAGCGGCCCATCACATACGAGGAAG
CCAGAGCCCTGGCCCTCGAAGCCACCGGCCACGCCTCTGTGCAGAGCTTTGTCGAGGCCTTTGGCAAACA
GGGCAGAAAGGGCACCCTGATCCTGTTCATGGAGGACACCAAAACAGGCGCCTTCCCCTCCAACGAGTTC
GACTATAAGCTGAAGAAGCTGAAGGAGGACGCAGAGCGGGTGGGCAGAAAGGGCATCATCCCACATCGG
GACGTGATCGCCTCTTACCTCCGGAACCAGACCGGAGCCGACATCGAGTACAACAGCAAGGCCTGGTGCG
AAAGCTACTGCTGCGCCGTTTCTGAATACAACAGCAAGATGAGCAACAACGTGCGGTTCGCTACAGAGAA
GAGCCTGGACCTGACTAAGCTGGACGAGACAATCAGGGAAACCCCAAAGATCAGCGAGGCCATGCTGGTG
TTCGAGAACTACATGGCCAGAATCGATGCCGACCTGAGGTTCATCGTGTCGAAGCACCACCTGGGAAACCT
GGCCAAGTTCCGGCAAACAATGATGCACGTGTCCGCCAGCGAGTTCGAGGAAGCCTTCAAGGCCATGTGG
GCCGATTACCTGGCTGGCTTGGAGTATGGCGAGAAACCTGCTATCTGCGAGCTGGTTAGATACGTGCTGACC
CACGGCAATGACCTGCCTGTGGAAGCCTTTTACGCCGCCTGCAAGTTTCTGTCCCTGGACGACAAGATCAA
GAACAGATACCCTCATCCTTTCGTGCCCGGCAACAAGGGCTATACATTCGGCGCAAAGAACCTCTGGGCCG
AGATCAACGACCCTTTCAAGCCTATCAGACAGGGCAATCCTGAGGTAGCCGGCCAAAGACCCATGATGTGG
GCCACAGCTGATCTGCTGGACAACAACAAGTGGGTGCTGCACCATATTCCTTTTGCCTCGAGCAGATACTTT
GAGGAAGTGTACTACACAGACCCATCTCTCCCAACCGCCCAGAAGGCCAGAGACGGCAAGCACGGCTACA
GACTGGGAAAGGTGCTGGATGAGGCCGCCAGAGAAAGACTGAAGGCCAACAACAGACAAAGAAAGGCC
GCCAAGGCCATCGAGCGGATCAAGGCCAATTGCGAGCACAATGTGGCCTGGGACCCCTACCACCACCTTCAT
GCTGCAACTGGACAGCGAGGGCAACGTGAAGATGACCATCAACCACAGACACATCGCCTACCGGGCTCCT
AAGGAAATCGGCGTGGGCGACCGGGTTATCGGCATCGACCAGAACGAAACCGCCCCTACAACATACGCCAT
CTTGGAAAGAACGGAAAACCCCCGGGACCTGGAATATAACGGCAAGTACTACAGAGTGGTGAAGATGGGC
AGCGTGACCTCTCCTAACGTGTCCAAATACAGAACCGTGGACGCCCTGACTTACGACGGCGTGTCTCTGAG
CGACGACGCCAGCGGAGCCGTGAACTTCGTCGTGCTGTGCAGAGAGTTCTTCGCCGCTCATGGCGACGAC
GAGGGCCGGAAATACCTGGAGAGAACCCTGGGCTGGAGCTCCAGCCTGTATAGCTTCCACGGCAACTACTT
CAAGTGCCTGACCCAGATGATGCGGAGAAGCGCCCGCTCTGGCGGCGATCTGACCGTGTACCGCGCTCACC
TGCAGCAGATCCTGTTTCAGCACAACCTGTCCCCTCTGAGAATGCACAGCCTGAGCCTGCGGAGCATGGAA
TCTACCATGAAGGTGATCAGCTGCATGAAGTCTTACATGAGCCTGTGCGGCTGGAAAACCGATGCTGACAG
AATCGCCAACGACCGGAGCCTGTTCGAAGCCGCCAGAAAGCTGTACACATCTCTGGTCAATCGGCGGACC
GAAAGAGTGCGGGTGACAGCAGGCATCCTTATGAGACTGTGTCTGGAGCACAATGTGCGGTTTATCCACAT
GGAGGACGAGCTGCCTGTGGCTGAAACCGGCAAAAGCAAAAAAAGCAACGGCGCCAAGATGCACTGGTG
TGCCCGGGAGCTGGCAGTTAGACTGTCTCAGATGGCCGAAGTGACCAGCGTTAAGTTCACCGGAGTGAGC
CCCCACTACACTAGTCACCAGGACCCCTTCGTGCACTCTAAAACCAGCAAAGTGATGCGCGCCAGATGGTC
CTGGCGGAACCGGGCCGACTTCACAGATAAGGACGCCGAGAGAATCCGGACTATCCTGGGCGGCGATGAC
GCCGGGACCAAAGCTTACTACAGAAGCGCCCTGGCCGAGTTCGCCAGCAGATACGGCCTGGATATGGAGC
AAATGAGAAAGAGACGGGATGCCCAGTGGTACCAGGAGAGACTGCCTGAAACCTTCATCATCCCCCAGAG
AGGCGGGAGAGTGTACCTGAGCTCCCACGACCTGGGCAGCGGCCAGAAAGTGGACGGCATCTACGGCGG
AAGGGCCTTCGTGAATCACGCTGATGAGGTGGCCGCCCTTAACGTGGCTCTGGTCCGCCTC

SEQ ID NO: 44

>Sa3Cas12i Codon Optimized
ATGAAAACAGAGACACTGATCCGCCCTTACCCCGGCAAGCTGAACCTGCAGCCTCGGCGGGCCCAATTCCT
GGAGGATTCAATCCAGTACCACCAGAAAATGACCGAGTTCTTCTACCAGTTCCTGCAGGCCGTAGGCGGCG
CGACCACACATCAGAACATCAGCGATTTCATTGACAACAAGGCCACTGATGAGCACCAGGCCACCCTTCTC
TTCCAGGTCGTGTCCAAGGACAGCACCACCCCTGAGTGCCCTGCCGAGGAACTGCTGGCCAGATTCGCCC
AGTACACCGGCAAACAGCCCAACGAGGCCGTGACCCACTACCTGACCAGCAGAATCAACACCGACAAGTA
CAGATGGCAGGACAATAGACTACTGGCCCAGAACATCGCCAGCCAACTTAACATCTCCGAGACACAATTCC
AGGAAATCGCGCACGCTATCCTCAGCAACAACCTGTACATCGGACAGACCGCCAGCAACGCTGCCGCCAA
CTTCATCTCTCAGGTGACCGGCACCGGCCAGAAAGCCCCAAAGGCTGCCAGACTGGACGTGCTGTTCCAG
ACGAACCAAGCCCTGGCCAAAACCCAGCCTACAACCTTTGGCCAGCTCCAGCAGATTATCGTGCAGGCTTG
TGGAGAAAGCACCACCGACGCCGTGCTGGCCAAGTTCGGCAACAAAGGTGCCGCCACCTCGCTGCAGCTG
GCTCTGAAAACCGACCCCAACACCACCCTGGATCAGAAAAAGTATGAGGCCCTGCAAAAGAAATTCGCCG
AGGACGAAACAAAGTACCGGAACAAGGTTGACATTCCCCACAAAACGCAGCTGAGAAATCTGATCCTGAA
CACAAGCAATCAATTTTGCAACTGGCACACAAAGCCTGCCATCGAGGCTTTTAAGTGCGCCATCGCCGACA
TCCAGAGCAAGGTGTCCAACAACCTGAGGATCATGCAGGAGAAGGCCAAGCTGTACGAGGCCTTCAGAAA
CGTGGACCCCCAGGTGCAGATCGCTGTCCAAGCCCTGGAGAATCACATGAACACCCTCGAAGAACCCTAC
GCCCCTTACGCCCACAGCTTCGGCAGCGTGAAGGACTTCTATGAGGACCTGAACAACGGCAGCAATCTGG
ACGAGGCAATTCAGACCATCGTGCACGATTCTGATAACTTCAACCGGAAGCCTGATCCTAACTGGCTGAGA
ATCATCGCCCCACTGCACTCTAGCCACAGCGCCTCTCAGATCATGGAAGCTGTGAAATACCTGAGCAGCAA
GCAGGACTACGAACTGAGGAAGCCCTTCCCATTCGTGGCCACCAACCTGCCTGCCACATACGGCAAGTTCA
ATATCCCCGGCACCCTGAACCCTCCTACAGACTCTCTGCACGGCAGACTGAACGGCTCTCACAGCAACATG
TGGCTGACAGCCCTGCTGCTGGACGGCAGAGACTGGAAGAACCACCACCTGTGCTTCGCCAGCAGCAGAT
ACTTCGAAGAAGTCTACTTCACCAACCCTAGCCTGCCCACCACCGATAAAGTGCGGTCCCCAAAGTGCGGC
TTTACCCTGAAGAGCGTGCTGGACAGCGAGGCTAAGGATAGAATCCGTAATGCCCCTAAGAGCAGAACCAA
GGCCGTGAAGGCCATCGAGAGAATTAAGGCTAATTCTACCCACAACGTGGCCTGGAACCCCGAGACAAGC
TTCCAGATGCAGAAGAGAAACGACGAGTTCTACATCACAATCAACCACAGGATCGAGATGGAAAAGATCC
CCGGCCAAAAGAAAACAGACGACGGCTTCACCATCCACCCCAAGGGCCTGTTTGCTATCCTGAAGGAAGG
AGATAGAATCCTGAGCCAGGATCTGAATCAGACAGCCGCTACACACTGCGCCGTGTACGAGGTGGCCAAGC -continued

| SEQUENCE LISTING | |
|---|---|
| | CTGACCAGAACACCTTCAACCACCATGGCATCCACCTGAAGCTGATCGCCACCGAAGAACTGAAGATGCCT<br>CTGAAAACCAAGAAGTCTACCATCCCAGATGCCCTGTCATACCAGGGCATCCACGCCCACGACCGGGAAA<br>ACGGCCTGCAGCAGCTGAAGGACGCTTGCGGAGCCTTCATCTCACCTAGACTGGACCCCAAGCAGAAGGC<br>CACCTGGGACAACAGCGTGTCCAAGAAAGAAAACCTGTACCCTTTCATCACCGCCTACATGAAGCTGCTGA<br>AGAAGGTGATGAAGGCGGGCCGGCAGGAGCTGAAGCTGTTTCGGACTCATCTGGATCACATCCTGTTCAA<br>ACACAATCTCAGCCCTCTGAAACTGCACGGCGTGAGCATGATCGGCCTGGAGAGCAGCAGAGCTACAAAA<br>AGCGTGATCAACAGCTTCTTCAACCTGCAGAACGCTAAGACTGAGCAGCAGCAGATCGCCTTAGACAGAC<br>CCCTGTTCGAGGCCGGCAAGACACTGATCAATAATCAGACCAGAAGAAGGCAGGAAAGAGTGCGGCTGGA<br>AACATCTCTGACCATGAGACTGGCCCATAAGTATAACGCTAAAGCCATCATCATTGAGGGAGAGCTGCCTCA<br>CAGCTCCACCGGCACATCTCAGTACCAGAACAACGTGCGGCTGGATTGGAGTGCCAAGAAGAGCGCCAAG<br>CTGAAAACCGAAAGCGCCAACTGCGCTGGAATCGCCATCTGCCAGATCGACCCTTGTCACACCTCCCACCA<br>GAACCCTTTTCGGCACACCCCTACAAACCCTGACCTGCGGCCACGGTTCGCCCAGGTGAAGAAAGGCAAG<br>ATGTTCCAGTACCAGCTTAATGGCCTCCAGCGGCTGCTGAATCCTAGATCAAAGTCTAGCACAGCAATCTAC<br>TACCGGCAGGCCGTGCAAAGCTTTTGTGCCCACCACAACCTGACCGAGAGAGACATCACCTCTGCCAAATT<br>TCCCAGCGACCTGGAAAAGAAGATCAAGGACGACACCTACCTGATCCCTCAGAGAGGCGGCCGGATCTAC<br>ATCAGTAGCTTCCCTGTTACAAGCTGCGCCAGACCTTGCACAAGCAACCATTATTTCGGCGGAGGCCAGTT<br>CGAGTGTAATGCTGATGCCGTGGCCGCCGTGAACATCATGCTGAAGGTCCACCCT |
| SEQ ID NO: 45 | >WaCas12i Codon Optimized<br>ATGCCTATCCGGGGCTATAAGTGCACCGTGGTGCCTAATGTGCGGAAAAAGAAACTGCTGGAGAAAACATA<br>CAGCTACCTGCAGGAGGGCAGCGACGTGTTTTTCGATCTGTTCCTGTCACTGTATGGCGGCATCGCCCCTAA<br>GATGATCCCTCAGGATCTGGGCATCAACGAGCAAGTGATCTGTGCCGCAAACTGGTTCAAGATCGTGGAAA<br>AGACCAAGGACTGCATCGCCGACGACGCCCTGCTGAACCAGTTTGCCCAGTACTACGGCGAGAAGCCTAA<br>CGAGAAGGTTGTGCAGTTTCTGACAGCTTCTTATAACAAAGATAAGTACGTGTGGGTCGACTGCCGTCAAA<br>AGTTCTACACCCTGCAGAAAGACCTGGGAGTGCAGAACCTCGAGAACGACCTGGAGTGCCTGATCCGCGA<br>GGACCTGCTGCCTGTGGGATCTGATAAGGAAGTGAATGGATGGCACAGCATCAGCAAACTCTTCGGCTGCG<br>GCGAGAAGGAGGACAGAACCATCAAGGCCAAGATTCTGAACGGCCTGTGGGAGCGGATCGAGAAGGAAG<br>ATATTCTGACCGAGGAGGACGCCAGAAACGAGCTGCTGCATAGCGCTGGCGTGCTGACCCCTAAGGAGTTC<br>AGAAAGGTGTACAAGGGCGCCGCCGGCGGACGGGACTGCTACCACACCCTGCTGGTTGACGGCAGAAAC<br>TTCACCTTCAACCTGAAAACCCTGATCAAGCAGACCAAGGACAAGCTCAAGGAAAAGTCCGTGGATGTGG<br>AAATCCCCAACAAGGAGGCCCTGAGGCTGTACCTGGAAAAGCGAATCGGAAGATCTTTCGAGCAGAAGCC<br>TTGGTCCGAGATGTACAAAACCGCCCTGAGCGCTGTTATGCCCAAGAACACCCTGAATTACTGCTTTGCCAT<br>CGATAGACACGCCCAGTACACGAAGATCCAGACCCTGAAGCAACCTTACGACTCTGCCATCACCGCCCTGA<br>ACGGCTTCTTCGAGAGCGAATGCTTCACCGGGAGCGACGTGTTCGTGATCAGCCCTAGCCACCTGGGAAA<br>AACCCTGAAGAAGCTGTACAACTACAAGGACGTTGAGAGCGGAATCAGCGAGATCGTCGAGGACGAGGAT<br>AATAGCCTGCGGAGCGGCGTGAACGTGAATCTGCTTCGGTACATCTTCACACTGAAGGATATGTTCAGCGC<br>CGAGGACTTCATCAAGGCCGCCGAGTACAACGTAGTGTTTGAGAGATACAATAGACAGAAAGTCCACCCTA<br>CAGTGAAGGGCAATCAAAGCTTCACATTTGGCAACAGCGCTCTGTCTGGCAAGGTGATCCCTCCATCTAAG<br>TGTCTGAGCAACCTGCCTGGACAGATGTGGCTGGCCATCAATCTGCTGGACCAGGGCGAGTGGAAGGAGC<br>ACCACATTCCCTTCCACAGCGCCAGATTCTACGAGGAAATCTACGCTACATCTGATAACCAGAACAACCCCG<br>TGGACCTGCGGACCAAGAGATTCGGCTGTTCTCTGAACAAGACCTTCAGCGCCGCTGACATCGAGAAGGT<br>GAAGGAGTCTGCCAAGAAAAAGCACGGAAAGGCCGCTAAGAGAATCCTGCGTGCCAAGAACACAAACAC<br>CGCCGTGAACTGGGTGGATTGCGGCTTCATGCTGGAAAAGACCGAAGTGAACTTCAAAATCACCGTCAATT<br>ACAAACTGCCCGATCAGAAGCTGGGCAAGTTCGAGCCTATCGTGGGCACAAAAATCCTGGCTTATGACCAG<br>AATCAGACCGCCCCAGATGCCTACGCCATCCTGGAAATTTGCGACGATTCTGAAGCCTTCGACTACAAGGG<br>CTACAAAATCAAATGTCTGAGCACCGGGGACCTGGCCAGCAAGTCCCTGACAAAGCAGACAGAAGTGGAC<br>CAGCTGGCATATAAGGGCGTAGACAAAACCAGCAACTTCTACAAGAAGTGGAAGCAGCAGCGGAGACTTT<br>TTGTGAAGAGCCTGAATATCCCAGACGCCCTGAAATCTTTTGAAAACATCAACAAGGAGTACCTGTACGGC<br>TTTAACAATAGTTACCTGAAGCTACTGAAGCAAATTCTGAGAGGCAAATTCGGACCTATCCTGGTGGACATC<br>AGACCTGAGCTGATCGAGATGTGCCAGGGCATCGGCAGCATCATGCGGCTGTCCAGCTTGAACCACGACAG<br>CCTGGACGCCATTCAGTCCCTGAAGAGCCTGCTGCACTCTTACTTCGACCTGAAGGTGAAGGAAGAAATCA<br>AGACCGAAGAGCTGAGAGAGAAGGCCGATAAGGAAGTGTTTAAGCTGCTGCAACAGGTGATCCAGAAGC<br>AGAAGAATAAGAGAAAGGAAAAGGTGAACAGAACAGTGGATGCTATCCTGACACTGGCCGCCGACGAGC<br>AAGTGCAGGTGATCGTGGGCGAAGGCGACCTGTGCGTGTCCACCAAGGGCACCAAAAAGAGACAGAACA<br>ACCGGACAATCGACTGGTGCGCGAGAGCCGTGGTCGAGAAACTGGAAAAAGCCTGCAAGCTGCACGGCC<br>TGCACTTCAAGGAAATCCCCCCCCACTACACCAGCCACCAGGACTGTTTCGAGCACAACAAGGACATCGA<br>GAATCCTAAGGAAGTGATGAAGTGTAGATTCAACAGCAGCGAGAACGTGGCCCCTTGGATGATTAAGAAGT<br>TCGCCAACTACCTTAAATGCGAGACAAAATACTACGTGCAGGGCATGCAGGACTTCCTGGAACATTACGGC<br>CTGGTGGAATACAAGGACCATATCAAGAAGGGAAAGATCAGTATCGGCGATTTTCAGAAACTGATCAAGCT<br>GGCCCTGGAAAAAGTAGGCGAGAAGGAAATCGTGTTTCCTTGCAAAGGCGGCAGAATCTACCTGAGCACC<br>TACTGTCTGACCAACGAGTCCAAACCCATCGTGTTCAACGGCAGACGGTGCTATGTGAACAACGCCGACCA<br>CGTGGCCGCTATCAACGTGGGCATCTGCCTGTTGAATTTCAACGCCAGAGCTAAGGTGGCTGAAAAGACAC<br>CA |
| SEQ ID NO: 46 | >Wa2Cas12i Codon Optimized<br>ATGGCCAAGAAGGACTTCATCGCCAGACCTTACAACAGCTTTCTGCTGCCTAACGACAGAAAGCTGGCTTA<br>CCTGGAAGAAACATGGACCGCCTACAAGAGCATCAAGACCGTGCTGCACAGATTTCTGATCGCGGCCTATG<br>GCGCCATCCCCTTCCAGACATTCGCCAAAACCATTGAAAACACCCAAGAGGACGAGCTGCAACTGGCCTAT<br>GCCGTGCGGATGTTCAGACTGGTGCCCAAGGACTTCAGCAAGAACGAGAACAACATTCCACCTGACATGC<br>TGATCAGCAAGCTGGCCAGCTACACCAATATCAACCAGTCCCCAACAAACGTTCTCAGCTACGTGAATAGC<br>AACTACGACCCAGAGAAATACAAGTGGATCGATTCTAGAAACGAGGCCATCAGCCTGAGCAAGGAGATCG<br>GCATCAAGCTGGACGAGCTCGCTGATTACGCCACCACCATGCTGTGGGAGGATTGGCTGCCCCTGAACAAG<br>GACACAGTGAACGGCTGGGGAACCACCTCTGGCCTGTTCGGCGCCGGCAAAAAAGAGGATAGGACCCAA<br>AAGGTGCAGATGCTGAACGCCCTGCTGCTGGGCCTGAAAAACAACCCCCCCAAGGATTACAAGCAGTACA<br>GCACCATCCTACTGAAGGCATTTGATGCCAAGAGCTGGGAAGAGGCCGTGAAGATTTACAAAGGCGAGTG<br>TTCTGGCCGAACAAGTAGTTACCTGACTGAGAAGCACGGTGACATCAGCCCTGAGACACTGGAAAAGCTG<br>ATCCAGAGCATCCAGCGGGACATCGCCGACAAACAGCACCCAATCAACCTGCCAAAGAGAGAAGAAATCA |

-continued

SEQUENCE LISTING

AAGCCTACCTGGAGAAACAGTCTGGCACCCCATACAACCTGAACCTGTGGAGCCAGGCCCTGCACAACGC
CATGAGCTCTATCAAGAAAACCGACACCAGAAATTTCAACTCTACCCTGGAGAAGTACGAGAAGGAAATCC
AGCTGAAGGAGTGCCTTCAAGATGGCGACGATGTGGAGCTGCTGGGGAACAAGTTTTTCTCTTCTCCTTAC
CACAAGACAAATGATGTGTTCGTGATCTGCTCTGAACACATCGGAACAAATAGAAAGTACAACGTGGTCGA
GCAGATGTATCAGCTGGCCAGCGAGCACGCCGACTTCGAGACAGTTTTCACCCTGCTGAAGGACGAGTATG
AGGAAAAGGGCATCAAGACACCCATCAAAAACATCCTGGAGTACATCTGGAACAACAAGAACGTCCCTGT
GGGCACATGGGGCCGGATCGCTAAATACAACCAGCTGAAGGACAGATTAGCAGGGATCAAGGCCAATCCC
ACAGTGGAATGCAACAGAGGCATGACATTTGGCAACAGCGCCATGGTGGGCGAAGTGATGCGCTCCAACC
GGATCAGCACCAGCACCAAGAACAAGGGCCAGATCTTGGCCCAGATGCACAACGACCGGCCTGTGGGCAG
CAACAACATGATTTGGCTGGAAATGACCCTCCTGAACAACGGCAAGTGGCAGAAGCACCACATCCCCACA
CACAACAACAAATTTTTCGAGGAAGTGCACGCCTTCAACCCTGAACTGAAGCAGAGCGTGAACGTGAGAA
ACAGAATGTACAGAAGCCAGAACTACTCACAGCTGCCTACCAGCCTGACCGACGGCCTGCAGGGAAATCC
TAAGGCCAAGATCTTCAAGAGACAGTACAGAGCCCTGAACAACATGACCGCTAATGTGATCGACCCTAAGC
TGTCCTTCATCGTGAACAAGAAAGATGGAAGATTCGAGATCAGCATCATCCACAACGTGGAAGTGATCCGA
GCCAGACGGGACGTGCTGGTCGGCGACTACCTGGTGGGCATGGACCAAAACCAGACGGCTTCTAATACCT
ACGCCGTCATGCAGGTGGTGCAGCCTAACACCCCCGACAGCCATGAGTTCAGAAACCAGTGGGTCAAGTT
CATCGAGAGCGGCAAGATCGAGAGCTCAACACTGAACTCCCGGGGTGAGTACATCGACCAGCTGAGCCAC
GATGGCGTCGACCTGCAGGAGATTAAGGATTCTGAGTGGATTCCTGCCGCCGAAAAATTCCTGAACAAGCT
AGGAGCTATCAACAAAGACGGCACCCCCATCAGCATCTCCAACACCAGCAAACGGGCCTACACATTCAATA
GCATCTATTTCAAAATCCTGCTGAATTATCTGAGAGCCAACGACGTGGACCTGAATCTGGTGCGGGAAGAG
ATCCTGCGGATCGCCAACGGCAGATTCAGCCCTATGCGGCTGGGATCTCTGTCCTGGACCACACTAAAAAT
GCTGGGCAATTTCCGGAACCTAATTCACAGCTACTTCGACCACTGTGGCTTTAAGGAAATGCCTGAGAGAG
AAAGCAAGGACAAGACCATGTACGATCTGCTGATGCACACCATCACCAAGCTGACCAACAAGCGGGCCGA
GCGCACCAGCAGAATCGCTGGAAGCCTGATGAACGTGGCTCACAAGTACAAGATCGGCACAAGCGTGGTC
CACGTGGTGGTGGAAGGCTCTCTGAGCAAAACCGACAAGAGCAGCTCCAAGGGCAACAATCGGAATACCA
CAGACTGGTGCAGCCGGGCCGTGGTGAAGAAGCTTGAAGATATGTGCGTGTTCTACGGCTTCAACCTGAAA
GCCGTGAGCGCCCACTACACCAGCCACCAGGACCCTCTGGTTCATAGAGCCGATTACGATGATCCTAAGTT
GGCCCTGAGATGCAGATACTCTTCTTACAGCAGAGCTGATTTTGAGAAGTGGGGCGAAAAATCTTTCGCCG
CCGTGATCAGATGGGCCACAGACAAGAAGAGCAACACCTGCTACAAGGTGGGAGCCGTAGAGTTCTTCAA
GAACTACAAAATCCCTGAGGACAAGATCACCAAAAAGCTGACCATCAAAGAGTTCCTGGAAATTATGTGCG
CTGAGAGCCACTACCCTAATGAGTACGACGACATTCTGATCCCTAGAAGGGGCGGCAGAATCTACCTCACA
ACTAAGAAGCTGCTGTCCGATAGCACCCACCAGAGAGAGTCTGTGCATAGCCATACCGCCGTGGTGAAGAT
GAACGGCAAGGAATACTATAGCAGCGACGCCGATGAGGTGGCTGCTATCAATATCTGCCTGCACGACTGGG
TGGTCCCCCTGAATTGGACAAATCACTGCCTGCCTGCCGGATGGTGTAGCGACCACCTGAAGGAATGCGTG
CAATGTCACACCCCTGATCCTGTGAGAATCAGCATG

SEQ ID NO: 47
>SiCas12i-crRNA
CUAGCAAUGACUCAGAAAUGUGUCCCCAGUUGACACCCAUUACAGUAGGAGCAUAC

SEQ ID NO: 48
>Si2Cas12i-crRNA
AUCGCAACAUCUUAGAAAUCCGUCCUUAGUUGACGGCCAUUACAGUAGGAGCAUAC

SEQ ID NO: 49
>WiCas12i-crRNA
UCUCAACGAUAGUCAGACAUGUGUCCCCAGUGACACCCAUUACAGUAGGAGCAUAC

SEQ ID NO: 50
>Wi2Cas12i-crRNA
CUCAAAGUGUCAAAAGAAUGUCCCUGCUAAUGGGACCCAUUACAGUAGGAGCAUAC

SEQ ID NO: 51
>Wi3Cas12i-crRNA
UCCCAAAGUGGCAAAAGAAUCUCCCUGUUAAUGGGAGCCAUUACAGUAGGAGCAUAC

SEQ ID NO: 52
>SaCas12i-crRNA
GUCUAACUGCCAUAGAAUCGUGCCUGCAAUUGGCACCCAUUACAGUAGGAGCAUAC

SEQ ID NO: 53
>Sa2Cas12i-crRNA
UCGGGGCACCAAAAUAAUCUCCUUGGUAAUGGGAGCCAUUACAGUAGGAGCAUAC

SEQ ID NO: 54
>Sa3Cas12i-crRNA
CCACAACAACCAAAAGAAUGUCCCUGAAAGUGGGACCCAUUACAGUAGGAGCAUAC

SEQ ID NO: 55
>WaCas12i-crRNA
GUAACAGUGGCUAAGUAAUGUGUCUUCCAAUGACACCCAUUACAGUAGGAGCAUAC

SEQ ID NO: 56
>Wa2Cas12i-crRNA
GAGAGAAUGUGUGCAAAGUCACACCCAUUACAGUAGGAGCAUAC

SEQ ID NO: 57
>SpCas9 Codon Optimized
ATGGACAAGAAGTACAGCATCGGCCTGGACATCGGCACCAACTCTGTGGGCTGGGCCGTGATCACCGACG
AGTACAAGGTGCCCAGCAAGAAATTCAAGGTGCTGGGCAACACCGACCGGCACAGCATCAAGAAGAACC
TGATCGGAGCCCTGCTGTTCGACAGCGGCGAAACAGCCGAGGCCACCCGGCTGAAGAGAACCGCCAGAA
GAAGATACACCAGACGGAAGAACCGGATCTGCTATCTGCAAGAGATCTTCAGCAACGAGATGGCCAAGGT
GGACGACAGCTTCTTCCACAGACTGGAAGAGTCCTTCCTGGTGGAAGAGGATAAGAAGCACGAGCGGCAC
CCCATCTTCGGCAACATCGTGGACGAGGTGGCCTACCACGAGAAGTACCCCACCATCTACCACCTGAGAAA
GAAACTGGTGGACAGCACCGACAAGGCCGACCTGCGGCTGATCTATCTGGCCCTGGCCCACATGATCAAGT
TCCGGGGCCACTTCCTGATCGAGGGCGACCTGAACCCCGACAACAGCGACGTGGACAAGCTGTTCATCCA
GCTGGTGCAGACCTACAACCAGCTGTTCGAGGAAAACCCCATCAACGCCAGCGGCGTGGACGCCAAGGCC
ATCCTGTCTGCCAGACTGAGCAAGAGCAGACGGCTGGAAAATCTGATCGCCCAGCTGCCCGGCGAGAAGA -continued

SEQUENCE LISTING

AGAATGGCCTGTTCGGAAACCTGATTGCCCTGAGCCTGGGCCTGACCCCCAACTTCAAGAGCAACTTCGAC
CTGGCCGAGGATGCCAAACTGCAGCTGAGCAAGGACACCTACGACGACGACCTGGACAACCTGCTGGCCC
AGATCGGCGACCAGTACGCCGACCTGTTTCTGGCCGCCAAGAACCTGTCCGACGCCATCCTGCTGAGCGAC
ATCCTGAGAGTGAACACCGAGATCACCAAGGCCCCCCTGAGCGCCTCTATGATCAAGAGATACGACGAGCA
CCACCAGGACCTGACCCTGCTGAAAGCTCTCGTGCGGCAGCAGCTGCCTGAGAAGTACAAAGAGATTTTC
TTCGACCAGAGCAAGAACGGCTACGCCGGCTACATTGACGGCGGAGCCAGCCAGGAAGAGTTCTACAAGT
TCATCAAGCCCATCCTGGAAAAGATGGACGGCACCGAGGAACTGCTCGTGAAGCTGAACAGAGAGGACCT
GCTGCGGAAGCAGCGGACCTTCGACAACGGCAGCATCCCCCACCAGATCCACCTGGGAGAGCTGCACGCC
ATTCTGCGGCGGCAGGAAGATTTTTACCCATTCCTGAAGGACAACCGGGAAAAGATCGAGAAGATCCTGAC
CTTCCGCATCCCCTACTACGTGGGCCCTCTGGCCAGGGGAAACAGCAGATTCGCCTGGATGACCAGAAAGA
GCGAGGAAACCATCACCCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAAGCACAGCCTGCTGTAC
GAGTACTTCACCGTGTATAACGAGCTGACCAAAGTGAAATACGTGACCGAGGGAATGAGAAAGCCCGCCT
TCCTGAGCGGCGAGCAGAAAAAGGCCATCGTGGACCTGCTGTTCAAGACCAACCGGAAAGTGACCGTGA
AGCAGCTGAAAGAGGACTACTTCAAGAAAATCGAGTGCTTCGACTCCGTGGAAATCTCCGGCGTGGAAGA
TCGGTTCAACGCCTCCCTGGGCACATACCACGATCTGCTGAAAATTATCAAGGACAAGGACTTCCTGGACA
ATGAGGAAAACGAGGACATTCTGGAAGATATCGTGCTGACCCTGACACTGTTTGAGGACAGAGAGATGATC
GAGGAACGGCTGAAAACCTATGCCCACCTGTTCGACGACAAAGTGATGAAGCAGCTGAAGCGGCGGAGAT
ACACCGGCTGGGGCAGGCTGAGCCGGAAGCTGATCAACGGCATCCGGGACAAGCAGTCCGGCAAGACAA
TCCTGGATTTCCTGAAGTCCGACGGCTTCGCCAACAGAAACTTCATGCAGCTGATCCACGACGACAGCCTG
ACCTTTAAAGAGGACATCCAGAAAGCCCAGGTGTCCGGCCAGGGCGATAGCCTGCACGAGCACATTGCCA
ATCTGGCCGGCAGCCCCGCCATTAAGAAGGGCATCCTGCAGACAGTGAAGGTGGTGGACGAGCTCGTGAA
AGTGATGGGCCGGCACAAGCCCGAGAACATCGTGATCGAAATGGCCAGAGAGAACCAGACCACCCAGAA
GGGACAGAAGAACAGCCGCGAGAGAATGAAGCGGATCGAAGAGGGCATCAAAGAGCTGGGCAGCCAGAT
CCTGAAAGAACACCCCGTGGAAAACACCCAGCTGCAGAACGAGAAGCTGTACCTGTACTACCTGCAGAAT
GGGCGGGATATGTACGTGGACCAGGAACTGGACATCAACCGGCTGTCCGACTACGATGTGGACCATATCGT
GCCTCAGAGCTTTCTGAAGGACGACTCCATCGACAACAAGGTGCTGACCAGAAGCGACAAGAACCGGGG
CAAGAGCGACAACGTGCCCTCCGAAGAGGTCGTGAAGAAGATGAAGAACTACTGGCGGCAGCTGCTGAA
CGCCAAGCTGATTACCCAGAGAAAGTTCGACAATCTGACCAAGGCCGAGAGAGGCGGCCTGAGCGAACTG
GATAAGGCCGGCTTCATCAAGAGACAGCTGGTGGAAACCCGGCAGATCACAAAGCACGTGGCACAGATCC
TGGACTCCCGGATGAACACTAAGTACGACGAGAATGACAAGCTGATCCGGGAAGTGAAAGTGATCACCCT
GAAGTCCAAGCTGGTGTCCGATTTCCGGAAGGATTTCCAGTTTTACAAAGTGCGCGAGATCAACAACTACC
ACCACGCCCACGACGCCTACCTGAACGCCGTCGTGGGAACCGCCCTGATCAAAAAGTACCCTAAGCTGGA
AAGCGAGTTCGTGTACGGCGACTACAAGGTGTACGACGTGCGGAAGATGATCGCCAAGAGCGAGCAGGAA
ATCGGCAAGGCTACCGCCAAGTACTTCTTCTACAGCAACATCATGAACTTTTTCAAGACCGAGATTACCCTG
GCCAACGGCGAGATCCGGAAGCGGCCTCTGATCGAGACAAACGGCGAAACCGGGGAGATCGTGTGGGATA
AGGGCCGGGATTTTGCCACCGTGCGGAAAGTGCTGAGCATGCCCCAAGTGAATATCGTGAAAAAGACCGA
GGTGCAGACAGGCGGCTTCAGCAAAGAGTCTATCCTGCCCAAGAGGAACAGCGATAAGCTGATCGCCAGA
AAGAAGGACTGGGACCCTAAGAAGTACGGCGGCTTCGACAGCCCCACCGTGGCCTATTCTGTGCTGGTGG
TGGCCAAAGTGGAAAAGGGCAAGTCCAAGAAACTGAAGAGTGTGAAAGAGCTGCTGGGGATCACCATCA
TGGAAAGAAGCAGCTTCGAGAAGAATCCCATCGACTTTCTGGAAGCCAAGGGCTACAAAGAAGTGAAAA
AGGACCTGATCATCAAGCTGCCTAAGTACTCCCTGTTCGAGCTGGAAAACGGCCGGAAGAGAATGCTGGC
CTCTGCCGGCGAACTGCAGAAGGGAAACGAACTGGCCCTGCCCTCCAAATATGTGAACTTCCTGTACCTGG
CCAGCCACTATGAGAAGCTGAAGGGCTCCCCCGAGGATAATGAGCAGAAACAGCTGTTTGTGGAACAGCA
CAAGCACTACCTGGACGAGATCATCGAGCAGATCAGCGAGTTCTCCAAGAGAGTGATCCTGGCCGACGCTA
ATCTGGACAAAGTGCTGTCCGCCTACAACAAGCACCGGGATAAGCCCATCAGAGAGCAGGCCGAGAATATC
ATCCACCTGTTTACCCTGACCAATCTGGGAGCCCCTGCCGCCTTCAAGTACTTTGACACCACCATCGACCGG
AAGAGGTACACCAGCACCAAAGAGGTGCTGGACGCCACCCTGATCCACCAGAGCATCACCGGCCTGTACG
AGACACGGATCGACCTGTCTCAGCTGGGAGGCGAC

SEQ ID NO: 58

>LbCas12a Codon Optimized
ATGCCATCCCTGTGGGCAAGACCCAGGAGAACATCGACAATAAGCGGCTGCTGGTGGAGGACGAGAAGAG
AGCCGAGGATTATAAGGGCGTGAAGAAGCTGCTGGATCGCTACTATCTGTCTTTTATCAACGACGTGCTGCA
CAGCATCAAGCTGAAGAATCTGAACAATTACATCAGCCTGTTCCGGAAGAAAACCAGAACCGAGAAGGAG
AATAAGGAGCTGGAGAACCTGGAGATCAATCTGCGGAAGGAGATCGCCAAGGCCTTCAAGGGCAACGAGG
GCTACAAGTCCCTGTTTAAGAAGGATATCATCGAGACAATCCTGCCAGAGTTCCTGGACGATAAGGACGAG
ATCGCCCTGGTGAACAGCTTCAATGGCTTTACCACAGCCTTCACCGGCTTCTTTGATAACAGAGAGAATATG
TTTTCCGAGGAGGCCAAGAGCACATCCATCGCCTTCAGGTGTATCAACGAGAATCTGACCCGCTACATCTCT
AATATGGACATCTTCGAGAAGGTGGACGCCATCTTTGATAAGCACGAGGTGCAGGAGATCAAGGAGAAGAT
CCTGAACAGCGACTATGATGTGGAGGATTTCTTTGAGGGCGAGTTCTTTAACTTTGTGCTGACACAGGAGG
GCATCGACGTGTATAACGCCATCATCGGCGGCTTCGTGACCGAGAGCGGCGAGAAGATCAAGGGCCTGAA
CGAGTACATCAACCTGTATAATCAGAAAACCAAGCAGAAGCTGCCTAAGTTTAAGCCACTGTATAAGCAGG
TGCTGAGCGATCGGGAGTCTCTGAGCTTCTACGGCGAGGGCTATACATCCGATGAGGAGGTGCTGGAGGTG
TTTAGAAACACCCTGAACAAGAACAGCGAGATCTTCAGCTCCATCAAGAAGCTGGAGAAGCTGTTCAAGA
ATTTTGACGAGTACTCTAGCGCCGGCATCTTTGTGAAGAACGGCCCCGCCATCAGCACAATCTCCAAGGATA
TCTTCGGCGAGTGGAACGTGATCCGGGACAAGTGGAATGCCGAGTATGACGATATCCACCTGAAGAAGAA
GGCCGTGGTGACCGAGAAGTACGAGGACGATCGGAGAAAGTCCTTCAAGAAGATCGGCTCCTTTTCTCTG
GAGCAGCTGCAGGAGTACGCCGACGCCGATCTGTCTGTGGTGGAGAAGCTGAAGGAGATCATCATCCAGA
AGGTGGATGAGATCTACAAGGTGTATGGCTCCTCTGAGAAGCTGTTCGACGCCGATTTTGTGCTGGAGAAG
AGCCTGAAGAAGAACGACGCCGTGGTGGCCATCATGAAGGACCTGCTGGATTCTGTGAAGAGCTTCGAGA
ATTACATCAAGGCCTTCTTTGGCGAGGGCAAGGAGACAAACAGGGACGAGTCCTTCTATGGCGATTTTGTG
CTGGCCTACGACATCCTGCTGAAGGTGGACCACATCTACGATGCCATCCGCAATTATGTGACCCAGAAGCCC
TACTCTAAGGATAAGTTCAAGCTGTATTTTCAGAACCCTCAGTTCATGGGCGGCTGGGACAAGGATAAGGA
GACAGACTATCGGGCCACCATCCTGAGATACGGCTCCAAGTACTATCTGGCCATCATGGATAAGAAGTACGC
CAAGTGCCTGCAGAAGATCGACAAGGACGATGTGAACGGCAATTACGAGAAGATCAACTATAAGCTGCTG
CCCGGCCCTAATAAGATGCTGCCAAAGGTGTTCTTTTCTAAGAAGTGGATGGCCTACTATAACCCCAGCGAG
GACATCCAGAAGATCTACAAGAATGGCACATTCAAGAAGGGCGATATGTTTAACCTGAATGACTGTCACAA -continued

SEQUENCE LISTING

| | |
|---|---|
| | GCTGATCGACTTCTTTAAGGATAGCATCTCCCGGTATCCAAAGTGGTCCAATGCCTACGATTTCAACTTTTCT<br>GAGACAGAGAAGTATAAGGACATCGCCGGCTTTTACAGAGAGGTGGAGGAGCAGGGCTATAAGGTGAGCT<br>TCGAGTCTGCCAGCAAGAAGGAGGTGGATAAGCTGGTGGAGGAGGGCAAGCTGTATATGTTCCAGATCTAT<br>AACAAGGACTTTTCCGATAAGTCTCACGGCACACCCAATCTGCACACCATGTACTTCAAGCTGCTGTTTGA<br>CGAGAACAATCACGGACAGATCAGGCTGAGCGGAGGAGCAGAGCTGTTCATGAGGCGCGCCTCCCTGAAG<br>AAGGAGGAGCTGGTGGTGCACCCAGCCAACTCCCCTATCGCCAACAAGAATCCAGATAATCCCAAGAAAA<br>CCACAACCCTGTCCTACGACGTGTATAAGGATAAGAGGTTTTCTGAGGACCAGTACGAGCTGCACATCCCA<br>ATCGCCATCAATAAGTGCCCCAAGAACATCTTCAAGATCAATACAGAGGTGCGCGTGCTGCTGAAGCACGA<br>CGATAACCCCTATGTGATCGGCATCGacAGGGGCGAGCGCAATCTGCTGTATATCGTGGTGGTGGACGGCAA<br>GGGCAACATCGTGGAGCAGTATTCCCTGAACGAGATCATCAACAACTTCAACGGCATCAGGATCAAGACAG<br>ATTACCACTCTCTGCTGGACAAGAAGGAGAAGGAGAGGTTCGAGGCCCGCCAGAACTGGACCTCCATCGA<br>GAATATCAAGGAGCTGAAGGCCGGCTATATCTCTCAGGTGGTGCACAAGATCTGCGAGCTGGTGGAGAAGT<br>ACGATGCCGTGATCGCCCTGGAGGACCTGAACTCTGGCTTTAAGAATAGCCGCGTGAAGGTGGAGAAGCA<br>GGTGTATCAGAAGTTCGAGAAGATGCTGATCGATAAGCTGAACTACATGGTGGACAAGAAGTCTAATCCTT<br>GTGCAACAGGCGGCGCCCTGAAGGGCTATCAGATCACCAATAAGTTCGAGAGCTTTAAGTCCATGTCTACC<br>CAGAACGGCTTCATCTTTTACATCCCTGCCTGGCTGACATCCAAGATCGATCCATCTACCGGCTTTGTGAAC<br>CTGCTGAAAACCAAGTATACCAGCATCGCCGATTCCAAGAAGTTCATCAGCTCCTTTGACAGGATCATGTAC<br>GTGCCCGAGGAGGATCTGTTCGAGTTTGCCCTGGACTATAAGAACTTCTCTCGCACAGACGCCGATTACATC<br>AAGAAGTGGAAGCTGTACTCCTACGGCAACCGGATCAGAATCTTCCGGAATCCTAAGAAGAACAACGTGTT<br>CGACTGGGAGGAGGTGTGCCTGACCAGCGCCTATAAGGAGCTGTTCAACAAGTACGGCATCAATTATCAGC<br>AGGGCGATATCAGAGCCCTGCTGTGCGAGCAGTCCGACAAGGCCTTCTACTCTAGCTTTATGGCCCTGATGA<br>GCCTGATGCTGCAGATGCGGAACAGCATCACAGGCCGCACCGACGTGGATTTTCTGATCAGCCCTGTGAAG<br>AACTCCGACGGCATCTTCTACGATAGCCGGAACTATGAGGCCCAGGAGAATGCCATCCTGCCAAAGAACGC<br>CGACGCCAATGGCGCCTATAACATCGCCAGAAAGGTGCTGTGGGCCATCGGCCAGTTCAAGAAGGCCGAG<br>GACGAGAAGCTGGATAAGGTGAAGATCGCCATCTCTAACAAGGAGTGGCTGGAGTACGCCCAGACCAGCG<br>TGAAGCAC |
| SEQ ID NO:<br>59 | >Cas12i.3 Codon Optimized<br>ATGAAGAAAGTGGAAGTGAGCAGACCCTACCAAAGCCTACTGCTGCCCAATCACCGGAAGTTCAAGTACC<br>TGGACGAAACCTGGAACGCCTACAAGTCCGTGAAGAGCCTGCTGCACAGATTCCTCGTTTGTGCCTATGGA<br>GCCGTCCCCTTCAATAAGTTTGTGGAAGTGGTGGAGAAAGTGGATAATGACCAACTGGTGCTGGCCTTCGC<br>TGTGAGACTGTTCAGACTTGTGCCTGTGGAGTCCACCAGCTTCGCCAAGGTGGACAAAGCCAACCTGGCT<br>AAGAGCCTGGCCAACCACCTGCCTGTGGGAACAGCTATCCCTGCAAACGTGCAGAGCTACTTCGACAGCA<br>ACTTCGACCCAAAGAAGTACATGTGGATCGACTGCGCCTGGGAGGCCGACCGGCTGGCCAGAGAAATGGG<br>ACTGAGCGCCTCTCAGTTTTCGGAGTACGCCACGACCATGCTGTGGGAAGATTGGCTGCCTCTGAACAAGG<br>ACGATGTGAATGGCTGGGGCTCCGTGTCTGGCCTGTTTGGGGAGGGTAAGAAGGAGGACAGACAGCAGAA<br>GGTGAAGATGCTGAACAACCTGCTGAACGGAATCAAAAAGAACCCTCCTAAGGACTATACACAGTACCTG<br>AAGATCCTGTTAAACGCCTTCGATGCCAAGAGCCACAAAGAAGCCGTTAAAAACTACAAGGGAGATAGCA<br>CCGGCAGAACCGCCAGCTACCTGAGCGAGAAGAGCGGCGAGATCACCGAGCTGATGCTGGAACAGCTGAT<br>GAGCAACATCCAGAGGGATATCGGAGACAAACAAAAAGAAATCAGCCTGCCAAAAAAAGATGTGGTTAAG<br>AAATACCTCGAAAGCGAAAGCGGAGTGCCTTACGATCAGAACCTGTGGAGCCAGGCCTACCGGAACGCCG<br>CTAGCTCTATCAAGAAAACCGATACAAGAAACTTTAACTCTACCCTGGAGAAGTTCAAGAACGAGGTGGAA<br>CTGAGAGGCCTGCTGAGCGAAGGCGATGACGTGGAAATCCTGCGGAGCAAGTTCTTCAGCTCTGAGTTCC<br>ACAAGACCCCTGACAAGTTCGTTATCAAGCCTGAGCACATCGGCTTCAACAACAAGTACAACGTGGTGGC<br>CGAGCTGTACAAGCTGAAGGCCGAGGCCACCGACTTCGAGAGTGCCTTCGCCACAGTGAAGGACGAGTTC<br>GAGGAAAAAGGCATCAAGCACCCTATCAAGAACATCCTGGAATACATCTGGAACAACGAGGTGCCCGTGG<br>AGAAGTGGGGCAGAGTGGCCAGATTCAACCAGTCTGAGGAGAAGCTGCTGAGAATTAAAGCTAATCCTAC<br>CGTGGAATGCAATCAGGGCATGACATTTGGCAACAGCGCCATGGTGGGCGAGGTGCTGAGAAGCAACTAC<br>GTGAGCAAAAAGGGCGCCCTGGTGAGCGGCGAGCACGGCGGCCGGCTGATCGGCCAGAATAACATGATCT<br>GGCTGGAAATGCGGCTGCTGAACAAGGGCAAGTGGGAGACACACCACGTGCCCACCCACAACATGAAGTT<br>CTTCGAAGAGGTGCACGCCTACAATCCTTCTCTGGCCGACTCTGTGAACGTGCGGAATAGACTGTACAGAA<br>GTGAGGATTATACACAGCTCCCAAGCAGCATCACCGATGGACTGAAAGGCAACCCCAAGGCCAAGCTGCT<br>GAAGAGACAACACTGTGCCCTGAATAACATGACCGCCAACGTGCTGAATCCCAAACTGAGCTTCACCATCA<br>ACAAGAAGAACGACGACTACACCGTGATCATCGTGCATAGCGTGGAGGTCTCCAAGCCCCGGAGAGAGGT<br>CCTCGTGGGCGACTACCTGGTGGGCATGGATCAGAACCAGACAGCCAGCAACACCTACGCCGTTATGCAGG<br>TGGTTAAGCCCAAGTCCACCGACGCCATTCCTTTCAGAAACATGTGGGTACGCTTCGTGGAGAGCGGCAGC<br>ATCGAGTCCCGGACCCTGAATAGCCGGGGCGAGTACGTGGATCAGCTGAATCATGATGGCGTGGACCTGTT<br>CGAAATCGGCGACACCGAGTGGGTCGACAGCGCCCGGAAGTTTTTCAACAAGTTGGGAGTGAAGCACAA<br>GGATGGCACCTTGGTGGACCTGAGCACCGCCCCTAGAAAGGCTTACGCCTTTAACAACTTCTACTTTAAGA<br>CCATGCTGAACCACCTGCGGAGCAACGAGGTCGACCTGACACTGCTGCGGAACGAGATCCTGAGAGTCGC<br>TAACGGCAGATTCAGCCCTATGCGGCTGGGCAGCCTGTCCTGGACCACCCTGAAGGCCCTGGGTTCCTTCA<br>AGTCACTCGTTCTGTCCTATTTCGACAGACTAGGCGCCAAAGAGATGGTGGACAAGGAGGCCAAGGACAA<br>GTCCCTGTTCGACCTGCTGGTGGCCATCAACAACAAGCGGAGCAACAAGCGCGAGGAACGGACCAGCAG<br>GATCGCCAGCAGCCTGATGACCGTGGCCCAGAAATACAAGGTTGACAACGCTGTGGTGCACGTGGTGGTG<br>GAGGGCAATCTCTCTTCCACAGACCGGAGCGCATCCAAGGCCCACAACAGAAACACAATGGACTGGTGCA<br>GCAGAGCCGTAGTCAAAAAGCTGGAAGATATGTGCAACCTGTACGGCTTCAACATCAAGGGTGTGCCTGCT<br>TTTTACACATCTCACCAGGACCCACTGGTGCACAGAGCCGACTACGACGATCCGAAGCCTGCTCTGAGATG<br>CAGATACTCTAGCTACTCTAGAGCCGATTTTAGTAAGTGGGGACAGAACGCCCTGGCTGCCGTGGTCAGAT<br>GGGCCAGCAACAAAAAAAGCAACACATGCTACAAGGTGGGCGCCGTGGAGTTCCTGAAGCAGCACGGCC<br>TGTTCGCCGATAAGAAACTGACCGTCGAGCAGTTCCTGTCTAAGGTGAAGGATGAAGAGATTCTCATCCCT<br>AGACGGGGCGGAAGAGTGTTCCTTACAACCCACAGGCTGCTGGCAGAGTCTACCTTTGTGTACCTGAATGG<br>CGTGAAATACCACAGCTGTAATGCCGACGAGGTGGCCGCTGTTAATATCTGCCTGAACGACTGGGTGATTCC<br>CTGCAAGAAAAAAATGAAGGAAGAGAGCAGCGCCAGCGGCGGCTCTGGGAGC |
| SEQ ID NO:<br>60 | >SpCas9-crRNA<br>CCAUUACAGUAGGAGCAUACGUUUUAGAGCUAGAAAUAGCAAGUUAAAAUAAGGCUAGUCCGUUAUC<br>AACUUGAAAAAGUGGCACCGAGUCGGUGC |

-continued

SEQUENCE LISTING

| SEQ ID NO: | Sequence |
|---|---|
| 61 | >LbCas12a-crRNA<br>UAAUUUCUACUAAGUGUAGAUCCAUUACAGUAGGAGCAUAC |
| 62 | >Cas12i.3-crRNA<br>AGAGAAUGUGUGCAUAGUCACACCCAUUACAGUAGGAGCAUAC |
| 63 | >SiCas12i-DMNT1-crRNA<br>AGAAAUGUGUCCCCAGUUGACACCCUCACUCCUGCUCGGUGAAUU |
| 64 | >SpCas9-DMNT1-gRNA<br>UCACUCCUGCUCGGUGAAUUGUUUUAGAGCUAGAAAUAGCAAGUUAAAAUAAGGCUAGUCCGUUAUC<br>AACUUGAAAAAGUGGCACCGAGUCGGUGC |
| 65 | >LbCas12a-DMNT1-crRNA<br>UAAUUUCUACUAAGUGUAGAUCCUCACUCCUGCUCGGUGAAUU |
| 66 | >Cas12i.3-DMNT1-crRNA<br>AGAGAAUGUGUGCAUAGUCACACCCUCACUCCUGCUCGGUGAAUU |
| 67 | >SiCas12i-TTR-crRNA<br>AGAAAUGUGUCCCCAGUUGACACAGAAAGGCUGCUGAUGACAC |
| 68 | >SpCas9-TTR-gRNA<br>AAAGGCUGCUGAUGACACCUGUUUUAGAGCUAGAAAUAGCAAGUUAAAAUAAGGCUAGUCCGUUAUC<br>AACUUGAAAAAGUGGCACCGAGUCGGUGC |
| 69 | >LbCas12a-TTR-crRNA<br>UAAUUUCUACUAAGUGUAGAUAGAAAGGCUGCUGAUGACAC |
| 70 | >Cas12i.3-TTR-crRNA<br>AGAGAAUGUGUGCAUAGUCACACAGAAAGGCUGCUGAUGACAC |
| 71 | >SiCas12i-PCSK9.1-crRNA<br>AGAAAUGUGUCCCCAGUUGACACCCCAGAGCAUCCCGUGGAAC |
| 72 | >SpCas9-PCSK9.1-gRNA<br>CCAGAGCAUCCCGUGGAACCGUUUUAGAGCUAGAAAUAGCAAGUUAAAAUAAGGCUAGUCCGUUAUC<br>AACUUGAAAAAGUGGCACCGAGUCGGUGC |
| 73 | >LbCas12a-PCSK9.1-crRNA<br>UAAUUUCUACUAAGUGUAGAUCCCAGAGCAUCCCGUGGAAC |
| 74 | >Cas12i.3-PCSK9.1-crRNA<br>AGAGAAUGUGUGCAUAGUCACACCCCAGAGCAUCCCGUGGAAC |
| 75 | >SiCas12i-PCSK9.2-crRNA<br>AGAAAUGUGUCCCCAGUUGACACCCUUGACAGUUGAGCACACG |
| 76 | >SpCas9-PCSK9.2-gRNA<br>CUUGACAGUUGAGCACACGCGUUUUAGAGCUAGAAAUAGCAAGUUAAAAUAAGGCUAGUCCGUUAUC<br>AACUUGAAAAAGUGGCACCGAGUCGGUGC |
| 77 | >LbCas12a-PCSK9.2-crRNA<br>UAAUUUCUACUAAGUGUAGAUCCUUGACAGUUGAGCACACG |
| 78 | >Cas12i.3-PCSK9.2-crRNA<br>AGAGAAUGUGUGCAUAGUCACACCCUUGACAGUUGAGCACACG |
| 79 | >dSiCas12i(D700A)<br>MSSDVVRPYNTKLLPDNRKHNMFLQTFKRLNSISLNHFDLLICLYAAITNKKAEEYKSEKEAHVTADSLCAINW<br>FRPMSKRYSKYATTTFNMLELFKEYSGHEPDAYSKNYLMSNIDSDRFVWVDCRKFAKDFAYQMELGFHEFTVL<br>AETLLANSILVLNESTKANWAWGTVSALYGGGDKEDSTLKSKILLAFVDALNNHELKTKREILNQVCESLKYQ<br>SYQDMYVDFRSVVDENGNKKSPNGSMPIVTKFETDDLISDNQRKAMISNFTKNAAAKAAKKPIPYLDRLKEH<br>MVSLCDEYNVYAWAAAITNSNADVTARNTRNLTFIGEQNSRRKELSVLQTTTNEKAKDILNKINDNLIQEVRYT<br>PAPKHLGRDLANLFDTLKEKDINNIENEEEKQNVINDCIEQYVDDCRSLNRNPIAALLKHISRYYEDFSAKNFLD<br>GAKLNVLTEVVNRQKAHPTIWSEKAYTWISKFDKNRRQANSSLVGWVVPPEEVHKEKIAGQQSMMWVTLTLL<br>DDGKWVKHHIPFSDSRYYSEVYAYNPNLPYLDGGIPRQSKFGNKPTTNLTAESQALLANSKYKKANKSFLRAK<br>ENATHNVRVSPNTSLCIRLLKDSAGNQMFDKIGNVLFGMQINHKITVGKPNYKIEVGDRFLGFDQNQSENHTY<br>AVLQRVSESSHDTHHFNGWDVKVLEKGKVTSDVIVRDEVYAQLSYEGVPYDSSKFAEWRDKRRRFVLENLSIQ<br>LEEGKTFLTEFDKLNKDSLYRWNMNYLKLLRKAIRAGGKEFAKIAKTEIFELAVERFGPINLGSLSQISLKMIASF<br>KGVVQSYFSVSGCVDDASKKAHDSMLFTFMCAAEEKRTNKREEKTNRAASFILQKAYLHGCKMIVCEDDLPV<br>ADGKTGKAQNADRMDWCARALAKKVNDGCVAMSICYRAIPAYMSSHQDPFVHMQDKKTSVLRPRFMEVNK<br>DSIRDYHVAGLRRMLNSKSDAGTSVYYRQAALHFCEALGVSPELVKNKKTHAAELGKHMGSAMLMPWRGG<br>RVYIASKKLTSDAKSVKYCGEDMWQYHADEIAAVNIAMYEVCCQTGAFGKKQKKSDELPG |

-continued

| SEQUENCE LISTING | |
|---|---|
| SEQ ID NO: 80 | >dSiCas12i(D650A)<br>MSSDVVRPYNTKLLPDNRKHNMFLQTFKRLNSISLNHFDLLICLYAAITNKKAEEYKSEKEAHVTADSLCAINW<br>FRPMSKRYSKYATTTFNMLELFKEYSGHEPDAYSKNYLMSNIDSDRFVWVDCRKFAKDFAYQMELGFHEFTVL<br>AETLLANSILVLNESTKANWAWGTVSALYGGGDKEDSTLKSKILLAFVDALNNHELKTKREILNQVCESLKYQ<br>SYQDMYVDFRSVVDENGNKKSPNGSMPIVTKFETDDLISDNQRKAMISNFTKNAAAKAAKKPIPYLDRLKEH<br>MVSLCDEYNVYAWAAAITNSNADVTARNTRNLTFIGEQNSRRKELSVLQTTTNEKAKDILNKINDNLIQEVRYT<br>PAPKHLGRDLANLFDTLKEKDINNIENEEEKQNVINDCIEQYVDDCRSLNRNPIAALLKHISRYYEDFSAKNFLD<br>GAKLNVLTEVVNRQKAHPTIWSEKAYTWISKFDKNRRQANSSLVGWVVPPEEVHKEKIAGQQSMMWVTLTLL<br>DDGKWVKHHIPFSDSRYYSEVYAYNPNLPYLDGGIPRQSKFGNKPTTNLTAESQALLANSKYKKANKSFLRAK<br>ENATHNVRVSPNTSLCIRLLKDSAGNQMFDKIGNVLFGMQINHKITVGKPNYKIEVGDRFLGFAQNQSENHTYA<br>VLQRVSESSHDTHHFNGWDVKVLEKGKVTSDVIVRDEVYDQLSYEGVPYDSSKFAEWRDKRRRFVLENLSIQ<br>LEEGKTFLTEFDKLNKDSLYRWNMNYLKLLRKAIRAGGKEFAKIAKTEIFELAVERFGPINLGSLSQISLKMIASF<br>KGVVQSYFSVSGCVDDASKKAHDSMLFTFMCAAEEKRTNKREEKTNRAASFILQKAYLHGCKMIVCEDDLPV<br>ADGKTGKAQNADRMDWCARALAKKVNDGCVAMSICYRAIPAYMSSHQDPFVHMQDKKTSVLRPRFMEVNK<br>DSIRDYHVAGLRRMLNSKSDAGTSVYYRQAALHFCEALGVSPELVKNKKTHAAELGKHMGSAMLMPWRGG<br>RVYIASKKLTSDAKSVKYCGEDMWQYHADEIAAVNIAMYEVCCQTGAFGKKQKKSDELPG |
| SEQ ID NO: 81 | >dSiCas12i(E875A)<br>MSSDVVRPYNTKLLPDNRKHNMFLQTFKRLNSISLNHFDLLICLYAAITNKKAEEYKSEKEAHVTADSLCAINW<br>FRPMSKRYSKYATTTFNMLELFKEYSGHEPDAYSKNYLMSNIDSDRFVWVDCRKFAKDFAYQMELGFHEFTVL<br>AETLLANSILVLNESTKANWAWGTVSALYGGGDKEDSTLKSKILLAFVDALNNHELKTKREILNQVCESLKYQ<br>SYQDMYVDFRSVVDENGNKKSPNGSMPIVTKFETDDLISDNQRKAMISNFTKNAAAKAAKKPIPYLDRLKEH<br>MVSLCDEYNVYAWAAAITNSNADVTARNTRNLTFIGEQNSRRKELSVLQTTTNEKAKDILNKINDNLIQEVRYT<br>PAPKHLGRDLANLFDTLKEKDINNIENEEEKQNVINDCIEQYVDDCRSLNRNPIAALLKHISRYYEDFSAKNFLD<br>GAKLNVLTEVVNRQKAHPTIWSEKAYTWISKFDKNRRQANSSLVGWVVPPEEVHKEKIAGQQSMMWVTLTLL<br>DDGKWVKHHIPFSDSRYYSEVYAYNPNLPYLDGGIPRQSKFGNKPTTNLTAESQALLANSKYKKANKSFLRAK<br>ENATHNVRVSPNTSLCIRLLKDSAGNQMFDKIGNVLFGMQINHKITVGKPNYKIEVGDRFLGFDQNQSENHTY<br>AVLQRVSESSHDTHHFNGWDVKVLEKGKVTSDVIVRDEVYDQLSYEGVPYDSSKFAEWRDKRRRFVLENLSI<br>QLEEGKTFLTEFDKLNKDSLYRWNMNYLKLLRKAIRAGGKEFAKIAKTEIFELAVERFGPINLGSLSQISLKMIAS<br>FKGVVQSYFSVSGCVDDASKKAHDSMLFTFMCAAEEKRTNKREEKTNRAASFILQKAYLHGCKMIVCADDLP<br>VADGKTGKAQNADRMDWCARALAKKVNDGCVAMSICYRAIPAYMSSHQDPFVHMQDKKTSVLRPRFMEVN<br>KDSIRDYHVAGLRRMLNSKSDAGTSVYYRQAALHFCEALGVSPELVKNKKTHAAELGKHMGSAMLMPWRG<br>GRVYIASKKLTSDAKSVKYCGEDMWQYHADEIAAVNIAMYEVCCQTGAFGKKQKKSDELPG |
| SEQ ID NO: 82 | >dSiCas12i(D1049A)<br>MSSDVVRPYNTKLLPDNRKHNMFLQTFKRLNSISLNHFDLLICLYAAITNKKAEEYKSEKEAHVTADSLCAINW<br>FRPMSKRYSKYATTTFNMLELFKEYSGHEPDAYSKNYLMSNIDSDRFVWVDCRKFAKDFAYQMELGFHEFTVL<br>AETLLANSILVLNESTKANWAWGTVSALYGGGDKEDSTLKSKILLAFVDALNNHELKTKREILNQVCESLKYQ<br>SYQDMYVDFRSVVDENGNKKSPNGSMPIVTKFETDDLISDNQRKAMISNFTKNAAAKAAKKPIPYLDRLKEH<br>MVSLCDEYNVYAWAAAITNSNADVTARNTRNLTFIGEQNSRRKELSVLQTTTNEKAKDILNKINDNLIQEVRYT<br>PAPKHLGRDLANLFDTLKEKDINNIENEEEKQNVINDCIEQYVDDCRSLNRNPIAALLKHISRYYEDFSAKNFLD<br>GAKLNVLTEVVNRQKAHPTIWSEKAYTWISKFDKNRRQANSSLVGWVVPPEEVHKEKIAGQQSMMWVTLTLL<br>DDGKWVKHHIPFSDSRYYSEVYAYNPNLPYLDGGIPRQSKFGNKPTTNLTAESQALLANSKYKKANKSFLRAK<br>ENATHNVRVSPNTSLCIRLLKDSAGNQMFDKIGNVLFGMQINHKITVGKPNYKIEVGDRFLGFDQNQSENHTY<br>AVLQRVSESSHDTHHFNGWDVKVLEKGKVTSDVIVRDEVYDQLSYEGVPYDSSKFAEWRDKRRRFVLENLSI<br>QLEEGKTFLTEFDKLNKDSLYRWNMNYLKLLRKAIRAGGKEFAKIAKTEIFELAVERFGPINLGSLSQISLKMIAS<br>FKGVVQSYFSVSGCVDDASKKAHDSMLFTFMCAAEEKRTNKREEKTNRAASFILQKAYLHGCKMIVCEDDLP<br>VADGKTGKAQNADRMDWCARALAKKVNDGCVAMSICYRAIPAYMSSHQDPFVHMQDKKTSVLRPRFMEVN<br>KDSIRDYHVAGLRRMLNSKSDAGTSVYYRQAALHFCEALGVSPELVKNKKTHAAELGKHMGSAMLMPWRG<br>GRVYIASKKLTSDAKSVKYCGEDMWQYHAAEIAAVNIAMYEVCCQTGAFGKKQKKSDELPG |
| SEQ ID NO: 83 | >Spacer-20nt<br>GUUUAAACACACCGGGUUAA |
| SEQ ID NO: 84 | >Spacer-23nt<br>GUUUAAACACACCGGGUUAAUAA |
| SEQ ID NO: 85 | >TadA8e-dSiCas12i(D1049A)<br>SEVEFSHEYWMRHALTLAKRARDEREVPVGAVLVLNNRVIGEGWNRAIGLHDPTAHAEIMALRQGGLVMQNY<br>RLIDATLYVTFEPCVMCAGAMIHSRIGRVVFGWRNSKRGAAGSLMNVLNYPGMNHRVEITEGILADECAALLC<br>DFYRMPRQVFNAQKKAQSSINSGGSSGGSSGSETPGTSESATPESSGGSSGGSSMSSDVVRPYNTKLLPDNRKH<br>NMFLQTFKRLNSISLNHFDLLICLYAAITNKKAEEYKSEKEAHVTADSLCAINWFRPMSKRYSKYATTTFNMLEL<br>FKEYSGHEPDAYSKNYLMSNIDSDRFVWVDCRKFAKDFAYQMELGFHEFTVLAETLLANSILVLNESTKANWA<br>WGTVSALYGGGDKEDSTLKSKILLAFVDALNNHELKTKREILNQVCESLKYQSYQDMYVDFRSVVDENGNKK<br>SPNGSMPIVTKFETDDLISDNQRKAMISNFTKNAAAKAAKKPIPYLDRLKEHMVSLCDEYNVYAWAAAITNSN<br>ADVTARNTRNLTFIGEQNSRRKELSVLQTTTNEKAKDILNKINDNLIQEVRYTPAPKHLGRDLANLFDTLKEKDI<br>NNIENEEEKQNVINDCIEQYVDDCRSLNRNPIAALLKHISRYYEDFSAKNFLDGAKLNVLTEVVNRQKAHPTIW<br>SEKAYTWISKFDKNRRQANSSLVGWVVPPEEVHKEKIAGQQSMMWVTLTLLDDGKWVKHHIPFSDSRYYSEV<br>YAYNPNLPYLDGGIPRQSKFGNKPTTNLTAESQALLANSKYKKANKSFLRAKENATHNVRVSPNTSLCIRLLKD<br>SAGNQMFDKIGNVLFGMQINHKITVGKPNYKIEVGDRFLGFDQNQSENHTYAVLQRVSESSHDTHHFNGWDV<br>KVLEKGKVTSDVIVRDEVYDQLSYEGVPYDSSKFAEWRDKRRRFVLENLSIQLEEGKTFLTEFDKLNKDSLYR<br>WNMNYLKLLRKAIRAGGKEFAKIAKTEIFELAVERFGPINLGSLSQISLKMIASFKGVVQSYFSVSGCVDDASK<br>KAHDSMLFTFMCAAEEKRTNKREEKTNRAASFILQKAYLHGCKMIVCEDDLPVADGKTGKAQNADRMDWCA<br>RALAKKVNDGCVAMSICYRAIPAYMSSHQDPFVHMQDKKTSVLRPRFMEVNKDSIRDYHVAGLRRMLNSKSD<br>AGTSVYYRQAALHFCEALGVSPELVKNKKTHAAELGKHMGSAMLMPWRGGRVYIASKKLTSDAKSVKYCGE<br>DMWQYHAAEIAAVNIAMYEVCCQTGAFGKKQKKSDELPG |

-continued

| SEQUENCE LISTING | |
|---|---|
| SEQ ID NO: 86 | >TadA8e-dCas12i.3<br>SEVEFSHEYWMRHALTLAKRARDEREVPVGAVLVLNNRVIGEGWNRAIGLHDPTAHAEIMALRQGGLVMQNY<br>RLIDATLYVTFEPCVMCAGAMIHSRIGRVVFGWRNSKRGAAGSLMNVLNYPGMNHRVEITEGILADECAALLC<br>DFYRMPRQVFNAQKKAQSSINSGGSSGGSSGSETPGTSESATPESSGGSSGGSSMGPKKKRKVMDYKDHDGDY<br>KDHDIDYKDDDDKKKVEVSRPYQSLLLPNHRKFKYLDETWNAYKSVKSLLHRFLVCAYGAVPFNKFVEVVEK<br>VDNDQLVLAFAVRLFRLVPVESTSFAKVDKANLAKSLANHLPVGTAIPANVQSYFDSNFDPKKYMWIDCAWEA<br>DRLAREMGLSASQFSEYATTMLWEDWLPLNKDDVNGWGSVSGLFGEGKKEDRQQKVKMLNNLLNGIKKNPP<br>KDYTQYLKILLNAFDAKSHKEAVKNYKGDSTGRTASYLSEKSGEITELMLEQLMSNIQRDIGDKQKEISLPKKD<br>VVKKYLESESGVPYDQNLWSQAYRNAASSIKKTDTRNFNSTLEKFKNEVELRGLLSEGDDVEILRSKFFSSEFH<br>KTPDKFVIKPEHIGFNNKYNVVAELYKLKAEATDFESAFATVKDEFEEKGIKHPIKNILEYIWNNEVPVEKWGRV<br>ARFNQSEEKLLRIKANPTVECNQGMTFGNSAMVGEVLRSNYVSKKGALVSGEHGGRLIGQNNMIWLEMRLLN<br>KGKWETHHVPTHNMKFFEEVHAYNPSLADSVNVRNRLYRSEDYTQLPSSITDGLKGNPKAKLLKRQHCALNN<br>MTANVLNPKLSFTINKKNDDYTVIIVHSVEVSKPRREVLVGDYLVGMAQNQTASNTYAVMQVVKPKSTDAIPF<br>RNMWVRFVESGSIESRTLNSRGEYVDQLNHDGVDLFEIGDTEWVDSARKFFNKLGVKHKDGTLVDLSTAPRK<br>AYAFNNFYFKTMLNHLRSNEVDLTLLRNEILRVANGRFSPMRLGSLSWTTLKALGSFKSLVLSYFDRLGAKEM<br>VDKEAKDKSLFDLLVAINNKRSNKREERTSRIASSLMTVAQKYKVDNAVVHVVVEGNLSSTDRSASKAHNRNT<br>MDWCSRAVVKKLEDMCNLYGFNIKGVPAFYTSHQDPLVHRADYDDPKPALRCRYSSYSRADFSKWGQNALA<br>AVVRWASNKKSNTCYKVGAVEFLKQHGLFADKKLTVEQFLSKVKDEEILIPRRGGRVFLTTHRLLAESTFVYLN<br>GVKYHSCNADEVAAVNICLNDWVIPCKKKMKEESSASGGSGS |
| SEQ ID NO: 87 | >SiCas12i-KLF4-crRNA<br>AGAAAUGUGUCCCCAGUUGACACGUUUAAACACACCGGGUUAA |
| SEQ ID NO: 88 | >Cas12i.3-KLF4-crRNA<br>AGAGAAUGUGUGCAUAGUCACACGUUUAAACACACCGGGUUAA |
| SEQ ID NO: 89 | crRNA coding sequence: DR-P + spacer<br>AGAAATGTGTCCCCAGTTGACACCCATTACAGTAGGAGCATACGGGA |
| SEQ ID NO: 90 | crRNA coding sequence: DR-A + spacer<br>AGAAATCCGTCCTTAGTTGACGGCCATTACAGTAGGAGCATACGGGA |
| SEQ ID NO: 91 | crRNA coding sequence: DR-B + spacer<br>AGACATGTGTCCCCAGTGACACCCATTACAGTAGGAGCATACGGGA |
| SEQ ID NO: 92 | crRNA coding sequence: DR-C + spacer<br>AGAAATGTTTCCCCAGTTGAAACCCATTACAGTAGGAGCATACGGGA |
| SEQ ID NO: 93 | crRNA coding sequence: DR-D + spacer<br>AGAAATGTGTTCCCAGTTAACACCCATTACAGTAGGAGCATACGGGA |
| SEQ ID NO: 94 | crRNA coding sequence: DR-E + spacer<br>AGAAATTTGTCCCCAGTTGACAACCATTACAGTAGGAGCATACGGGA |
| SEQ ID NO: 95 | crRNA: DR-P + spacer RNA sequence<br>AGAAAUGUGUCCCCAGUUGACACCCAUUACAGUAGGAGCAUACGGGA |
| SEQ ID NO: 96 | crRNA: DR-A + spacer RNA sequence<br>AGAAAUCCGUCCUUAGUUGACGGCCAUUACAGUAGGAGCAUACGGGA |
| SEQ ID NO: 97 | crRNA: DR-B + spacer RNA sequence<br>AGACAUGUGUCCCCAGUGACACCCAUUACAGUAGGAGCAUACGGGA |
| SEQ ID NO: 98 | crRNA: DR-C + spacer RNA sequence<br>AGAAAUGUUUCCCCAGUUGAAACCCAUUACAGUAGGAGCAUACGGGA |
| SEQ ID NO: 99 | crRNA: DR-D + spacer RNA sequence<br>AGAAAUGUGUUCCCAGUUAACACCCAUUACAGUAGGAGCAUACGGGA |
| SEQ ID NO: 100 | crRNA: DR-E + spacer RNA sequence<br>AGAAAUUUGUCCCCAGUUGACAACCAUUACAGUAGGAGCAUACGGGA |
| SEQ ID NO: 101 | DR-P RNA sequence<br>AGAAAUGUGUCCCCAGUUGACAC |
| SEQ ID NO: 102 | DR-A RNA sequence<br>AGAAAUCCGUCCUUAGUUGACGG |
| SEQ ID NO: 103 | DR-B RNA sequence<br>AGACAUGUGUCCCCAGUGACAC |
| SEQ ID NO: 104 | DR-C RNA sequence<br>AGAAAUGUUUCCCCAGUUGAAAC |
| SEQ ID NO: 105 | DR-D RNA sequence<br>AGAAAUGUGUUCCCAGUUAACAC |

-continued

| SEQUENCE LISTING | |
|---|---|
| SEQ ID NO: 106 | DR-E RNA sequence<br>AGAAAUUUGUCCCCAGUUGACAA |
| SEQ ID NO: 107 | **TTC**CCATTACAGTAGGAGCATAC**GGG** |
| SEQ ID NO: 108 | DR-A coding sequence<br>AGAAATCCGTCCTTAGTTGACGG |
| SEQ ID NO: 109 | DR-B coding sequence<br>AGACATGTGTCCCCAGTGACAC |
| SEQ ID NO: 110 | DR-C coding sequence<br>AGAAATGTTTCCCCAGTTGAAAC |
| SEQ ID NO: 111 | DR-D coding sequence<br>AGAAATGTGTTCCCAGTTAACAC |
| SEQ ID NO: 112 | DR-E coding sequence<br>AGAAATTTGTCCCCAGTTGACAA |
| SEQ ID NO: 113 | DR-P coding sequence<br>AGAAATGTGTCCCCAGTTGACAC |
| SEQ ID NO: 114 | CUCCCNNNNNNUGGGAG |
| SEQ ID NO: 115 | CUCCUNNNNNNUGGGAG |
| SEQ ID NO: 116 | GUCCCNNNNNNUGGGAC |
| SEQ ID NO: 117 | GUGUCNNNNNNUGACAC |
| SEQ ID NO: 118 | GUGCCNNNNNNUGGCAC |
| SEQ ID NO: 119 | UGUGUNNNNNNUCACAC |
| SEQ ID NO: 120 | CCGUCNNNNNNUGACGG |
| SEQ ID NO: 121 | GUUUCNNNNNNUGAAAC |
| SEQ ID NO: 122 | GUGUUNNNNNNUAACAC |
| SEQ ID NO: 123 | UUGUCNNNNNNUGACAA |
| SEQ ID NO: 176 (5'UTR-NLS-SiCas12i-NLS-3'UTR-PolyA mRNA) | ACAUUUGCUUCUGACACAACUGUGUUCACUAGCAACCUCAAACAGACACCGCCACCAUGGCCCCAAAG<br>AAGAAGCGGAAGGUCGGUAUCCACGGAGUCCCAGCAGCCAUGAGUUCUGAUGUGGUGCGGCCUUAUAA<br>CACAAAGCUGCUCCCAGAUAACAGAAAGCACAAUAUGUUCCUGCAGACCUUCAAGCGGCUGAACAGCA<br>UCUCUCUGAACCACUUCGACCUGCUGAUCUGCCUGUACGCUGCAAUCACCAACAAGAAGGCCGAGGAA<br>UACAAGUCUGAAAAGGAAGCCCACGUGACCGCCGAUAGCCUGUGUGCCAUCAAUUGGUUCAGACCCAU<br>GAGCAAGAGAUACAGCAAAUACGCCACCACCACCUUCAACAUGUUAGAACUGUUUAAGGAGUACAGCG<br>GCCACGAGCCUGAUGCCUAUUCCAAGAACUACCUGAUGAGCAAUAUCGACAGCGACAGAUUCGUGUGG<br>GUGGAUUGUAGGAAGUUCGCUAAGGACUUUGCCUAUCAGAUGGAACUGGGUUUCCACGAGUUCACCG<br>UGUUGGCCGAAACCCUGCUGGCUAAUUCUAUCCUGGUGCUGAACGAGAGCACCAAGGCCAAUUGGGCU<br>UGGGGAACCGUGUCUGCCCUGUACGGCGGCGGAGAUAAGGAGGACAGCACACUGAAGAGCAAGAUUCU<br>GCUGGCCUUCGUGGACGCCCUGAACAACCACGAGCUGAAAACAAAGAGAGAAAUCUUGAAUCAAGUGU<br>GUGAAUCUCUGAAAUACCAGAGCUACCAGGACAUGUACGUGGAUUUUAGAAGCGUGGUUGACGAAAA<br>CGGCAACAAGAAGUCUCCUAACGGCUCUAUGCCUAUCGUGACCAAGUUCGAGACAGACGACCUGAUCA<br>GCGACAACCAAAGAAAGGCCAUGAUCAGCAACUUCACUAAGAACGCCGCUGCCAAGGCAGCUAAGAAA<br>CCUAUCCCUUACUUGGACCGCCUGAAGGAGCACAUGGUGUCCCUGUGCGACGAGUACAAUGUGUAUGC<br>CUGGGCCGCGGCCAUCACAAACAGCAACGCCGACGUGACCGCCCGGAAUACCAGAAACCUGACAUUCA<br>UCGGCGAACAGAACAGCAGACGAAAGGAACUGAGCGUGCUGCAGACAACAACCAACGAGAAGGCUAAG<br>GACAUCCUGAACAAGAUCAACGACAACCUGAUUCAGGAGGUGCGGUACACCCCUGCCCCUAAGCACCU<br>GGGCAGAGAUCUGGCCAACCUGUUUGAUACACUGAAGGAAAAGGACAUCAACAACAUCGAGAACGAA<br>GAAGAGAAACAGAACGUGAUCAAUGACUGUAUCGAGCAGUACGUGGACGAUUGCAGAAGCCUCAACC<br>GGAACCCCAUCGCAGCCCUCCUGAAGCACAUCUCUAGGUACUACGAGGAUUUCAGCGCCAAGAAUUUC<br>CUGGACGGCGCCAAGCUGAACGUGCUGACUGAGGUGGUGAACCGGCAGAAGGCCCACCCCACCAUCUG<br>GAGCGAGAAGGCUUACACCUGGAUCAGCAAGUUCGACAAGAACCGGAGACAGGCCAACAGCAGCCUGG |

-continued

SEQUENCE LISTING

UCGGAUGGGUUGUGCCCCCCGAGGAGGUGCACAAGGAGAAAAUCGCCGGACAGCAGAGCAUGAUGUGG
GUGACCCUCACCCUGCUGGACGACGGCAAGUGGGUCAAACAUCACAUCCCCUUCAGCGACAGCAGAUA
CUACAGCGAAGUGUACGCCUACAACCCUAAUCUGCCUUAUCUGGACGGAGGCAUCCCAAGACAGAGCA
AGUUCGGCAACAAACCAACAACCAACCUGACAGCCGAGUCCCAGGCCCUCCUGGCUAAUUCUAAGUAC
AAGAAAGCCAACAAGAGCUUCCUGCGGGCUAAAGAGAAUGCCACACACAACGUGCGGGUGUCCCCUAA
CACCUCUCUGUGCAUUAGACUGCUGAAGGACAGCGCCGGAAACCAGAUGUUCGACAAAAUCGGCAACG
UGCUCUUCGGCAUGCAGAUCAACCACAAGAUCACCGUGGGAAAACCUAACUACAAGAUCGAGGUGGGC
GACAGAUUCCUGGGCUUCGAUCAGAACCAGAGCGAGAACCACACCUACGCCGUGCUGCAGAGAGUGUC
CGAGAGCAGUCACGACACCCACCACUUUAACGGCUGGGACGUGAAGGUGCUGGAAAAGGGCAAAGUGA
CCAGCGAUGUGAUCGUGCGGGACGAGGUCUACGACCAACUGUCUUACGAGGGCGUCCCCUACGAUAGC
AGCAAGUUCGCCGAGUGGCGGGACAAGCGCAGAAGAUUUGUGCUUGAGAACCUGAGCAUCCAGCUGGA
AGAGGGCAAGACCUUCCUGACAGAGUUCGACAAGCUGAAUAAGGACAGCCUGUACCGCUGGAACAUGA
ACUACCUGAAACUGCUGAGAAAGGCCAUCCGGGCCGGAGGCAAAGAGUUCGCCAAGAUCGCUAAGACA
GAGAUCUUCGAGCUGGCGGUGGAAAGAUUCGGCCCUAUUAACCUGGGCAGCCUGUCCCAGAUCAGCCU
UAAGAUGAUUGCCUCCUUUAAGGGCGUGGUCCAGUCCUACUUCUCCGUGAGCGGCUGCGUGGAUGAUG
CCUCCAAAAAGGCCCAUGAUUCUAUGCUGUUCACAUUUAUGUGCGCCGCCGAAGAAAAGCGGACCAAC
AAGAGAGAAGAAAAGACCAACAGAGCCGCCAGCUUUAUCCUGCAAAAAGCCUACCUGCAUGGCUGCAA
GAUGAUCGUGUGCGAGGACGACCUUCCUGUGGCCGACGGCAAGACAGGCAAAGCCCAGAAUGCCGACC
GGAUGGACUGGUGCGCCAGAGCCCUGGCCAAGAAGGUGAACGACGGCUGUGUUGCCAUGAGCAUCUGC
UACAGAGCUAUCCCUGCCUACAUGAGCAGCCACCAGGACCCCUUUGUGCACAUGCAGGAUAAGAAAAC
CAGCGUGCUGCGGCCUAGAUUCAUGGAAGUUAAUAAGGAUAGCAUCAGAGACUACCACGUGGCGGGCC
UGAGAAGAAUGCUGAACAGCAAGAGUGACGCUGGCACCAGUGUUUAUUACCGGCAAGCUGCCCUGCAU
UUCUGCGAAGCCCUGGGCGUGAGCCCUGAACUGGUGAAAAACAAGAAAACCCACGCCGCCGAACUGGG
CAAGCACAUGGGCAGCGCUAUGCUGAUGCCCUGGAGAGGCGGUAGAGUGUACAUCGCCAGCAAAAAGC
UGACCUCCGAUGCCAAAUCAGUGAAGUACUGCGGCGAGGAUAUGUGGCAGUACCACGCCGAUGAGAUC
GCCGCUGUUAACAUCGCCAUGUAUGAGGUGUGCUGCCAGACCGGCGCUUUCGGAAAGAAACAGAAAAA
AUCGGACGAGCUGCCUGGAAAAAGGCCGGCGGCCACGAAgAAGGCCGGCCAGGCAAAgAAGAAgAAGUA
AGCUCGCUUUCUUGCUGUCCAAUUUCUAUUAAAGGUUCCUUUGUUCCCUAAGUCCAACUACUAAACUG
GGGGAUAUUAUGAAGGGCCUUGAGCAUCUGGAUUCUGCCUAAUAAAAAACAUUUAUUUUCAUUGCAA
AAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAA

SEQ ID NO: 177 (short SiCas12i-mTTR-gRNA)

mA*mU*mG*ACUCAGAAAUGUGUCCCCAGUUGACACUAGAAGGAGUGUACAGAGUAU*mU*mU*mU

SEQ ID NO: 178 (long SiCas12i-mTTR-gRNA)

mC*mG*mC*GGUUCUAUCUAGUUACGCGUUAAACCAACUAGAAACCUCUUCUAUGACUCAGAAAUGUG
UCCCCAGUUGACACUAGAAGGAGUGUACAGAGUAU*mU*mU*mU

SEQ ID NO: 179 SV40 NLS

PKKKRKV

SEQ ID NO: 180 BP NLS

KRTADGSEFESPKKKRKV

SEQ ID NO: 181 BP NLS

KRTADGSESEPKKKRKV

SEQ ID NO: 182 TadA8e

SEVEFSHEYWMRHALTLAKRARDEREVPVGAVLVLNNRVIGEGWNRAIGLHDPTAHAEIMALRQGGLVMQNY
RLIDATLYVTFEPCVMCAGAMIHSRIGRVVFGWRNSKRGAAGSLMNVLNYPGMNHRVEITEGILADECAALLC
DFYRMPRQVFNAQKKAQSSIN

SEQ ID NO: 183 linker

SGGSSGGSSGSETPGTSESATPESSGGSSGGSS

SEQ ID NO: 184 TadA8e-dSiCas12i (E875A)

SEVEFSHEYWMRHALTLAKRARDEREVPVGAVLVLNNRVIGEGWNRAIGLHDPTAHAEIMALRQGGLVMQNY
RLIDATLYVTFEPCVMCAGAMIHSRIGRVVFGWRNSKRGAAGSLMNVLNYPGMNHRVEITEGILADECAALLC
DFYRMPRQVFNAQKKAQSSINSGGSSGGSSGSETPGTSESATPESSGGSSGGSSMSSDVVRPYNTKLLPDNRKH
NMFLQTFKRLNSISLNHFDLLICLYAAITNKKAEEYKSEKEAHVTADSLCAINWFRPMSKRYSKYATTTFNMLEL
FKEYSGHEPDAYSKNYLMSNIDSDRFVWVDCRKFAKDFAYQMELGFHEFTVLAETLLANSILVLNESTKANWA
WGTVSALYGGGDKEDSTLKSKILLAFVDALNNHELKTKREILNQVCESLKYQSYQDMYVDFRSVVDENGNKK
SPNGSMPIVTKFETDDLISDNQRKAMISNFTKNAAAKAAKKPIPYLDRLKEHMVSLCDEYNVYAWAAAITNSN
ADVTARNTRNLTFIGEQNSRRKELSVLQTTTNEKAKDILNKINDNLIQEVRYTPAPKHLGRDLANLFDTLKEKDI
NNIENEEEKQNVINDCIEQYVDDCRSLNRNPIAALLKHISRYYEDFSAKNFLDGAKLNVLTEVVNRQKAHPTIW
SEKAYTWISKFDKNRRQANSSLVGWVVPPEEVHKEKIAGQQSMMWVTLTLLDDGKWVKHHIPFSDSRYYSEV
YAYNPNLPYLDGGIPRQSKFGNKPTTNLTAESQALLANSKYKKANKSFLRAKENATHNVRVSPNTSLCIRLLKD
SAGNQMFDKIGNVLFGMQINHKITVGKPNYKIEVGDRFLGFDQNQSENHTYAVLQRVSESSHDTHHFNGWDV
KVLEKGKVTSDVIVRDEVYDQLSYEGVPYDSSKFAEWRDKRRRFVLENLSIQLEEGKTFLTEFDKLNKDSLYR

-continued

| SEQUENCE LISTING | |
|---|---|
| | WNMNYLKLLRKAIRAGGKEFAKIAKTEIFELAVERFGPINLGSLSQISLKMIASFKGVVQSYFSVSGCVDDASK<br>KAHDSMLFTFMCAAEEKRTNKREEKTNRAASFILQKAYLHGCKMIVCADDLPVADGKTGKAQNADRMDWC<br>ARALAKKVNDGCVAMSICYRAIPAYMSSHQDPFVHMQDKKTSVLRPRFMEVNKDSIRDYHVAGLRRMLNSKS<br>DAGTSVYYRQAALHFCEALGVSPELVKNKKTHAAELGKHMGSAMLMPWRGGRVYIASKKLTSDAKSVKYCG<br>EDMWQYHADEIAAVNIAMYEVCCQTGAFGKKQKKSDELPG |
| SEQ ID NO: 185 | (spacer corresponding to target sequence SEQ ID NO: 33)<br>CCAUUACAGUAGGAGCAUAC |
| SEQ ID NO: 186 | (non-target; NT)<br>GGTCTTCGATAAGAAGACCT |
| SEQ ID NO: 187 | (spacer-NT)<br>GGUCUUCGAUAAGAAGACCU |
| SEQ ID NO: 188 | (SiCas12i crRNA-NT; SEQ ID NO: 21 + SEQ ID NO: 187)<br>CUAGCAAUGACUCAGAAAUGUGUCCCCAGUUGACACGGUCUUCGAUAAGAAGACCU |
| SEQ ID NO: 189 | (Cas12i.3-DR)<br>AGAGAAUGUGUGCAUAGUCACAC |

SEQUENCE LISTING

```
Sequence total quantity: 192
SEQ ID NO: 1            moltype = AA  length = 1080
FEATURE                 Location/Qualifiers
source                  1..1080
                        mol_type = protein
                        organism = unidentified
SEQUENCE: 1
MSSDVVRPYN TKLLPDNRKH NMFLQTFKRL NSISLNHFDL LICLYAAITN KKAEEYKSEK  60
EAHVTADSLC AINWFRPMSK RYSKYATTTF NMLELFKEYS GHEPDAYSKN YLMSNIDSDR  120
FVWVDCRKFA KDFAYQMELG FHEFTVLAET LLANSILVLN ESTKANWAWG TVSALYGGGD  180
KEDSTLKSKI LLAFVDALNN HELKTKREIL NQVCESLKYQ SYQDMYVDFR SVVDENGNKK  240
SPNGSMPIVT KFETDDLISD NQRKAMISNF TKNAAAKAAK KPIPYLDRLK EHMVSLCDEY  300
NVYAWAAAIT NSNADVTARN TRNLTFIGEQ NSRRKELSVL QTTTNEKAKD ILNKINDNLI  360
QEVRYTPAPK HLGRDLANLF DTLKEKDINN IENEEEKQNV INDCIEQYVD DCRSLNRNPI  420
AALLKHISRY YEDFSAKNFL DGAKLNVLTE VVNRQKAHPT IWSEKAYTWI SKFDKNRRQA  480
NSSLVGWVVP PEEVHKEKIA GQQSMMWVTL TLLDDGKWVK HHIPFSDSRY YSEVYAYNPN  540
LPYLDGGIPR QSKFGNKPTT NLTAESQALL ANSKYKKANK SFLRAKENAT HNVRVSPNTS  600
LCIRLLKDSA GNQMFDKIGN VLFGMQINHK ITVGKPNYKI EVGDRFLGFD QNQSENHTYA  660
VLQRVSESSH DTHHFNGWDV KVLEKGKVTS DVIVRDEVYD QLSYEGVPYD SSKFAEWRDK  720
RRRFVLENLS IQLEEGKTFL TEFDKLNKDS LYRWNMNYLK LLRKAIRAGG KEFAKIAKTE  780
IFELAVERFG PINLGSLSQI SLKMIASFKG VVQSYFSVSG CVDDASKKAH DSMLFTFMCA  840
AEEKRTNKRE EKTNRAASFI LQKAYLHGCK MIVCEDDLPV ADGKTGKAQN ADRMDWCARA  900
LAKKVNDGCV AMSICYRAIP AYMSSHQDPF VHMQDKKTSV LRPRFMEVNK DSIRDYHVAG  960
LRRMLNSKSD AGTSVYYRQA ALHFCEALGV SPELVKNKKT HAAELGKHMG SAMLMPWRGG  1020
RVYIASKKLT SDAKSVKYCG EDMWQYHADE IAAVNIAMYE VCCQTGAFGK KQKKSDELPG  1080

SEQ ID NO: 2            moltype = AA  length = 1061
FEATURE                 Location/Qualifiers
source                  1..1061
                        mol_type = protein
                        organism = unidentified
SEQUENCE: 2
MSSDVVRPYN TKLLPDNRKY NMFLQTFKRL NLISSNHFDL LVCLYAAITN KKAEEYKSEK  60
EDHVTADSLC AINWFRPMSK RYIKYATTTF KMLELFKEYS GHEPDTYSKN YLMSNIVSDR  120
FVWVDCRKFA KDFANQMELS FHEFTTLSET LLANSILVLN ESTKANWAWG AVSALYGGGD  180
KEDSTLKSKI LLAFVDALNN PELKTRREIL NHVCESLKYQ SYQDMYVDFR SVVDDKGNKK  240
SPNGSMPIVT KFESDDLIGD NQRKTMISSF TKNAAAKASK KPIPYLDILK DHMISLCEEY  300
NVYAWAAAIT NSNADVTARN TRNLTFIGEQ NTRRKELSVL QTSTNEKAKD ILNKINDNLI  360
PEVRYTPAPK HLGRDLANLF EMFKEKDINQ IGNEEEKQNV INDCIEQYVD DCRSLNRNPV  420
AALLKHISGY YEDFSAKNFL DGAKLNVLTE VVNRQKAHPT ICSEKAYTWI SKIDKNRRQA  480
NSSLVGWVVP PEEVHKEKIA GQQSMMWVTL TLLDDGKWVK HHIPFADSRY YSEVYAYNPN  540
LPYLEGGIPR QSKFGNKPTT NLTAESQALL ANSKHKKANK TFLRAKENIT HNVRVSPNTS  600
LCIRPLKDSA GNQMFDNIGN MLFGMQINHR ITVGKPNYKI EVGDRFLGFD QNQSENHTYA  660
VLQRVSESSH GTHHFNGWDV KVIEKGKVTS DVVVRDEVYD QLSYEGVPYD SPKFTEWREK  720
RRKFVLENMS IQIEEGKTFL TEFDKLNKDS LYRWNMNYMK LLRKAIRAGG KEFAKITKAE  780
IFELGVMRFG PMNLGSLSQV SLKMIAAFKG VIQSYFSVSG CIDDASKKAH DSMLFAFLCS  840
ADEKRTNKRE EKTNRAASFI LQKAYSHGCK MIVCEDDLPI ADGKVGKAQN ADRMDWCARS  900
LAKKVNDGCV AMSICYRAIP AYMSSHQDPF THMQDKKTSV LRPRFMEVGK DSIRDHHVAG  960
LRRMLNSKGN TGTSVYYREA ALRFCEALGV LPELVKNKKT HASELGKHMG SAMLMPWRGG  1020
RIYVASKKLT SDAKSIKYCG EDMWQYHADE IAAINIAMYE V                     1061
```

```
SEQ ID NO: 3            moltype = AA  length = 1075
FEATURE                 Location/Qualifiers
source                  1..1075
                        mol_type = protein
                        organism = unidentified
SEQUENCE: 3
MGISISRPYG TKLRPDARKK EMLDKFFTTL AKGQRVFADL GLCIYGSLTL EMVKRLEPES  60
DSELVCAIGW FRLVDKVTWS ENEIKQENLV RQYETYSGKE ASEVIKTYLS SPSSDKYVWI  120
DCRQKFLRFQ RDLGTRNLSE DFECMLFEQY LRLTKGELDG HTAMSNMFGT KTKEDRATKL  180
RYAARMKEWL EANEEITWEQ YHQALQDKLD ANTLEEAVDN YKGKAGGSNP FFSYTLLNRG  240
QIDKKTHEQQ LKKFNKVLKT KSKNLNFPNK EKLKQYLETA IGIPVDAQVY GQMFNNGVSE  300
VQPKTTRNMS FSMEKLELLN ELKSLNKTDG FERANEVLNG FFDSELHTTE DKFNITSRYL  360
GGDRNNRLPK LYELWKKEGV DREEGIQQFS QAIQDKMGQI PVKNVLRYIW EFRETVSAED  420
FEAAAKANQL EEKITRTKAH PVVISNRYWT FGSSALVGNI MPADKMHKDQ YAGQSFKMWL  480
EAELHYDGKK VKHHLPFYNA RFFEEVYCYH PSVAEVTPFK TKQFGYAIGK DIPADVSVVL  540
KDNPYKKATK RFLRAISNPV ANTVDVNKPT VCSFMIKREN DEYKLVINRK IGVDRPKRIK  600
VGRKVMGYDR NQTASDTYWI GELVPHGTTG AYRIGEWSVQ YIKSGPVLSS TQGVNDSTTD  660
QLIYNGMPSS SERFKAWKKS RMSFIRKLIR QLNAEGLESK GQDYVPENPS SFDVRGETLY  720
VFNSNYMKAL VSKHRKAKKP VEGILEEIEA LTSKAKDSCS LMRLSSLSDA AMQGIASLKS  780
LINSYFNKNG CKTIEDKEKF NPDLYVKLVE VEQKRTNKRK EKVGRIAGSL EQLALLNGVD  840
VVIGEADLGE VKKGKSKKQN SRNMDWCAKQ VAERLEYKLT FHCIGYFGVN PMYTSHQDPF  900
EHRRVADHLV MRARFEEVNV SNVSEWHMRN FSNYLRADSG TGLYYKQATL DFLKHYDLEE  960
HADDLEKQNI KFYDFRKILE DKQLTSVIVP KRGGRIYMAT NPVTSDSTPV TYAGKTYNRC  1020
NADEVAAANI AISVLAPHSK KEEKEDKIPI ISKKPKSKNT PKARKNLKTS QLPQK       1075

SEQ ID NO: 4            moltype = AA  length = 1003
FEATURE                 Location/Qualifiers
source                  1..1003
                        mol_type = protein
                        organism = unidentified
SEQUENCE: 4
MASKHVVRPF NGKVTATGKR LAYLEETFHY LEKAAGGVST LFAALGSYLD ATTISNLINK  60
NQDLAVVIFR YHVVPKGEAH TLPVGTDMVS RFVADYGMEP NEFQRAYLDS PIDQEKYCWQ  120
DNRDVGCWLG EQLGVSEADM RAIAVTFYNN QMLYDCVKGT GSGNAVSLLF GSGKKSDYSM  180
KGVIAGKAAS VLAKYRPATY QDARKMILEA NGFTSVKDLV TSYGITGRSS ALQIFMEGIE  240
SGPISSKTLD ARIKKFTEDS ERNGRKNLVP HAGAIRNWLI EQAGSSVENY QMAWCEVYGN  300
VSADWNAKVE SNFNFVAEKV KALTELSNIQ KSTPDLGKAL KLFEEYLTTC QDEFAIAPYH  360
FSVMEEVRME MATGREFNDA YDDALNSLDM ESKQPIQPLC KFLIERGGSI SFDTFKSAAK  420
YLKTQSKIAG RYPHPFVKGN QGFTFGSKNI WAAINDPMME YADGRIAGGS AMMWVTATLL  480
DGKKWVRHHI PFANTRYFEE VYASKKGLPV LPCARDGKHS FKLGNNLSVE RVEKVKEGGR  540
TKATKAQERI LSNLTHNVQF DSSTTFIIRR QEESFVICVN HRHPAPLMKK EMEVGDKIIG  600
IDQNVTAPTT YAIVERVASG GIERNGKQYK VTAMGAISSV QKTRGGEVDV LSYMGVELSD  660
SKNGFQSLWN KCLDFVTKHG TENDVKYYNN TAVWANKLYV WHKMYFRLLK QLMRRAKDLK  720
PFRDHLQHLL FHPNLSPLQR HSLSLTSLEA TKIVRNCIHS YFSLLGLKTL DERKAADINL  780
LEVLEKLYAG LVERRKERTK LTAGLLVRLC NEHGISFAAI EGDLPVVGEG KSKAANNTQQ  840
DWTARELEKR LSEMAEVVGI KVIAVLPHYT SHQDPFVYSK NTKKMRCRWN WRTTKTFTDR  900
DALSIRRILS KPETGTNLYY QKGLKAFAEK HGLDLAEMKK RKDAQWYLER IQDKNFLVPM  960
NGGRVYLSSV KLAGKETIDM GGEILYLNDA DQVAALNVLL VKI                    1003

SEQ ID NO: 5            moltype = AA  length = 1018
FEATURE                 Location/Qualifiers
source                  1..1018
                        mol_type = protein
                        organism = unidentified
SEQUENCE: 5
MAKKEHIIRP FKGTLPLRGD RLRYLQDTMK YMKKVEDTIT ELCAAVIAYA KPTIIQQILG  60
EEIETTSTFC SFRLVGIHEN FTMPLTTNMI KHFQKTFNIN PSEKQAIYLS SGFDSDKYRW  120
QDTSEVSRNF ANKCRLTNQE FQEFAEQALL NMCFIGCSGS PGATNAVSQI FGTGEKSDYQ  180
RKSQIAKIAA DTLENHKPST YESARLMVLN TLGHKTIEDC VNDYGAIGAK SAFRLFMESK  240
EIGPITSEQL TTKIKKFRED HKKNSIKKQL PHVEKVRNAL LSQFKEQYLP SAWAEAWCNI  300
MGEFNSKLSN NNNFIDQKTK MVNDCDNIKK SNPQLDKAVN MLDEWKYKNW DDNSAIHPYH  360
IGDLKKLMAI FNINNEGTFD ERFSASWEQF STSLEYGEKP PVRDLLAHII KNMNDLTYTD  420
VINAAKFLKL QDNIRNKYPH PFVMPNKGCT FGKDNLWGEI NDPTAKIKST EEVAGQRPMM  480
WLTAKLLDNG KWVEHHIPFA SSRYFAEVYY TNPALPTLPI ARDGKHSYKL TKTIDANTAK  540
TLVNNPRDKA AKLIARTKAN TTHNVKWIKP TYRIQKENNQ FVITINHRHP CITPPKEIIL  600
GDRILSFDQN ETAPTAFSIL EKTTKGTEFC GHHIKVLKTG MLEAKIKTSK KSIDAFTYMG  660
PMEDDHASGF PTLLNICEKF ISENGDEKDK SFSSRKLPFK RSLYFFHGSH FDLLKKMIRK  720
AKNDPKKLKL VRIHINEILF NSNLSPIKLH SLSIHSMENT KKVIAAISCY MNVHEWKTID  780
EQKNADITLY NAKEKLYNNL VNRRKERVKV TAGMLIRLAR ENNCRFMVGE AELPTQQQGK  840
SKKNNNSKQD WCARDIAQRC EDMCEVVGIK WNGVTPHNTS HQNPFIYKNT SGQQMRCRYS  900
LVKKSEMTDK MAEKIRNILH AEPVGTTAYY REGILEFAKH HGLDLGMMKK RRDAKYYDNL  960
PDEFLLPTRG GRIYLSENQL GGNETIVING KKYFVNQADQ VAAVNIGLLY LLPKKNQS    1018

SEQ ID NO: 6            moltype = AA  length = 1047
FEATURE                 Location/Qualifiers
source                  1..1047
                        mol_type = protein
                        organism = unidentified
```

```
SEQUENCE: 6
MSEKKFHIRP YRCSISPNAR KADMLKATIS YLDSLTSVFR SGFTALLAGI DPSTVSRLAP  60
SGAVGSPDLW SAVNWFRIVP LAEAGDARVG QASLKNLFRG YAGHEPDEEA SIYMESRVDD  120
KRHAWVDCRA MFRAMALECG LEEAQLASDV FALASREVIV FKDGEINGWG IASLLFGEGE  180
KADSQKKVAL LRSVRLALEG DYATYEELSG LMLAKTGASS GSDLLDEYKR SEKGGSSGGR  240
HPFFDEVFRR GGRVKQEERE RLLKSCDTAI QKQGQALPLS HVASWRQWFL RRVTLLRNRR  300
QESFAVCITN ALMDLQPKNL RNVHYVTNPK SEKDKGVLEL RVDVKNNEGP DVAGAQAVFD  360
AYMARLAPDL RFSVMPRHLG SLKDLYALWA KLGRDEAIEE YLEGYEGPFS KRPIAGILQI  420
IHAHRGKVGH DSLLRAARLN RAMDRLERKR AHACAAGNKG YVYGKSSMVG RINPQSLEVG  480
GRKSGRSPMM WVTLDLVDGD RFAQHHLPFQ SARFFSEVYC HGDGLPATRV PGMVRNRRNG  540
LAIGNGLGEG GLSALRAGSD RRKRANKRTL RALENITHNV EIDPSTSFTL REDGIIISHR  600
IEKIEPKLVA FGDRALGFDL NQTGAHTFAV LQKVDSGGLD VGHSRVSIVL TGTVRSICKG  660
NQASGGRDYD LLSYDGPERD DGAFTAWRSD RQAFLMSAIR ELPTPAEGEK DYKADLLSQM  720
ASLDHYRRLY AYNRKCLGIY IGALRRATRR QAVAAFKDEI LSIANHRCGP LMRGSLSVNG  780
MESLANLKGL ATAYLSKFKD SKSEDLLSKD EEMADLYRAC ARRMTGKRKE RYRRAASEIV  840
RLANEHGCLF VFGEKELPTT SKGNKSKQNQ RNTDWSARAI VKAVKEACEG CGLGFKPVWK  900
EYSSLTDPFE RDGDGRPALR CRFAKVAAPD SELPPRLTKA VGSYVKNALK ADKAEKKQTC  960
YQRGAIEFCS RHGIDVRKAT DKAIRKAVRG SSDLLVPFDG GRTFLLSTRL SPESRKVEWA  1020
GRTLYEFPSD MVAAINIACR GLEPRKA                                     1047

SEQ ID NO: 7            moltype = AA  length = 1029
FEATURE                 Location/Qualifiers
source                  1..1029
                        mol_type = protein
                        organism = unidentified
SEQUENCE: 7
MDEQAVVSSG SDKTLKIVRP YRAKVTATGI RLEGIKNTLN YLKRTEICLS RLNAACGAFL  60
TPAIVEQICK DDPALVCAIA RFQLVPVGSE ATLSDSGLMR HFKAALGELT PLQEAYLNSS  120
YNDELYAWQD TLVLARQIIA ETGLTEDQFR AFAHACFKNG NIIGCAGGPG ASNAISGIFG  180
EGIKSDYSLR SEMTAAVAKV FEEKRPITYE EARALALEAT GHASVQSFVE AFGKQGRKGT  240
LILFMEDTKT GAFPSNEFDY KLKKLKEDAE RVGRKGIIPH RDVIASYLRN QTGADIEYNS  300
KAWCESYCCA VSEYNSKMSN NVRFATEKSL DLTKLDETIR ETPKISEAML VFENYMARID  360
ADLRFIVSKH HLGNLAKFRQ TMMHVSASEF EEAFKAMWAD YLAGLEYGEK PAICELVRYV  420
LTHGNDLPVE AFYAACKFLS LDDKIKNRYP HPFVPGNKGY TFGAKNLWAE INDPFKPIRQ  480
GNPEVAGQRP MMWATADLLD NNKWVLHHIP FASSRYFEEV YYTDPSLPTA QKARDGKHGY  540
RLGKVLDEAA RERLKANNRQ RKAAKAIERI KANCEHNVAW DPTTTFMLQL DSEGNVKMTI  600
NHRHIAYRAP KEIGVGDRVI GIDQNETAPT TYAILERTEN PRDLEYNGKY YRVVKMGSVT  660
SPNVSKYRTV DALTYDGVSL SDDASGAVNF VVLCREFFAA HGDDEGRKYL ERTLGWSSSL  720
YSFHGNYFKC LTQMMRRSAR SGGDLTVYRA HLQQILFQHN LSPLRMHSLS LRSMESTMKV  780
ISCMKSYMSL CGWKTDADRI ANDRSLFEAA RKLYTSLVNR RTERVRVTAG ILMRLCLEHN  840
VRFIHMEDEL PVAETGKSKK SNGAKMHWCA RELAVRLSQM AEVTSVKFTG VSPHYTSHQD  900
PFVHSKTSKV MRARWSWRNR ADFTDKDAER IRTILGGDDA GTKAYYRSAL AEFASRYGLD  960
MEQMRKRRDA QWYQERLPET FIIPQRGGRV YLSSHDLGSG QKVDGIYGGR AFVNHADEVA  1020
ALNVALVRL                                                         1029

SEQ ID NO: 8            moltype = AA  length = 1029
FEATURE                 Location/Qualifiers
source                  1..1029
                        mol_type = protein
                        organism = unidentified
SEQUENCE: 8
MKTETLIRPY PGKLNLQPRR AQFLEDSIQY HQKMTEFFYQ FLQAVGGATT HQNISDFIDN  60
KATDEHQATL LFQVVSKDST TPECPAEELL ARFAQYTGKQ PNEAVTHYLT SRINTDKYRW  120
QDNRLLAQNI ASQLNISETQ FQEIAHAILS NNLYIGQTAS NAAANFISQV TGTGQKAPKA  180
ARLDVLFQTN QALAKTQPTT FGQLQQIIVQ ACGESTTDAV LAKFGNKGAA TSLQLALKTD  240
PNTTLDQKKY EALQKKFAED ETKYRNKVDI PHKTQLRNLI LNTSNQFCNW HTKPAIEAFK  300
CAIADIQSKV SNNLRIMQEK AKLYEAFRNV DPQVQIAVQA LENHMNTLEE PYAPYAHSFG  360
SVKDFYEDLN NGSNLDEAIQ TIVHDSDNFN RKPDPNWLRI IAPLHSSHSA SQIMEAVKYL  420
SSKQDYELRK PFPFVATNLP ATYGKFNIPG TLNPPTDSLH GRLNGSHSNM WLTALLLDGR  480
DWKNHHLCFA SSRYFEEVYF TNPSLPTTDK VRSPKCGFTL KSVLDSEAKD RIRNAPKSRT  540
KAVKAIERIK ANSTHNVAWN PETSFQMQKR NDEFYITINH RIEMEKIPGQ KKTDDGFTIH  600
PKGLFAILKE GDRILSQDLN QTAATHCAVY EVAKPDQNTF NHHGIHLKLI ATEELKMPLK  660
TKKSTIPDAL SYQGIHAHDR ENGLQQLKDA CGAFISPRLD PKQKATWDNS VSKKENLYPF  720
ITAYMKLLKK VMKAGRQELK LFRTHLDHIL FKHNLSPLKL HGVSMIGLES SRATKSVINS  780
FFNLQNAKTE QQQIALDRPL FEAGKTLINN QTRRRQERVR LETSLTMRLA HKYNAKAIII  840
EGELPHSSTG TSQYQNNVRL DWSAKKSAKL KTESANCAGI AICQIDPCHT SHQNPFRHTP  900
TNPDLRPRFA QVKKGKMFQY QLNGLQRLLN PRSKSSTAIY YRQAVQSFCA HHNLTERDIT  960
SAKFPSDLEK KIKDDTYLIP QRGGRIYISS FPVTSCARPC TSNHYFGGGQ FECNADAVAA  1020
VNIMLKVHP                                                         1029

SEQ ID NO: 9            moltype = AA  length = 1011
FEATURE                 Location/Qualifiers
source                  1..1011
                        mol_type = protein
                        organism = unidentified
SEQUENCE: 9
MPIRGYKCTV VPNVRKKKLL EKTYSYLQEG SDVFFDLFLS LYGGIAPKMI PQDLGINEQV  60
ICAANWFKIV EKTKDCIADD ALLNQFAQYY GEKPNEKVVQ FLTASYNKDK YVWVDCRQKF  120
YTLQKDLGVQ NLENDLECLI REDLLPVGSD KEVNGWHSIS KLFGCGEKED RTIKAKILNG  180
```

-continued

LWERIEKEDI LTEEDARNEL LHSAGVLTPK EFRKVYKGAA GGRDCYHTLL VDGRNFTFNL 240
KTLIKQTKDK LKEKSVDVEI PNKEALRLYL EKRIGRSFEQ KPWSEMYKTA LSAVMPKNTL 300
NYCFAIDRHA QYTKIQTLKQ PYDSAITALN GFFESECFTG SDVFVISPSH LGKTLKKLYN 360
YKDVESGISE IVEDEDNSLR SGVNVNLLRY IFTLKDMFSA EDFIKAAEYN VVFERYNRQK 420
VHPTVKGNQS FTFGNSALSG KVIPPSKCLS NLPGQMWLAI NLLDQGEWKE HHIPFHSARF 480
YEEIYATSDN QNNPVDLRTK RFGCSLNKTF SAADIEKVKE SAKKKHGKAA KRILRAKNTN 540
TAVNWVDCGF MLEKTEVNFK ITVNYKLPDQ KLGKFEPIVG TKILAYDQNQ TAPDAYAILE 600
ICDDSEAFDY KGYKIKCLST GDLASKSLTK QTEVDQLAYK GVDKTSNFYK KWKQQRRLFV 660
KSLNIPDALK SFENINKEYL YGFNNSYLKL LKQILRGKFG PILVDIRPEL IEMCQGIGSI 720
MRLSSLNHDS LDAIQSLKSL LHSYFDLKVK EEIKTEELRE KADKEVFKLL QQVIQKQKNK 780
RKEKVNRTVD AILTLAADEQ VQVIVGEGDL CVSTKGTKKR QNNRTIDWCA RAVVEKLEKA 840
CKLHGLHFKE IPPHYTSHQD CFEHNKDIEN PKEVMKCRFN SSENVAPWMI KKFANYLKCE 900
TKYYVQGMQD FLEHYGLVEY KDHIKKGKIS IGDFQKLIKL ALEKVGEKEI VFPCKGGRIY 960
LSTYCLTNES KPIVFNGRRC YVNNADHVAA INVGICLLNF NARAKVAEKT P 1011

SEQ ID NO: 10 moltype = AA length = 1093
FEATURE Location/Qualifiers
source 1..1093
mol_type = protein
organism = unidentified
SEQUENCE: 10
MAKKDFIARP YNSFLLPNDR KLAYLEETWT AYKSIKTVLH RFLIAAYGAI PFQTFAKTIE 60
NTQEDELQLA YAVRMFRLVP KDFSKNENNI PPDMLISKLA SYTNINQSPT NVLSYVNSNY 120
DPEKYKWIDS RNEAISLSKE IGIKLDELAD YATTMLWEDW LPLNKDTVNG WGTTSGLFGA 180
GKKEDRTQKV QMLNALLLGL KNNPPKDYKQ YSTILLKAFD AKSWEEAVKI YKGECSGRTS 240
SYLTEKHGDI SPETLEKLIQ SIQRDIADKQ HPINLPKREE IKAYLEKQSG TPYNLNLWSQ 300
ALHNAMSSIK KTDTRNFNST LEKYEKEIQL KECLQDGDDV ELLGNKFFSS PYHKTNDVFV 360
ICSEHIGTNR KYNVVEQMYQ LASEHADFET VFTLLKDEYE EKGIKTPIKN ILEYIWNNKN 420
VPVGTWGRIA KYNQLKDRLA GIKANPTVEC NRGMTFGNSA MVGEVMRSNR ISTSTKNKGQ 480
ILAQMHNDRP VGSNNMIWLE MTLLNNGKWQ KHHIPTHNNK FFEEVHAFNP ELKQSVNVRN 540
RMYRSQNYSQ LPTSLTDGLQ GNPKAKIFKR QYRALNNMTA NVIDPKLSFI VNKKDGRFEI 600
SIIHNVEVIR ARRDVLVGDY LVGMDQNQTA SNTYAVMQVV QPNTPDSHEF RNQWVKFIES 660
GKIESSTLNS RGEYIDQLSH DGVDLQEIKD SEWIPAAEKF LNKLGAINKD GTPISISNTS 720
KRAYTFNSIY FKILLNYLRA NDVDLNLVRE EILRIANGRF SPMRLGSLSW TTLKMLGNFR 780
NLIHSYFDHC GFKEMPERES KDKTMYDLLM HTITKLTNKR AERTSRIAGS LMNVAHKYKI 840
GTSVVHVVVE GSLSKTDKSS SKGNNRNTTD WCSRAVVKKL EDMCVFYGFN LKAVSAHYTS 900
HQDPLVHRAD YDDPKLALRC RYSSYSRADF EKWGEKSFAA VIRWATDKKS NTCYKVGAVE 960
FFKNYKIPED KITKKLTIKE FLEIMCAESH YPNEYDDILI PRRGGRIYLT TKKLLSDSTH 1020
QRESVHSHTA VVKMNGKEYY SSDADEVAAI NICLHDWVVP LNWTNHCLPA GWCSDHLKEC 1080
VQCHTPDPVR ISM 1093

SEQ ID NO: 11 moltype = DNA length = 3243
FEATURE Location/Qualifiers
source 1..3243
mol_type = unassigned DNA
organism = unidentified
SEQUENCE: 11
atgtctagtg atgtcgttcg tccatataac accaaactgc ttccagataa tcgcaaacac 60
aatatgtttt tgcaaacttt caagcgactt aattctattt ctcttaatca ttttgatctc 120
ttaatttgtc tttatgctgc cattaccaac aagaaggcag aagaatataa gtctgaaaaa 180
gaagctcatg taaccgctga tagcctttgt gctatcaatt ggttccgtcc tatgtccaag 240
cgttacagca aatacgcaac tacaactttc aatatgcttg aattgttcaa agaatactct 300
gggcatgaac cagatgctta ttccaagaat tatcttatgt ccaatattga ctcagacagg 360
tttgtctggg ttgattgccg taaatttgcc aaagatttg cgtatcaaat ggaacttggt 420
ttccatgaat ttacagtctt ggcagaaacc ttgttggcaa atagtattct tgtactcaac 480
gaatcaacta aggcaaattg ggcatggggc accgtttctg cactttacgg tggaggcgat 540
aaggaagatt ctacgctgaa gtcgaaaatc cttttggctt ttgttgatgc actcaataac 600
cacgaactta aaactaagcg tgaaattctc aatcaagttt gtgaatcact aaaatatcaa 660
tcataccaag acatgtatgt tgatttccgt tctgttgttg acgaaaatgg aaacaagaag 720
tctcccaatg gctcaatgcc aatcgtcacc aagtttgaaa cagatgattt gatttctgat 780
aatcaacgca aagcaatgat ttctaatttc acaaagaatg ctgctgctaa agcggctaaa 840
aaacctattc cctacctaga cagactcaag gaacatatgg tttccttgtg cgatgaatat 900
aatgtttatg cttgggcagc agctatcact aactctaatg ccgatgtaac agctaggaat 960
actcgcaatt taacattcat cggggaacaa aattctcgaa ggaaagaact atcggtttta 1020
caaactacaa caaacgaaaa agcaaaagat atcttgaata agattaatga caatcttatt 1080
caagaagtaa ggtataccccc tgcccccaag cacttggggc gtgatcttgc caatcttttt 1140
gatactctga aagaaaaaga tatcaataat attgaaaacg aagaagagaa gcagaatgta 1200
attaatgatt gcattgagca atatgttgat gattgccgtt cactgaaccg caatcccatt 1260
gctgctttgc tcaagcacat tagccgatac tatgaagatt tttcagccaa gaatttcttg 1320
gatggtgcca agttgaatgt cttgactgaa gttgtaaatc gtcaaaaggc acatccaact 1380
atttggtctg aaaaggctta tacttggatt tccaagtttg acaagaatag gcgacaagca 1440
aactcttctt tggttggatg ggttgttcca ccagaagaag tccataaaga gaagattgct 1500
ggtcaacaaa gcatgatgtg ggtcactttg actctgcttg atgatggcaa gtgggtaaag 1560
caccatattc ctttttcaga ttccagatat tattctgaag tctatgccta caatccaaat 1620
ttgccatatc ttgatggtgg tattccacgc cagtcaaagt ttggcaataa accaaccact 1680
aatctgactg ctgaaagtca agcgttactt gcaaacagca agtataaaaa ggcaaataag 1740
tcatttctcc gtgccaagga aaatgctact cacaatgtcc gtgttagtcc aaacacttcc 1800
ttgtgcattc gtttgctcaa ggatagtgct ggtaatcaaa tgtttgataa gattggcaat 1860
gttctgtttg gaatgcagat caaccataaa atcaccgttg gcaagcccaa ctacaagatc 1920

-continued

```
gaagttggtg ataggttcct tggtttcgac cagaaccaaa gtgaaaacca cacttatgct  1980
gtcttgcaac gagtctctga aagctctcat gacactcatc attttaatgg atgggatgtc  2040
aaggttcttg aaaagggcaa agtaacaagt gatgtcatcg ttagagatga ggtctatgac  2100
caacttagct atgagggcgt tccttatgat tcttcaaagt ttgcagaatg gagagacaag  2160
aggagaaggt ttgttttgga aaacttgtct atccagttgg aagaaggcaa aacattcttg  2220
actgaattcg acaaattaaa taaagattct ctttatcgtt ggaatatgaa ttatctgaaa  2280
ctgctcagga aagctattcg tgccggtggc aaggaatttg ccaagattgc taagactgag  2340
atttttgaat tggcagttga aaggtttgga ccaatcaacc ttggtagttt gtcacaaatt  2400
agcttgaaga tgattgcatc tttcaaggga gtggttcagt cttacttttc tgtatctggt  2460
tgtgttgatg acgcatccaa gaaggcacat gattccatgc tcttcacttt catgtgtgca  2520
gcagaagaaa aaaggacaaa caaaagagaa gaaaagacta atcgtgcagc atcttttatc  2580
ttgcagaaag catatttgca tggctgcaag atgattgttt gcgaagacga tcttcctgtt  2640
gctgatggaa aaacaggcaa ggcacaaaat gcggatcgta tggactggtg tgcccgtgct  2700
ttggcaaaga aagtcaacga tggttgtgtg gcaatgtcta tctgctatcg tgccattcca  2760
gcttatatgt ctagccacca agatccattt gttcacatgc aagacaaaaa gacttctgtt  2820
ttgcgtccaa ggttcatgga agttaacaag gatagcatca gggattatca tgttgctggt  2880
ttgcggagaa tgctgaacag caagagtgat gcaggcactt ccgtttacta tcgtcaggca  2940
gctttgcatt tctgcgaagc gttgggcgtg tctccagaat tagtcaagaa caaaaagact  3000
catgctgccg aattaggaaa gcatatgggt tctgccatgt tgatgccttg gcggggtggc  3060
agggtttata ttgccagcaa gaagttgact tcggatgcta aaagtgtaaa atactgtgga  3120
gaagatatgt ggcagtatca tgctgatgag attgctgctg tcaatatcgc aatgtatgaa  3180
gtttgctgcc agacaggtgc gtttggcaag aagcaaaaga agagtgatga actaccggga  3240
taa                                                                3243

SEQ ID NO: 12          moltype = DNA  length = 3244
FEATURE                Location/Qualifiers
source                 1..3244
                       mol_type = unassigned DNA
                       organism = unidentified
SEQUENCE: 12
catgtctagt gatgttgttc gtccatataa cactaagctg cttcctgata atcgcaaata  60
caatatgttt ttgcaaactt tcaaaagact caatttgatt tcatcaaatc attttgatct  120
cttggtttgt ctttatgctg ctatcaccaa caaaaaagct gaagaatata agtcagaaaa  180
agaagatcat gtaaccgctg atagcctttg cgccatcaat tggttccgtc ctatgtccaa  240
gcgttatatc aaatacgcaa ccactacttt taagatgctt gaattgttta aggagtactc  300
tggtcatgaa ccagatactt attccaagaa ttatctcatg tccaatatcg tctcagatag  360
gtttgtttgg gttgattgcc gcaaatttgc caaagatttt gccaatcaaa tggaacttag  420
tttccacgaa tttaccactt tgtcagagac tttgttggca aatagtatcc ttgtactcaa  480
tgagtcaacc aaggcaaatt gggcatgggg tgctgtttca gcactttatg gtggaggcga  540
caaagaagat tctacgctga agtccaaaat ccttttggct tttgttgatg ctctcaataa  600
tcctgaactt aaaactaggc gggaaattct caatcatgtt tgtgaatcac taaaatatca  660
atcataccaa gatatgtatg ttgattttcg atctgtcgtt gatgataagg gaaacaagaa  720
gtctcccaat ggctcaatgc caatcgtcac taagtttgaa tcagatgatt tgattggtga  780
caatcaacgc aaaactatga tttctagttt cacaaaaaac gccgctgcca aagcgtctaa  840
gaagcccatt ccatatctag acattctaaa agaccacatg atttccttgt gcgaggaata  900
caatgtctat gcttgggcag cagctattac caattccaat gctgatgtaa ctgctagaaa  960
cactcgcaat ctgacattca tcggggaaca aaatacccga aggaaagaac tatcggtttt  1020
acaaacttct acaaacgaaa aagcaaaaga tatcttaaat aagattaacg acaatcttat  1080
tccagaagta aggtacaccc ctgctcccaa gcacttgggg cgtgatcttg ccaatctttt  1140
tgaaatgttc aaagaaaaag atataaatca gattggaaat gaagaagaaa agcaaaatgt  1200
gatcaatgat tgcattgagc aatatgtcga tgattgccgt tcattgaacc gcaatcctgt  1260
tgcagctttg ctcaagcata ttagcggata ttatgaagat tttcagcca agaatttctt  1320
ggatggtgcc aagttgaatg tcttgacgga agttgtcaat cgtcaaaagg cacatccaac  1380
tatttgttct gaaaaggctt atacttggat ttccaagatt gacaagaata ggcgacaagc  1440
aaactcttct ttggttggat gggttgttcc accggaggaa gtccataagg aaaaaattgc  1500
cggtcaacaa agcatgatgt gggtcacttt gactttgctt gatgacggca agtgggtaaa  1560
gcatcatatt ccttttgcag actcaagata ttattctgaa gtctatgcct ataatccaaa  1620
tttgccatat cttgaaggtg gtattccacg acaatcaaag tttggcaata aaccaacaac  1680
taatttgacc gctgaaagcc aagcattact tgccaacagt aagcacaaga aagccaacaa  1740
gacatttctc cgtgccaagg agaatatcac tcacaatgtt cgtgttagtc caaatacttc  1800
attgtgcatt cgtcccctca aggatagtgc tggtaatcaa atgtttgaca acattggtaa  1860
tatgttgttt ggaatgcaga tcaatcacag aattactgtc ggcaagccaa actacaagat  1920
cgaagttggt gatcggttcc ttggttttga ccagaaccaa agcgaaaacc acacctatgc  1980
agttcttcaa cgagtatccg aaagctctca tggcactcat catttcaatg gttgggatgt  2040
caaagtgatt gagaagggca aggtgacaag tgatgtcgtc gtcagagatg aagtctatga  2100
tcaattaagc tacgagggtg tcccttacga ttctccaaag tttacagaat ggagagagaa  2160
gaggcgaaag tttgtcttgg aaaatatgtc aatccagatt gaagaaggca aaacattctt  2220
gactgaattt gacaagttaa acaaagactc tttgtatcgt tggaacatga attacatgaa  2280
attgcttagg aaggcaattc gtgctggtgg caaggaattt gccaagatta caaaggctga  2340
gatttttgaa ctaggagtta tgagatttgg accaatgaac ttgggcagct tgtcgcaagt  2400
cagcttgaag atgattgctg cttttaaggg agttattcag tcttactttt ccgtatctgg  2460
ttgcattgat gacgcatcca agaaagctca tgattcgatg ttattcgctt tcttgtgttc  2520
agcagatgag aaaaggacaa acaagaggga agaaaagaca aatcgtgcag catctttcat  2580
attgcagaaa gcatactcgc atggttgcaa gatgattgtt tgcgaggatg atcttcccat  2640
tgccgatggc aaggtgggca aggcacaaaa tgcggatcgc atggactggt gcgcccgttc  2700
attggcaaag aaagtcaacg atggttgtgt ggctatgtcc atatgttatc gtgccattcc  2760
agcatatatg tcaagccatc aagatccatt tactcatatg caagataaaa agacttctgt  2820
tttgcgtcca aggttcatgg aagtcggcaa ggatagcatt agggatcatc atgttgctgg  2880
tctgcggaga atgctgaaca gtaaaggtaa tactggcact tctgtttact atcgtgaggc  2940
```

```
agctttgcgt ttctgcgaag cgttgggtgt gcttcccgaa ttagtcaaga acaaaaagac  3000
tcatgcttcg gaattaggaa agcatatggg ttctgccatg ttgatgcctt ggcggggtgg  3060
caggatctat gtcgccagca agaaattgac ttcggatgcc aagagtataa aatattgtgg  3120
agaagatatg tggcaatatc atgctgatga gattgctgct atcaatatcg caatgtatga  3180
ggtctgctgt cagacaggtg cttttggcaa aaaacaaaag aagagtgatg aactaccggg  3240
ataa                                                               3244

SEQ ID NO: 13           moltype = DNA  length = 3225
FEATURE                 Location/Qualifiers
source                  1..3225
                        mol_type = unassigned DNA
                        organism = unidentified
SEQUENCE: 13
atgggtatta gcatttcacg tccgtacggt acaaagttgc gtcctgatgc tcgtaagaag  60
gaaatgttgg ataagttttt caccacgcta gcaaaaggtc agcgtgtttt tgcggatctg  120
ggactgtgca tttacggcag ccttacttta gaaatggtaa agcggcttga gccagaatcc  180
gattctgaac ttgtctgtgc aattggttgg tttcgtcttg tagataaggt aacttggtct  240
gagaatgaaa ttaaacaaga gaacctggtt agacaatatg agacgtattc aggaaaagaa  300
gcgtctgagg ttatcaagac ttacctaagc tctccaagtt cagacaagta tgtgtggata  360
gactgccgac aaaagtttct taggtttcaa agggatctgg gaacacgtaa tctgtctgaa  420
gactttgagt gcatgctttt tgaacagtac ctcagactca caaagggaga gcttgatggg  480
cataccgcta tgtccaacat gtttggaaca aaaacaaaag aagatcgcgc cacaaaactg  540
agatatgccg caaggatgaa agaatggctc gaggctaacg aagaaattac ttgggaacaa  600
tatcaccaag cgttgcaaga taaattagac gccaatactt tagaggaggc tgttgataat  660
tacaaaggca aagcgggagg ctctaatcca ttttttagtt acacgctttt aaacagaggt  720
cagattgata aaaaaactca cgagcagcaa ttaaagaaat tcaacaaagt tctaaaaacc  780
aaatccaaaa atttaaattt tccaaacaaa gagaagttaa aacaatattt agaaacagca  840
attggtattc ctgttgatgc tcaggtctac ggtcagatgt ttaataacgg cgtttctgaa  900
gttcaaccaa agacaacgcg caacatgtct ttttctatgg agaagcttga gcttttaaac  960
gagttgaaaa gtctcaacaa gactgacggt tttgaacgcg ctaatgaagt cttgaatggt  1020
ttctttgatt ctgaacttca cactactgaa gacaagttca acatcacttc caggtatttg  1080
ggtggagaca gaaacaatcg gctaccaaag ctgtacgagc tttggaaaaa ggaaggagta  1140
gatcgtgagg aaggtatcca gcaattcagc caagcaatcc aagataagat gggtcagata  1200
cctgttaaga atgtccttag gtatatttgg gaatttcgtg agactgtttc tgccgaagac  1260
tttgaagcgg cagcgaaagc gaatcagttg gaagaaaaaa tcacgcgtac caaagcgcac  1320
cccgttgtta tatctaacag gtattggaca tttggctctt cggctcttgt tggtaatatc  1380
atgccagcag acaagatgca caaagaccag tacgcaggtc aaagtttcaa gatgtggctt  1440
gaagccgaac tgcactacga cggtaagaaa gtcaaacatc acttgccgtt ctacaacgcc  1500
aggttctttg aagaggtcta ctgctatcac ccgagcgtag ctgaagttac accattcaaa  1560
accaagcagt ttggttatgc aattggaaaa gatattccag ctgacgtttc ggttgtactg  1620
aaagacaatc cttataaaaa ggcaaccaag cgcttccttc gggctatcag caatccagtc  1680
gccaacacag tggatgtaaa caagcctaca gtttgctcat tcatgattaa acgagaaaat  1740
gacgaataca aactagtcat taatcgaaag atcggtgttg atcgcccaaa gcgtattaaa  1800
gtaggtagga aggtcatggg ctatgaccgt aaccaaactg cttctgatac ttactggatt  1860
ggagagcttg ttccacatgg aacaaccgga gcgtaccgta ttggagaatg gagcgtccag  1920
tatatcaaga gcggtcccgt gttgtcttct acgcaaggcg taaatgacag tactacggat  1980
caacttatat acaacggaat gccgagctcc agcgaacgtt ttaaagcttg gaagaaatct  2040
aggatgtctt tcattcgtaa gttgatacgc caactgaacg ccgaaggctt ggaaagtaaa  2100
ggacaggact atgttcctga aaatccaagt agctttgatg ttaggggcga aacactttac  2160
gtattcaaca gcaactatat gaaagctttg gtgtctaagc atcgaaaagc caagaaacct  2220
gttgaaggta ttcttgaaga aatagaagcc ttgacaagca aagctaaaga ttcttgttcg  2280
ttgatgcgtt tgagttcttt gtctgatgcg gctatgcaag gtattgcttc gttgaagagt  2340
ttgatcaact catacttcaa caagaatggt tgcaaaacaa ttgaagacaa agaaaagttt  2400
aacccagatc tgtatgtgaa acttgttgaa gttgagcaaa agagaactaa caagagaaaa  2460
gaaaaagttg gtcgaatcgc cggttctctt gaacagttag ctttgcttaa cggtgttgac  2520
gttgttatcg gtgaagctga tcttggcgaa gtcaagaaag gcaaatccaa aaaacaaaat  2580
agtcgaaaca tggactggtg tgccaagcaa gtcgctgagc ggcttgagta caagctgacc  2640
ttccattgta ttggttattt tggtgtcaac ccgatgtata cgtctcatca agatccattt  2700
gaacatcgtc gcgttgctga ccacctagta atgcgtgcga ggtttgaaga agtgaatgta  2760
agtaatgttt cggaatggca catgcgaaac ttctcaaact atctgcgtgc ggactcaggt  2820
actggtttgt attacaaaca agctaccttg gatttcctca agcattatga tttggaagag  2880
cacgccgatg atttggaaaa gcagaatatc aaattctatg acttcaggaa aattcttgaa  2940
gacaaacaat tgacttctgt tattgttcca aaacgtggcg gtcgcattta catggcgact  3000
aacccggtaa cttccgatag tacgcctgtc acttatgccg gtaaaactta caaccggtgt  3060
aatgctgacg aagtggctgc ggctaacatc gctatcagcg tcttagctcc tcactctaag  3120
aaagaagaaa aggaagataa gatcccgatt atttctaaga agcctaagtc taagaatact  3180
cccaaggccc ggaagaattt aaagacttct caacttcctc agaaa                  3225

SEQ ID NO: 14           moltype = DNA  length = 3012
FEATURE                 Location/Qualifiers
source                  1..3012
                        mol_type = unassigned DNA
                        organism = unidentified
SEQUENCE: 14
atggctagca aacatgtagt gcgtcccttt aatggcaaag taacagctac tggcaagcgt  60
ttggcatact tggaagaaac ttttcattat ttggaaaaag ctgctggtgg tgttagtact  120
ttgtttgctg cccttggttc ttatcttgat gcaaccacaa taagcaattt aattaataaa  180
aatcaagatt tagccgttgt aatatttcgt tatcatgtgg ttcccaaagg tgaggctcat  240
actttacctg taggtacaga catggttagt cgttttgttg ccgactatgg tatggagccg  300
```

```
aatgagtttc agagagctta tttggacagt ccgattgacc aagaaaagta ttgttggcag  360
gataataggg atgttggttg ttggttgggt gagcaattgg gtgttagcga agcggacatg  420
cgggcaatag cagtaacttt ttataacaat cagatgcttt atgattgtgt aaaaggtact  480
gggagtggta atgctgtgag tcttttgttt ggcagtggta aaaagtctga ttacagtatg  540
aagggcgtta tagcaggtaa ggctgcttca gtactggcaa aatatcgccc agctacctat  600
caagatgccc gaaagatgat tttggaagct aatggtttca cctcagtaaa agatttggtt  660
acttcttatg gaataactgg aaggtctagt gctttgcaga tatttatgga agggattgaa  720
agtggtccta ttagcagcaa gacattagat gctcgtatta agaagttcac agaggattcg  780
gagcgcaatg gcaggaagaa tctagtccct catgctgggg ctatacgaaa ttggctgatt  840
gagcaagctg gtagtagtgt agaaaactat cagatggcat ggtgcgaggt ttacggtaat  900
gtgtctgccg actggaatgc caaagtagaa agtaatttca atttcgtagc ggagaaagta  960
aaggcattaa cagaattatc caacattcag aaatcgactc ctgatttggg taaggctttg  1020
aaattatttg aagaatattt gactacttgt caggatgaat ttgctattgc gccttatcat  1080
tttagcgtca tggaagaggt gcgaatggaa atggcaacag gcagggaatt caatgatgct  1140
tatgatgacg ccctaaatag cttggacatg gagtctaagc agcccattca gcctttgtgt  1200
aagtttttga ttgagcgtgg aggtagtatc agttttgata ctttcaagag tgcagccaag  1260
tatttgaaaa cacagagcaa gattgctggt cgatatccac atccatttgt aaaaggtaat  1320
cagggattta cttttggttc caaaaacatt tgggcagcca tcaacgatcc tatgatggag  1380
tatgcagatg gtcgtattgc tggtggttct gcaatgatgt gggtgacggc tacattgttg  1440
gatgggaaaa agtgggttcg ccatcatatc ccatttgcca atactcgata ctttgaggag  1500
gtttatgcta gcaagaaagg gttgcctgta ttgccttgtg ctagagatgg caaacactca  1560
tttaaattgg gcaataattt gagtgtagag agagttgaaa aggtcaaaga aggcggtaga  1620
actaaagcaa ccaaggcaca agagcgtatt ttaagcaact tgactcacaa tgtgcagttt  1680
gacagttcga caactttat tattcgtcgt caggaagaaa gtttgtaat ttgcgtgaat  1740
catcgacatc cagctccgct catgaagaag gagatggaag ttggcgacaa aatcattggt  1800
atcgaccaga atgtgacggc acccacaacc tatgccatag ttgagcgtgt ggcttctggc  1860
ggcattgagc gtaacggcaa gcagtacaaa gtgacggcga tgggagccat ttccagcgtt  1920
cagaagacca gaggcggtga ggtggatgtt ttgagttata tgggggttga actttctgac  1980
agcaaaaatg gatttcaaag cttgtggaat aaatgtttgg actttgttac caaacatggc  2040
actgaaaatg atgttaaata ttataacaac actgctgtct gggccaacaa gctgtatgtg  2100
tggcacaaga tgtatttccg gcttttgaag cagttgatgc gtcgggcaaa ggacttgaaa  2160
cctttcaggg accatttaca gcatctatta ttccatccta atcttagtcc cttgcaacgc  2220
catagcttgt ccttaacaag tctggaagca actaagatag tgcggaattg cattcattcg  2280
tatttcagtc tattggggtt gaagaccttg gatgaacgca aagccgctga catcaattta  2340
ttggaagttt tggaaaagct gtatgctggt ttggttgaga ggcgaaaaga aagaaccaaa  2400
ctaaccgctg ggctattggt tcgcttatgt aatgagcatg ggatttcttt tgcagctatt  2460
gagggtgatt tgccggtcgt tggagagggc aaatctaaag ctgccaacaa tacacaacag  2520
gattggacag ccagagagtt agagaagcga ttatctgaga tggcggaggt ggttggcatc  2580
aaggtaatag ctgttttgcc ccactatacc agtcatcagg acccatttgt ttatagtaaa  2640
aataccaaga aaatgagatg tcgttggaac tggaggacca ccaagacctt cactgatcgt  2700
gatgctttga gtatacgcag gatattaagc aagcctgaga cgggtacaaa tttgtattat  2760
cagaagggct tgaaagcatt tgctgaaaag catggtctgg atttggcaga gatgaagaag  2820
cgcaaggatg ctcaatggta tcttgagcgc attcaagaca agaatttttt ggtgccaatg  2880
aatggtggta gagtttattt gagttctgtc aaattagccg ggaaagaaac aattgacatg  2940
ggtggcgaaa ttttatatct taacgatgcc gatcaagtcg cagcgttgaa tgttttgtta  3000
gtgaagattt ga                                                      3012

SEQ ID NO: 15          moltype = DNA  length = 3058
FEATURE                Location/Qualifiers
source                 1..3058
                       mol_type = unassigned DNA
                       organism = unidentified
SEQUENCE: 15
atggctaaga aagaacatat tataagacca ttcaaaggaa cactaccact tcgtggtgat  60
agactaaggt atcttcaaga taccatgaaa tatatgaaaa aggttgaaga tactatcaca  120
gaactctgcg ccgctgttat cgcctatgcc aaacccacca tcattcaaca aatacttggc  180
gaagaaattg aaaccaccag cacattttgt agcttccgct tagtaggcat tcatgaaaac  240
tttaccatgc cactaaccac aaatatgata aaacacttcc agaaaacctt taacataaac  300
ccatcagaaa aacaagcaat ctatctctcc agtggattcg attcagataa atatcgctgg  360
caagatactt ccgaagtatc cagaaacttc gccaacaaat gccgacttac taatcaagaa  420
ttccaagaat ttgccgaaca agcactactc aatatgtgct tcataggttg ctctggtagc  480
cccggtgcaa ctaatgccgt ctcacaaatc tttggcacag gcgaaaaaag cgattaccaa  540
cgcaaaagcc aaatcgctaa aattgctgct gataccctcg aaaaccacaa acctagcacc  600
tatgagtctg ctagattaat ggttcttaat acacttggac acaaaacaat agaagattgt  660
gtcaatgact atggcgcaat aggagccaaa tccgccttcc gactattcat ggaatcaaaa  720
gaaataggac caattacatc tgaacaactc acaaccaaaa ttaagaagtt cagagaagat  780
cataaaaaga actccatcaa gaaacaactt ccacatgtag aaaaagttcg taacgctttg  840
ctatcacaat tcaaagaaca atacctgccc tcagcatggg cagaagcatg gtgcaatatc  900
atgggcgaat ttaactccaa attatcaaat aataataact tcatcgacca aaaaacaaaa  960
atggtcaatg actgcgataa tattaaaaaa tctaatccac aactagacaa agctgttaat  1020
atgctcgatg aatggaaata taaaaactgg gatgataatt ctgctataca cccatatcat  1080
attggcgatc ttaaaaaact catggcaata ttcaatatca ataacgaagg aaccttcgac  1140
gaaagatttt cagctagctg ggaacaattc tccacatcac tagaatacgg ggagaaacca  1200
cccgttcgtg atctactagc ccatatcatc aaaaatatga atgacctcac ctacacagac  1260
gtaatcaacg ccgcaaaatt tctcaaactt caagataata taagaaataa atacccacac  1320
cctttcgtta tgccaaataa aggatgtacc tttggtaaag ataacctttg gggcgaaatt  1380
aatgacccca cagccaaaat caaatcaaca gaagaagttg ctggacaaag acctatgatg  1440
tggctgacag ccaaacttct cgataatgga aaatgggtag aacaccacat ccctttcgcc  1500
tccagtagat actttgccga agtttattat accaatccag cactccccac tctaccaata  1560
```

```
gctagagatg gaaaacattc atacaaatta acaaaaacta tagatgccaa tactgcaaaa  1620
actctagtaa ataatcctag agataaagca gctaaactaa tcgcacgaac taaagccaat  1680
actacacaca atgtaaaatg gattaaacct acatacagaa tccaaaaaga aaataaccaa  1740
ttcgttatta ctatcaatca tcgacaccca tgcataacac caccaaagga aatcatactc  1800
ggagatcgta tcctatcctt cgaccaaaac gaaacagccc ccacagcatt ctccattctc  1860
gaaaaaaacaa ccaaaggtac agaattctgt ggccaccaca ttaaagtgct aaagactggt  1920
atgctagaag ctaaaattaa aaccagtaag aaatcaatag atgcattcac atacatggga  1980
ccaatggaag atgatcatgc gtctggcttc ccaacactac tcaacatatg tgaaaaattc  2040
atatcagaga atggagatga aaaagacaaa agtttctctt ctcgtaaatt gccctttaaa  2100
aggtctttgt acttctttca tggctcacac ttcgatttac taaagaaaat gatcagaaag  2160
gccaaaaatg accccaagaa attgaagtta gtaagaattc atatcaatga aattctattc  2220
aattccaatt tgtcaccaat aaaactacac agtctgtcta ttcacagcat ggaaaatacc  2280
aaaaaagtta tagctgctat tagctgctat atgaatgttc atgaatggaa aactatcgat  2340
gaacaaaaga atgctgatat aacattgtat aatgctaaag aaaaactata caacaacctt  2400
gttaaccgcc gtaaagaaag agtaaaagta actgcaggta tgttgattcg attagctaga  2460
gaaaacaatt gcagattcat ggtcggggaa gcagaattac ccacccaaca acaaggcaaa  2520
tcaaaaaaga acaataactc caaacaggat tggtgcgcca gagatatagc acaacgatgt  2580
gaagatatgt gcgaagtcgt aggtataaaa tggaatggcg ttactccgca taataccagc  2640
catcaaaacc cattcatcta taaaaatact agtggacaac aaatgcgatg ccgttatagt  2700
ctcgtaaaga agtcagaaat gacagacaag atggcagaaa aaattagaaa tattttacac  2760
gctgaacctg taggcactac agcatactac cgtgaaggca ttttggaatt cgccaaacat  2820
catggattag atctgggaat gatgaaaaaa cgaagagatg ctaagtatta tgataatctt  2880
ccagatgagt ttctgcttcc tactagaggt ggtagaatct atctgtccga aaatcaacta  2940
ggcggaaacg aaaccattgt tattaatggg aaaaaatatt ttgtcaatca ggcagatcaa  3000
gtcgctgccg taaatattgg cctgctttat cttctgccga agaaaaacca gagttaag    3058

SEQ ID NO: 16           moltype = DNA  length = 3144
FEATURE                 Location/Qualifiers
source                  1..3144
                        mol_type = unassigned DNA
                        organism = unidentified
SEQUENCE: 16
atgtccgaga agaagttcca catcaggccc taccgctgct cgataagccc gaacgcccgc  60
aaggccgata tgctcaaggc gacgatctcc taccttgact ccctgacctc cgtgttcagg  120
tcgggattca ccgcactact tgcgggcata gacccgtcga cggtgagccg cctggcgcct  180
tcgggggccg tcggcagccc ggacctgtgg agcgccgtca actggttccg catcgtgccg  240
ctcgcagagg ccggcgacgc ccgagtcggc caggcatcgc tcaagaacct cttccgtggc  300
tacgcaggcc acgagcccga cgaagaggcg tcgatctata tggagtcgag agtggacgat  360
aagaggcacg cgtgggtgga ctgccgtgcc atgttcaggg cgatggcgct cgagtgcggg  420
ctggaggagg cccagctcgc ctccgacgtg ttcgccctcg cctcaaggga ggtcatagtc  480
ttcaaggacg gcgagatcaa cggctggggc atagcctccc tgctgttcgg cgagggcgag  540
aaggccgact cgcaaaagaa ggtcgccctg ctccgctccg tgaggctggc ccttgagggg  600
gactacgcga cctacgagga actctccggg ctcatgctgg ccaagaccgg agcctccagc  660
ggctccgacc tccttgacga gtacaagagg agcgagaagg gcggcagcag cggcggcagg  720
cacccccttct tcgacgaggt cttccggagg ggcggcaggg tcaagcagga ggagcgcgag  780
aggctgctga agagctgcga cacagcgatc cagaagcagg ggcaggcgct gccgctgtcg  840
cacgtcgcat cttggaggca atggttcctg cgcagggtca cgctgctgcg caaccgcagg  900
caagagtcgt tcgcagtctg catcaccaac gccctcatgg acctacagcc caagaaccta  960
cgcaacgtcc actacgtgac gaaccccaag agcgagaagg acaagggcgt gctcgagctg  1020
cgcgtcgacg tcaagaacaa cgaggggccg gacgtggcgg gcgcgcaggc ggtcttcgac  1080
gcctacatgg cgaggctggc acccgacctg cgcttctccg tgatgccacg gcacctcggc  1140
tccctcaagg acctctacgc cctttgggcc aagctcgggc gggacgaggc catcgaggag  1200
tacctcgagg gctacgaggg accattcagc aagaggccca tcgcaggcat tctacaaatc  1260
atccacgcac accgtggcaa ggtgggctac gatagcctgt tgcgtgcggc gaggctcaac  1320
agggcgatgg acaggctgga gaggaagagg gcccacgcct gcgcagccgg caacaagggt  1380
tacgtctacg gcaagagctc gatggtcggc cgcatcaacc cgcagagcct cgaggtcggc  1440
ggccgcaagt cgggccgaag cccgatgatg tgggtgaccc tcgacctggt ggacggcgac  1500
aggttcgcgc agcaccacct tcccttccag agcgcccgct tcttctccga ggtctactgc  1560
cacggcgacg ggctcccggc cacccgtgtc cccggcatgg tcaggaaccg tcgcaacggg  1620
ctggcgatag ggaacgggct cggggagggt ggactctcag cgctgcgcgc aggcagcgac  1680
aggaggaaga gggccaacaa gaggacgctg cgcgccctcg agaacatcac gcacaacgtg  1740
gagatcgacc ccagcacctc cttcacgctg cgggaggacg ggataatcat ttcgcacagg  1800
atcgagaaga ttgagccgaa gcttgtcgcc ttcggggaca gggcgctcgg cttcgacctc  1860
aaccagacag gggctcatac gtttgcggtg ctccagaagg tggactcggg cggcctagac  1920
gtcggccact ctcgcgtgtc gatcgtgctc accggcactg ttcgcagcat ctgcaagggc  1980
aaccaggcga gcggcggacg ggactacgac ctgctttcct acgacggccc cgagcgcgac  2040
gacggggcgt tcacggcatg gaggtcggac aggcaggcct tcctgatgtc tgccatacgg  2100
gagctgccca cgcccgccga gggggaaaag gactacaagg cagacctcct ctcccagatg  2160
gcgagccttg accactacag gcgactgtac gcgtacaaca ggaagtgcct cggcatctac  2220
atcggggcct tgagacgcgc gaccaggagg caggccgtgg ccgcattcaa ggacgagata  2280
ctctcgatcg cgaatcaccg ctgcgggcct ctcatgcgtg ggagcctttc ggtgaacggc  2340
atggagtccc tcgcgaacct caagggccta gccacggcat acctgagcaa gttcaaggac  2400
agcaagtccg aggacctgct gtcgaaggac gaggagatgg ccgacctgta cagggcttgc  2460
gcgcgcagaa tgactggcaa gcgcaaggag aggtacagga gggcggctag cgagatcgtc  2520
cggctggcca acgagcacgg ctgcctgttc gtcttcggcg agaaagagct gcccaccacc  2580
agcaagggca acaagagcaa gcagaaccag aggaacaccg actggtcggc ccgtgccata  2640
gtgaaggcgg tcaaggaggc ctgcgagggc tgcggtctcg gcttcaagcc cgtgtggaag  2700
gagtactcga gcctcacgga cccgttcgag agggacgggg acggaaggcc tgccctccgc  2760
tgccggttcg ccaaggtggc cgcacccgac tccgaactcc cgcctcgcct gacgaaggcc  2820
```

```
gtcggctcct atgtgaagaa cgccctcaag gccgacaagg cggagaagaa gcagacctgc  2880
taccagcgtg gcgccatcga gttctgctca aggcacggca tcgacgtccg gaaggcgacc  2940
gacaaggcca ttcgcaaggc agtccgtggc tcctccgacc tgcttgtgcc gttcgacggg  3000
gggaggacct tcctgctctc gacgaggctg tccccggagt cgcgaaaggt ggagtgggcc  3060
gggcgcaccc tgtacgagtt ccccagcgac atggtcgccg caatcaacat cgcctgcagg  3120
ggcctagagc cacgcaaggc ctag                                          3144

SEQ ID NO: 17          moltype = DNA  length = 3090
FEATURE                Location/Qualifiers
source                 1..3090
                       mol_type = unassigned DNA
                       organism = unidentified
SEQUENCE: 17
atggacgagc aagctgttgt ttcctctggt tccgacaaga ccctcaagat cgtacgccct  60
tacagggcaa aagtaaccgc tactggaatt cgccttgagg gaattaaaaa taccctgaat  120
tacctgaagc gtacagaaat ttgtctgtca cgcctgaatg cagcttgtgg agcttttctc  180
actcctgcca tcgtggagca gatctgtaag gacgatcctg ccctagtttg tgccattgct  240
cgctttcaat tggttccggt tggtagtgaa gccactttgt ccgacagtgg gctaatgcgt  300
cattttaagg ctgctctcgg tgaattgacc ccgctacaag aagcctacct gaatagcagc  360
tataacgacg aattgtacgc atggcaggat actcttgtct tagcgcgaca gattattgct  420
gaaaccggat tgactgaaga tcaattccgc gcctttgctc atgcctgttt caagaacggc  480
aatattatcg ggtgcgctgg tggtcccggt gccagcaacg ccatctctgg catttttggc  540
gagggaatta aatccgatta ttcactccga agtgaaatga ccgctgccgt tgcaaaggtg  600
tttgaagaga aacgtcctat cacttacgaa gaagctcggg ctctcgctct ggaagcaact  660
ggacacgcca gcgttcagtc tttcgtggaa gcatttggta aacaggggcg taaaggcact  720
ctgattcttt tcatggaaga taccaagaca ggcgcattcc caagcaatga attcgattac  780
aagctcaaga aactgaagga ggatgcagag cgtgtcgggc gtaagggtat catcccgcac  840
cgcgatgtga ttgcttctta tctccgcaat cagactggtg ctgatattga atacaactcc  900
aaggcatggt gcgagtccta ctgttgtgcc gtgagcgaat acaactcaaa gatgagcaac  960
aatgttcgat ttgccacgga aaaaagtctt gatttgacca agcttgatga aacgatcagg  1020
gaaacgccca agatcagtga agccatgctt gtttttgaaa actacatggc gcgaattgat  1080
gccgatctcc ggttcattgt gagcaagcat catctcggca atctcgccaa attccgtcag  1140
accatgatgc atgtctctgc atcagaattt gaagaggctt ttaaggcgat gtgggctgat  1200
tacttggctg gtctggaata cggtgaaaaa cccgcgatct gtgaactggt gcggtatgtc  1260
ctgacccatg gcaacgattt gcctgtcgaa gcgttttacg ctgcgtgcaa gttccttagc  1320
ttggatgaca agatcaagaa tcgttaccct cacccattg ttccgggtaa caaaggctac  1380
acctttggcg cgaaaaactt gtgggcagaa atcaatgatc ccttcaagcc catccgtcaa  1440
ggcaacccag aggttgctgg tcaacgcccc atgatgtggg ctaccgccga ccttctggac  1500
aacaacaaat gggtcttgca tcacatcccc tttgcctcca gcaggtattt cgaggaagtg  1560
tactacaccg atccctcgct tcctacggct caaaaggcgc gagacggcaa gcatggctat  1620
cggttgggca aagtgctgga tgaggctgct cgggagcgtt taaaagcaaa taatcgccag  1680
cgcaaggcag ctaaagccat cgagcggatc aaagccaact gtgagcacaa tgtggcttgg  1740
gatccgacca ccaccttcat gcttcagttg gattctgagg gtaatgtgaa aatgacgatc  1800
aatcatcgtc acattgccta tcgcgcaccc aaggaaattg gtgttgggga cagggtgatt  1860
ggcatcgacc aaaacgagac tgctcctaca acctacgcca ttcttgagcg cacggaaaat  1920
cctcgcgatc ttgaatacaa cggcaagtat taccgtgtag tcaagatggg tagtgtgact  1980
tcaccgaatg tcagcaagta tcgcacggtg gacgctttga cttacgatgg cgtgtccttg  2040
tcggatgatg cttctggtgc tgtgaacttt gtggtattgt gtcgcgagtt ttttgcagca  2100
catggcgacg atgagggtcg caagtacctt gagaggactt tggggtggag ttcaagcctg  2160
tattccttcc atggaaacta tttcaagtgc cttacgcaga tgatgcgtcg atccgctcgt  2220
tctggtggtg atttgacggt ctatcgcgcc catttgcagc agatcctgtt ccaacacaat  2280
ctgtcgccct tgaggatgca cagcttgtct ttaaggagca tggaatcgac gatgaaggtc  2340
atcagttgca tgaagagcta catgtctctt tgtggctgga agaccgacgc ggatcggatt  2400
gccaatgata ggtcgctgtt tgaggctgct cgtaagcttt acaccagttt ggtaaatcgt  2460
cggacggagc gggttcgtgt gactgctggc attctgatgc gtctgtgctt ggagcacaac  2520
gttaggttta ttcacatgga ggatgaactt cctgtggctg aaacgggcaa aagcaagaaa  2580
agcaatggcg cgaagatgca ttggtgtgcc cgggagcttg ccgttcgttt gtcccagatg  2640
gcagaggtga cgagcgtcaa gttcacaggt gtgtcaccgc attacactag ccatcaagac  2700
ccatttgtgc attccaagac tagtaaggta atgcgtgccc gttggagttg gcggaatcgt  2760
gccgatttca cggacaagga tgcggagcgt attcggacga ttctgggtgg tgatgacgca  2820
gggacgaagg cttattatcg ctcggcgttg gctgaatttg cctcgcgcta tggtctggac  2880
atggagcaga tgcggaagag gcgcgatgct cagtggtatc aagagagact gccagaaacc  2940
tttattattc ctcagcgggg tggtagagtg tacttgtctt ctcacgatct gggatcaggt  3000
caaaaagttg acgggattta tggtggtcgt gctttcgtga atcacgctga cgaggttgct  3060
gcgctgaatg tggcgttggt caggctgtga                                    3090

SEQ ID NO: 18          moltype = DNA  length = 3090
FEATURE                Location/Qualifiers
source                 1..3090
                       mol_type = unassigned DNA
                       organism = unidentified
SEQUENCE: 18
atgaagactg aaactcttat ccgtccctac cccggcaaac tcaacctcca accccgtcga  60
gcacaattcc tcgaagactc cattcaatat caccagaaaa tgacggaatt tttctaccaa  120
ttcctccaag cagtcggcgg tgccaccacg caccaaaaca tcagcgattt catcgacaat  180
aaagccaccg atgaacacca agccactctc ctcttccaag tagtctccaa agacagcaca  240
acaccagaat gccccgcaga agaactccta gcccgatttg cccaatacac cggcaaacaa  300
cccaatgagg ctgtcaccca ctacctgacc agcagaatca atacagataa ataccgctgg  360
caggacaatc gactcctcgc ccaaaacatc gcttcacaac tgaacatctc cgaaactcaa  420
```

-continued

```
ttccaagaga tcgctcacgc aatcctgtcc aacaacctat acatcggtca aactgcatcc  480
aacgcagcag ccaacttcat cagccaagtc acaggcacag gccagaaagc ccccaaggca  540
gcacggctcg atgtcctgtt ccagaccaac caagccctcg ccaaaacaca acccacaacc  600
ttcggccaac tccaacagat catcgtacaa gcctgcggtg aatccaccac cgatgcagtc  660
ctcgccaaat tcggcaacaa aggcgctgca accagccttc aactggccct taaaaccgac  720
cccaacacaa cgctggatca gaagaagtac gaagccctgc aaaagaaatt tgcagaggac  780
gaaaccaaat atcgcaacaa ggtcgatatc ccccacaaga cccaactgcg caacctcatc  840
ctcaacacct caaaccaatt ctgcaactgg cacaccaagc cagccatcga agcctttaag  900
tgcgccatcg ctgacatcca gtccaaagtc agcaacaacc tccgcatcat gcaggaaaag  960
gccaaactct acgaggcatt cagaaatgtc gatccacaag tccagatcgc cgtccaagct  1020
cttgaaaacc acatgaacac acttgaggaa ccctacgcac cctacgccca ctcgttcggc  1080
agcgtcaaag acttctacga agacctcaac aacggctcca acttagatga ggccattcaa  1140
accatcgtcc acgattccga caacttcaac aggaagccag accccaactg gctccgcatc  1200
atcgcacctc tccactcatc ccattccgca agccaaatca tggaggcagt aaaatacctg  1260
tccagcaaac aggattacga actccgtaaa cccttcccat tcgtcgccac taacctgcca  1320
gcaacctacg ggaaatttaa cattcccggc accctcaacc cacccaccga cagccttcac  1380
ggcagactga acggtagcca ctccaatatg tggctcacag ccctgctcct cgacggcagg  1440
gattggaaaa accaccacct ttgcttcgcc tcaagccgct acttcgagga ggtctacttc  1500
acaaaccccca gcctgcccac tacagacaaa gtccgtagcc ccaaatgcgg cttcacactc  1560
aagagcgtgc tcgactccga agccaaagac aggattcgca acgctcccaa atcccgcacc  1620
aaggccgtga aagccatcga acgcatcaag gccaactcca cccacaatgt ggcgtggaac  1680
cccgaaacct ctttccagat gcagaaaaga aacgatgagt tctacatcac catcaaccac  1740
cgcatcgaaa tggaaaaaat ccccggtcag aaaaagaccg atgacggttt cacaatccac  1800
cccaaaggtc tcttcgccat cctcaaggaa ggcgacagaa tcctgtcaca agacctcaac  1860
cagaccgcag ccacacattg cgccgtctat gaagtcgcca aacccgacca gaacaccttc  1920
aaccaccacg gcattcacct caagctgatt gccacagaag aactcaaaat gcccctcaag  1980
accaaaaagt ccacaatccc agatgccctc tcctaccaag gcatccacgc ccacgaccgt  2040
gaaaacggct tacaacaact caaagatgcc tgcggagctt tcatcagccc cagactcgat  2100
cccaaacaaa aggctacttg ggacaactcc gtctccaaga aggagaatct ctatccattc  2160
atcaccgcct acatgaaact cctcaagaag gtcatgaagg caggtcgtca agaactgaaa  2220
cttttcagga cacaccttga ccacatcctc tttaaacaca acctcagccc cctcaagctg  2280
cacggtgtgt ccatgatcgg tctggaatca tccagagcaa ccaaatccgt catcaacagc  2340
ttcttcaacc ttcagaacgc caagacggaa cagcagcaga tcgccctcga ccgacccctg  2400
tttgaggccg gtaaaaccct catcaacaac caaacccgcc gacgacagga aagggtcagg  2460
ttagaaacca gtctcaccat gagactggca cacaaataca acgccaaggc aatcatcatc  2520
gagggtgaac tgccacactc cagcaccgga acctcgcagt accagaacaa tgtccgtctg  2580
gactggtctg ccaagaaatc cgcaaagctg aaaaccgaat cagccaactg tgcaggcatt  2640
gccatatgcc agatcgatcc gtgccacaca agccaccaaa atcccttccg gcacactcca  2700
actaacccag acctcagacc acgatttgcg caagtcaaaa agggcaaaat gttccagtat  2760
caactcaatg gactacagag gctgctcaac cccagaagca aatcctcaac tgccatctac  2820
tacaggcagg cagtccaaag tttctgcgcc caccacaacc tgacggagag ggacatcacc  2880
tctgccaaat tccccagcga tctggagaaa aaaatcaagg atgacaccta tctgattccc  2940
cagagaggtg gtagaatata catcagcagc ttccccgtca ctagctgcgc ccgtccctgc  3000
accagcaacc attatttcgg gggtggacaa ttcgagtgca atgctgacgc tgtcgcagcc  3060
gtcaacatca tgctgaaggt tcacccgtaa                                  3090

SEQ ID NO: 19          moltype = DNA  length = 3036
FEATURE                Location/Qualifiers
source                 1..3036
                       mol_type = unassigned DNA
                       organism = unidentified
SEQUENCE: 19
atgcccattc gcggatataa atgcactgtt gtcccaaacg tacgcaaaaa gaaactcttg  60
gaaaaaacct atagctactt acaagagggt tctgatgtat tttttgatct tttcttgagt  120
ctgtatggtg ggatcgcccc aaaaatgatt ccacaagacc tggggatcaa tgaacaagta  180
atttgtgctg ccaattggtt caaaattgtt gaaaaaacga aagattgcat cgctgatgat  240
gcgttgttga atcaatttgc tcaatattat ggggaaaaac ccaatgaaaa ggttgttcaa  300
tttttgacgg catcttacaa taaagacaaa tatgtttggg tcgattgtcg tcaaaaattt  360
tacactctgc aaaaggattt gggagtccaa aacctagaaa acgacctgga gtgtttgatt  420
cgagaagatt tgttgcccgt aggaagcgac aaagaagtta atggatggca ctcgatatca  480
aaattgtttg gttgtggaga aaaagaagac agaacaatta aggctaaaat tctgaatggc  540
ctatgggaaa gaattgagaa agaagatatt ctaacagaag aagacgcaag aaatgaacta  600
ttgcactctg ctggggtgtt gactccaaaa gaatttagaa aagtatataa aggggctgct  660
ggtgggcgtg attgttatca cacgttgctg gtagatggga gaaacttcac ttttaacctt  720
aaaacactca ttaagcagac caaggataaa ttaaaagaaa agtctgttga tgttgaaatc  780
cccaataaag aagcattgcg tctatatctc gaaaaacgaa ttggacggtc tttcgagcaa  840
aagccatgga gcgaaatgta taaaacggcc ctctcagccg ttatgccaaa aaatacgcta  900
aattattgtt tcgccattga taggcacgcc caatatacaa aaattcaaac actaaagcag  960
ccatatgatt cggcaattac tgccctaaat gggtttttttg agtctgaatg ctttacaggc  1020
tcagatgttt ttgttatttc tccctcccat ttggggaaaa ctcttaaaaa actttataat  1080
tacaaagatg ttgaatctgg cattagcgaa attgttgaag atgaagacaa tagtttgcga  1140
tctggggtaa atgtaaattt acttagatat atttttactc ttaaagatat gttttctgct  1200
gaggatttca tcaaagcggc agaatataat gttgtatttg aacgctacaa caggcaaaaa  1260
gtccacccta cagtaaaagg gaatcaatcg ttcactttcg gcaattccgc attgagcggt  1320
aaagttattc ctccatcaaa atgcttgtcc aatttgcctg gacaaatgtg gctggccatt  1380
aatctacttg accagggcga atggaaagaa catcacattc cttttcacag tgcaagattc  1440
tatgaagaaa tctatgcaac aagtgacaat caaaataatc ccgtagattt gcgaactaaa  1500
cgttttggct gctctcttaa caagactttt tctgctgctg acatcgaaaa ggtgaaagaa  1560
agtgccaaga aaaaacatgg caaagcagct aaacgtattt tgagagccaa aaacaccaat  1620
```

```
acagccgtaa attgggttga ttgcggtttt atgttggaaa aaacagaggt taactttaaa  1680
attactgtta actacaaact tccagaccaa aagttgggaa aatttgaacc aattgttggg  1740
acgaagattt tggcttatga ccaaaatcaa accgctcctg atgcttatgc gattcttgaa  1800
atttgcgatg atagcgaagc ttttgattac aagggatata aaatcaaatg tttgtctact  1860
ggtgatttgg cttcaaagtc attgaccaaa caaacagaag ttgatcagct agcttataag  1920
ggtgtggaca aaactagcaa tttttacaaa aagtggaaac agcaacgaag gctttttgtc  1980
aaaagtctta acattccaga tgccctaaag agttttgaaa acatcaataa agaatatctt  2040
tatgggttca acaattcgta tctgaagttg cttaaacaaa ttttacgggg caaatttgga  2100
ccaattcttg ttgatattcg accagaactt attgaaatgt gtcagggaat tggctctatc  2160
atgcgattgt ctagtctaaa ccatgatagt ttggacgcaa ttcaatctct caaatccttg  2220
cttcactcct attttgatct caaagtaaag gaagaaatca aaacagaaga attgagagaa  2280
aaagcagata aagaggtttt taagttgctt caacaagtga ttcaaaaaca aaagaataaa  2340
cgcaaagaaa aagttaatag aactgttgat gccattttga ctttggcggc tgatgagcaa  2400
gtacaagtca ttgtaggaga gggagatctt tgtgtttcca ccaaaggaac aaaaaagaga  2460
caaaacaaca gaaccattga ttggtgtgcc agagcagttg tggaaaaact agaaaaagca  2520
tgcaaactac atgggttgca ttttaaggaa attccaccac attacacttc acatcaagat  2580
tgttttgaac acaacaagga tattgaaaat ccaaaagaag tcatgaagtg tcgtttcaat  2640
agcagcgaaa atgtagctcc ttggatgatc aagaaattcg caaattatct taaatgcgaa  2700
acaaaatatt atgttcaagg aatgcaagat tttctagagc attatggtct agtagaatac  2760
aaagatcaca tcaaaaaggg aaaaatctca attggggatt ttcaaaaact tatcaaactt  2820
gctcttgaga aagttggaga aaaagagatt gtttttccat gtaaaggtgg tagaatctat  2880
ttgtcaacct attgcttaac aaatgagtct aaacccattg ttttcaatgg cagaagatgc  2940
tatgttaata atgcagacca tgttgctgcg attaatgttg gcatttgtct tttgaatttt  3000
aatgcgagag ccaaggtggc ggaaaaaacc ccttga                            3036

SEQ ID NO: 20          moltype = DNA  length = 3282
FEATURE                Location/Qualifiers
source                 1..3282
                       mol_type = unassigned DNA
                       organism = unidentified
SEQUENCE: 20
atggctaaga aggattttat cgctcgtccc tacaattcat tcctgctccc caacgacaga  60
aagcttgctt atctggaaga aacttggact gcctacaagt caatcaaaac agtactgcac  120
cgtttcctca tcgcagcata cggcgctatt cccttccaga cctttgcaaa aaccatcgaa  180
aacacacaag aagacgaatt gcaattggca tatgccgtta gaatgttcag actagttcca  240
aaagacttct ccaagaatga aaacaacata ccccccgata tgctcattag caagcttgct  300
agctatacaa atataaatca atcaccaacc aatgtcttga gctatgtaaa cagcaactac  360
gatccagaaa agtataagtg gatcgactca cgcaacgaag ccatctcatt gtccaaagaa  420
atcggcatca aactcgatga gttggcagac tacgctacca ccatgctttg ggaggactgg  480
cttccactta acaaagacac agtcaacggt tggggcacca ctagcggcct attcggcgca  540
ggaaaaaaag aggatcgtac ccaaaaggta caaatgctca acgcattgct tttggggctt  600
aaaaacaacc ctcccaagga ctacaaacag tattcgacca tccttctcaa ggcatttgat  660
gccaaatcat gggaagaggc tgttaaaatt tataaaggcg aatgctcagg tagaaccagt  720
agctacctga cagaaaagca tggagacatt tccccagaaa ctttggaaaa actaattcaa  780
agtattcaga gagatattgc tgacaaacaa caccccatca atctacctaa aagagaagaa  840
attaaggcat acttggaaaa gcagagtggt actccataca atctcaatct ctggtcacaa  900
gccctacaca acgctatgtc ttctatcaag aagacagata ctcgcaattt caatagcaca  960
ctagaaaaat atgaaaaaga aattcaactc aaggagtgct tgcaagatgg tgatgatgta  1020
gaattacttg gcaacaaatt cttttcatct ccatatcata agaccaacga tgtctttgtc  1080
atttgctctg agcatatcgg caccaatcgc aaatacaatg tcgttgagca gatgtaccaa  1140
ctcgctagcg aacatgccga ttttgaaaca gtgttcactc tcctcaaaga tgaatacgaa  1200
gaaaaaggta tcaaaacccc aatcaaaaac attcttgaat acatttggaa caacaagaat  1260
gtgcctgtag gcacttgggg tagaattgcc aaatacaatc agctgaaaga tagattggct  1320
ggaatcaaag ccaatcctac cgttgaatgc aaccgtggca tgacatttgg caattctgcg  1380
atggttggcg aagttatgcg atccaatcgc atttcgacca gcacgaagaa taaaggccag  1440
attttggccc aaatgcacaa cgataggccc gttgggtcaa acaacatgat ctggctggaa  1500
atgacgcttt taaacaacgg gaaatggcaa aaacaccaca tcccgaccca caataataag  1560
ttctttgaag aagtccatgc tttcaatcca gaactgaagc aatccgtgaa tgtgcgaaat  1620
agaatgtatc gttctcaaaa ctattcgcaa cttccaacat ctctgaccga tgggctgcaa  1680
ggcaacccaa aagccaagat tttcaagcgt caatatcgtg cgctcaataa catgacggca  1740
aacgtgattg atccaaagtt gagttttatt gttaacaaaa aggatggcag attcgaaatt  1800
agcatcattc acaatgttga agtgatcagg gccagacgag atgttctggt cggggattac  1860
ttggtcggca tggatcaaaa ccagactgcc agcaacactt acgctgtcat gcaggtggtt  1920
cagccaaaca ctcctgactc ccatgaattt cgcaaccaat gggtgaagtt tattgagagt  1980
ggcaagattg aatcttctac tctcaattct agaggcgaat acattgacca gttgagtcat  2040
gatggcgtgg atttgcaaga aatcaaggat tctgaatgga ttccagctgc tgagaaattc  2100
ttaaacaagt tgggagcaat caacaaggac ggcactccaa tcagcatctc taatacttca  2160
aagagggctt acaccttcaa ctccatatat ttcaaaatct tattgaatta tcttcgtgct  2220
aatgatgttg atctgaattt ggtgagagag gagattctgc gtattgccaa cggcaggttt  2280
tcgcccatgc gtctgggtag tctgtcgtgg actactctta agatgttggg caactttaga  2340
aatttgattc atagttattt cgatcactgt ggtttcaagg aaatgcctga aagggaatct  2400
aaagacaaaa ccatgtacga tctgttgatg cataccatca caaagctgac aaacaagcgt  2460
gccgaaagaa cgagtaggat tgctggttct ttgatgaatg tagcccataa gtataaaatt  2520
ggcacaagcg ttgtgcatgt tgtcgttgaa ggcagtctaa gcaagaccga caaatccagc  2580
agcaagggta ataaccgaaa taccactgat tggtgctcaa gggctgtagt caaaaagctg  2640
gaagacatgt gcgtctttta tgggttcaat ttgaaagcag tttcggcgca ttacactagt  2700
caccaagacc cattggttca tcgggctgat tatgatgatc ccaagcttgc tttgcggtgt  2760
cgatattcgt cgtatagtcg ggctgatttt gaaaagtggg gtgagaagtc gtttgctgct  2820
gtgattcgtt gggctaccga caaaaagagc aatacttgtt acaaggttgg ggctgtggag  2880
```

-continued

```
ttctttaaaa attataaaat cccagaggac aagatcacca agaagctgac cataaaggaa  2940
ttccttgaga taatgtgtgc agagtcacac tatccgaatg agtatgacga tattttgatt  3000
cctcgccgtg gaggcaggat ttatctgaca acgaagaagt tgctaagtga ttcgacccac  3060
caaagagaaa gtgtgcatag tcacacggct gttgtcaaaa tgaacgggaa agagtattat  3120
tcctcagatg cagatgaggt ggctgcgatc aacatctgcc tacatgactg ggttgtccca  3180
ctgaattgga ccaatcactg cctacctgct ggctggtgct ctgaccacct gaaagaatgt  3240
gtgcaatgtc acactccaga cccagtacga atatccatgt aa                     3282

SEQ ID NO: 21          moltype = RNA  length = 36
FEATURE                Location/Qualifiers
source                 1..36
                       mol_type = unassigned RNA
                       organism = unidentified
SEQUENCE: 21
ctagcaatga ctcagaaatg tgtccccagt tgacac                            36

SEQ ID NO: 22          moltype = RNA  length = 36
FEATURE                Location/Qualifiers
source                 1..36
                       mol_type = unassigned RNA
                       organism = unidentified
SEQUENCE: 22
atcgcaacat cttagaaatc cgtccttagt tgacgg                            36

SEQ ID NO: 23          moltype = RNA  length = 36
FEATURE                Location/Qualifiers
source                 1..36
                       mol_type = unassigned RNA
                       organism = unidentified
SEQUENCE: 23
tctcaacgat agtcagacat gtgtccccag tgacac                            36

SEQ ID NO: 24          moltype = RNA  length = 36
FEATURE                Location/Qualifiers
source                 1..36
                       mol_type = unassigned RNA
                       organism = unidentified
SEQUENCE: 24
ctcaaagtgt caaaagaatg tccctgctaa tgggac                            36

SEQ ID NO: 25          moltype = RNA  length = 37
FEATURE                Location/Qualifiers
source                 1..37
                       mol_type = unassigned RNA
                       organism = unidentified
SEQUENCE: 25
tcccaaagtg gcaaaagaat ctccctgtta atgggag                           37

SEQ ID NO: 26          moltype = RNA  length = 36
FEATURE                Location/Qualifiers
source                 1..36
                       mol_type = unassigned RNA
                       organism = unidentified
SEQUENCE: 26
gtctaactgc catagaatcg tgcctgcaat tggcac                            36

SEQ ID NO: 27          moltype = RNA  length = 35
FEATURE                Location/Qualifiers
source                 1..35
                       mol_type = unassigned RNA
                       organism = unidentified
SEQUENCE: 27
tcggggcacc aaaataatct ccttggtaat gggag                             35

SEQ ID NO: 28          moltype = RNA  length = 36
FEATURE                Location/Qualifiers
source                 1..36
                       mol_type = unassigned RNA
                       organism = unidentified
SEQUENCE: 28
ccacaacaac caaaagaatg tccctgaaag tgggac                            36

SEQ ID NO: 29          moltype = RNA  length = 36
FEATURE                Location/Qualifiers
source                 1..36
                       mol_type = unassigned RNA
                       organism = unidentified
SEQUENCE: 29
gtaacagtgg ctaagtaatg tgtcttccaa tgacac                            36
```

```
SEQ ID NO: 30          moltype = RNA  length = 24
FEATURE                Location/Qualifiers
source                 1..24
                       mol_type = unassigned RNA
                       organism = unidentified
SEQUENCE: 30
gagagaatgt gtgcaaagtc acac                                      24

SEQ ID NO: 31          moltype = DNA  length = 1979
FEATURE                Location/Qualifiers
source                 1..1979
                       mol_type = other DNA
                       organism = synthetic construct
SEQUENCE: 31
atgagcgagc tgattaagga gaacatgcac atgaagctgt atatggaggg caccgtggac  60
aaccatcact tcaagtgcac atccgagggc gaaggcaagc cctacgaggg cacccagacc  120
atgagaatca aggtggtcga gggcggccct ctccccttcg ccttcgacat cctggctact  180
agcttcctct acggcagcaa gaccttcatc aaccacaccc agggcatccc cgacttcttc  240
aagcagtcct tccctgaggg cttcacatgg gagagagtca ccacatacga ggacgggggc  300
gtgctgaccg ctacccagga caccagcctc caggacggct gcctcatcta caacgtcaag  360
atcagagggg tgaacttcac atccaacggc cctgtgatgc agaagaaaac actcggctgg  420
gaggccttca ccgagacact gtaccccgct gacggcggcc tggaaggcag aaacgacatg  480
gccctgaagc tcgtgggcgg gagccatctg atcgcaaaca tcaagaccac atatagatcc  540
aagaaacccg ctaagaacct caagatgcct ggcgtctact atgtggacta cagactggaa  600
agaatcaagg aggccaacaa cgagacatac gtcgagcagc acgaggtggc agtggccaga  660
tactgcgacc tccctagcaa actggggcac aagctgaatg aattcgaggg caggggcagc  720
ctgctgacct gcggcgacgt ggaggagaac cccggcccca tggtgagcaa gggcgaggag  780
ctgttcaccg gggtggtgcc catcctggtc gagctggacg gcgacgtaaa cggccacaag  840
ttcagcgtgt ccggcgaggg cgagggcgat gccacctacg gcaagctgac cctgaagttc  900
atctgcacca ccggcaagct gcccgtgccc tggcccaccc tcgtgaccac cctgacctac  960
ggcgtgcagt gcttcagccg ctaccccgac cacatgaagc agcacgactt cttcaagtcc  1020
gccatgcccg aaggctacgt ccaggagcgc accatcttct tcaaggacga cggcaactac  1080
aagacccgcg ccgaggtgaa gttcgagggc gacaccctgg tgaaccgcat cgagctgaag  1140
ggcatcgact tcaaggagga cggcaacatc ctggggcaca agctggagta caactacaac  1200
agccacaacg tctatatcat ggccgacaag cagaagaacg gcatcaaggt gaacttcaag  1260
atccgccaca acatcgagga cggcagcgtg cagctcgccg accactacca gcagaacacc  1320
ggatccgtgt ctttcccatt acagtaggag catacgggag acaagctttg gccacctacg  1380
gcaagctgac cctgaagttc atctgcacca ccggcaagct gcccgtgccc tggcccaccc  1440
tcgtgaccac cctgacctac ggcgtgcagt gcttcagccg ctaccccgac cacatgaagc  1500
agcacgactt cttcaagtcc gccatgcccg aaggctacgt ccaggagcgc accatcttct  1560
tcaaggacga cggcaactac aagacccgcg ccgaggtgaa gttcgagggc gacaccctgg  1620
tgaaccgcat cgagctgaag ggcatcgact tcaaggagga cggcaacatc ctggggcaca  1680
agctggagta caactacaac agccacaacg tctatatcat ggccgacaag cagaagaacg  1740
gcatcaaggt gaacttcaag atccgccaca acatcgagga cggcagcgtg cagctcgccg  1800
accactacca gcagaacacc cccatcggcg acggccccgt gctgctgccc gacaaccact  1860
acctgagcac ccagtccgcc ctgagcaaag accccaacga gaagcgcgat cacatggtcc  1920
tgctggagtt cgtgaccgcc gccgggatca ctctcggcat ggacgagctg tacaagtaa   1979

SEQ ID NO: 32          moltype = DNA  length = 50
FEATURE                Location/Qualifiers
source                 1..50
                       mol_type = other DNA
                       organism = synthetic construct
SEQUENCE: 32
ggatccgtgt ctttcccatt acagtaggag catacgggag acaagctttg            50

SEQ ID NO: 33          moltype = DNA  length = 20
FEATURE                Location/Qualifiers
source                 1..20
                       mol_type = other DNA
                       organism = synthetic construct
SEQUENCE: 33
ccattacagt aggagcatac                                           20

SEQ ID NO: 34          moltype = AA  length = 1368
FEATURE                Location/Qualifiers
source                 1..1368
                       mol_type = protein
                       organism = Streptococcus pyogenes
SEQUENCE: 34
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
```

-continued

```
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 35          moltype = AA  length = 1209
FEATURE                Location/Qualifiers
source                 1..1209
                       mol_type = protein
                       organism = unidentified
REGION                 1..1209
                       note = Lachnospiraceae bacterium
SEQUENCE: 35
MAIPVGKTQE NIDNKRLLVE DEKRAEDYKG VKKLLDRYYL SFINDVLHSI KLKNLNNYIS  60
LFRKKTRTEK ENKELENLEI NLRKEIAKAF KGNEGYKSLF KKDIIETILP EFLDDKDEIA  120
LVNSFNGFTT AFTGFFDNRE NMFSEEAKST SIAFRCINEN LTRYISNMDI FEKVDAIFDK  180
HEVQEIKEKI LNSDYDVEDF FEGEFFNFVL TQEGIDVYNA IIGGFVTESG EKIKGLNEYI  240
NLYNQKTKQK LPKFKPLYKQ VLSDRESLSF YGEGYTSDEE VLEVFRNTLN KNSEIFSSIK  300
KLEKLFKNFD EYSSAGIFVK NGPAISTISK DIFGEWNVIR DKWNAEYDDI HLKKKAVVTE  360
KYEDDRRKSF KKIGSFSLEQ LQEYADADLS VVEKLKEIII QKVDEIYKVY GSSEKLFDAD  420
FVLEKSLKKN DAVVAIMKDL LDSVKSFENY IKAFFGEGKE TNRDESFYGD FVLAYDILLK  480
VDHIYDAIRN YVTQKPYSKD KFKLYFQNPQ FMGGWDKDKE TDYRATILRY GSKYYLAIMD  540
KKYAKCLQKI DKDDVNGNYE KINYKLLPGP NKMLPKVFFS KKWMAYYNPS EDIQKIYKNG  600
TFKKGDMFNL NDCHKLIDFF KDSISRYPKW SNAYDFNFSE TEKYKDIAGF YREVEEQGYK  660
VSFESASKKE VDKLVEEGKL YMFQIYNKDF SDKSHGTPNL HTMYFKLLFD ENNHGQIRLS  720
GGAELFMRRA SLKKEELVVH PANSPIANKN PDNPKKTTTL SYDVYKDKRF SEDQYELHIP  780
IAINKCPKNI FKINTEVRVL LKHDDNPYVI GIDRGERNLL YIVVVDGKGN IVEQYSLNEI  840
INNFNGIRIK TDYHSLLDKK EKERFEARQN WTSIENIKEL KAGYISQVVH KICELVEKYD  900
AVIALEDLNS GFKNSRVKVE KQVYQKFEKM LIDKLNYMVD KKSNPCATGG ALKGYQITNK  960
FESFKSMSTQ NGFIFYIPAW LTSKIDPSTG FVNLLKTKYT SIADSKKFIS SFDRIMYVPE  1020
EDLFEFALDY KNFSRTDADY IKKWKLYSYG NRIRIFRNPK KNNVFDWEEV CLTSAYKELF  1080
NKYGINYQQG DIRALLCEQS DKAFYSSFMA LMSLMLQMRN SITGRTDVDF LISPVKNSDG  1140
IFYDSRNYEA QENAILPKNA DANGAYNIAR KVLWAIGQFK KAEDEKLDKV KIAISNKEWL  1200
EYAQTSVKH                                                         1209

SEQ ID NO: 36          moltype = AA  length = 1049
FEATURE                Location/Qualifiers
source                 1..1049
                       mol_type = protein
                       organism = unidentified
SEQUENCE: 36
MKKVEVSRPY QSLLLPNHRK FKYLDETWNA YKSVKSLLHR FLVCAYGAVP FNKFVEVVEK  60
VDNDQLVLAF AVRLFRLVPV ESTSFAKVDK ANLAKSLANH LPVGTAIPAN VQSYFDSNFD  120
PKKYMWIDCA WEADRLAREM GLSASQFSEY ATTMLWEDWL PLNKDDVNGW GSVSGLFGEG  180
KKEDRQQKVK MLNNLLNGIK KNPPKDYTQY LKILLNAFDA KSHKEAVKNY KGDSTGRTAS  240
YLSEKSGEIT ELMLEQLMSN IQRDIGDKQK EISLPKKDVV KKYLESESGV PYDQNLWSQA  300
YRNAASSIKK TDTRNFNSTL EKFKNEVELR GLLSEGDDVE ILRSKFFSSE FHKTPDKFVI  360
KPEHIGFNNK YNVVAELYKL KAEATDFESA FATVKDEFEE KGIKHPIKNI LEYIWNNEVP  420
VEKWGRVARF NQSEEKLLRI KANPTVECNQ GMTFGNSAMV GEVLRSNYVS KKGALVSGEH  480
GGRLIGQNNM IWLEMRLLNK GKWETHHVPT HNMKFFEEVH AYNPSLADSV NVRNRLYRSE  540
DYTQLPSSIT DGLKGNPKAK LLKRQHCALN NMTANVLNPK LSFTINKKND DYTVIIVHSV  600
EVSKPRREVL VGDYLVGMDQ NQTASNTYAV MQVVKPKSTD AIPFRNMWVR FVESGSIESR  660
TLNSRGEYVD QLNHDGVDLF EIGDTEWVDS ARKFFNKLGV KHKDGTLVDL STAPRKAYAF  720
NNFYFKTMLN HLRSNEVDLT LLRNEILRVA NGRFSPMRLG SLSWTTLKAL GSFKSLVLSY  780
FDRLGAKEMV DKEAKDKSLF DLLVAINNKR SNKREERTSR IASSLMTVAQ KYKVDNAVVH  840
VVVEGNLSST DRSASKAHNR NTMDWCSRAV VKKLEDMCNL YGFNIKGVPA FYTSHQDPLV  900
HRADYDDPKP ALRCRYSSYS RADFSKWGQN ALAAVVRWAS NKKSNTCYKV GAVEFLKQHG  960
LFADKKLTVE QFLSKVKDEE ILIPRRGGRV FLTTHRLLAE STFVYLNGVK YHSCNADEVA  1020
AVNICLNDWV IPCKKKMKEE SSASGGSGS                                   1049

SEQ ID NO: 37          moltype = DNA  length = 3240
FEATURE                Location/Qualifiers
source                 1..3240
                       mol_type = other DNA
                       organism = synthetic construct
SEQUENCE: 37
atgagttctg atgtggtgcg gccttataac acaaagctgc tcccagataa cagaaagcac  60
aatatgttcc tgcagacctt caagcggctg aacagcatct ctctgaacca cttcgacctg  120
```

-continued

```
ctgatctgcc tgtacgctgc aatcaccaac aagaaggccg aggaatacaa gtctgaaaag  180
gaagcccacg tgaccgccga tagcctgtgt gccatcaatt ggttcagacc catgagcaag  240
agatacagca aatacgccac caccaccttc aacatgttag aactgtttaa ggagtacagc  300
ggccacgagc ctgatgccta ttccaagaac tacctgatga gcaatatcga cagcgacaga  360
ttcgtgtggg tggattgtag gaagttcgct aaggactttg cctatcagat ggaactgggt  420
ttccacgagt tcaccgtgtt ggccgaaacc ctgctggcta attctatcct ggtgctgaac  480
gagagcacca aggccaattg ggcttgggga accgtgtctg ccctgtacgg cggcggagat  540
aaggaggaca gcacactgaa gagcaagatt ctgctggcct tcgtggacgc cctgaacaac  600
cacgagctga aaacaaagag agaaatcttg aatcaagtgt gtgaatctct gaaataccag  660
agctaccagg acatgtacgt ggattttaga agcgtggttg acgaaaacgg caacaagaag  720
tctcctaacg gctctatgcc tatcgtgacc aagttcgaga cagacgacct gatcagcgac  780
aaccaaagaa aggccatgat cagcaacttc actaagaacg ccgctgccaa ggcagctaag  840
aaacctatcc cttacttgga ccgcctgaag gagcacatgg tgtccctgtg cgacgagtac  900
aatgtgtatg cctgggccgc ggccatcaca aacagcaacg ccgacgtgac cgcccggaat  960
accagaaacc tgacattcat cggcgaacag aacagcagac gaaaggaact gagcgtgctg  1020
cagacaacaa ccaacgagaa ggctaaggac atcctgaaca agatcaacga caacctgatt  1080
caggaggtgc ggtacacccc tgcccctaag cacctgggca gagatctggc caacctgttt  1140
gatacactga aggaaaagga catcaacaac atcgagaacg aagaagagaa acagaacgtg  1200
atcaatgact gtatcgagca gtacgtggac gattgcagaa gcctcaaccg gaaccccatc  1260
gcagccctcc tgaagcacat ctctaggtac tacgaggatt tcagcgccaa gaatttcctg  1320
gacggcgcca agctgaacgt gctgactgag gtggtgaacc ggcagaaggc ccaccccacc  1380
atctggagcg agaaggctta cacctggatc agcaagttcg acaagaaccg gagacaggcc  1440
aacagcagcc tggtcggatg ggttgtgccc cccgaggagg tgcacaagga gaaaatcgcc  1500
ggacagcaga gcatgatgtg ggtgaccctc accctgctgg acgacggcaa gtgggtcaaa  1560
catcacatcc ccttcagcga cagcagatac tacagcgaag tgtacgccta caaccctaat  1620
ctgccttatc tggacggagg catcccaaga cagagcaagt tcggcaacaa accaacaacc  1680
aacctgacag ccgagtccca ggccctcctg gctaattcta agtacaagaa agccaacaag  1740
agcttcctgc gggctaaaga gaatgccaca cacaacgtgc gggtgtcccc taacacctct  1800
ctgtgcatta gactgctgaa ggacagcgcc ggaaaccaga tgttcgacaa aatcggcaac  1860
gtgctcttcg gcatgcagat caaccacaag atcaccgtgg gaaaacctaa ctacaagatc  1920
gaggtgggcg acagattcct gggcttcgat cagaaccaga gcgagaacca cacctacgcc  1980
gtgctgcaga gagtgtccga gagcagtcac gacacccacc actttaacgg ctgggacgtg  2040
aaggtgctgg aaaagggcaa agtgaccagc gatgtgatcg tgcgggacga ggtctacgac  2100
caactgtctt acgagggcgt cccctacgat agcagcaagt tcgccgagtg gcgggacaag  2160
cgcagaagat ttgtgcttga gaacctgagc atccagctgg aagagggcaa gaccttcctg  2220
acagagttcg acaagctgaa taaggacagc ctgtaccgct ggaacatgaa ctacctgaaa  2280
ctgctgagaa aggccatccg ggccggaggc aaagagttcg ccaagatcgc taagacagag  2340
atcttcgagc tggcggtgga aagattcggc cctattaacc tgggcagcct gtcccagatc  2400
agccttaaga tgattgcctc ctttaagggc gtggtccagt cctacttctc cgtgagcggc  2460
tgcgtggatg atgcctccaa aaaggcccat gattctatgc tgttcacatt tatgtgcgcc  2520
gccgaagaaa agcggaccaa caagagagaa gaaaagacca acagagccgc cagctttatc  2580
ctgcaaaaag cctacctgca tggctgcaag atgatcgtgt gcgaggacga ccttcctgtg  2640
gccgacggca agacaggcaa agcccagaat gccgaccgga tggactggtg cgccagagcc  2700
ctggccaaga aggtgaacga cggctgtgtt gccatgagca tctgctacag agctatccct  2760
gcctacatga gcagccacca ggaccccttt gtgcacatgc aggataagaa aaccagcgtg  2820
ctgcggccta gattcatgga agttaataag gatagcatca gagactacca cgtggcgggc  2880
ctgagaagaa tgctgaacag caagagtgac gctggcacca gtgtttatta ccggcaagct  2940
gccctgcatt tctgcgaagc cctgggcgtg agccctgaac tggtgaaaaa caagaaaacc  3000
cacgccgccg aactgggcaa gcacatgggc agcgctatgc tgatgccctg gagaggcggt  3060
agagtgtaca tcgccagcaa aaagctgacc tccgatgcca aatcagtgaa gtactgcggc  3120
gaggatatgt ggcagtacca cgccgatgag atcgccgctg ttaacatcgc catgtatgag  3180
gtgtgctgcc agaccggcgc tttcggaaag aaacagaaaa aatcggacga gctgcctgga  3240

SEQ ID NO: 38          moltype = DNA  length = 3183
FEATURE                Location/Qualifiers
source                 1..3183
                       mol_type = other DNA
                       organism = synthetic construct
SEQUENCE: 38
atgagctctg acgtggtgcg gccttacaat accaagctgc tgccagacaa ccggaagtac  60
aacatgtttc tgcagacctt caagagactg aacctgatct ccagcaacca cttcgacctg  120
ctggtgtgcc tgtacgccgc tatcaccaac aagaaagctg aggaatacaa gagcgaaaaa  180
gaggatcacg ttacagccga cagcctgtgt gccatcaact ggttccggcc tatgtctaag  240
cggtacatca agtacgctac aaccaccttt aagatgctgg aactgttcaa ggagtacagc  300
ggccacgagc ctgacaccta cagcaagaac tacctgatgt ctaatatcgt gagcgatagg  360
ttcgtgtggg tggactgccg gaaattcgct aaggacttcg ccaatcaaat ggaactgtcc  420
ttccacgagt tcaccaccct gagtgaaacc ctgctggcta acagcatcct ggtgctaaat  480
gagtctacaa aggccaactg ggcctggggc gccgtgagtg ctctgtacgg cggcggcgac  540
aaagaggact ctacactgaa aagcaagatc cttctggcct ttgtggacgc cctgaacaac  600
cctgaactga aaacacgtag agaaattctg aaccacgtgt gcgaatctct gaagtatcag  660
agctaccagg acatgtacgt cgatttcaga agcgtggtcg atgataaggg caacaagaag  720
agcccaaacg gcagcatgcc tatcgtgacc aagttcgaga gcgatgatct gatcggcgat  780
aaccagagaa agacaatgat ctctagcttt acgaagaacg ccgccgccaa ggccagcaag  840
aagcccatcc catacctgga catcctcaag gaccacatga tcagcctgtg tgaagagtac  900
aacgtgtatg cctgggccgc tgccatcacc aacagcaacg ccgacgtgac agcccgcaac  960
accagaaacc tgacattcat cggagaacag aacacccgga ggaaggaact gagcgtgctg  1020
cagacaagca ccaacgagaa ggctaaagac atcctgaaca aaatcaacga caacctgatc  1080
cctgaggtgc ggtacacacc tgcccctaag cacctgggtc gggacctggc caatctgttc  1140
gagatgttca aggaaaagga catcaaccag atcggcaacg aggaggagaa gcagaacgtg  1200
```

```
atcaacgact gcatcgaaca gtacgtggac gactgtagaa gcctgaacag aaacccagtg  1260
gccgccctgc taaagcacat cagcggatac tacgaggatt tcagcgccaa aaatttcctg  1320
gacggcgcca agctgaatgt gctgaccgaa gtggtcaaca gacagaaggc tcatcctaca  1380
atctgcagcg aaaaggccta cacctggatt agcaagatcg ataagaaccg gcggcaggcc  1440
aattcctccc tggtcggatg ggtggtgccc cccgaggaag tgcacaagga aaagattgcc  1500
ggccagcaga gcatgatgtg ggtgacactg acactgctgg acgacggcaa gtgggttaag  1560
caccacatcc ccttcgccga ttctagatac tacagcgagg tgtatgccta taatcctaac  1620
ctgccttatc tcgagggcgg catccccaga cagtctaagt ttggcaacaa acctaccacc  1680
aacctgaccg ccgaatctca ggccctgttg gccaactcca agcacaaaaa agccaacaag  1740
accttcctga gggccaaaga gaacatcacc cacaacgtga gagtgtctcc taataccagc  1800
ctgtgcatca gaccactgaa ggactctgct ggcaatcaaa tgttcgacaa catcggcaac  1860
atgctgttcg gtatgcagat caaccataga atcaccgtag gaaaacccaa ctacaagata  1920
gaggtgggcg atagatttct cggattcgac cagaatcaga gcgagaacca cacctacgca  1980
gtgctgcaaa gagtatctga gagcagccac ggcacacacc actttaacgg ctgggacgtg  2040
aaagtgatcg agaagggcaa ggtgaccagc gacgtggtgg tgcgggacga ggtgtacgat  2100
cagctgtcct acgaaggcgt tccttacgac tcccctaagt ttaccgaatg gcgggaaaaa  2160
cggagaaagt tcgtgctgga aaacatgagc atccagatcg aggagggcaa gacttttctg  2220
accgagttcg ataagctgaa taaagacagc ctgtatagat ggaacatgaa ctacatgaaa  2280
ctgctgagga aggccatcag agccggcgga aaagagttcg ccaagatcac caaggccgag  2340
atcttcgaac tgggcgtgat gagattcggg cctatgaacc tgggcagcct gagccaagtg  2400
agtctcaaga tgatcgccgc cttcaaggga gtgatccaga gctacttctc tgtgtctggc  2460
tgcatcgatg atgcttccaa gaaggcccac gacagcatgc tgttcgcctt cctgtgtagc  2520
gccgatgaaa agcggaccaa caagcgggaa gaaaagacca atcgggccgc cagcttcatc  2580
cttcaaaagg cctactccca cggctgtaaa atgattgtgt gcgaggacga ccttcctatc  2640
gccgatggca aagtgggaaa ggcccagaac gccgacagaa tggactggtg cgcccggagc  2700
ctggctaaga aagtgaacga tggctgcgtg gccatgtcca tctgctacag agccatcccc  2760
gcctacatga gctcccacca ggacccccttc acccatatgc aggataagaa aaccagcgtg  2820
ctgcggccta gatttatgga agttggcaag gacagcatcc gggaccacca cgtggctggc  2880
ctgagacgga tgctgaatag caagggcaac acaggcacca gcgtgtacta cagagaggcc  2940
gcactgcgct tctgcgaggc cctgggcgtg ctgcctgagc tggtgaagaa taagaaaaca  3000
cacgccagcg agctgggaaa gcatatgggc agcgcaatgc tgatgccttg gagaggcggc  3060
agaatctacg tggccagcaa gaaactgaca agcgacgcca aatctatcaa gtactgcggc  3120
gaggatatgt ggcagtacca cgccgacgag atcgctgcta tcaacatcgc catgtacgag  3180
gtc                                                                3183

SEQ ID NO: 39          moltype = DNA  length = 3225
FEATURE                Location/Qualifiers
source                 1..3225
                       mol_type = other DNA
                       organism = synthetic construct
SEQUENCE: 39
atgggcatct ctatcagcag accttacggc accaaactgc ggcctgatgc cagaaagaaa  60
gaaatgctgg ataaattctt caccaccctg gccaaaggcc agagagtgtt cgccgacctg  120
ggcctgtgca tctacggcag cctgacactg gagatggtga aaagactgga gcctgagagc  180
gacagcgagc tggtgtgcgc catcggctgg ttccggctgg tggataaagt gacctggagc  240
gaaaacgaga tcaagcagga aaacctggtg cggcagtacg aaacctactc tggcaaggaa  300
gccagcgagg tgatcaagac ctatctgagc agtccctctt ctgataagta cgtgtggata  360
gattgcagac agaagtttct gcggttccag cgggacctgg gcacaagaaa cctgtccgag  420
gatttcgagt gcatgctgtt cgagcagtat ctgagactga ctaagggcga gctggatgga  480
cacaccgcca tgagcaatat gttcggcacc aagacaaagg aggatagagc caccaagctg  540
cgatacgccg ccagaatgaa ggagtggctg gaagctaatg aggagatcac ctgggaacag  600
taccaccagg ccctgcagga taagctcgac gcgaacactc tggaggaagc cgtggataac  660
tacaagggca aggctggcgg aagcaaccct ttctttagct acaccctgct gaaccgagga  720
cagatcgaca agaaaaccca cgagcagcag ctgaagaagt tcaacaaggt gctgaaaacc  780
aagtctaaga acctgaactt ccctaacaaa gagaagctaa agcagtacct cgagacagcg  840
atcggaatcc ccgtggacgc tcaggtgtac ggccagatgt ttaacaacgg cgtgtctgag  900
gttcaaccta agacaaccag aaacatgtcc tttagcatgg aaaagctgga gctcctgaac  960
gaactgaaga gcctgaacaa gaccgacgga ttcgagagag ccaacgaggt gctcaatggc  1020
ttcttcgaca gcgaactgca cacaacagag gacaaattca atatcacaag cagatacctg  1080
ggcggcgaca gaaacaaccg gctccctaag ctgtatgagt tgtggaagaa ggagggcgtg  1140
gacagagagg agggcatcca gcaattttcc caagccatcc aggacaagat gggccaaatc  1200
cctgttaaga acgtgctccg ctacatctgg gagttccggg aaaccgtgag cgcagaagat  1260
ttcgaggctg ctgccaaggc caaccagctg gaggaaaaga tcacccggac caaagcccac  1320
cccgtcgtga tcagcaacag atactggacc ttcgggtcca gcgccctggt gggcaacatc  1380
atgcctgccg acaagatgca caaggaccag tacgccggcc agagctttaa gatgtggctg  1440
gaagctgagc tgcactacga cggcaagaag gtgaagcacc acctgccctt ctacaatgcc  1500
agattcttcg aggaggtgta ctgctaccac cccatcagtgg ccgaagtgac cccttttaag  1560
accaagcagt tcggatatgc catcggcaag gacatcccag ctgacgtgtc tgtggtgctg  1620
aaagataacc cctacaagaa ggccaccaag agatttctga gggccatcag caatccagtc  1680
gccaacactg tggacgtgaa caagcctaca gtgtgtagct tcatgatcaa gcgggaaaac  1740
gacgagtaca agctggtgat caacagaaag atcggagtgg acagacccaa gagaatcaag  1800
gtgggcagaa aagtgatggg ctacgacaga aaccagaccg ccagcgacac atattggatc  1860
ggcgagctgg ttcctcatgg gaccacaggc gcctacagaa tcggagaatg gagcgtgcaa  1920
tacattaaaa gcggccctgt gctttcttct acacagggcg tgaacgattc taccaccgat  1980
cagctgatct acaacggaat gcccagcagc agcgagcggt tcaaggcctg gaagaagtcc  2040
agaatgagct tcatccggaa gctgatcaga cagctgaatg ccgaaggcct ggaaagcaaa  2100
ggacaggact acgtgcccga gaaccctagc agcttcgacg tcagaggaga aacactgtac  2160
gtgtttaaca gcaactacat gaaagccctg gtgtccaagc acaggaaggc caagaagccc  2220
gtggaaggca tcctggaaga aatcgaggct ctgacctcca aagccaagga cagctgcagc  2280
```

```
ctgatgcgcc tgagctctct gagcgacgcc gccatgcagg gcatcgccag cctgaagtcc  2340
ctgatcaact cttatttcaa caagaatggc tgtaaaacca tcgaggacaa ggaaaagttc  2400
aaccccgacc tgtacgtgaa gctggtcgag gtcgaacaga aaagaaccaa caagcggaag  2460
gagaaggtgg gccggatcgc cggcagcctg gaacagctcg ccctgctgaa tggtgttgac  2520
gtggtgatcg gcgaggccga tctgggggaa gtcaagaaag gcaagtctaa gaagcagaat  2580
agcagaaaca tggactggtg cgccaagcag gtcgctgagc gcctggaata caaactgacc  2640
ttccactgta tcggctactt cggcgtgaac cctatgtaca caagccacca agatcctttt  2700
gaacaccgga gagtggccga ccacctggtg atgagagcta ggttcgaaga ggtgaacgtt  2760
agcaacgtaa gcgaatggca catgagaaac ttcagcaatt acctgcgggc cgacagcggc  2820
acaggtctgt actacaagca agccaccctg gactttctga aacattacga cctggaggag  2880
cacgccgacg acctggagaa acagaatatc aagttctacg atttcagaaa gatcctggag  2940
gacaagcagc tgacatctgt tatagtgcct aagcggggcg gcagaatcta catggccaca  3000
aaccccgtga catcagacag cacccctgtg acctacgccg gcaagaccta caatagatgc  3060
aacgccgatg aggtggctgc cgctaatatc gctatttctg tgctggcccc tcacagcaag  3120
aaggaagaga aagaggataa gatccctatc atcagcaaga agcctaagtc caagaacacc  3180
ccaaaggcta gaaagaacct gaaaacaagc cagctgcctc agaag                 3225
```

```
SEQ ID NO: 40          moltype = DNA  length = 3009
FEATURE                Location/Qualifiers
source                 1..3009
                       mol_type = other DNA
                       organism = synthetic construct
SEQUENCE: 40
atggccagca aacacgtggt gcggcctttt aacggcaaag tgaccgctac cggcaagcgg  60
ctggcctacc tggaggaaac ctttcattac ctggagaagg ccgccggcgg cgtgtctacc  120
ctgttcgccg ctctgggcag ctacctcgac gccacaacca tcagcaacct gatcaacaag  180
aaccaggact tggctgtcgt gatcttccgg taccacgtgg tgcctaaggg cgaagcccac  240
acactgcccg tgggcaccga catggtgtca aggttcgtgg ccgactacgg catggagcct  300
aatgagttcc aaagagccta cctggatagc ccatcgatc aggagaagta ctgctggcag  360
gacaatcggg acgtgggatg ttggctgggc gaacagctgg gtgtttctga ggccgacatg  420
cgggctatcg ccgtgacttt ttacaacaac cagatgctgt acgactgtgt gaagggaact  480
ggcagcggca atgccgtctc tctgctgttt ggcagcggca agaagtccga ctacagcatg  540
aagggagtca ttgccggcaa ggctgcctca gtgctggcta agtatagacc tgccacctac  600
caggatgcca gaaagatgat cctggaagct aatggcttca ccagcgtgaa agatctggtc  660
acatcttacg gcatcaccgg cagaagcagc gccctgcaaa tcttcatgga aggcattgaa  720
agcggaccta tctcctccaa aacattggac gccagaatca agaagttcac ggaagatagt  780
gagcggaacg gccgcaagaa cctggtcccc cacgccggcg ccattagaaa ttggctgatc  840
gagcaggccg gttcttctgt ggaaaactac caaatggcct ggtgcgaggt ttacggcaac  900
gtgagcgctg actggaacgc caaggtggaa agcaacttca acttcgtggc cgagaaggtg  960
aaagccctga ccgagctgag caatatccag aagagcaccc ctgatctggg caaggctctg  1020
aaactgtttg aggagtacct gaccacatgc caggacgagt tcgccatcgc cccataccac  1080
ttcagcgtga tggaagaggt gcggatggaa atggccacag gcagagagtt taacgatgca  1140
tacgacgacg ctctgaacag cctggacatg gaaagcaagc agcctatcca gcctctgtgt  1200
aaattcctga tcgagcgggg cggaagcatc agcttcgaca ccttcaagag cgccgccaaa  1260
tacctgaaaa cccagagcaa gattgccggc agataccctc atccattcgt gaagggaaac  1320
cagggcttca cattcggctc caagaacatc tgggccgcca taaacgaccc catgatggag  1380
tacgccgacg gccggatcgc cggcggctct gccatgatgt gggtcaccgc taccctgctg  1440
gacggcaaga agtgggtgag acaccacatc cccttcgcca acacaagata cttcgaggag  1500
gtttacgcca gcaagaaggg cctgcctgtc ctgccgtgcg ccagagatgg caagcacagc  1560
tttaagctgg gtaacaacct gagcgtggag agagtggaaa aggtgaagga aggcggcaga  1620
acaaaggcca caaaggctca ggagagaatc ctgagcaacc tgacacacaa cgtgcagttc  1680
gacagcagca ccaccttcat catccggaga caggaggaat cctttgtgat ctgcgtgaac  1740
cacagacacc ccgcccctct gatgaagaag gagatggaag tgggcgacaa gatcatcggc  1800
atcgaccaga acgtgaccgc ccctaccacc tacgccatcg tggagagggt ggccagcgga  1860
ggcatcgagc ggaacggcaa acagtacaag gtgacagcca tgggcgccat ctcctctgtg  1920
cagaaaacca gaggcggaga ggtggacgtg ctgagctaca tgggtgtgga gctgtccgac  1980
tcgaagaacg gattccagag cctgtggaac aagtgtctgg acttcgtgac caagcacggc  2040
acagagaacg acgtgaagta ctacaacaac acagccgtgt gggccaacaa gctttacgtg  2100
tggcacaaga tgtacttcag actgctcaag caactgatga gaagagccaa ggacctgaag  2160
cctttcagag atcacctgca acacctgctg ttccacccta acctgtctcc tctgcagcgg  2220
catagcctgt ctcttacaag cctggaggct accaagatcg tgcgcaattg catccacagc  2280
tatttcagcc ttctcgggct gaaaaccctg gatgagagaa aggcagccga catcaacctg  2340
ctcgaggtgc tggaaaagct gtatgccggc cttgtggaaa gaaggaagga gagaaccaag  2400
ctgacagccg gcctgctggt cagactgtgc aacgagcacg gaattagctt tgccgccatc  2460
gaaggcgacc tgcctgtggt gggcgaaggc aagagcaagg ccgctaacaa cacccagcag  2520
gactggaccg cccgggaact ggagaagaga ctgagcgaaa tggctgaggt ggtgggcatc  2580
aaggtgatcg ctgttctacc acactacacc agccaccagg accctttcgt ttactccaag  2640
aataccaaga aaatgcggtg cagatggaat tggcggacca ccaagacctt caccgataga  2700
gatgccctga gcatccggag aatcctgagc aagcccgaaa ccggaaccaa cctgtattac  2760
cagaagggac tgaaggcctt cgccgagaag cacggcctgg atctggccga aatgaagaag  2820
cggaaggacg cccagtggta cctggaaaga atccaggata agaacttcct ggtgcccatg  2880
aacggcggaa gagtgtacct gagcagcgtg aagctggccg gcaaagagac aatcgacatg  2940
ggcggcgaga ttctgtacct gaacgacgcc gatcaggtgg ccgccctcaa cgtgctgctg  3000
gtgaagatc                                                          3009
```

```
SEQ ID NO: 41          moltype = DNA  length = 3054
FEATURE                Location/Qualifiers
source                 1..3054
                       mol_type = other DNA
```

```
                        organism = synthetic construct
SEQUENCE: 41
atggccaaaa aggaacacat tatcagacct ttcaagggca ccctgccact gcggggggac  60
agactgagat acctgcagga caccatgaag tacatgaaga aggttgagga caccatcacc  120
gagctgtgcg ccgccgtgat cgcctacgcc aagcctacaa tcatccagca gattctggga  180
gaagaaatcg agactacctc caccttctgc agcttcagac tggttgggat tcatgagaac  240
ttcactatgc ccctgacaac caatatgatc aagcacttcc agaaaacctt caacatcaat  300
ccttctgaga agcaggccat ctatctgagc agcggatttg atagcgacaa atacagatgg  360
caggatacaa gcgaggtgtc tagaaatttc gctaataagt gccgcctgac caaccaggag  420
ttccaggagt tcgccgagca agctctgtta aacatgtgct ttatcggctg tagcggatct  480
cctggcgcca caaacgccgt gtcccagatc ttcggcaccg gcgaaaagtc tgattaccag  540
cggaagtctc agatcgccaa gatcgccgct gataccctcg agaaccacaa acctagcaca  600
tacgagtctg ctaggctgat ggtgctgaac acactgggac acaagacgat cgaagattgc  660
gtgaacgact acggcgctat tggagccaag tccgccttcc ggctgtttat ggaaagtaaa  720
gaaatcggcc caatcaccag cgaacaactg accacaaaaa tcaagaaatt cagagaggac  780
cacaagaaga acagcatcaa gaagcagctg cctcatgtgg aaaaggtgcg gaacgcacta  840
ctgagccagt tcaaggagca gtacctgcca agcgcctggg ccgaggcctg gtgtaacatc  900
atgggagagt tcaatagcaa gctgtccaac aacaacaatt tcatcgacca aaaaaccaag  960
atggtcaacg actgcgacaa catcaaaaaa tctaaccccc agctggataa ggccgtgaat  1020
atgctggacg aatggaagta caagaattgg gacgacaatt ctgccatcca cccctaccac  1080
atcggcgatc tgaaaaagct gatggccatc ttcaacatca acaatgaggg caccttcgac  1140
gagagattca gcgccagctg ggagcagttt tctaccagcc tggagtacgg cgagaagccc  1200
cccgtgcggg acctgctggc ccacatcatc aagaacatga acgacctgac ttacaccgac  1260
gtgatcaatg ccgctaagtt cctgaagctg caagataata tcagaaacaa gtatcctcac  1320
ccttttgtga tgcctaacaa gggatgtacc ttcggcaagg ataacctgtg gggcgagatc  1380
aatgatccta cagctaagat caagtccaca gaggaagtgg ccggccagcg gcctatgatg  1440
tggctgaccg ccaagctcct ggacaacggc aaatgggtcg agcaccatat ccccttcgcc  1500
tctagcagat acttcgccga agtgtactac accaaccccg ccctgcctac cttacccatc  1560
gcccgcgacg gcaagcacag ctacaagctg accaagacca tcgacgccaa caccgccaaa  1620
accctggtga acaaccctag agacaaggcc gccaagctca ttgccagaac aaaggcgaac  1680
accacccaca acgtgaagtg gatcaaacct acatacagaa tccagaaaga gaacaaccag  1740
ttcgtgatca ccatcaatca cagacaccca tgtatcaccc ctcctaagga aatcatcttg  1800
ggcgatagaa tcctgtcatt cgaccaaaac gagacagccc ctaccgcctt tagcatcctg  1860
gaaaagacca ccaagggcac agagttctgc ggccaccaca tcaaagtgct gaaaaccggc  1920
atgctggaag ccaagatcaa gacatcgaag aaatccatcg acgccttcac ctacatgggc  1980
cctatggagg acgaccacgc cagcggtttc cccaccctgc tgaacatctg tgaaaagttc  2040
atcagcgaga acggcgacga gaaggacaag agcttcagca gcagaaagct gccttttaag  2100
agaagcctgt atttttcca cggcagccac ttcgacctgc tgaagaagat gatccggaag  2160
gctaaaaatg accctaagaa actgaagctg gtgagaatcc acatcaacga gatcctattc  2220
aacagcaacc tgtcccctat caagctgcac agcctgagca tccactctat ggagaacaca  2280
aaaaaggtga tcgctgccat ctcttgctac atgaacgtac acgagtggaa aaccatcgat  2340
gagcaaaaaa acgccgacat cacactgtac aacgccaagg aaaagctgta caacaacctg  2400
gttaatagaa gaaaggaaag agtgaaggtg accgctggca tgctgatccg gctggcccgg  2460
gaaaacaact gcagattcat ggtgggcgaa gccgaactgc caacacagca gcagggcaag  2520
agcaagaaga acaacaacag caagcaggac tggtgcgcca gagacatcgc acagagatgc  2580
gaggatatgt gcgaggtggt gggcatcaaa tggaacggcg tgacacctca caacaccagc  2640
caccagaatc cattcatcta caagaacacc tccggccagc agatgcggtg cagatacagc  2700
ctggtcaaaa agtctgagat gaccgataag atggctgaga agatccggaa cattctgcac  2760
gccgagcctg tgggcacaac cgcttattac agagagggca tcctggagtt tgccaagcac  2820
cacggactgg acctgggcat gatgaagaaa agaagagatg ccaagtatta cgacaacctg  2880
cccgacgaat ttctgctgcc gacaagaggc ggaagaatat acctgtcgga aaaccagctg  2940
ggcggcaacg agacaatcgt gatcaacggc aagaaatact tcgtgaatca ggccgaccag  3000
gtggccgccg tgaacatagg gctgctgtac ctgctgccta agaagaacca gagc        3054

SEQ ID NO: 42           moltype = DNA  length = 3141
FEATURE                 Location/Qualifiers
source                  1..3141
                        mol_type = other DNA
                        organism = synthetic construct
SEQUENCE: 42
atgagcgaga agaaattcca catcagaccc tacagatgca gcatctcccc taacgcccgg  60
aaggccgaca tgctgaaggc taccatctcc tacctggaca gcctgacctc tgtgttcaga  120
agcgggttta ccgccctgct ggctggaatc gatcctagca ccgtgtccag gctggctcct  180
agcggcgccg tgggcagccc cgacctgtgg agcgccgtga actggttcag aatcgtgccc  240
ctggccgaag ccggcgatgc cagagtcggc caggcaagcc tgaaaaacct gtttagaggc  300
tacgccgggc acgaacctga cgaggaagcc agcatctaca tggaaagcag agtggacgac  360
aaacggcacg cctgggtcga ctgcagggcc atgttcagag ctatggccct cgagtgcggc  420
ctggaggaag cccagctggc ttccgacgtg ttcgccctgg ccagcagaga ggtgatcgtg  480
ttcaaggacg gcgaaatcaa cggctggggc atcgccagtc tgctgttcgg cgaaggagag  540
aaggctgatt ctcagaaaaa ggtggccctg ctgagaagcg tgagactggc cctcgagggc  600
gattacgcta cctacgagga gctgtctggc ctgatgctgg ccaagaccgg cgccagctct  660
ggctccgatc tgctggacga gtacaaacgg tccgaaaaag gtggctcttc tggaggcaga  720
catcctttct ttgacgaggt gtttcggaga ggcggcagag ttaaacagga ggaaagagag  780
agactcctga aaagctgcga caccgcaatc cagaagcagg gacaggccct gcctctgtct  840
cacgtggcca gctggcggca gtggttcctg agaagagtga ccctgctgag gaatagacgg  900
caggagagct tcgctgtgtg catcacaaac gccctgatgg acctgcaacc caagaacctg  960
agaaatgtgc actacgtgac caaccccaag agcgagaagg ataaggggggt tctggaactg  1020
cgggtggacg tcaaaaacaa cgagggccct gatgtggctg gcgcccaagc cgtgtttgac  1080
gcctacatgg ccagacttgc cccagatctg agattcagcg tgatgcctag acatctgggc  1140
```

```
tcactgaagg acctgtacgc cttgtgggcc aagctgggaa gagatgaggc gatcgaggag  1200
tacctggaag gctatgaggg ccctttcagc aaaagaccaa tcgccggcat cctgcagatc  1260
atccacgccc atcggggcaa ggtggggcac gacagcctgt tgagagccgc cagacttaac  1320
agagctatgg atagactgga gagaaaaaga gcccacgcct gtgccgccgg caacaaggga  1380
tatgtgtacg gcaagagcag catggtgggc cggatcaacc ctcagagcct tgaagtgggc  1440
ggacggaagt ctggccggag ccccatgatg tgggtgacac tggacctggt cgacggcgac  1500
agattcgccc agcaccacct gccctttcaa tctgcccggt tcttcagcga agtgtactgc  1560
cacggagacg gcctgcccgc caccagagtg ccaggcatgg tcagaaaccg gagaaatggc  1620
ctggccatcg gaaatggcct gggcgaggga ggactgagtg ctctgagagc cggaagcgac  1680
cggagaaagc gggctaacaa gagaacactg agagccctgg agaatatcac ccacaacgtg  1740
gaaatcgatc ctagcacatc cttcacactg agagaggacg gcatcatcat cagccacaga  1800
atcgagaaga tcgagcctaa gctggtggct tttggagaca gagctctggg cttcgacctg  1860
aaccagaccg gcgcccacac ctttgccgtg ctgcagaagg tggacagcgg cgggctggat  1920
gtgggtcaca gccgggtcag cattgtgctg accggcaccg tgcggagcat ctgcaagggc  1980
aatcaggcca gcgggggccg ggactacgac ctgctgtctt acgacggccc cgagagagat  2040
gatggcgctt ttaccgcctg gaggtctgac agacaggcct ttctgatgag cgccattcgg  2100
gaactgccta cccctgccga gggcgagaaa gattacaagg ccgacctgct gtcccagatg  2160
gccagcctgg accactaccg gaggctgtac gcctacaaca gaaagtgcct gggcatctac  2220
atcggtgccc tgcggcgcgc cacaagacgg caggccgttg ccgccttcaa ggacgagatt  2280
ctgtccatcg ccaaccacag atgcggcccc ctgatgagag gctccctgag cgtcaacggc  2340
atggaaagcc tggccaacct gaagggcctg gcaaccgctt atctgtctaa gttcaaggac  2400
agcaagtccg aggacctgct gagtaaggac gaagaaatgg ccgacctgta cagagcttgc  2460
gccagacgca tgaccggaaa aagaaaggaa cggtaccggc gtgctgccag cgaaatcgtg  2520
agactggcta acgagcacgg ctgtctgttc gtgttcggcg agaaggaact gcctacaacc  2580
agcaagggca acaagtctaa acagaaccag cggaacaccg actggtcggc ccgggccatc  2640
gtgaaggccg tgaaggaggc ctgcgaggga tgtggcctgg gcttcaagcc ggtgtggaag  2700
gaatactcta gcttgaccga ccccttcgag agggacggcg atggccggcc tgctctgaga  2760
tgtagattcg ccaaggtggc tgctcccgac agcgagctcc cacctagact gacaaaggcc  2820
gtgggaagct atgtgaagaa cgccctaaag gccgataagg ccgagaagaa acaaacatgt  2880
taccagagag gagccatcga gttctgcagc aggcacggca tcgacgtccg gaaagctaca  2940
gataaggcca ttcggaaagc tgtgcggggt agcagtgacc tattagtgcc tttcgatgga  3000
ggcagaacct tcctgctatc aacaagactg agccctgaga gcagaaaggt ggaatgggcc  3060
ggaagaacac tgtacgagtt cccttctgat atggtggccg ccatcaacat cgcctgccgg  3120
ggcctggaac ctagaaaggc a                                            3141
```

```
SEQ ID NO: 43          moltype = DNA  length = 3087
FEATURE                Location/Qualifiers
source                 1..3087
                       mol_type = other DNA
                       organism = synthetic construct
SEQUENCE: 43
atggacgagc aggccgtggt gagcagcggc tctgataaga ccctgaagat cgtgaggccc  60
tacagagcta aggtgaccgc tactggaatc agattggaag ggatcaaaaa caccctgaat  120
tacctgaaga gaacagagat ttgtctgtcc agactgaacg ccgcttgcgg cgcctttctg  180
acccctgcca tcgtggagca gatctgtaaa gacgatcccg ccctggtgtg cgccatagct  240
agattccagc tggtgcctgt gggcagcgaa gctaccctga gcgatagcgg actgatgcgg  300
cacttcaagg cggcgctggg cgaactgacc cctctgcagg aagcctacct gaacagcagt  360
tataacgatg agctgtacgc ctggcaggat accctggtgc tggccagaca gatcatcgcg  420
gaaaccggcc tgaccgagga ccagttccgg gcatttgccc acgcctgctt caagaacggt  480
aatatcatcg gttgtgccgg aggccctggc gcaagcaatg ccattagcgg catcttcggc  540
gagggaatca agagcgacta cagcctccgc agcgagatga cagccgctgt ggctaaggtg  600
ttcgaggaaa agcggcccat cacatacgag gaagccagag ccctggccct cgaagccacc  660
ggccacgcct ctgtgcagag ctttgtcgag gcctttggca aacagggcag aaagggcacc  720
ctgatcctgt tcatggagga caccaaaaca ggcgccttcc cctccaacga gttcgactat  780
aagctgaaga agctgaagga ggacgcagag cgggtgggca gaaagggcat catcccacat  840
cgggacgtga tcgcctctta cctccggaac cagaccggag ccgacatcga gtacaacagc  900
aaggcctggt gcgaaagcta ctgctgcgcc gtttctgaat acaacagcaa gatgagcaac  960
aacgtgcggt tcgctacaga gaagagcctg gacctgacta agctggacga gacaatcagg  1020
gaaaccccaa agatcagcga ggccatgctg gtgttcgaga actacatggc cagaatcgat  1080
gccgacctga ggttcatcgt gtcgaagcac cacctgggaa acctggccaa gttccggcaa  1140
acaatgatgc acgtgtccgc cagcgagttc gaggaagcct tcaaggccat gtgggccgat  1200
tacctggctg gcttggagta tggcgagaaa cctgctatct gcgagctggt tagatacgtg  1260
ctgacccacg gcaatgacct gcctgtggaa gccttttacg ccgcctgcaa gtttctgtcc  1320
ctggacgaca agatcaagaa cagataccct catcctttcg tgcccggcaa caagggctat  1380
acattcggcg caaagaacct ctgggccgag atcaacgacc ctttcaagcc tatcagacag  1440
ggcaatcctg aggtagccgg ccaaagaccc atgatgtggg ccacagctga tctgctggac  1500
aacaacaagt gggtgctgca ccatattcct tttgcctcga gcagatactt tgaggaagtg  1560
tactacacag acccatctct cccaaccgcc cagaaggcca gagacggcaa gcacggctac  1620
agactgggaa aggtgctgga tgaggccgcc agagaaagac tgaaggccaa caacagacaa  1680
agaaaggccg ccaaggccat cgagcggatc aaggccaatt gcgagcacaa tgtggcctgg  1740
gaccctacca ccaccttcat gctgcaactg gacagcgagg gcaacgtgaa gatgaccatc  1800
aaccacagac acatcgccta ccgggctcct aaggaaatcg gcgtgggcga ccgggttatc  1860
ggcatcgacc agaacgaaac cgcccctaca acatacgcca tcttggaaag aacggaaaac  1920
ccccgggacc tggaatataa cggcaagtac tacagagtgg tgaagatggg cagcgtgacc  1980
tctcctaacg tgtccaaata cagaaccgtg gacgccctga cttacgacgg cgtgtctctg  2040
agcgacgacg ccagcggagc cgtgaacttc gtcgtgctgt gcagagagtt cttcgccgct  2100
catggcgacg acgagggccg gaaatacctg gagagaaccc tgggctggag ctccagcctg  2160
tatagcttcc acggcaacta cttcaagtgc ctgacccaga tgatgcggag aagcgcccgc  2220
tctggcggcg atctgaccgt gtaccgcgct cacctgcagc agatcctgtt tcagcacaac  2280
```

-continued

```
ctgtcccctc tgagaatgca cagcctgagc ctgcggagca tggaatctac catgaaggtg  2340
atcagctgca tgaagtctta catgagcctg tgcggctgga aaaccgatgc tgacagaatc  2400
gccaacgacc ggagcctgtt cgaagccgcc agaaagctgt acacatctct ggtcaatcgg  2460
cggaccgaaa gagtgcgggt gacagcaggc atccttatga gactgtgtct ggagcacaat  2520
gtgcggttta tccacatgga ggacgagctg cctgtggctg aaaccggcaa aagcaaaaaa  2580
agcaacggcg ccaagatgca ctggtgtgcc cgggagctgg cagttagact gtctcagatg  2640
gccgaagtga ccagcgttaa gttcaccgga gtgagccccc actacactag tcaccaggac  2700
cccttcgtgc actctaaaac cagcaaagtg atgcgcgcca gatggtcctg gcggaaccgg  2760
gccgacttca cagataagga cgccgagaga atccggacta tcctgggcgg cgatgacgcc  2820
gggaccaaag cttactacag aagcgccctg gccgagttcg ccagcagata cggcctggat  2880
atggagcaaa tgagaaagag acgggatgcc cagtggtacc aggagagact gcctgaaacc  2940
ttcatcatcc cccagagagg cgggagagtg tacctgagct cccacgacct gggcagcggc  3000
cagaaagtgg acggcatcta cggcggaagg gccttcgtga atcacgctga tgaggtggcc  3060
gcccttaacg tggctctggt ccgcctc                                      3087
```

```
SEQ ID NO: 44           moltype = DNA  length = 3087
FEATURE                 Location/Qualifiers
source                  1..3087
                        mol_type = other DNA
                        organism = synthetic construct
SEQUENCE: 44
atgaaaacag agacactgat ccgcccttac ccggcaagc tgaacctgca gcctcggcgg  60
gcccaattcc tggaggattc aatccagtac caccagaaaa tgaccgagtt cttctaccag  120
ttcctgcagg ccgtaggcgg cgcgaccaca catcagaaca tcagcgattt cattgacaac  180
aaggccactg atgagcacca ggccaccctt ctcttccagg tcgtgtccaa ggacagcacc  240
acccctgagt gccctgccga ggaactgctg gccagattcg cccagtacac cggcaaacag  300
cccaacgagg ccgtgaccca ctacctgacc agcagaatca acaccgacaa gtacagatgg  360
caggacaata gactactggc ccagaacatc gccagccaac ttaacatctc cgagacacaa  420
ttccaggaaa tcgcgcacgc tatcctcagc aacaacctgt acatcggaca gaccgccagc  480
aacgctgccg ccaacttcat ctctcaggtg accggcaccg gccagaaagc cccaaaggct  540
gccagactgg acgtgctgtt ccagacgaac caagccctgg ccaaaaccca gcctacaacc  600
tttggccagc tccagcagat tatcgtgcag gcttgtggag aaagcaccac cgacgccgtg  660
ctggccaagt tcggcaacaa aggtgccgcc acctcgctgc agctggctct gaaaaccgac  720
cccaacacca ccctggatca gaaaaagtat gaggccctgc aaaagaaatt cgccgaggac  780
gaaacaaagt accggaacaa ggttgacatt ccccacaaaa cgcagctgag aaatctgatc  840
ctgaacacaa gcaatcaatt ttgcaactgg cacacaaagc ctgccatcga ggcttttaag  900
tgcgccatcg ccgacatcca gagcaaggtg tccaacaacc tgaggatcat gcaggagaag  960
gccaagctgt acgaggcctt cagaaacgtg gacccccagg tgcagatcgc tgtccaagcc  1020
ctggagaatc acatgaacac cctcgaagaa ccctacgccc cttacgccca cagcttcggc  1080
agcgtgaagg acttctatga ggacctgaac aacggcagca atctggacga ggcaattcag  1140
accatcgtgc acgattctga taacttcaac cggaagcctg atcctaactg gctgagaatc  1200
atcgccccac tgcactctag ccacagcgcc tctcagatca tggaagctgt gaaatacctg  1260
agcagcaagc aggactacga actgaggaag cccttcccat tcgtggccac caacctgcct  1320
gccacatacg gcaagttcaa tatccccggc accctgaacc ctcctacaga ctctctgcac  1380
ggcagactga acggctctca cagcaacatg tggctgacag ccctgctgct ggacggcaga  1440
gactggaaga accaccacct gtgcttcgcc agcagcagat acttcgaaga agtctacttc  1500
accaacccta gcctgcccac caccgataaa gtgcggtccc caaagtgcgg ctttaccctg  1560
aagagcgtgc tggacagcga ggctaaggat agaatccgta atgcccctaa gagcagaacc  1620
aaggccgtga aggccatcga gagaattaag gctaattcta cccacaacgt ggcctggaac  1680
cccgagacaa gcttccagat gcagaagaga aacgacgagt tctacatcac aatcaaccac  1740
aggatcgaga tggaaaagat ccccggccaa aagaaaacag acgacggctt caccatccac  1800
cccaagggcc tgtttgctat cctgaaggaa ggagatagaa tcctgagcca ggatctgaat  1860
cagacagccg ctacacactg cgccgtgtac gaggtggcca agcctgacca gaacaccttc  1920
aaccaccatg gcatccacct gaagctgatc gccaccgaag aactgaagat gcctctgaaa  1980
accaagaagt ctaccatccc agatgccctg tcataccagg gcatccacgc ccacgaccgg  2040
gaaaacggcc tgcagcagct gaaggacgct tgcggagcct tcatctcacc tagactggac  2100
cccaagcaga aggccacctg ggacaacagc gtgtccaaga aagaaaacct gtaccctttc  2160
atcaccgcct acatgaagct gctgaagaag gtgatgaagg cgggccggca ggagctgaag  2220
ctgtttcgga ctcatctgga tcacatcctg ttcaaacaca atctcagccc tctgaaactg  2280
cacggcgtga gcatgatcgg cctggagagc agcagagcta caaaaagcgt gatcaacagc  2340
ttcttcaacc tgcagaacgc taagactgag cagcagcaga tcgccttaga cagacccctg  2400
ttcgaggccg gcaagacact gatcaataat cagaccagaa gaaggcagga aagagtgcgg  2460
ctggaaacat ctctgaccat gagactggcc cataagtata acgctaaagc catcatcatt  2520
gagggagagc tgcctcacag ctccaccggc acatctcagt accagaacaa cgtgcggctg  2580
gattggagtg ccaagaagag cgccaagctg aaaaccgaaa gcgccaactg cgctggaatc  2640
gccatctgcc agatcgaccc ttgtcacacc tcccaccaga acccttttcg gcacacccct  2700
acaaaccctg acctgcggcc acggttcgcc caggtgaaga aaggcaagat gttccagtac  2760
cagcttaatg gcctccagcg gctgctgaat cctagatcaa agtctagcac agcaatctac  2820
taccggcagg ccgtgcaaag cttttgtgcc caccacaacc tgaccgagag agacatcacc  2880
tctgccaaat ttcccagcga cctggaaaag aagatcaagg acgacaccta cctgatccct  2940
cagagaggcg gccggatcta catcagtagc ttccctgtta caagctgcgc cagaccttgc  3000
acaagcaacc attatttcgg cggaggccag ttcgagtgta atgctgatgc cgtggccgcc  3060
gtgaacatca tgctgaaggt ccaccct                                      3087
```

```
SEQ ID NO: 45           moltype = DNA  length = 3033
FEATURE                 Location/Qualifiers
source                  1..3033
                        mol_type = other DNA
                        organism = synthetic construct
```

-continued

```
SEQUENCE: 45
atgcctatcc ggggctataa gtgcaccgtg gtgcctaatg tgcggaaaaa gaaactgctg  60
gagaaaacat acagctacct gcaggagggc agcgacgtgt tttcgatct gttcctgtca  120
ctgtatggcg gcatcgcccc taagatgatc cctcaggatc tgggcatcaa cgagcaagtg  180
atctgtgccg caaactggtt caagatcgtg gaaaagacca aggactgcat cgccgacgac  240
gccctgctga accagtttgc ccagtactac ggcgagaagc ctaacgagaa ggttgtgcag  300
tttctgacag cttcttataa caaagataag tacgtgtggg tcgactgccg tcaaaagttc  360
tacaccctgc agaaagacct gggagtgcag aacctcgaga acgacctgga gtgcctgatc  420
cgcgaggacc tgctgcctgt gggatctgat aaggaagtga atggatggca cagcatcagc  480
aaactcttcg gctgcggcga gaaggaggac agaaccatca aggccaagat tctgaacggc  540
ctgtgggagc ggatcgagaa ggaagatatt ctgaccgagg aggacgccag aaacgagctg  600
ctgcatagcg ctggcgtgct gacccctaag gagttcagaa aggtgtacaa gggcgccgcc  660
ggcggacggg actgctacca caccctgctg gttgacggca gaaacttcac cttcaacctg  720
aaaaccctga tcaagcagac caaggacaag ctcaaggaaa agtccgtgga tgtggaaatc  780
cccaacaagg aggccctgag gctgtacctg gaaaagcgaa tcggaagatc tttcgagcag  840
aagccttggt ccgagatgta caaaaccgcc ctgagcgctg ttatgcccaa gaacaccctg  900
aattactgct ttgccatcga tagacacgcc cagtacacga agatccagac cctgaagcaa  960
ccttacgact ctgccatcac cgccctgaac ggcttcttcg agagcgaatg cttcaccggg  1020
agcgacgtgt tcgtgatcag ccctagccac ctgggaaaaa ccctgaagaa gctgtacaac  1080
tacaaggacg ttgagagcgg aatcagcgag atcgtcgagg acgaggataa tagcctgcgg  1140
agcggcgtga acgtgaatct gcttcggtac atcttcacac tgaaggatat gttcagcgcc  1200
gaggacttca tcaaggccgc cgagtacaac gtagtgtttg agagatacaa tagacagaaa  1260
gtccacccta cagtgaaggg caatcaaagc ttcacatttg gcaacagcgc tctgtctggc  1320
aaggtgatcc ctccatctaa gtgtctgagc aacctgcctg gacagatgtg gctggccatc  1380
aatctgctgg accagggcga gtggaaggag caccacattc ccttccacag cgccagattc  1440
tacgaggaaa tctacgctac atctgataac cagaacaacc ccgtggacct gcggaccaag  1500
agattcggct gttctctgaa caagaccttc agcgccgctg acatcgagaa ggtgaaggag  1560
tctgccaaga aaaagcacgg aaaggccgct aagagaatcc tgcgtgccaa gaacacaaac  1620
accgccgtga actgggtgga ttgcggcttc atgctggaaa agaccgaagt gaacttcaaa  1680
atcaccgtca attacaaact gcccgatcag aagctgggca agttcgagcc tatcgtgggc  1740
acaaaaatcc tggcttatga ccagaatcag accgccccag atgcctacgc catcctggaa  1800
atttgcgacg attctgaagc cttcgactac aagggctaca aaatcaaatg tctgagcacc  1860
ggggacctgg ccagcaagtc cctgacaaag cagacagaag tggaccagct ggcatataag  1920
ggcgtagaca aaaccagcaa cttctacaag aagtggaagc agcagcggag actttttgtg  1980
aagagcctga atatcccaga cgccctgaaa tcttttgaaa acatcaacaa ggagtacctg  2040
tacggcttta acaatagtta cctgaagcta ctgaagcaaa ttctgagagg caaattcgga  2100
cctatcctgg tggacatcag acctgagctg atcgagatgt gccagggcat cggcagcatc  2160
atgcggctgt ccagcttgaa ccacgacagc ctggacgcca ttcagtccct gaagagcctg  2220
ctgcactctt acttcgacct gaaggtgaag gaagaaatca agaccgaaga gctgagagag  2280
aaggccgata aggaagtgtt taagctgctg caacaggtga tccagaagca gaagaataag  2340
agaaaggaaa aggtgaacag aacagtggat gctatcctga cactggccgc cgacgagcaa  2400
gtgcaggtga tcgtgggcga aggcgacctg tgcgtgtcca ccaagggcac caaaaagaga  2460
cagaacaacc ggacaatcga ctggtgcgcg agagccgtgg tcgagaaact ggaaaaagcc  2520
tgcaagctgc acggcctgca cttcaaggaa atcccccccc actacaccag ccaccaggac  2580
tgtttcgagc acaacaagga catcgagaat cctaaggaag tgatgaagtg tagattcaac  2640
agcagcgaga acgtggcccc ttggatgatt aagaagttcg ccaactacct taaatgcgag  2700
acaaaatact acgtgcaggg catgcaggac ttcctggaac attacggcct ggtggaatac  2760
aaggaccata tcaagaaggg aaagatcagt atcggcgatt ttcagaaact gatcaagctg  2820
gccctggaaa aagtaggcga gaaggaaatc gtgtttcctt gcaaaggcgg cagaatctac  2880
ctgagcacct actgtctgac caacgagtcc aaacccatcg tgttcaacgg cagacggtgc  2940
tatgtgaaca acgccgacca cgtggccgct atcaacgtgg gcatctgcct gttgaatttc  3000
aacgccagag ctaaggtggc tgaaaagaca cca                               3033

SEQ ID NO: 46           moltype = DNA  length = 3279
FEATURE                 Location/Qualifiers
source                  1..3279
                        mol_type = other DNA
                        organism = synthetic construct
SEQUENCE: 46
atggccaaga aggacttcat cgccagacct tacaacagct ttctgctgcc taacgacaga  60
aagctggctt acctggaaga aacatggacc gcctacaaga gcatcaagac cgtgctgcac  120
agatttctga tcgcggccta tggcgccatc cccttccaga cattcgccaa aaccattgaa  180
aacacccaag aggacgagct gcaactggcc tatgccgtgc ggatgttcag actggtgccc  240
aaggacttca gcaagaacga gaacaacatt ccacctgaca tgctgatcag caagctggcc  300
agctacacca atatcaacca gtccccaaca aacgttctca gctacgtgaa tagcaactac  360
gacccagaga aatacaagtg gatcgattct agaaacgagg ccatcagcct gagcaaggag  420
atcggcatca agctggacga gctcgctgat tacgccacca ccatgctgtg ggaggattgg  480
ctgcccctga acaaggacac agtgaacggc tggggaacca cctctggcct gttcggcgcc  540
ggcaaaaaag aggataggac ccaaaaggtg cagatgctga acgccctgct gctgggcctg  600
aaaaacaacc cccccaagga ttacaagcag tacagcacca tcctactgaa ggcatttgat  660
gccaagagct gggaagaggc cgtgaagatt tacaaaggcg agtgttctgg ccgaacaagt  720
agttacctga ctgagaagca cggtgacatc agccctgaga cactggaaaa gctgatccag  780
agcatccagc gggacatcgc cgacaaacag cacccaatca acctgccaaa gagagaagaa  840
atcaaagcct acctggagaa acagtctggc accccataca acctgaacct gtggagccag  900
gccctgcaca acgccatgag ctctatcaag aaaaccgaca ccagaaattt caactctacc  960
ctggagaagt acgagaagga aatccagctg aaggagtgcc ttcaagatgg cgacgatgtg  1020
gagctgctgg ggaacaagtt tttctcttct ccttaccaca agacaaatga tgtgttcgtg  1080
atctgctctg aacacatcgg aacaaataga aagtacaacg tggtcgagca gatgtatcag  1140
ctggccagcg agcacgccga cttcgagaca gttttcaccc tgctgaagga cgagtatgag  1200
```

```
gaaaagggca tcaagacacc catcaaaaac atcctggagt acatctggaa caacaagaac  1260
gtccctgtgg gcacatgggg ccggatcgct aaatacaacc agctgaagga cagattagca  1320
gggatcaagg ccaatcccac agtggaatgc aacagaggca tgacatttgg caacagcgcc  1380
atggtgggcg aagtgatgcg ctccaaccgg atcagcacca gcaccaagaa caagggccag  1440
atcttggccc agatgcacaa cgaccggcct gtgggcagca acaacatgat ttggctggaa  1500
atgaccctcc tgaacaacgg caagtggcag aagcaccaca tccccacaca caacaacaaa  1560
tttttcgagg aagtgcacgc cttcaaccct gaactgaagc agagcgtgaa cgtgagaaac  1620
agaatgtaca gaagccagaa ctactcacag ctgcctacca gcctgaccga cggcctgcag  1680
ggaaatccta aggccaagat cttcaagaga cagtacagag ccctgaacaa catgaccgct  1740
aatgtgatcg accctaagct gtccttcatc gtgaacaaga aagatggaag attcgagatc  1800
agcatcatcc acaacgtgga agtgatccga gccagacggg acgtgctggt cggcgactac  1860
ctggtgggca tggaccaaaa ccagacggct tctaatacct acgccgtcat gcaggtggtg  1920
cagcctaaca cccccgacag ccatgagttc agaaaccagt gggtcaagtt catcgagagc  1980
ggcaagatcg agagctcaac actgaactcc cggggtgagt acatcgacca gctgagccac  2040
gatggcgtcg acctgcagga gattaaggat tctgagtgga ttcctgccgc cgaaaaattc  2100
ctgaacaagc taggagctat caacaaagac ggcaccccca tcagcatctc caacaccagc  2160
aaacgggcct acacattcaa tagcatctat ttcaaaatcc tgctgaatta tctgagagcc  2220
aacgacgtgg acctgaatct ggtgcgggaa gagatcctgc ggatcgccaa cggcagattc  2280
agccctatgc ggctgggatc tctgtcctgg accacactaa aaatgctggg caatttccgg  2340
aacctaattc acagctactt cgaccactgt ggctttaagg aaatgcctga gagagaaagc  2400
aaggacaaga ccatgtacga tctgctgatg cacaccatca ccaagctgac caacaagcgg  2460
gccgagcgca ccagcagaat cgctggaagc ctgatgaacg tggctcacaa gtacaagatc  2520
ggcacaagcg tggtccacgt ggtggtggaa ggctctctga gcaaaaccga caagagcagc  2580
tccaagggca acaatcggaa taccacagac tggtgcagcc gggccgtggt gaagaagctt  2640
gaagatatgt gcgtgttcta cggcttcaac ctgaaagccg tgagcgccca ctacaccagc  2700
caccaggacc ctctggttca tagagccgat tacgatgatc ctaagttggc cctgagatgc  2760
agatactctt cttacagcag agctgatttt gagaagtggg gcgaaaaatc tttcgccgcc  2820
gtgatcagat gggccacaga caagaagagc aacacctgct acaaggtggg agccgtagag  2880
ttcttcaaga actacaaaat ccctgaggac aagatcacca aaaagctgac catcaaagag  2940
ttcctggaaa ttatgtgcgc tgagagccac taccctaatg agtacgacga cattctgatc  3000
cctagaaggg gcggcagaat ctacctcaca actaagaagc tgctgtccga tagcacccac  3060
cagagagagt ctgtgcatag ccataccgcc gtggtgaaga tgaacggcaa ggaatactat  3120
agcagcgacg ccgatgaggt ggctgctatc aatatctgcc tgcacgactg ggtggtcccc  3180
ctgaattgga caaatcactg cctgcctgcc ggatggtgta gcgaccacct gaaggaatgc  3240
gtgcaatgtc acacccctga tcctgtgaga atcagcatg                         3279

SEQ ID NO: 47          moltype = RNA  length = 56
FEATURE                Location/Qualifiers
source                 1..56
                       mol_type = other RNA
                       organism = synthetic construct
SEQUENCE: 47
ctagcaatga ctcagaaatg tgtccccagt tgacacccat tacagtagga gcatac      56

SEQ ID NO: 48          moltype = RNA  length = 56
FEATURE                Location/Qualifiers
source                 1..56
                       mol_type = other RNA
                       organism = synthetic construct
SEQUENCE: 48
atcgcaacat cttagaaatc cgtccttagt tgacggccat tacagtagga gcatac      56

SEQ ID NO: 49          moltype = RNA  length = 56
FEATURE                Location/Qualifiers
source                 1..56
                       mol_type = other RNA
                       organism = synthetic construct
SEQUENCE: 49
tctcaacgat agtcagacat gtgtccccag tgacacccat tacagtagga gcatac      56

SEQ ID NO: 50          moltype = RNA  length = 56
FEATURE                Location/Qualifiers
source                 1..56
                       mol_type = other RNA
                       organism = synthetic construct
SEQUENCE: 50
ctcaaagtgt caaaagaatg tccctgctaa tgggacccat tacagtagga gcatac      56

SEQ ID NO: 51          moltype = RNA  length = 57
FEATURE                Location/Qualifiers
source                 1..57
                       mol_type = other RNA
                       organism = synthetic construct
SEQUENCE: 51
tcccaaagtg gcaaaagaat ctccctgtta atgggagcca ttacagtagg agcatac     57

SEQ ID NO: 52          moltype = RNA  length = 56
FEATURE                Location/Qualifiers
source                 1..56
```

```
                        mol_type = other RNA
                        organism = synthetic construct
SEQUENCE: 52
gtctaactgc catagaatcg tgcctgcaat tggcacccat tacagtagga gcatac      56

SEQ ID NO: 53           moltype = RNA  length = 55
FEATURE                 Location/Qualifiers
source                  1..55
                        mol_type = other RNA
                        organism = synthetic construct
SEQUENCE: 53
tcggggcacc aaaataatct ccttggtaat gggagccatt acagtaggag catac       55

SEQ ID NO: 54           moltype = RNA  length = 56
FEATURE                 Location/Qualifiers
source                  1..56
                        mol_type = other RNA
                        organism = synthetic construct
SEQUENCE: 54
ccacaacaac caaaagaatg tccctgaaag tgggacccat tacagtagga gcatac      56

SEQ ID NO: 55           moltype = RNA  length = 56
FEATURE                 Location/Qualifiers
source                  1..56
                        mol_type = other RNA
                        organism = synthetic construct
SEQUENCE: 55
gtaacagtgg ctaagtaatg tgtcttccaa tgacacccat tacagtagga gcatac      56

SEQ ID NO: 56           moltype = RNA  length = 44
FEATURE                 Location/Qualifiers
source                  1..44
                        mol_type = other RNA
                        organism = synthetic construct
SEQUENCE: 56
gagagaatgt gtgcaaagtc acacccatta cagtaggagc atac                   44

SEQ ID NO: 57           moltype = DNA  length = 4104
FEATURE                 Location/Qualifiers
source                  1..4104
                        mol_type = other DNA
                        organism = synthetic construct
SEQUENCE: 57
atggacaaga agtacagcat cggcctggac atcggcacca actctgtggg ctgggccgtg  60
atcaccgacg agtacaaggt gcccagcaag aaattcaagg tgctgggcaa caccgaccgg  120
cacagcatca agaagaacct gatcggagcc ctgctgttcg acagcggcga aacagccgag  180
gccacccggc tgaagagaac cgccagaaga agatacacca gacggaagaa ccggatctgc  240
tatctgcaag agatcttcag caacgagatg gccaaggtgg acgacagctt cttccacaga  300
ctggaagagt ccttcctggt ggaagaggat aagaagcacg agcggcaccc catcttcggc  360
aacatcgtgg acgaggtggc ctaccacgag aagtacccca ccatctacca cctgagaaag  420
aaactggtgg acagcaccga caaggccgac ctgcggctga tctatctggc cctggcccac  480
atgatcaagt tccggggcca cttcctgatc gagggcgacc tgaaccccga caacagcgac  540
gtggacaagc tgttcatcca gctggtgcag acctacaacc agctgttcga ggaaaacccc  600
atcaacgcca gcggcgtgga cgccaaggcc atcctgtctg ccagactgag caagagcaga  660
cggctggaaa atctgatcgc ccagctgccc ggcgagaaga agaatggcct gttcggaaac  720
ctgattgccc tgagcctggg cctgaccccc aacttcaaga gcaacttcga cctggccgag  780
gatgccaaac tgcagctgag caaggacacc tacgacgacg acctggacaa cctgctggcc  840
cagatcggcg accagtacgc cgacctgttt ctggccgcca agaacctgtc cgacgccatc  900
ctgctgagcg acatcctgag agtgaacacc gagatcacca aggccccccct gagcgcctct  960
atgatcaaga gatacgacga gcaccaccag gacctgaccc tgctgaaagc tctcgtgcgg  1020
cagcagctgc ctgagaagta caaagagatt ttcttcgacc agagcaagaa cggctacgcc  1080
ggctacattg acggcggagc cagccaggaa gagttctaca agttcatcaa gcccatcctg  1140
gaaaagatgg acggcaccga ggaactgctc gtgaagctga acagagagga cctgctgcgg  1200
aagcagcgga ccttcgacaa cggcagcatc ccccaccaga tccacctggg agagctgcac  1260
gccattctgc ggcggcagga agatttttac ccattcctga aggacaaccg ggaaaagatc  1320
gagaagatcc tgaccttccg catcccctac tacgtgggcc ctctggccag gggaaacagc  1380
agattcgcct ggatgaccag aaagagcgag gaaaccatca ccccctggaa cttcgaggaa  1440
gtggtggaca agggcgcttc cgcccagagc ttcatcgagc ggatgaccaa cttcgataag  1500
aacctgccca acgagaaggt gctgcccaag cacagcctgc tgtacgagta cttcaccgtg  1560
tataacgagc tgaccaaagt gaaatacgtg accgagggaa tgagaaagcc cgccttcctg  1620
agcggcgagc agaaaaaggc catcgtggac ctgctgttca agaccaaccg gaaagtgacc  1680
gtgaagcagc tgaaagagga ctacttcaag aaaatcgagt gcttcgactc cgtggaaatc  1740
tccggcgtgg aagatcggtt caacgcctcc ctgggcacat accacgatct gctgaaaatt  1800
atcaaggaca aggacttcct ggacaatgag gaaaacgagg acattctgga agatatcgtg  1860
ctgaccctga cactgtttga ggacagagag atgatcgagg aacggctgaa aacctatgcc  1920
cacctgttcg acgacaaagt gatgaagcag ctgaagcggc ggagatacac cggctggggc  1980
aggctgagcc ggaagctgat caacggcatc cgggacaagc agtccggcaa gacaatcctg  2040
gatttcctga agtccgacgg cttcgccaac agaaacttca tgcagctgat ccacgacgac  2100
agcctgacct ttaaagagga catccagaaa gcccaggtgt ccggccaggg cgatagcctg  2160
```

```
cacgagcaca ttgccaatct ggccggcagc cccgccatta agaagggcat cctgcagaca  2220
gtgaaggtgg tggacgagct cgtgaaagtg atgggccggc acaagcccga gaacatcgtg  2280
atcgaaatgg ccagagagaa ccagaccacc cagaagggac agaagaacag ccgcgagaga  2340
atgaagcgga tcgaagaggg catcaaagag ctgggcagcc agatcctgaa agaacacccc  2400
gtggaaaaca cccagctgca gaacgagaag ctgtacctgt actacctgca gaatgggcgg  2460
gatatgtacg tggaccagga actggacatc aaccggctgt ccgactacga tgtggaccat  2520
atcgtgcctc agagctttct gaaggacgac tccatcgaca acaaggtgct gaccagaagc  2580
gacaagaacc ggggcaagag cgacaacgtg ccctccgaag aggtcgtgaa gaagatgaag  2640
aactactggc ggcagctgct gaacgccaag ctgattaccc agagaaagtt cgacaatctg  2700
accaaggccg agagaggcgg cctgagcgaa ctggataagg ccggcttcat caagagacag  2760
ctggtggaaa cccggcagat cacaaagcac gtggcacaga tcctggactc ccggatgaac  2820
actaagtacg acgagaatga caagctgatc cgggaagtga aagtgatcac cctgaagtcc  2880
aagctggtgt ccgatttccg gaaggatttc cagttttaca aagtgcgcga gatcaacaac  2940
taccaccacg cccacgacgc ctacctgaac gccgtcgtgg gaaccgccct gatcaaaaag  3000
taccctaagc tggaaagcga gttcgtgtac ggcgactaca aggtgtacga cgtgcggaag  3060
atgatcgcca agagcgagca ggaaatcggc aaggctaccg ccaagtactt cttctacagc  3120
aacatcatga actttttcaa gaccgagatt accctggcca acggcgagat ccggaagcgg  3180
cctctgatcg agacaaacgg cgaaaccggg gagatcgtgt gggataaggg ccgggatttt  3240
gccaccgtgc ggaaagtgct gagcatgccc caagtgaata tcgtgaaaaa gaccgaggtg  3300
cagacaggcg gcttcagcaa agagtctatc ctgcccaaga ggaacagcga taagctgatc  3360
gccagaaaga aggactggga ccctaagaag tacggcggct tcgacagccc caccgtggcc  3420
tattctgtgc tggtggtggc caaagtggaa aagggcaagt ccaagaaact gaagagtgtg  3480
aaagagctgc tggggatcac catcatggaa agaagcagct tcgagaagaa tcccatcgac  3540
tttctggaag ccaagggcta caaagaagtg aaaaaggacc tgatcatcaa gctgcctaag  3600
tactccctgt tcgagctgga aaacggccgg aagagaatgc tggcctctgc cggcgaactg  3660
cagaagggaa acgaactggc cctgccctcc aaatatgtga acttcctgta cctggccagc  3720
cactatgaga agctgaaggg ctcccccgag gataatgagc agaaacagct gtttgtggaa  3780
cagcacaagc actacctgga cgagatcatc gagcagatca gcgagttctc caagagagtg  3840
atcctggccg acgctaatct ggacaaagtg ctgtccgcct acaacaagca ccgggataag  3900
cccatcagag agcaggccga gaatatcatc cacctgttta ccctgaccaa tctgggagcc  3960
cctgccgcct tcaagtactt tgacaccacc atcgaccgga agaggtacac cagcaccaaa  4020
gaggtgctgg acgccaccct gatccaccag agcatcaccg gcctgtacga gacacggatc  4080
gacctgtctc agctgggagg cgac                                         4104

SEQ ID NO: 58          moltype = DNA  length = 3626
FEATURE                Location/Qualifiers
source                 1..3626
                       mol_type = other DNA
                       organism = synthetic construct
SEQUENCE: 58
atgccatccc tgtgggcaag acccaggaga acatcgacaa taagcggctg ctggtggagg  60
acgagaagag agccgaggat tataagggcg tgaagaagct gctggatcgc tactatctgt  120
cttttatcaa cgacgtgctg cacagcatca agctgaagaa tctgaacaat tacatcagcc  180
tgttccggaa gaaaaccaga accgagaagg agaataagga gctggagaac ctggagatca  240
atctgcggaa ggagatcgcc aaggccttca agggcaacga gggctacaag tccctgttta  300
agaaggatat catcgagaca atcctgccag agttcctgga cgataaggac gagatcgccc  360
tggtgaacag cttcaatggc tttaccacag ccttcaccgg cttctttgat aacagagaga  420
atatgttttc cgaggaggcc aagagcacat ccatcgcctt caggtgtatc aacgagaatc  480
tgacccgcta catctctaat atggacatct tcgagaaggt ggacgccatc tttgataagc  540
acgaggtgca ggagatcaag gagaagatcc tgaacagcga ctatgatgtg gaggatttct  600
ttgagggcga gttctttaac tttgtgctga cacaggaggg catcgacgtg tataacgcca  660
tcatcggcgg cttcgtgacc gagagcggcg agaagatcaa gggcctgaac gagtacatca  720
acctgtataa tcagaaaacc aagcagaagc tgcctaagtt taagccactg tataagcagg  780
tgctgagcga tcgggagtct ctgagcttct acggcgaggg ctatacatcc gatgaggagg  840
tgctggaggt gtttagaaac accctgaaca agaacagcga gatcttcagc tccatcaaga  900
agctggagaa gctgttcaag aattttgacg agtactctag cgccggcatc tttgtgaaga  960
acggccccgc catcagcaca atctccaagg atatcttcgg cgagtggaac gtgatccggg  1020
acaagtggaa tgccgagtat gacgatatcc acctgaagaa gaaggccgtg gtgaccgaga  1080
agtacgagga cgatcggaga aagtccttca agaagatcgg ctccttttct ctggagcagc  1140
tgcaggagta cgccgacgcc gatctgtctg tggtggagaa gctgaaggag atcatcatcc  1200
agaaggtgga tgagatctac aaggtgtatg gctcctctga gaagctgttc gacgccgatt  1260
ttgtgctgga gaagagcctg aagaagaacg acgccgtggt ggccatcatg aaggacctgc  1320
tggattctgt gaagagcttc gagaattaca tcaaggcctt ctttggcgag ggcaaggaga  1380
caaacaggga cgagtccttc tatggcgatt ttgtgctggc ctacgacatc ctgctgaagg  1440
tggaccacat ctacgatgcc atccgcaatt atgtgaccca gaagccctac tctaaggata  1500
agttcaagct gtattttcag aaccctcagt tcatgggcgg ctgggacaag gataaggaga  1560
cagactatcg ggccaccatc ctgagatacg gctccaagta ctatctggcc atcatggata  1620
agaagtacgc caagtgcctg cagaagatcg acaaggacga tgtgaacggc aattacgaga  1680
agatcaacta taagctgctg cccggcccta ataagatgct gccaaaggtg ttcttttcta  1740
agaagtggat ggcctactat aaccccagcg aggacatcca gaagatctac aagaatggca  1800
cattcaagaa gggcgatatg tttaacctga atgactgtca caagctgatc gacttcttta  1860
aggatagcat ctcccggtat ccaaagtggt ccaatgccta cgatttcaac ttttctgaga  1920
cagagaagta taaggacatc gccggctttt acagagaggt ggaggagcag ggctataagg  1980
tgagcttcga gtctgccagc aagaaggagg tggataagct ggtggaggag ggcaagctgt  2040
atatgttcca gatctataac aaggactttt ccgataagtc tcacggcaca cccaatctgc  2100
acaccatgta cttcaagctg ctgtttgacg agaacaatca cggacagatc aggctgagcg  2160
gaggagcaga gctgttcatg aggcgcgcct ccctgaagaa ggaggagctg gtggtgcacc  2220
cagccaactc ccctatcgcc aacaagaatc cagataatcc caagaaaacc acaaccctgt  2280
cctacgacgt gtataaggat aagaggtttt ctgaggacca gtacgagctg cacatcccaa  2340
```

```
tcgccatcaa taagtgcccc aagaacatct tcaagatcaa tacagaggtg cgcgtgctgc  2400
tgaagcacga cgataacccc tatgtgatcg gcatcgacag gggcgagcgc aatctgctgt  2460
atatcgtggt ggtggacggc aagggcaaca tcgtggagca gtattccctg aacgagatca  2520
tcaacaactt caacggcatc aggatcaaga cagattacca ctctctgctg gacaagaagg  2580
agaaggagag gttcgaggcc cgccagaact ggacctccat cgagaatatc aaggagctga  2640
aggccggcta tatctctcag gtggtgcaca agatctgcga gctggtggag aagtacgatg  2700
ccgtgatcgc cctggaggac ctgaactctg gctttaagaa tagccgcgtg aaggtggaga  2760
agcaggtgta tcagaagttc gagaagatgc tgatcgataa gctgaactac atggtggaca  2820
agaagtctaa tccttgtgca acaggcggcg ccctgaaggg ctatcagatc accaataagt  2880
tcgagagctt taagtccatg tctacccaga acggcttcat cttttacatc cctgcctggc  2940
tgacatccaa gatcgatcca tctaccggct ttgtgaacct gctgaaaacc aagtatacca  3000
gcatcgccga ttccaagaag ttcatcagct cctttgacag gatcatgtac gtgcccgagg  3060
aggatctgtt cgagtttgcc ctggactata agaacttctc tcgcacagac gccgattaca  3120
tcaagaagtg gaagctgtac tcctacggca accggatcag aatcttccgg aatcctaaga  3180
agaacaacgt gttcgactgg gaggaggtgt gcctgaccag cgcctataag gagctgttca  3240
acaagtacgg catcaattat cagcagggcg atatcagagc cctgctgtgc gagcagtccg  3300
acaaggcctt ctactctagc tttatggccc tgatgagcct gatgctgcag atgcggaaca  3360
gcatcacagg ccgcaccgac gtggattttc tgatcagccc tgtgaagaac tccgacggca  3420
tcttctacga tagccggaac tatgaggccc aggagaatgc catcctgcca aagaacgccg  3480
acgccaatgg cgcctataac atcgccagaa aggtgctgtg ggccatcggc cagttcaaga  3540
aggccgagga cgagaagctg gataaggtga agatcgccat ctctaacaag gagtggctgg  3600
agtacgccca gaccagcgtg aagcac                                       3626

SEQ ID NO: 59          moltype = DNA  length = 3147
FEATURE                Location/Qualifiers
source                 1..3147
                       mol_type = other DNA
                       organism = synthetic construct
SEQUENCE: 59
atgaagaaag tggaagtgag cagaccctac caaagcctac tgctgcccaa tcaccggaag  60
ttcaagtacc tggacgaaac ctggaacgcc tacaagtccg tgaagagcct gctgcacaga  120
ttcctcgttt gtgcctatgg agccgtcccc ttcaataagt ttgtggaagt ggtggagaaa  180
gtggataatg accaactggt gctggccttc gctgtgagac tgttcagact tgtgcctgtg  240
gagtccacca gcttcgccaa ggtggacaaa gccaacctgg ctaagagcct ggccaaccac  300
ctgcctgtgg gaacagctat ccctgcaaac gtgcagagct acttcgacag caacttcgac  360
ccaaagaagt acatgtggat cgactgcgcc tgggaggccg accggctggc cagagaaatg  420
ggactgagcg cctctcagtt ttcggagtac gccacgacca tgctgtggga agattggctg  480
cctctgaaca aggacgatgt gaatggctgg ggctccgtgt ctggcctgtt tggggagggt  540
aagaaggagg acagacagca gaaggtgaag atgctgaaca acctgctgaa cggaatcaaa  600
aagaaccctc ctaaggacta tacacagtac ctgaagatcc tgttaaacgc cttcgatgcc  660
aagagccaca aagaagccgt taaaaactac aagggagata gcaccggcag aaccgccagc  720
tacctgagcg agaagagcgg cgagatcacc gagctgatgc tggaacagct gatgagcaac  780
atccagaggg atatcggaga caaacaaaaa gaaatcagcc tgccaaaaaa agatgtggtt  840
aagaaatacc tcgaaagcga aagcggagtg ccttacgatc agaacctgtg gagccaggcc  900
taccggaacg ccgctagctc tatcaagaaa accgatacaa gaaactttaa ctctaccctg  960
gagaagttca agaacgaggt ggaactgaga ggcctgctga gcgaaggcga tgacgtggaa  1020
atcctgcgga gcaagttctt cagctctgag ttccacaaga cccctgacaa gttcgttatc  1080
aagcctgagc acatcggctt caacaacaag tacaacgtgg tggccgagct gtacaagctg  1140
aaggccgagg ccaccgactt cgagagtgcc ttcgccacag tgaaggacga gttcgaggaa  1200
aaaggcatca agcaccctat caagaacatc ctggaataca tctggaacaa cgaggtgccc  1260
gtggagaagt ggggcagagt ggccagattc aaccagtctg aggagaagct gctgagaatt  1320
aaagctaatc ctaccgtgga atgcaatcag ggcatgacat ttggcaacag cgccatggtg  1380
ggcgaggtgc tgagaagcaa ctacgtgagc aaaaagggcg ccctggtgag cggcgagcac  1440
ggcggccggc tgatcggcca gaataacatg atctggctgg aaatgcggct gctgaacaag  1500
ggcaagtggg agacacacca cgtgcccacc cacaacatga agttcttcga agaggtgcac  1560
gcctacaatc cttctctggc cgactctgtg aacgtgcgga atagactgta cagaagtgag  1620
gattatacac agctcccaag cagcatcacc gatggactga aaggcaaccc caaggccaag  1680
ctgctgaaga gacaacactg tgccctgaat aacatgaccg ccaacgtgct gaatcccaaa  1740
ctgagcttca ccatcaacaa gaagaacgac gactacaccg tgatcatcgt gcatagcgtg  1800
gaggtctcca agccccggag agaggtcctc gtgggcgact acctggtggg catggatcag  1860
aaccagacag ccagcaacac ctacgccgtt atgcaggtgg ttaagcccaa gtccaccgac  1920
gccattcctt tcagaaacat gtgggtacgc ttcgtggaga gcggcagcat cgagtcccgg  1980
accctgaata gccggggcga gtacgtggat cagctgaatc atgatggcgt ggacctgttc  2040
gaaatcggcg acaccgagtg ggtcgacagc gcccggaagt ttttcaacaa gttgggagtg  2100
aagcacaagg atggcacctt ggtggacctg agcaccgccc ctagaaaggc ttacgccttt  2160
aacaacttct actttaagac catgctgaac cacctgcgga gcaacgaggt cgacctgaca  2220
ctgctgcgga acgagatcct gagagtcgct aacggcagat tcagccctat gcggctgggc  2280
agcctgtcct ggaccaccct gaaggccctg ggttccttca agtcactcgt tctgtcctat  2340
ttcgacagac taggcgccaa agagatggtg gacaaggagg ccaaggacaa gtccctgttc  2400
gacctgctgg tggccatcaa caacaagcgg agcaacaagc gcgaggaacg gaccagcagg  2460
atcgccagca gcctgatgac cgtggcccag aaatacaagg ttgacaacgc tgtggtgcac  2520
gtggtggtgg agggcaatct ctcttccaca gaccggagcg catccaaggc ccacaacaga  2580
aacacaatgg actggtgcag cagagccgta gtcaaaaagc tggaagatat gtgcaacctg  2640
tacggcttca acatcaaggg tgtgcctgct ttttacacat ctcaccagga cccactggtg  2700
cacagagccg actacgacga tccgaagcct gctctgagat gcagatactc tagctactct  2760
agagccgatt ttagtaagtg gggacagaac gccctggctg ccgtggtcag atgggccagc  2820
aacaaaaaaa gcaacacatg ctacaaggtg ggcgccgtgg agttcctgaa gcagcacggc  2880
ctgttcgccg ataagaaact gaccgtcgag cagttcctgt ctaaggtgaa ggatgaagag  2940
attctcatcc ctagacgggg cggaagagtg ttccttacaa cccacaggct gctggcagag  3000
```

```
tctacctttg tgtacctgaa tggcgtgaaa taccacagct gtaatgccga cgaggtggcc  3060
gctgttaata tctgcctgaa cgactgggtg attccctgca agaaaaaaat gaaggaagag  3120
agcagcgcca gcggcggctc tgggagc                                      3147

SEQ ID NO: 60          moltype = RNA  length = 96
FEATURE                Location/Qualifiers
source                 1..96
                       mol_type = other RNA
                       organism = synthetic construct
SEQUENCE: 60
ccattacagt aggagcatac gttttagagc tagaaatagc aagttaaaat aaggctagtc  60
cgttatcaac ttgaaaaagt ggcaccgagt cggtgc                            96

SEQ ID NO: 61          moltype = RNA  length = 41
FEATURE                Location/Qualifiers
source                 1..41
                       mol_type = other RNA
                       organism = synthetic construct
SEQUENCE: 61
taatttctac taagtgtaga tccattacag taggagcata c                      41

SEQ ID NO: 62          moltype = RNA  length = 43
FEATURE                Location/Qualifiers
source                 1..43
                       mol_type = other RNA
                       organism = synthetic construct
SEQUENCE: 62
agagaatgtg tgcatagtca cacccattac agtaggagca tac                    43

SEQ ID NO: 63          moltype = RNA  length = 45
FEATURE                Location/Qualifiers
source                 1..45
                       mol_type = other RNA
                       organism = synthetic construct
SEQUENCE: 63
agaaatgtgt ccccagttga caccctcact cctgctcggt gaatt                  45

SEQ ID NO: 64          moltype = RNA  length = 96
FEATURE                Location/Qualifiers
source                 1..96
                       mol_type = other RNA
                       organism = synthetic construct
SEQUENCE: 64
tcactcctgc tcggtgaatt gttttagagc tagaaatagc aagttaaaat aaggctagtc  60
cgttatcaac ttgaaaaagt ggcaccgagt cggtgc                            96

SEQ ID NO: 65          moltype = RNA  length = 43
FEATURE                Location/Qualifiers
source                 1..43
                       mol_type = other RNA
                       organism = synthetic construct
SEQUENCE: 65
taatttctac taagtgtaga tcctcactcc tgctcggtga att                    43

SEQ ID NO: 66          moltype = RNA  length = 45
FEATURE                Location/Qualifiers
source                 1..45
                       mol_type = other RNA
                       organism = synthetic construct
SEQUENCE: 66
agagaatgtg tgcatagtca caccctcact cctgctcggt gaatt                  45

SEQ ID NO: 67          moltype = RNA  length = 43
FEATURE                Location/Qualifiers
source                 1..43
                       mol_type = other RNA
                       organism = synthetic construct
SEQUENCE: 67
agaaatgtgt ccccagttga cacagaaagg ctgctgatga cac                    43

SEQ ID NO: 68          moltype = RNA  length = 96
FEATURE                Location/Qualifiers
source                 1..96
                       mol_type = other RNA
                       organism = synthetic construct
SEQUENCE: 68
aaaggctgct gatgacacct gttttagagc tagaaatagc aagttaaaat aaggctagtc  60
cgttatcaac ttgaaaaagt ggcaccgagt cggtgc                            96
```

```
SEQ ID NO: 69          moltype = RNA  length = 41
FEATURE                Location/Qualifiers
source                 1..41
                       mol_type = other RNA
                       organism = synthetic construct
SEQUENCE: 69
taatttctac taagtgtaga tagaaaggct gctgatgaca c                      41

SEQ ID NO: 70          moltype = RNA  length = 43
FEATURE                Location/Qualifiers
source                 1..43
                       mol_type = other RNA
                       organism = synthetic construct
SEQUENCE: 70
agagaatgtg tgcatagtca cacagaaagg ctgctgatga cac                    43

SEQ ID NO: 71          moltype = RNA  length = 43
FEATURE                Location/Qualifiers
source                 1..43
                       mol_type = other RNA
                       organism = synthetic construct
SEQUENCE: 71
agaaatgtgt ccccagttga caccccagag catcccgtgg aac                    43

SEQ ID NO: 72          moltype = RNA  length = 96
FEATURE                Location/Qualifiers
source                 1..96
                       mol_type = other RNA
                       organism = synthetic construct
SEQUENCE: 72
ccagagcatc ccgtggaacc gttttagagc tagaaatagc aagttaaaat aaggctagtc  60
cgttatcaac ttgaaaaagt ggcaccgagt cggtgc                            96

SEQ ID NO: 73          moltype = RNA  length = 41
FEATURE                Location/Qualifiers
source                 1..41
                       mol_type = other RNA
                       organism = synthetic construct
SEQUENCE: 73
taatttctac taagtgtaga tcccagagca tcccgtggaa c                      41

SEQ ID NO: 74          moltype = RNA  length = 43
FEATURE                Location/Qualifiers
source                 1..43
                       mol_type = other RNA
                       organism = synthetic construct
SEQUENCE: 74
agagaatgtg tgcatagtca caccccagag catcccgtgg aac                    43

SEQ ID NO: 75          moltype = RNA  length = 43
FEATURE                Location/Qualifiers
source                 1..43
                       mol_type = other RNA
                       organism = synthetic construct
SEQUENCE: 75
agaaatgtgt ccccagttga cacccttgac agttgagcac acg                    43

SEQ ID NO: 76          moltype = RNA  length = 96
FEATURE                Location/Qualifiers
source                 1..96
                       mol_type = other RNA
                       organism = synthetic construct
SEQUENCE: 76
cttgacagtt gagcacacgc gttttagagc tagaaatagc aagttaaaat aaggctagtc  60
cgttatcaac ttgaaaaagt ggcaccgagt cggtgc                            96

SEQ ID NO: 77          moltype = RNA  length = 41
FEATURE                Location/Qualifiers
source                 1..41
                       mol_type = other RNA
                       organism = synthetic construct
SEQUENCE: 77
taatttctac taagtgtaga tccttgacag ttgagcacac g                      41

SEQ ID NO: 78          moltype = RNA  length = 43
FEATURE                Location/Qualifiers
source                 1..43
                       mol_type = other RNA
                       organism = synthetic construct
```

```
SEQUENCE: 78
agagaatgtg tgcatagtca cacccttgac agttgagcac acg                   43

SEQ ID NO: 79           moltype = AA  length = 1080
FEATURE                 Location/Qualifiers
source                  1..1080
                        mol_type = protein
                        organism = synthetic construct
SEQUENCE: 79
MSSDVVRPYN TKLLPDNRKH NMFLQTFKRL NSISLNHFDL LICLYAAITN KKAEEYKSEK  60
EAHVTADSLC AINWFRPMSK RYSKYATTTF NMLELFKEYS GHEPDAYSKN YLMSNIDSDR  120
FVWVDCRKFA KDFAYQMELG FHEFTVLAET LLANSILVLN ESTKANWAWG TVSALYGGGD  180
KEDSTLKSKI LLAFVDALNN HELKTKREIL NQVCESLKYQ SYQDMYVDFR SVVDENGNKK  240
SPNGSMPIVT KFETDDLISD NQRKAMISNF TKNAAAKAAK KPIPYLDRLK EHMVSLCDEY  300
NVYAWAAAIT NSNADVTARN TRNLTFIGEQ NSRRKELSVL QTTTNEKAKD ILNKINDNLI  360
QEVRYTPAPK HLGRDLANLF DTLKEKDINN IENEEEKQNV INDCIEQYVD DCRSLNRNPI  420
AALLKHISRY YEDFSAKNFL DGAKLNVLTE VVNRQKAHPT IWSEKAYTWI SKFDKNRRQA  480
NSSLVGWVVP PEEVHKEKIA GQQSMMWVTL TLLDDGKWVK HHIPFSDSRY YSEVYAYNPN  540
LPYLDGGIPR QSKFGNKPTT NLTAESQALL ANSKYKKANK SFLRAKENAT HNVRVSPNTS  600
LCIRLLKDSA GNQMFDKIGN VLFGMQINHK ITVGKPNYKI EVGDRFLGFD QNQSENHTYA  660
VLQRVSESSH DTHHFNGWDV KVLEKGKVTS DVIVRDEVYA QLSYEGVPYD SSKFAEWRDK  720
RRRFVLENLS IQLEEGKTFL TEFDKLNKDS LYRWNMNYLK LLRKAIRAGG KEFAKIAKTE  780
IFELAVERFG PINLGSLSQI SLKMIASFKG VVQSYFSVSG CVDDASKKAH DSMLFTFMCA  840
AEEKRTNKRE EKTNRAASFI LQKAYLHGCK MIVCEDDLPV ADGKTGKAQN ADRMDWCARA  900
LAKKVNDGCV AMSICYRAIP AYMSSHQDPF VHMQDKKTSV LRPRFMEVNK DSIRDYHVAG  960
LRRMLNSKSD AGTSVYYRQA ALHFCEALGV SPELVKNKKT HAAELGKHMG SAMLMPWRGG  1020
RVYIASKKLT SDAKSVKYCG EDMWQYHADE IAAVNIAMYE VCCQTGAFGK KQKKSDELPG  1080

SEQ ID NO: 80           moltype = AA  length = 1080
FEATURE                 Location/Qualifiers
source                  1..1080
                        mol_type = protein
                        organism = synthetic construct
SEQUENCE: 80
MSSDVVRPYN TKLLPDNRKH NMFLQTFKRL NSISLNHFDL LICLYAAITN KKAEEYKSEK  60
EAHVTADSLC AINWFRPMSK RYSKYATTTF NMLELFKEYS GHEPDAYSKN YLMSNIDSDR  120
FVWVDCRKFA KDFAYQMELG FHEFTVLAET LLANSILVLN ESTKANWAWG TVSALYGGGD  180
KEDSTLKSKI LLAFVDALNN HELKTKREIL NQVCESLKYQ SYQDMYVDFR SVVDENGNKK  240
SPNGSMPIVT KFETDDLISD NQRKAMISNF TKNAAAKAAK KPIPYLDRLK EHMVSLCDEY  300
NVYAWAAAIT NSNADVTARN TRNLTFIGEQ NSRRKELSVL QTTTNEKAKD ILNKINDNLI  360
QEVRYTPAPK HLGRDLANLF DTLKEKDINN IENEEEKQNV INDCIEQYVD DCRSLNRNPI  420
AALLKHISRY YEDFSAKNFL DGAKLNVLTE VVNRQKAHPT IWSEKAYTWI SKFDKNRRQA  480
NSSLVGWVVP PEEVHKEKIA GQQSMMWVTL TLLDDGKWVK HHIPFSDSRY YSEVYAYNPN  540
LPYLDGGIPR QSKFGNKPTT NLTAESQALL ANSKYKKANK SFLRAKENAT HNVRVSPNTS  600
LCIRLLKDSA GNQMFDKIGN VLFGMQINHK ITVGKPNYKI EVGDRFLGFA QNQSENHTYA  660
VLQRVSESSH DTHHFNGWDV KVLEKGKVTS DVIVRDEVYD QLSYEGVPYD SSKFAEWRDK  720
RRRFVLENLS IQLEEGKTFL TEFDKLNKDS LYRWNMNYLK LLRKAIRAGG KEFAKIAKTE  780
IFELAVERFG PINLGSLSQI SLKMIASFKG VVQSYFSVSG CVDDASKKAH DSMLFTFMCA  840
AEEKRTNKRE EKTNRAASFI LQKAYLHGCK MIVCEDDLPV ADGKTGKAQN ADRMDWCARA  900
LAKKVNDGCV AMSICYRAIP AYMSSHQDPF VHMQDKKTSV LRPRFMEVNK DSIRDYHVAG  960
LRRMLNSKSD AGTSVYYRQA ALHFCEALGV SPELVKNKKT HAAELGKHMG SAMLMPWRGG  1020
RVYIASKKLT SDAKSVKYCG EDMWQYHADE IAAVNIAMYE VCCQTGAFGK KQKKSDELPG  1080

SEQ ID NO: 81           moltype = AA  length = 1080
FEATURE                 Location/Qualifiers
source                  1..1080
                        mol_type = protein
                        organism = synthetic construct
SEQUENCE: 81
MSSDVVRPYN TKLLPDNRKH NMFLQTFKRL NSISLNHFDL LICLYAAITN KKAEEYKSEK  60
EAHVTADSLC AINWFRPMSK RYSKYATTTF NMLELFKEYS GHEPDAYSKN YLMSNIDSDR  120
FVWVDCRKFA KDFAYQMELG FHEFTVLAET LLANSILVLN ESTKANWAWG TVSALYGGGD  180
KEDSTLKSKI LLAFVDALNN HELKTKREIL NQVCESLKYQ SYQDMYVDFR SVVDENGNKK  240
SPNGSMPIVT KFETDDLISD NQRKAMISNF TKNAAAKAAK KPIPYLDRLK EHMVSLCDEY  300
NVYAWAAAIT NSNADVTARN TRNLTFIGEQ NSRRKELSVL QTTTNEKAKD ILNKINDNLI  360
QEVRYTPAPK HLGRDLANLF DTLKEKDINN IENEEEKQNV INDCIEQYVD DCRSLNRNPI  420
AALLKHISRY YEDFSAKNFL DGAKLNVLTE VVNRQKAHPT IWSEKAYTWI SKFDKNRRQA  480
NSSLVGWVVP PEEVHKEKIA GQQSMMWVTL TLLDDGKWVK HHIPFSDSRY YSEVYAYNPN  540
LPYLDGGIPR QSKFGNKPTT NLTAESQALL ANSKYKKANK SFLRAKENAT HNVRVSPNTS  600
LCIRLLKDSA GNQMFDKIGN VLFGMQINHK ITVGKPNYKI EVGDRFLGFD QNQSENHTYA  660
VLQRVSESSH DTHHFNGWDV KVLEKGKVTS DVIVRDEVYD QLSYEGVPYD SSKFAEWRDK  720
RRRFVLENLS IQLEEGKTFL TEFDKLNKDS LYRWNMNYLK LLRKAIRAGG KEFAKIAKTE  780
IFELAVERFG PINLGSLSQI SLKMIASFKG VVQSYFSVSG CVDDASKKAH DSMLFTFMCA  840
AEEKRTNKRE EKTNRAASFI LQKAYLHGCK MIVCADDLPV ADGKTGKAQN ADRMDWCARA  900
LAKKVNDGCV AMSICYRAIP AYMSSHQDPF VHMQDKKTSV LRPRFMEVNK DSIRDYHVAG  960
LRRMLNSKSD AGTSVYYRQA ALHFCEALGV SPELVKNKKT HAAELGKHMG SAMLMPWRGG  1020
RVYIASKKLT SDAKSVKYCG EDMWQYHADE IAAVNIAMYE VCCQTGAFGK KQKKSDELPG  1080

SEQ ID NO: 82           moltype = AA  length = 1080
```

```
FEATURE                Location/Qualifiers
source                 1..1080
                       mol_type = protein
                       organism = synthetic construct
SEQUENCE: 82
MSSDVVRPYN TKLLPDNRKH NMFLQTFKRL NSISLNHFDL LICLYAAITN KKAEEYKSEK  60
EAHVTADSLC AINWFRPMSK RYSKYATTTF NMLELFKEYS GHEPDAYSKN YLMSNIDSDR  120
FVWVDCRKFA KDFAYQMELG FHEFTVLAET LLANSILVLN ESTKANWAWG TVSALYGGGD  180
KEDSTLKSKI LLAFVDALNN HELKTKREIL NQVCESLKYQ SYQDMYVDFR SVVDENGNKK  240
SPNGSMPIVT KFETDDLISD NQRKAMISNF TKNAAAKAAK KPIPYLDRLK EHMVSLCDEY  300
NVYAWAAAIT NSNADVTARN TRNLTFIGEQ NSRRKELSVL QTTTNEKAKD ILNKINDNLI  360
QEVRYTPAPK HLGRDLANLF DTLKEKDINN IENEEEKQNV INDCIEQYVD DCRSLNRNPI  420
AALLKHISRY YEDFSAKNFL DGAKLNVLTE VVNRQKAHPT IWSEKAYTWI SKFDKNRRQA  480
NSSLVGWVVP PEEVHKEKIA GQQSMMWVTL TLLDDGKWVK HHIPFSDSRY YSEVYAYNPN  540
LPYLDGGIPR QSKFGNKPTT NLTAESQALL ANSKYKKANK SFLRAKENAT HNVRVSPNTS  600
LCIRLLKDSA GNQMFDKIGN VLFGMQINHK ITVGKPNYKI EVGDRFLGFD QNQSENHTYA  660
VLQRVSESSH DTHHFNGWDV KVLEKGKVTS DVIVRDEVYD QLSYEGVPYD SSKFAEWRDK  720
RRRFVLENLS IQLEEGKTFL TEFDKLNKDS LYRWNMNYLK LLRKAIRAGG KEFAKIAKTE  780
IFELAVERFG PINLGSLSQI SLKMIASFKG VVQSYFSVSG CVDDASKKAH DSMLFTFMCA  840
AEEKRTNKRE EKTNRAASFI LQKAYLHGCK MIVCEDDLPV ADGKTGKAQN ADRMDWCARA  900
LAKKVNDGCV AMSICYRAIP AYMSSHQDPF VHMQDKKTSV LRPRFMEVNK DSIRDYHVAG  960
LRRMLNSKSD AGTSVYYRQA ALHFCEALGV SPELVKNKKT HAAELGKHMG SAMLMPWRGG  1020
RVYIASKKLT SDAKSVKYCG EDMWQYHAAE IAAVNIAMYE VCCQTGAFGK KQKKSDELPG  1080

SEQ ID NO: 83          moltype = RNA  length = 20
FEATURE                Location/Qualifiers
source                 1..20
                       mol_type = other RNA
                       organism = synthetic construct
SEQUENCE: 83
gtttaaacac accgggttaa                                            20

SEQ ID NO: 84          moltype = RNA  length = 23
FEATURE                Location/Qualifiers
source                 1..23
                       mol_type = other RNA
                       organism = synthetic construct
SEQUENCE: 84
gtttaaacac accgggttaa taa                                        23

SEQ ID NO: 85          moltype = AA  length = 1279
FEATURE                Location/Qualifiers
source                 1..1279
                       mol_type = protein
                       organism = synthetic construct
SEQUENCE: 85
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGWRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSSM SSDVVRPYNT KLLPDNRKHN MFLQTFKRLN SISLNHFDLL  240
ICLYAAITNK KAEEYKSEKE AHVTADSLCA INWFRPMSKR YSKYATTTFN MLELFKEYSG  300
HEPDAYSKNY LMSNIDSDRF VWVDCRKFAK DFAYQMELGF HEFTVLAETL LANSILVLNE  360
STKANWAWGT VSALYGGGDK EDSTLKSKIL LAFVDALNNH ELKTKREILN QVCESLKYQS  420
YQDMYVDFRS VVDENGNKKS PNGSMPIVTK FETDDLISDN QRKAMISNFT KNAAAKAAKK  480
PIPYLDRLKE HMVSLCDEYN VYAWAAAITN SNADVTARNT RNLTFIGEQN SRRKELSVLQ  540
TTTNEKAKDI LNKINDNLIQ EVRYTPAPKH LGRDLANLFD TLKEKDINNI ENEEEKQNVI  600
NDCIEQYVDD CRSLNRNPIA ALLKHISRYY EDFSAKNFLD GAKLNVLTEV VNRQKAHPTI  660
WSEKAYTWIS KFDKNRRQAN SSLVGWVVPP EEVHKEKIAG QQSMMWVTLT LLDDGKWVKH  720
HIPFSDSRYY SEVYAYNPNL PYLDGGIPRQ SKFGNKPTTN LTAESQALLA NSKYKKANKS  780
FLRAKENATH NVRVSPNTSL CIRLLKDSAG NQMFDKIGNV LFGMQINHKI TVGKPNYKIE  840
VGDRFLGFDQ NQSENHTYAV LQRVSESSHD THHFNGWDVK VLEKGKVTSD VIVRDEVYDQ  900
LSYEGVPYDS SKFAEWRDKR RRFVLENLSI QLEEGKTFLT EFDKLNKDSL YRWNMNYLKL  960
LRKAIRAGGK EFAKIAKTEI FELAVERFGP INLGSLSQIS LKMIASFKGV VQSYFSVSGC  1020
VDDASKKAHD SMLFTFMCAA EEKRTNKREE KTNRAASFIL QKAYLHGCKM IVCEDDLPVA  1080
DGKTGKAQNA DRMDWCARAL AKKVNDGCVA MSICYRAIPA YMSSHQDPFV HMQDKKTSVL  1140
RPRFMEVNKD SIRDYHVAGL RRMLNSKSDA GTSVYYRQAA LHFCEALGVS PELVKNKKTH  1200
AAELGKHMGS AMLMPWRGGR VYIASKKLTS DAKSVKYCGE DMWQYHAAEI AAVNIAMYEV  1260
CCQTGAFGKK QKKSDELPG                                             1279

SEQ ID NO: 86          moltype = AA  length = 1279
FEATURE                Location/Qualifiers
source                 1..1279
                       mol_type = protein
                       organism = synthetic construct
SEQUENCE: 86
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGWRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSSM GPKKKRKVMD YKDHDGDYKD HDIDYKDDDD KKKVEVSRPY  240
```

-continued

```
QSLLLPNHRK FKYLDETWNA YKSVKSLLHR FLVCAYGAVP FNKFVEVVEK VDNDQLVLAF  300
AVRLFRLVPV ESTSFAKVDK ANLAKSLANH LPVGTAIPAN VQSYFDSNFD PKKYMWIDCA  360
WEADRLAREM GLSASQFSEY ATTMLWEDWL PLNKDDVNGW GSVSGLFGEG KKEDRQQKVK  420
MLNNLLNGIK KNPPKDYTQY LKILLNAFDA KSHKEAVKNY KGDSTGRTAS YLSEKSGEIT  480
ELMLEQLMSN IQRDIGDKQK EISLPKKDVV KKYLESESGV PYDQNLWSQA YRNAASSIKK  540
TDTRNFNSTL EKFKNEVELR GLLSEGDDVE ILRSKFFSSE FHKTPDKFVI KPEHIGFNNK  600
YNVVAELYKL KAEATDFESA FATVKDEFEE KGIKHPIKNI LEYIWNNEVP VEKWGRVARF  660
NQSEEKLLRI KANPTVECNQ GMTFGNSAMV GEVLRSNYVS KKGALVSGEH GGRLIGQNNM  720
IWLEMRLLNK GKWETHHVPT HNMKFFEEVH AYNPSLADSV NVRNRLYRSE DYTQLPSSIT  780
DGLKGNPKAK LLKRQHCALN NMTANVLNPK LSFTINKKND DYTVIIVHSV EVSKPRREVL  840
VGDYLVGMAQ NQTASNTYAV MQVVKPKSTD AIPFRNMWVR FVESGSIESR TLNSRGEYVD  900
QLNHDGVDLF EIGDTEWVDS ARKFFNKLGV KHKDGTLVDL STAPRKAYAF NNFYFKTMLN  960
HLRSNEVDLT LLRNEILRVA NGRFSPMRLG SLSWTTLKAL GSFKSLVLSY FDRLGAKEMV  1020
DKEAKDKSLF DLLVAINNKR SNKREERTSR IASSLMTVAQ KYKVDNAVVH VVVEGNLSST  1080
DRSASKAHNR NTMDWCSRAV VKKLEDMCNL YGFNIKGVPA FYTSHQDPLV HRADYDDPKP  1140
ALRCRYSSYS RADFSKWGQN ALAAVVRWAS NKKSNTCYKV GAVEFLKQHG LFADKKLTVE  1200
QFLSKVKDEE ILIPRRGGRV FLTTHRLLAE STFVYLNGVK YHSCNADEVA AVNICLNDWV  1260
IPCKKKMKEE SSASGGSGS                                             1279

SEQ ID NO: 87          moltype = RNA  length = 43
FEATURE                Location/Qualifiers
source                 1..43
                       mol_type = other RNA
                       organism = synthetic construct
SEQUENCE: 87
agaaatgtgt ccccagttga cacgtttaaa cacaccgggt taa                  43

SEQ ID NO: 88          moltype = RNA  length = 43
FEATURE                Location/Qualifiers
source                 1..43
                       mol_type = other RNA
                       organism = synthetic construct
SEQUENCE: 88
agagaatgtg tgcatagtca cacgtttaaa cacaccgggt taa                  43

SEQ ID NO: 89          moltype = RNA  length = 47
FEATURE                Location/Qualifiers
source                 1..47
                       mol_type = other RNA
                       organism = synthetic construct
SEQUENCE: 89
agaaatgtgt ccccagttga cacccattac agtaggagca tacggga              47

SEQ ID NO: 90          moltype = RNA  length = 47
FEATURE                Location/Qualifiers
source                 1..47
                       mol_type = other RNA
                       organism = synthetic construct
SEQUENCE: 90
agaaatccgt ccttagttga cggccattac agtaggagca tacggga              47

SEQ ID NO: 91          moltype = RNA  length = 46
FEATURE                Location/Qualifiers
source                 1..46
                       mol_type = other RNA
                       organism = synthetic construct
SEQUENCE: 91
agacatgtgt ccccagtgac acccattaca gtaggagcat acggga               46

SEQ ID NO: 92          moltype = RNA  length = 47
FEATURE                Location/Qualifiers
source                 1..47
                       mol_type = other RNA
                       organism = synthetic construct
SEQUENCE: 92
agaaatgttt ccccagttga aacccattac agtaggagca tacggga              47

SEQ ID NO: 93          moltype = RNA  length = 47
FEATURE                Location/Qualifiers
source                 1..47
                       mol_type = other RNA
                       organism = synthetic construct
SEQUENCE: 93
agaaatgtgt tcccagttaa cacccattac agtaggagca tacggga              47

SEQ ID NO: 94          moltype = RNA  length = 47
FEATURE                Location/Qualifiers
source                 1..47
                       mol_type = other RNA
```

```
                         organism = synthetic construct
SEQUENCE: 94
agaaatttgt ccccagttga caaccattac agtaggagca tacggga                47

SEQ ID NO: 95            moltype = RNA  length = 47
FEATURE                  Location/Qualifiers
source                   1..47
                         mol_type = other RNA
                         organism = synthetic construct
SEQUENCE: 95
agaaatgtgt ccccagttga cacccattac agtaggagca tacggga                47

SEQ ID NO: 96            moltype = RNA  length = 47
FEATURE                  Location/Qualifiers
source                   1..47
                         mol_type = other RNA
                         organism = synthetic construct
SEQUENCE: 96
agaaatccgt ccttagttga cggccattac agtaggagca tacggga                47

SEQ ID NO: 97            moltype = RNA  length = 46
FEATURE                  Location/Qualifiers
source                   1..46
                         mol_type = other RNA
                         organism = synthetic construct
SEQUENCE: 97
agacatgtgt ccccagtgac acccattaca gtaggagcat acggga                 46

SEQ ID NO: 98            moltype = RNA  length = 47
FEATURE                  Location/Qualifiers
source                   1..47
                         mol_type = other RNA
                         organism = synthetic construct
SEQUENCE: 98
agaaatgttt ccccagttga aacccattac agtaggagca tacggga                47

SEQ ID NO: 99            moltype = RNA  length = 47
FEATURE                  Location/Qualifiers
source                   1..47
                         mol_type = other RNA
                         organism = synthetic construct
SEQUENCE: 99
agaaatgtgt tcccagttaa cacccattac agtaggagca tacggga                47

SEQ ID NO: 100           moltype = RNA  length = 47
FEATURE                  Location/Qualifiers
source                   1..47
                         mol_type = other RNA
                         organism = synthetic construct
SEQUENCE: 100
agaaatttgt ccccagttga caaccattac agtaggagca tacggga                47

SEQ ID NO: 101           moltype = RNA  length = 23
FEATURE                  Location/Qualifiers
source                   1..23
                         mol_type = other RNA
                         organism = synthetic construct
SEQUENCE: 101
agaaatgtgt ccccagttga cac                                          23

SEQ ID NO: 102           moltype = RNA  length = 23
FEATURE                  Location/Qualifiers
source                   1..23
                         mol_type = other RNA
                         organism = synthetic construct
SEQUENCE: 102
agaaatccgt ccttagttga cgg                                          23

SEQ ID NO: 103           moltype = RNA  length = 22
FEATURE                  Location/Qualifiers
source                   1..22
                         mol_type = other RNA
                         organism = synthetic construct
SEQUENCE: 103
agacatgtgt ccccagtgac ac                                           22

SEQ ID NO: 104           moltype = RNA  length = 23
FEATURE                  Location/Qualifiers
source                   1..23
```

```
                        mol_type = other RNA
                        organism = synthetic construct
SEQUENCE: 104
agaaatgttt ccccagttga aac                                                  23

SEQ ID NO: 105          moltype = RNA  length = 23
FEATURE                 Location/Qualifiers
source                  1..23
                        mol_type = other RNA
                        organism = synthetic construct
SEQUENCE: 105
agaaatgtgt tcccagttaa cac                                                  23

SEQ ID NO: 106          moltype = RNA  length = 23
FEATURE                 Location/Qualifiers
source                  1..23
                        mol_type = other RNA
                        organism = synthetic construct
SEQUENCE: 106
agaaatttgt ccccagttga caa                                                  23

SEQ ID NO: 107          moltype = DNA  length = 26
FEATURE                 Location/Qualifiers
source                  1..26
                        mol_type = other DNA
                        organism = synthetic construct
SEQUENCE: 107
ttcccattac agtaggagca tacggg                                               26

SEQ ID NO: 108          moltype = DNA  length = 23
FEATURE                 Location/Qualifiers
source                  1..23
                        mol_type = other DNA
                        organism = synthetic construct
SEQUENCE: 108
agaaatccgt ccttagttga cgg                                                  23

SEQ ID NO: 109          moltype = DNA  length = 22
FEATURE                 Location/Qualifiers
source                  1..22
                        mol_type = other DNA
                        organism = synthetic construct
SEQUENCE: 109
agacatgtgt ccccagtgac ac                                                   22

SEQ ID NO: 110          moltype = DNA  length = 23
FEATURE                 Location/Qualifiers
source                  1..23
                        mol_type = other DNA
                        organism = synthetic construct
SEQUENCE: 110
agaaatgttt ccccagttga aac                                                  23

SEQ ID NO: 111          moltype = DNA  length = 23
FEATURE                 Location/Qualifiers
source                  1..23
                        mol_type = other DNA
                        organism = synthetic construct
SEQUENCE: 111
agaaatgtgt tcccagttaa cac                                                  23

SEQ ID NO: 112          moltype = DNA  length = 23
FEATURE                 Location/Qualifiers
source                  1..23
                        mol_type = other DNA
                        organism = synthetic construct
SEQUENCE: 112
agaaatttgt ccccagttga caa                                                  23

SEQ ID NO: 113          moltype = DNA  length = 23
FEATURE                 Location/Qualifiers
source                  1..23
                        mol_type = other DNA
                        organism = synthetic construct
SEQUENCE: 113
agaaatgtgt ccccagttga cac                                                  23

SEQ ID NO: 114          moltype = RNA  length = 17
FEATURE                 Location/Qualifiers
```

```
source                  1..17
                        mol_type = other RNA
                        organism = synthetic construct
misc_difference         6..11
                        note = n = any nucleobase
SEQUENCE: 114
ctcccnnnnn ntgggag                                                   17

SEQ ID NO: 115          moltype = RNA  length = 17
FEATURE                 Location/Qualifiers
source                  1..17
                        mol_type = other RNA
                        organism = synthetic construct
misc_difference         6..11
                        note = n = any nucleobase
SEQUENCE: 115
ctcctnnnnn ntgggag                                                   17

SEQ ID NO: 116          moltype = RNA  length = 17
FEATURE                 Location/Qualifiers
source                  1..17
                        mol_type = other RNA
                        organism = synthetic construct
misc_difference         6..11
                        note = n = any nucleobase
SEQUENCE: 116
gtcccnnnnn ntgggac                                                   17

SEQ ID NO: 117          moltype = RNA  length = 17
FEATURE                 Location/Qualifiers
source                  1..17
                        mol_type = other RNA
                        organism = synthetic construct
misc_difference         6..11
                        note = n = any nucleobase
SEQUENCE: 117
gtgtcnnnnn ntgacac                                                   17

SEQ ID NO: 118          moltype = RNA  length = 17
FEATURE                 Location/Qualifiers
source                  1..17
                        mol_type = other RNA
                        organism = synthetic construct
misc_difference         6..11
                        note = n = any nucleobase
SEQUENCE: 118
gtgccnnnnn ntggcac                                                   17

SEQ ID NO: 119          moltype = RNA  length = 17
FEATURE                 Location/Qualifiers
source                  1..17
                        mol_type = other RNA
                        organism = synthetic construct
misc_difference         6..11
                        note = n = any nucleobase
SEQUENCE: 119
tgtgtnnnnn ntcacac                                                   17

SEQ ID NO: 120          moltype = RNA  length = 17
FEATURE                 Location/Qualifiers
source                  1..17
                        mol_type = other RNA
                        organism = synthetic construct
misc_difference         6..11
                        note = n = any nucleobase
SEQUENCE: 120
ccgtcnnnnn ntgacgg                                                   17

SEQ ID NO: 121          moltype = RNA  length = 17
FEATURE                 Location/Qualifiers
source                  1..17
                        mol_type = other RNA
                        organism = synthetic construct
misc_difference         6..11
                        note = n = any nucleobase
SEQUENCE: 121
gtttcnnnnn ntgaaac                                                   17

SEQ ID NO: 122          moltype = RNA  length = 17
```

-continued

```
FEATURE                Location/Qualifiers
source                 1..17
                       mol_type = other RNA
                       organism = synthetic construct
misc_difference        6..11
                       note = n = any nucleobase
SEQUENCE: 122
gtgttnnnnn ntaacac                                                 17

SEQ ID NO: 123         moltype = RNA  length = 17
FEATURE                Location/Qualifiers
source                 1..17
                       mol_type = other RNA
                       organism = synthetic construct
misc_difference        6..11
                       note = n = any nucleobase
SEQUENCE: 123
ttgtcnnnnn ntgacaa                                                 17

SEQ ID NO: 124         moltype = DNA  length = 10
FEATURE                Location/Qualifiers
source                 1..10
                       mol_type = other DNA
                       organism = synthetic construct
SEQUENCE: 124
ccattacagt                                                         10

SEQ ID NO: 125         moltype = DNA  length = 12
FEATURE                Location/Qualifiers
source                 1..12
                       mol_type = other DNA
                       organism = synthetic construct
SEQUENCE: 125
ccattacagt ag                                                      12

SEQ ID NO: 126         moltype = DNA  length = 14
FEATURE                Location/Qualifiers
source                 1..14
                       mol_type = other DNA
                       organism = synthetic construct
SEQUENCE: 126
ccattacagt agga                                                    14

SEQ ID NO: 127         moltype = DNA  length = 15
FEATURE                Location/Qualifiers
source                 1..15
                       mol_type = other DNA
                       organism = synthetic construct
SEQUENCE: 127
ccattacagt aggag                                                   15

SEQ ID NO: 128         moltype = DNA  length = 16
FEATURE                Location/Qualifiers
source                 1..16
                       mol_type = other DNA
                       organism = synthetic construct
SEQUENCE: 128
ccattacagt aggagc                                                  16

SEQ ID NO: 129         moltype = DNA  length = 17
FEATURE                Location/Qualifiers
source                 1..17
                       mol_type = other DNA
                       organism = synthetic construct
SEQUENCE: 129
ccattacagt aggagca                                                 17

SEQ ID NO: 130         moltype = DNA  length = 18
FEATURE                Location/Qualifiers
source                 1..18
                       mol_type = other DNA
                       organism = synthetic construct
SEQUENCE: 130
ccattacagt aggagcat                                                18

SEQ ID NO: 131         moltype = DNA  length = 19
FEATURE                Location/Qualifiers
source                 1..19
                       mol_type = other DNA
```

-continued

```
                        organism = synthetic construct
SEQUENCE: 131
ccattacagt aggagcata                                               19

SEQ ID NO: 132          moltype = DNA  length = 21
FEATURE                 Location/Qualifiers
source                  1..21
                        mol_type = other DNA
                        organism = synthetic construct
SEQUENCE: 132
ccattacagt aggagcatac g                                            21

SEQ ID NO: 133          moltype = DNA  length = 22
FEATURE                 Location/Qualifiers
source                  1..22
                        mol_type = other DNA
                        organism = synthetic construct
SEQUENCE: 133
ccattacagt aggagcatac gg                                           22

SEQ ID NO: 134          moltype = DNA  length = 23
FEATURE                 Location/Qualifiers
source                  1..23
                        mol_type = other DNA
                        organism = synthetic construct
SEQUENCE: 134
ccattacagt aggagcatac ggg                                          23

SEQ ID NO: 135          moltype = DNA  length = 24
FEATURE                 Location/Qualifiers
source                  1..24
                        mol_type = other DNA
                        organism = synthetic construct
SEQUENCE: 135
ccattacagt aggagcatac ggga                                         24

SEQ ID NO: 136          moltype = DNA  length = 26
FEATURE                 Location/Qualifiers
source                  1..26
                        mol_type = other DNA
                        organism = synthetic construct
SEQUENCE: 136
ccattacagt aggagcatac gggaga                                       26

SEQ ID NO: 137          moltype = DNA  length = 27
FEATURE                 Location/Qualifiers
source                  1..27
                        mol_type = other DNA
                        organism = synthetic construct
SEQUENCE: 137
ccattacagt aggagcatac gggagac                                      27

SEQ ID NO: 138          moltype = DNA  length = 28
FEATURE                 Location/Qualifiers
source                  1..28
                        mol_type = other DNA
                        organism = synthetic construct
SEQUENCE: 138
ccattacagt aggagcatac gggagaca                                     28

SEQ ID NO: 139          moltype = DNA  length = 30
FEATURE                 Location/Qualifiers
source                  1..30
                        mol_type = other DNA
                        organism = synthetic construct
SEQUENCE: 139
ccattacagt aggagcatac gggagacaag                                   30

SEQ ID NO: 140          moltype = DNA  length = 32
FEATURE                 Location/Qualifiers
source                  1..32
                        mol_type = other DNA
                        organism = synthetic construct
SEQUENCE: 140
ccattacagt aggagcatac gggagacaag ct                                32

SEQ ID NO: 141          moltype = DNA  length = 35
FEATURE                 Location/Qualifiers
source                  1..35
```

```
                        mol_type = other DNA
                        organism = synthetic construct
SEQUENCE: 141
ccattacagt aggagcatac gggagacaag ctttg                               35

SEQ ID NO: 142          moltype = DNA  length = 40
FEATURE                 Location/Qualifiers
source                  1..40
                        mol_type = other DNA
                        organism = synthetic construct
SEQUENCE: 142
ccattacagt aggagcatac gggagacaag ctttggccac                          40

SEQ ID NO: 143          moltype = DNA  length = 45
FEATURE                 Location/Qualifiers
source                  1..45
                        mol_type = other DNA
                        organism = synthetic construct
SEQUENCE: 143
ccattacagt aggagcatac gggagacaag ctttggccac ctacg                    45

SEQ ID NO: 144          moltype = DNA  length = 50
FEATURE                 Location/Qualifiers
source                  1..50
                        mol_type = other DNA
                        organism = synthetic construct
SEQUENCE: 144
ccattacagt aggagcatac gggagacaag ctttggccac ctacggcaag               50

SEQ ID NO: 145          moltype = DNA  length = 23
FEATURE                 Location/Qualifiers
source                  1..23
                        mol_type = unassigned DNA
                        organism = Mus musculus
SEQUENCE: 145
ttgcctcgct ggactggtat ttg                                            23

SEQ ID NO: 146          moltype = DNA  length = 23
FEATURE                 Location/Qualifiers
source                  1..23
                        mol_type = unassigned DNA
                        organism = Mus musculus
SEQUENCE: 146
ttgtgtctga agctggcccc gcg                                            23

SEQ ID NO: 147          moltype = DNA  length = 23
FEATURE                 Location/Qualifiers
source                  1..23
                        mol_type = unassigned DNA
                        organism = Mus musculus
SEQUENCE: 147
ttcccttcga ctcttcctcc ttt                                            23

SEQ ID NO: 148          moltype = DNA  length = 23
FEATURE                 Location/Qualifiers
source                  1..23
                        mol_type = unassigned DNA
                        organism = Mus musculus
SEQUENCE: 148
ttcctccttt gcctcgctgg act                                            23

SEQ ID NO: 149          moltype = DNA  length = 23
FEATURE                 Location/Qualifiers
source                  1..23
                        mol_type = unassigned DNA
                        organism = Mus musculus
SEQUENCE: 149
ttgaccatca gaggacattt gga                                            23

SEQ ID NO: 150          moltype = DNA  length = 23
FEATURE                 Location/Qualifiers
source                  1..23
                        mol_type = unassigned DNA
                        organism = Mus musculus
SEQUENCE: 150
ttggattctc cagcaccctg ggc                                            23

SEQ ID NO: 151          moltype = DNA  length = 23
FEATURE                 Location/Qualifiers
```

```
source                  1..23
                        mol_type = unassigned DNA
                        organism = Mus musculus
SEQUENCE: 151
ttacagccac gtctacagca ggg                                          23

SEQ ID NO: 152          moltype = DNA  length = 23
FEATURE                 Location/Qualifiers
source                  1..23
                        mol_type = unassigned DNA
                        organism = Mus musculus
SEQUENCE: 152
ttcaaaaaga cctctgaggg atc                                          23

SEQ ID NO: 153          moltype = DNA  length = 23
FEATURE                 Location/Qualifiers
source                  1..23
                        mol_type = unassigned DNA
                        organism = Mus musculus
SEQUENCE: 153
ttgaacactt ttacagccac gtc                                          23

SEQ ID NO: 154          moltype = DNA  length = 23
FEATURE                 Location/Qualifiers
source                  1..23
                        mol_type = unassigned DNA
                        organism = Mus musculus
SEQUENCE: 154
ttggtgtcca gttctactct gta                                          23

SEQ ID NO: 155          moltype = DNA  length = 23
FEATURE                 Location/Qualifiers
source                  1..23
                        mol_type = unassigned DNA
                        organism = Mus musculus
SEQUENCE: 155
ttctcatctg tggtgagccc gtg                                          23

SEQ ID NO: 156          moltype = DNA  length = 23
FEATURE                 Location/Qualifiers
source                  1..23
                        mol_type = unassigned DNA
                        organism = Mus musculus
SEQUENCE: 156
ttgtagaagg agtgtacaga gta                                          23

SEQ ID NO: 157          moltype = DNA  length = 23
FEATURE                 Location/Qualifiers
source                  1..23
                        mol_type = unassigned DNA
                        organism = Mus musculus
SEQUENCE: 157
ttctacaaac ttctcatctg tgg                                          23

SEQ ID NO: 158          moltype = DNA  length = 23
FEATURE                 Location/Qualifiers
source                  1..23
                        mol_type = unassigned DNA
                        organism = Mus musculus
SEQUENCE: 158
tttcacagcc aacgactctg gcc                                          23

SEQ ID NO: 159          moltype = DNA  length = 23
FEATURE                 Location/Qualifiers
source                  1..23
                        mol_type = unassigned DNA
                        organism = Homo sapiens
SEQUENCE: 159
ttgaccatca gaggacactt gga                                          23

SEQ ID NO: 160          moltype = DNA  length = 23
FEATURE                 Location/Qualifiers
source                  1..23
                        mol_type = unassigned DNA
                        organism = Homo sapiens
SEQUENCE: 160
ttcagaaagg ctgctgatga cac                                          23

SEQ ID NO: 161          moltype = DNA  length = 23
```

```
FEATURE                Location/Qualifiers
source                 1..23
                       mol_type = unassigned DNA
                       organism = Homo sapiens
SEQUENCE: 161
ttgtagaagg gatatacaaa gtg                                              23

SEQ ID NO: 162         moltype = DNA  length = 23
FEATURE                Location/Qualifiers
source                 1..23
                       mol_type = unassigned DNA
                       organism = Homo sapiens
SEQUENCE: 162
ttggcatctc cccattccat gag                                              23

SEQ ID NO: 163         moltype = DNA  length = 23
FEATURE                Location/Qualifiers
source                 1..23
                       mol_type = unassigned DNA
                       organism = Homo sapiens
SEQUENCE: 163
ttccagtaag atttggtgtc tat                                              23

SEQ ID NO: 164         moltype = DNA  length = 23
FEATURE                Location/Qualifiers
source                 1..23
                       mol_type = unassigned DNA
                       organism = Homo sapiens
SEQUENCE: 164
ttccaccacg gctgtcgtca cca                                              23

SEQ ID NO: 165         moltype = DNA  length = 22
FEATURE                Location/Qualifiers
source                 1..22
                       mol_type = unassigned DNA
                       organism = Homo sapiens
SEQUENCE: 165
aatccaagtg tcctctgatg gt                                               22

SEQ ID NO: 166         moltype = DNA  length = 22
FEATURE                Location/Qualifiers
source                 1..22
                       mol_type = unassigned DNA
                       organism = Homo sapiens
SEQUENCE: 166
aatgtggccg tgcatgtgtt ca                                               22

SEQ ID NO: 167         moltype = DNA  length = 22
FEATURE                Location/Qualifiers
source                 1..22
                       mol_type = unassigned DNA
                       organism = Homo sapiens
SEQUENCE: 167
tagatgctgt ccgaggcagt cc                                               22

SEQ ID NO: 168         moltype = DNA  length = 22
FEATURE                Location/Qualifiers
source                 1..22
                       mol_type = unassigned DNA
                       organism = Homo sapiens
SEQUENCE: 168
caccacggct gtcgtcacca at                                               22

SEQ ID NO: 169         moltype = DNA  length = 20
FEATURE                Location/Qualifiers
source                 1..20
                       mol_type = unassigned DNA
                       organism = Homo sapiens
SEQUENCE: 169
ttcctggctt cctggtgaag                                                  20

SEQ ID NO: 170         moltype = DNA  length = 20
FEATURE                Location/Qualifiers
source                 1..20
                       mol_type = unassigned DNA
                       organism = Homo sapiens
SEQUENCE: 170
ctggtgaaga tgagtggcga                                                  20
```

```
SEQ ID NO: 171         moltype = DNA  length = 20
FEATURE                Location/Qualifiers
source                 1..20
                       mol_type = unassigned DNA
                       organism = Homo sapiens
SEQUENCE: 171
aagttgcccc atgtcgacta                                              20

SEQ ID NO: 172         moltype = DNA  length = 20
FEATURE                Location/Qualifiers
source                 1..20
                       mol_type = unassigned DNA
                       organism = Homo sapiens
SEQUENCE: 172
cccagagcat cccgtggaac                                              20

SEQ ID NO: 173         moltype = DNA  length = 20
FEATURE                Location/Qualifiers
source                 1..20
                       mol_type = unassigned DNA
                       organism = Homo sapiens
SEQUENCE: 173
gcccagagca tcccgtggaa                                              20

SEQ ID NO: 174         moltype = DNA  length = 20
FEATURE                Location/Qualifiers
source                 1..20
                       mol_type = unassigned DNA
                       organism = Homo sapiens
SEQUENCE: 174
cccctccacg gtaccgggcg                                              20

SEQ ID NO: 175         moltype = DNA  length = 20
FEATURE                Location/Qualifiers
source                 1..20
                       mol_type = unassigned DNA
                       organism = Homo sapiens
SEQUENCE: 175
atccgcccgg taccgtggag                                              20

SEQ ID NO: 176         moltype = RNA  length = 3658
FEATURE                Location/Qualifiers
source                 1..3658
                       mol_type = other RNA
                       organism = synthetic construct
SEQUENCE: 176
acatttgctt ctgacacaac tgtgttcact agcaacctca aacagacacc gccaccatgg  60
ccccaaagaa gaagcggaag gtcggtatcc acggagtccc agcagccatg agttctgatg  120
tggtgcggcc ttataacaca aagctgctcc cagataacag aaagcacaat atgttcctgc  180
agaccttcaa gcggctgaac agcatctctc tgaaccactt cgacctgctg atctgcctgt  240
acgctgcaat caccaacaag aaggccgagg aatacaagtc tgaaaaggaa gcccacgtga  300
ccgccgatag cctgtgtgcc atcaattggt tcagacccat gagcaagaga tacagcaaat  360
acgccaccac caccttcaac atgttagaac tgtttaagga gtacagcggc cacgagcctg  420
atgcctattc caagaactac ctgatgagca atatcgacag cgacagattc gtgtgggtgg  480
attgtaggaa gttcgctaag gactttgcct atcagatgga actgggtttc cacgagttca  540
ccgtgttggc cgaaaccctg ctggctaatt ctatcctggt gctgaacgag agcaccaagg  600
ccaattgggc ttggggaacc gtgtctgccc tgtacggcgg cggagataag gaggacagca  660
cactgaagag caagattctg ctggccttcg tggacgccct gaacaaccac gagctgaaaa  720
caaagagaga aatcttgaat caagtgtgtg aatctctgaa ataccagagc taccaggaca  780
tgtacgtgga ttttagaagc gtggttgacg aaaacggcaa caagaagtct cctaacggct  840
ctatgcctat cgtgaccaag ttcgagacag acgacctgat cagcgacaac caaagaaagg  900
ccatgatcag caacttcact aagaacgccg ctgccaaggc agctaagaaa cctatccctt  960
acttggaccg cctgaaggag cacatggtgt ccctgtgcga cgagtacaat gtgtatgcct  1020
gggccgcggc catcacaaac agcaacgccg acgtgaccgc ccggaatacc agaaacctga  1080
cattcatcgg cgaacagaac agcagacgaa aggaactgag cgtgctgcag acaacaacca  1140
acgagaaggc taaggacatc ctgaacaaga tcaacgacaa cctgattcag gaggtgcggt  1200
acacccctgc ccctaagcac ctgggcagag atctggccaa cctgtttgat acactgaagg  1260
aaaaggacat caacaacatc gagaacgaag aagagaaaca gaacgtgatc aatgactgta  1320
tcgagcagta cgtggacgat tgcagaagcc tcaaccggaa ccccatcgca gccctcctga  1380
agcacatctc taggtactac gaggatttca gcgccaagaa tttcctggac ggcgccaagc  1440
tgaacgtgct gactgaggtg gtgaaccggc agaaggccca ccccaccatc tggagcgaga  1500
aggcttacac ctggatcagc aagttcgaca agaaccggag acaggccaac agcagcctgg  1560
tcggatgggt tgtgcccccc gaggaggtgc acaaggagaa aatcgccgga cagcagagca  1620
tgatgtgggt gaccctcacc ctgctggacg acggcaagtg ggtcaaacat cacatcccct  1680
tcagcgacag cagatactac agcgaagtgt acgcctacaa ccctaatctg ccttatctgg  1740
acggaggcat cccaagacag agcaagttcg gcaacaaacc aacaaccaac ctgacagccg  1800
agtcccaggc cctcctggct aattctaagt acaagaaagc caacaagagc ttcctgcggg  1860
ctaaagagaa tgccacacac aacgtgcggg tgtcccctaa cacctctctg tgcattagac  1920
tgctgaagga cagcgccgga aaccagatgt tcgacaaaat cggcaacgtg ctcttcggca  1980
```

-continued

```
tgcagatcaa ccacaagatc accgtgggaa aacctaacta caagatcgag gtgggcgaca  2040
gattcctggg cttcgatcag aaccagagcg agaaccacac ctacgccgtg ctgcagagag  2100
tgtccgagag cagtcacgac acccaccact ttaacggctg ggacgtgaag gtgctggaaa  2160
agggcaaagt gaccagcgat gtgatcgtgc gggacgaggt ctacgaccaa ctgtcttacg  2220
agggcgtccc ctacgatagc agcaagttcg ccgagtggcg ggacaagcgc agaagatttg  2280
tgcttgagaa cctgagcatc cagctggaag agggcaagac cttcctgaca gagttcgaca  2340
agctgaataa ggacagcctg taccgctgga acatgaacta cctgaaactg ctgagaaagg  2400
ccatccgggc cggaggcaaa gagttcgcca agatcgctaa gacagagatc ttcgagctgg  2460
cggtggaaag attcggccct attaacctgg gcagcctgtc ccagatcagc cttaagatga  2520
ttgcctcctt taagggcgtg gtccagtcct acttctccgt gagcggctgc gtggatgatg  2580
cctccaaaaa ggcccatgat tctatgctgt tcacatttat gtgcgccgcc gaagaaaagc  2640
ggaccaacaa gagagaagaa aagaccaaca gagccgccag ctttatcctg caaaaagcct  2700
acctgcatgg ctgcaagatg atcgtgtgcg aggacgacct tcctgtggcc gacggcaaga  2760
caggcaaagc ccagaatgcc gaccggatgg actggtgcgc cagagccctg gccaagaagg  2820
tgaacgacgg ctgtgttgcc atgagcatct gctacagagc tatccctgcc tacatgagca  2880
gccaccagga cccctttgtg cacatgcagg ataagaaaac cagcgtgctg cggcctagat  2940
tcatggaagt taataaggat agcatcagag actaccacgt ggcgggcctg agaagaatgc  3000
tgaacagcaa gagtgacgct ggcaccagtg tttattaccg gcaagctgcc ctgcatttct  3060
gcgaagccct gggcgtgagc cctgaactgg tgaaaaacaa gaaaacccac gccgccgaac  3120
tgggcaagca catgggcagc gctatgctga tgccctggag aggcggtaga gtgtacatcg  3180
ccagcaaaaa gctgacctcc gatgccaaat cagtgaagta ctgcggcgag gatatgtggc  3240
agtaccacgc cgatgagatc gccgctgtta acatcgccat gtatgaggtg tgctgccaga  3300
ccggcgcttt cggaaagaaa cagaaaaaat cggacgagct gcctggaaaa aggccggcgg  3360
ccacgaagaa ggccggccag gcaaagaaga agaagtaagc tcgctttctt gctgtccaat  3420
ttctattaaa ggttcctttg ttccctaagt ccaactacta aactggggga tattatgaag  3480
ggccttgagc atctggattc tgcctaataa aaaacattta ttttcattgc aaaaaaaaaa  3540
aaaaaaaaaa aaaaaaaaaa aaaaaaaaaa aaaaaaaaaa aaaaaaaaaa aaaaaaaaaa  3600
aaaaaaaaaa aaaaaaaaaa aaaaaaaaaa aaaaaaaaaa aaaaaaaaaa aaaaaaaa    3658
```

```
SEQ ID NO: 177         moltype = RNA  length = 54
FEATURE                Location/Qualifiers
source                 1..54
                       mol_type = other RNA
                       organism = synthetic construct
modified_base          1
                       mod_base = OTHER
                       note = 2'-O-methyladenosine
modified_base          2
                       mod_base = OTHER
                       note = 2'-O-methyluridine
modified_base          3
                       mod_base = OTHER
                       note = 2'-O-methylguanosine
modified_base          52..54
                       mod_base = OTHER
                       note = 2'-O-methyluridine
SEQUENCE: 177
atgactcaga aatgtgtccc cagttgacac tagaaggagt gtacagagta tttt        54

SEQ ID NO: 178         moltype = RNA  length = 100
FEATURE                Location/Qualifiers
source                 1..100
                       mol_type = other RNA
                       organism = synthetic construct
modified_base          1
                       mod_base = OTHER
                       note = 2'-O-methylcytidine
modified_base          2
                       mod_base = OTHER
                       note = 2'-O-methylguanosine
modified_base          3
                       mod_base = OTHER
                       note = 2'-O-methylcytidine
modified_base          98..100
                       mod_base = OTHER
                       note = 2'-O-methyluridine
SEQUENCE: 178
cgcggttcta tctagttacg cgttaaacca actagaaacc tcttctatga ctcagaaatg  60
tgtccccagt tgacactaga aggagtgtac agagtatttt                        100

SEQ ID NO: 179         moltype = AA  length = 7
FEATURE                Location/Qualifiers
source                 1..7
                       mol_type = protein
                       organism = Betapolyomavirus macacae
SEQUENCE: 179
PKKKRKV                                                            7

SEQ ID NO: 180         moltype = AA  length = 18
```

```
FEATURE                Location/Qualifiers
source                 1..18
                       mol_type = protein
                       organism = synthetic construct
SEQUENCE: 180
KRTADGSEFE SPKKKRKV                                            18

SEQ ID NO: 181         moltype = AA  length = 17
FEATURE                Location/Qualifiers
source                 1..17
                       mol_type = protein
                       organism = synthetic construct
SEQUENCE: 181
KRTADGSESE PKKKRKV                                             17

SEQ ID NO: 182         moltype = AA  length = 166
FEATURE                Location/Qualifiers
source                 1..166
                       mol_type = protein
                       organism = synthetic construct
SEQUENCE: 182
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGWRNSKR GAAGSLMNVL  120
NYPGMNHRVE ITEGILADEC AALLCDFYRM PRQVFNAQKK AQSSIN             166

SEQ ID NO: 183         moltype = AA  length = 33
FEATURE                Location/Qualifiers
source                 1..33
                       mol_type = protein
                       organism = synthetic construct
SEQUENCE: 183
SGGSSGGSSG SETPGTSESA TPESSGGSSG GSS                           33

SEQ ID NO: 184         moltype = AA  length = 1279
FEATURE                Location/Qualifiers
source                 1..1279
                       mol_type = protein
                       organism = synthetic construct
SEQUENCE: 184
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGWRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSSM SSDVVRPYNT KLLPDNRKHN MFLQTFKRLN SISLNHFDLL  240
ICLYAAITNK KAEEYKSEKE AHVTADSLCA INWFRPMSKR YSKYATTTFN MLELFKEYSG  300
HEPDAYSKNY LMSNIDSDRF VWVDCRKFAK DFAYQMELGF HEFTVLAETL LANSILVLNE  360
STKANWAWGT VSALYGGGDK EDSTLKSKIL LAFVDALNNH ELKTKREILN QVCESLKYQS  420
YQDMYVDFRS VVDENGNKKS PNGSMPIVTK FETDDLISDN QRKAMISNFT KNAAAKAAKK  480
PIPYLDRLKE HMVSLCDEYN VYAWAAAITN SNADVTARNT RNLTFIGEQN SRRKELSVLQ  540
TTTNEKAKDI LNKINDNLIQ EVRYTPAPKH LGRDLANLFD TLKEKDINNI ENEEEKQNVI  600
NDCIEQYVDD CRSLNRNPIA ALLKHISRYY EDFSAKNFLD GAKLNVLTEV VNRQKAHPTI  660
WSEKAYTWIS KFDKNRRQAN SSLVGWVVPP EEVHKEKIAG QQSMMWVTLT LLDDGKWVKH  720
HIPFSDSRYY SEVYAYNPNL PYLDGGIPRQ SKFGNKPTTN LTAESQALLA NSKYKKANKS  780
FLRAKENATH NVRVSPNTSL CIRLLKDSAG NQMFDKIGNV LFGMQINHKI TVGKPNYKIE  840
VGDRFLGFDQ NQSENHTYAV LQRVSESSHD THHFNGWDVK VLEKGKVTSD VIVRDEVYDQ  900
LSYEGVPYDS SKFAEWRDKR RRFVLENLSI QLEEGKTFLT EFDKLNKDSL YRWNMNYLKL  960
LRKAIRAGGK EFAKIAKTEI FELAVERFGP INLGSLSQIS LKMIASFKGV VQSYFSVSGC  1020
VDDASKKAHD SMLFTFMCAA EEKRTNKREE KTNRAASFIL QKAYLHGCKM IVCADDLPVA  1080
DGKTGKAQNA DRMDWCARAL AKKVNDGCVA MSICYRAIPA YMSSHQDPFV HMQDKKTSVL  1140
RPRFMEVNKD SIRDYHVAGL RRMLNSKSDA GTSVYYRQAA LHFCEALGVS PELVKNKKTH  1200
AAELGKHMGS AMLMPWRGGR VYIASKKLTS DAKSVKYCGE DMWQYHADEI AAVNIAMYEV  1260
CCQTGAFGKK QKKSDELPG                                           1279

SEQ ID NO: 185         moltype = RNA  length = 20
FEATURE                Location/Qualifiers
source                 1..20
                       mol_type = other RNA
                       organism = synthetic construct
SEQUENCE: 185
ccattacagt aggagcatac                                          20

SEQ ID NO: 186         moltype = DNA  length = 20
FEATURE                Location/Qualifiers
source                 1..20
                       mol_type = other DNA
                       organism = synthetic construct
SEQUENCE: 186
ggtcttcgat aagaagacct                                          20

SEQ ID NO: 187         moltype = RNA  length = 20
```

-continued

```
FEATURE                Location/Qualifiers
source                 1..20
                       mol_type = other RNA
                       organism = synthetic construct
SEQUENCE: 187
ggtcttcgat aagaagacct                                              20

SEQ ID NO: 188         moltype = RNA  length = 56
FEATURE                Location/Qualifiers
source                 1..56
                       mol_type = other RNA
                       organism = synthetic construct
SEQUENCE: 188
ctagcaatga ctcagaaatg tgtccccagt tgacacggtc ttcgataaga agacct      56

SEQ ID NO: 189         moltype = RNA  length = 23
FEATURE                Location/Qualifiers
source                 1..23
                       mol_type = other RNA
                       organism = synthetic construct
SEQUENCE: 189
agagaatgtg tgcatagtca cac                                          23

SEQ ID NO: 190         moltype = AA  length = 4
FEATURE                Location/Qualifiers
source                 1..4
                       mol_type = protein
                       organism = synthetic construct
VARIANT                3..4
                       note = Can be absent, or present in repeats of any integer
SEQUENCE: 190
GSGS                                                               4

SEQ ID NO: 191         moltype = AA  length = 4
FEATURE                Location/Qualifiers
source                 1..4
                       mol_type = protein
                       organism = synthetic construct
VARIANT                1..4
                       note = Can be present in repeats of any integer
SEQUENCE: 191
GGGS                                                               4

SEQ ID NO: 192         moltype = AA  length = 5
FEATURE                Location/Qualifiers
source                 1..5
                       mol_type = protein
                       organism = synthetic construct
VARIANT                1..5
                       note = Can be present in repeats of any integer
SEQUENCE: 192
GGGGS                                                              5
```

The invention claimed is:

1. An engineered, non-naturally occurring CRISPR-Cas system, comprising:

(1) a Cas12i protein or a polynucleotide encoding the Cas12i protein, wherein the Cas12i protein comprises an amino acid sequence having at least about 90% identity to any of SEQ ID NOs: 1-3 and 6;

(2) a CRISPR RNA (crRNA) or a polynucleotide encoding the crRNA, the crRNA comprising:

(i) a spacer capable of hybridizing to a target sequence of an eukaryotic target DNA, and (ii) a Direct Repeat (DR) linked to the spacer and capable of guiding the Cas12i protein to bind to the crRNA to form a CRISPR-Cas complex targeting the target sequence.

2. The engineered, non-naturally occurring CRISPR-Cas system of claim 1, wherein the DR has a secondary structure substantially identical to the secondary structure of the DR of any one of SEQ ID NOs: 21-23, 26, and 101-106.

3. The engineered, non-naturally occurring CRISPR-Cas system of claim 2, wherein the DR comprises a stem-loop structure near the 3' end of the DR selected from any of SEQ ID NOs: 114-123, where N is any nucleobase.

4. The engineered, non-naturally occurring CRISPR-Cas system of claim 1, wherein the complementary sequence of the target sequence is at the 3' end of a protospacer adjacent motif (PAM).

5. The engineered, non-naturally occurring CRISPR-Cas system of claim 4, wherein the PAM is selected from the group consisting of 5'-TTA, 5'-TTT, 5'-TTG, 5'-TTC, 5'-ATA, and 5'-ATG.

6. The engineered, non-naturally occurring CRISPR-Cas system of claim 1, wherein the engineered, non-naturally occurring CRISPR-Cas system comprises a polynucleotide encoding the Cas12i protein and a polynucleotide encoding the crRNA located on the same or different vectors.

7. The engineered, non-naturally occurring CRISPR-Cas system of claim 6, wherein the polynucleotide encoding the Cas12i protein and the polynucleotide encoding the crRNA located on the same vector are each operably linked to a regulatory element.

8. The engineered, non-naturally occurring CRISPR-Cas system of claim 1, wherein the spacer is at least about 16 nucleotides in length.

9. An engineered, non-naturally occurring CRISPR-Cas system, comprising:

(1) a Cas12i protein or a polynucleotide encoding the Cas12i protein, wherein the Cas12i protein comprises an amino acid sequence having at least about 90% identity to any of SEQ ID NOs: 1-3 and 6;

(2) a crRNA or a polynucleotide encoding the crRNA, the crRNA comprising:

(i) a spacer capable of hybridizing to a target sequence of a target DNA, and (ii) a DR linked to the spacer and capable of guiding the Cas12i protein to bind to the crRNA to form a CRISPR-Cas complex targeting the target sequence;

wherein the Cas12i protein substantially lacks the spacer-specific endonuclease cleavage activity of the corresponding parental Cas12i protein of any of SEQ ID NOs: 1-3 and 6 against the target sequence of the target DNA.

10. The engineered, non-naturally occurring CRISPR-Cas system of claim 9, wherein the Cas12i protein comprises an amino acid substitution at one or more positions selected from D700, D650, E875, and D1049 of the parental Cas12i protein sequence of SEQ ID NO: 1.

11. The engineered, non-naturally occurring CRISPR-Cas system of claim 10, wherein the amino acid substitution is selected from the group consisting of D700A, D700V, D650A, D650V, E875A, E875V, D1049A, D1049V, D700A+D650A, D700A+E875A, D700A+D1049A, D650A+E875A, D650A+D1049A, E875A+D1049A, D700A+D650A+E875A, D700A+D650A+D1049A, D650A+E875A+D1049A, and D700A+D650A+E875A+D1049A.

12. The engineered, non-naturally occurring CRISPR-Cas system of claim 10, wherein the Cas12i protein comprises the amino acid sequence of any one of SEQ ID NOs: 79-82.

13. The engineered, non-naturally occurring CRISPR-Cas system of claim 9, wherein the Cas12i protein is fused to one or more functional domains to form a fusion protein.

14. The engineered, non-naturally occurring CRISPR-Cas system of claim 13, wherein the functional domain is selected from the group consisting of an adenosine deaminase catalytic domain, a cytidine deaminase catalytic domain, a DNA methylation catalytic domain, a DNA demethylation catalytic domain, a transcription activation catalytic domain, a transcription inhibition catalytic domain, a nuclear export signal, and a nuclear localization signal.

15. The engineered, non-naturally occurring CRISPR-Cas system of claim 14, wherein the Cas12i protein is fused to TadA8e or a functional fragment thereof to form the fusion protein.

16. The engineered, non-naturally occurring CRISPR-Cas system of claim 15, wherein the fusion protein comprises the amino acid sequence of SEQ ID NO: 85 or 184.

17. An engineered, non-naturally occurring CRISPR-Cas system, comprising:

(1) a Cas12i protein or a polynucleotide encoding the Cas12i protein, wherein the Cas12i protein comprises an amino acid sequence having at least about 90% identity to any of SEQ ID NOs: 1-3 and 6;

(2) a crRNA or a polynucleotide encoding the crRNA, the crRNA comprising:

(i) a spacer capable of hybridizing to a target sequence of a target DNA, and (ii) a DR linked to the spacer and capable of guiding the Cas12i protein to bind to the crRNA to form a CRISPR-Cas complex targeting the target sequence;

wherein the Cas12i protein substantially lacks spacer non-specific endonuclease collateral activity of the parental Cas12i protein of any of SEQ ID NOs: 1-3 and 6 against a non-target DNA.

18. A method of modifying a target DNA, comprising contacting the target DNA with an engineered, non-naturally occurring CRISPR-Cas system, wherein the engineered, non-naturally occurring CRISPR-Cas system comprises:

(1) a Cas12i protein or a polynucleotide encoding the Cas12i protein, wherein the Cas12i protein comprises an amino acid sequence having at least about 90% identity to any of SEQ ID NOs: 1-3 and 6;

(2) a crRNA or a polynucleotide encoding the crRNA, the crRNA comprising:

(i) a spacer capable of hybridizing to a target sequence of the target DNA, and (ii) a DR linked to the spacer and capable of guiding the Cas12i protein to bind to the crRNA to form a CRISPR-Cas complex targeting the target sequence;

thereby modifying the target sequence of the target DNA.

19. The method of claim 18, wherein the modification comprises one or more of cleavage, single base editing, and repairing of the target DNA.

20. The method of claim 19, wherein the modification comprises repairing of the target DNA, and wherein the method further comprises introducing a repair template DNA.

21. The method of claim 18, wherein the modification occurs in vitro, ex vivo, or in vivo.

22. A cell or descendant thereof comprising the engineered, non-naturally occurring CRISPR-Cas system of claim 1.

23. A non-human multicellular organism comprising the cell or descendant thereof of claim 22.

24. A method of treating a condition or disease in a subject in need thereof, comprising administering to the subject an effective amount of an engineered, non-naturally occurring CRISPR-Cas system, wherein the condition or disease is associated with a target DNA, wherein the engineered, non-naturally occurring CRISPR-Cas system comprises:

(1) a Cas12i protein or a polynucleotide encoding the Cas12i protein, wherein the Cas12i protein comprises an amino acid sequence having at least about 90% identity to any of SEQ ID NOs: 1-3 and 6;

(2) a crRNA or a polynucleotide encoding the crRNA, the crRNA comprising:

(i) a spacer capable of hybridizing to a target sequence of the target DNA, and (ii) a DR linked to the spacer and capable of guiding the Cas12i protein to bind to the crRNA to form a CRISPR-Cas complex targeting the target sequence;

wherein the engineered, non-naturally occurring CRISPR-Cas system modifies the target sequence of the target DNA, and wherein the modification of the target DNA treats the condition or disease.

25. The method of claim 24, wherein the condition or disease is selected from the group consisting of transthyretin amyloidosis (ATTR), cystic fibrosis, hereditary angioedema, diabetes, progressive pseudohypertrophic muscular dystrophy, Becker muscular dystrophy, alpha-1-antitrypsin deficiency, Pompe disease, myotonic dystrophy, Huntington's disease, fragile X syndrome, Friedreich ataxia, amyotrophic lateral sclerosis, frontotemporal dementia, hereditary chronic kidney disease, hyperlipidemia, hypercholesterolemia, Leber congenital amaurosis, sickle cell disease, and beta thalassemia.

26. The method of claim 25, wherein the condition or disease is ATTR.

27. The method of claim 24, wherein the engineered, non-naturally occurring CRISPR-Cas system is administered in a lipid nanoparticle.

* * * * *